US012305169B2

(12) United States Patent
Yokota et al.

(10) Patent No.: US 12,305,169 B2
(45) Date of Patent: May 20, 2025

(54) BBB-CROSSING LIPID LIGAND OF HETERO NUCLEIC ACID

(71) Applicant: NATIONAL UNIVERSITY CORPORATION TOKYO MEDICAL AND DENTAL UNIVERSITY, Tokyo (JP)

(72) Inventors: Takanori Yokota, Tokyo (JP); Tetsuya Nagata, Tokyo (JP); Hideki Furukawa, Kanagawa (JP); Yasuo Nakagawa, Kanagawa (JP); Takatoshi Yogo, Kanagawa (JP); Ryosuke Tokunoh, Kanagawa (JP); Shigekazu Sasaki, Kanagawa (JP); Kosuke Hidaka, Kanagawa (JP); Tomohiro Seki, Kanagawa (JP); Kenichi Miyata, Kanagawa (JP); Yusuke Adachi, Kanagawa (JP); Naoto Arimura, Kanagawa (JP)

(73) Assignee: National University Corporation Tokyo Medical and Dental University, Tokyo (JP)

( * ) Notice: Subject to any disclaimer, the term of this patent is extended or adjusted under 35 U.S.C. 154(b) by 829 days.

(21) Appl. No.: 16/982,758

(22) PCT Filed: Mar. 22, 2019

(86) PCT No.: PCT/JP2019/011464
§ 371 (c)(1),
(2) Date: Feb. 8, 2021

(87) PCT Pub. No.: WO2019/182109
PCT Pub. Date: Sep. 26, 2019

(65) Prior Publication Data

US 2021/0163934 A1 Jun. 3, 2021

(30) Foreign Application Priority Data

Mar. 19, 2018 (JP) ................................ 2018-051338

(51) Int. Cl.

| | |
|---|---|
| ***C07H 21/04*** | (2006.01) |
| ***A61K 31/713*** | (2006.01) |
| ***A61P 25/28*** | (2006.01) |
| ***C12N 15/113*** | (2010.01) |

(52) U.S. Cl.
CPC .......... *C12N 15/113* (2013.01); *A61K 31/713* (2013.01); *A61P 25/28* (2018.01); *C12N 2310/31* (2013.01); *C12N 2310/32* (2013.01); *C12N 2310/341* (2013.01); *C12N 2310/346* (2013.01); *C12N 2310/3515* (2013.01)

(58) Field of Classification Search
CPC .............. C12N 15/113; C12N 2310/31; C12N 2310/32; C12N 2310/341; C12N 2310/346; A61P 25/28; A61K 31/713
See application file for complete search history.

(56) References Cited

U.S. PATENT DOCUMENTS

| | | | |
|---|---|---|---|
| 2008/0039415 A1 | 2/2008 | Stewart et al. | |
| 2015/0209441 A1 | 7/2015 | Carell | |
| 2019/0240352 A1 | 8/2019 | Yokota et al. | |
| 2019/0247414 A1 | 8/2019 | Yokota et al. | |

FOREIGN PATENT DOCUMENTS

| | | | | |
|---|---|---|---|---|
| EP | 3 517 610 A1 | 7/2019 | | |
| JP | 2015-502134 A | 1/2015 | | |
| JP | 2015-527314 A | 9/2015 | | |
| WO | WO-2013/089283 A1 | 6/2013 | | |
| WO | WO-2014/009429 A1 | 1/2014 | | |
| WO | WO-2017053999 A1 * | 3/2017 | ......... | A61K 31/7105 |
| WO | WO-2018/056442 A1 | 3/2018 | | |
| WO | WO-2018/062510 A1 | 4/2018 | | |

OTHER PUBLICATIONS

Bruun, Jonas, et al. ("Investigation of enzyme-sensitive lipid nanoparticles for delivery of siRNA to blood-brain barrier and glioma cells." International journal of nanomedicine (2015): 5995-6008).*

Nishina, Kazutaka, et al. ("DNA/RNA heteroduplex oligonucleotide for highly efficient gene silencing." Nature communications 6.1 (2015): 7969).*

D'Souza et al. (CNS delivery of nucleic acid therapeutics: beyond the blood-brain barrier and towards specific cellular targeting. Pharmaceutical Research 40.1 (2023): 77-105).*

Holm, Anja, et al. ("Clinical advances of RNA therapeutics for treatment of neurological and neuromuscular diseases." RNA biology 19.1 (2022): 594-608).*

Alterman et al. ("Hydrophobically modified siRNAs silence huntingtin mRNA in primary neurons and mouse brain." Molecular Therapy-Nucleic Acids 4 (2015)).*

(Continued)

*Primary Examiner* — Kimberly Chong
(74) *Attorney, Agent, or Firm* — Foley & Lardner LLP

(57) ABSTRACT

The object of the present invention is to provide a nucleic acid agent that can be efficiently delivered to the nervous system, particularly the central nervous system to which the BBB mechanism prevents drug delivery, and can produce an antisense effect on a target transcriptional product at the delivered site, and a composition comprising the same. Provided is a double-stranded nucleic acid complex formed by annealing a first nucleic acid strand capable of hybridizing to part of a target transcriptional product, and has an antisense effect on the target transcriptional product, to a second nucleic acid strand comprising a base sequence complementary to the first nucleic acid strand, and is bound to tocopherol or an analog thereof, cholesterol or an analog thereof, or a substituted or unsubstituted $C_{1-30}$ alkyl group, a substituted or unsubstituted $C_{2-30}$ alkenyl group, or a substituted or unsubstituted $C_{1-30}$ alkoxy group.

28 Claims, 4 Drawing Sheets

Specification includes a Sequence Listing.

(56) References Cited

OTHER PUBLICATIONS

International Search Report dated Jun. 18, 2019, in PCT/JP2019/012077.
Kuwahara et al., "Modulation of blood-brain barrier function by a heteroduplex oligonucleotide in vivo," Scientific Reports, Mar. 12, 2018, 8(4377):1-12.
Office Action dated Apr. 2, 2024 in JP 2023-061429, with English translation.
Yazawa, Kazuyoshi," Physiological functions of docosahexaenoic acid (DHA) and eicosapentaenoic acid (EPA)," Journal of the Japan Society of Food Science and Technology, 1996, 43(11):1231-1237, with English translation of indicated portions.
Kuwahara et al., "Modulation of blood-brain barrier function by a heteroduplex oligonucleotide in vivo," Scientific Reports, Mar. 12, 2018, 8(1):4377, 1-12, with Supplementary Information, 1-13.
Nagata et al., "Cholesterol-functionalized DNA/RNA heteroduplexes cross the blood-brain barrier and knock down genes in the rodent CNS," Nature Biotechnology, Dec. 2021 (online Aug. 12, 2021), 39:1529-1536, and Supplementary information, 11 pages.
Ostergaard et al., "Conjugation of hydrophobic moieties enhances potency of antisense oligonucleotides in the muscle of rodents and non-human primates," Nucleic Acids Research, May 11, 2019, 47(12):6045-6058.
Supplementary European Search Report dated Feb. 7, 2022 in EP 19772155.

* cited by examiner

LNA

ENA cEt

2'-O,4'-C-spirocyclopropylene bridged nucleic acid (scpBNA)

Amido-bridged nucleic acid (AmNA)

BNA$^{COC}$

BNA$^{NC}$

Phosphodiester

Phosphorothioate

Boranophosphate

Amide bond

Morpholino

RNA

2'-O-Me-RNA

2'-O-MOE-RNA

2'-O-allyl-RNA

2'-O-DNP-RNA

2'F-RNA

2'F-ANA

DNA

4'S-RNA

4'S-FANA

BBB-CROSSING LIPID LIGAND OF HETERO NUCLEIC ACID

CROSS REFERENCE TO RELATED APPLICATIONS

This application is a national stage application filed under 35 U.S.C. § 371 of PCT/JP2019/012077, filed Mar. 22, 2019, which claims priority from Japanese patent application JP 2018-055372, filed Mar. 22, 2018.

TECHNICAL FIELD

The present invention relates to e.g., a nucleic acid complex or a salt thereof that can produce an antisense effect in the nervous system, particularly in the central nervous system, and a composition comprising the same.

BACKGROUND ART

In recent years, an oligonucleotide has been drawing attention in the ongoing development of a pharmaceutical called a nucleic acid medicine, and in particular, development of a nucleic acid medicine utilizing the antisense method is actively pushed forward from the viewpoint of high selectivity on target genes and low toxicity. The antisense method is a method comprising selectively modifying or inhibiting the expression of a protein encoded by a target gene or the activity of miRNA by introducing into a cell an oligonucleotide complementary to a target sense strand that is a partial sequence of mRNA or miRNA transcribed from a target gene (antisense oligonucleotide, herein often referred to as "ASO").

Patent Literature 1 discloses a double-stranded nucleic acid molecule which consists of a first oligomeric compound, and a second oligomeric compound comprising a conjugated group such as cholesterol, and can regulate the amount or activity of a target nucleic acid in an extrahepatic tissue or an extrahepatic cell, or in a hepatic tissue or a hepatocyte, and an antisense compound consisting of the double-stranded nucleic acid molecule.

Meanwhile, in order to produce an antisense effect in the central nervous system including the brain, it is necessary to deliver the nucleic acid agent such as the aforementioned ASO to the central nervous system. However, in the brain there is a mechanism called a blood-brain barrier (hereinafter, often referred to as the "BBB") that selects and restricts substances that are to be transferred to the brain via the blood. While this BBB mechanism protects the brain from toxic substances, it also serves as a barrier for drug delivery to the brain. Therefore, a method of delivering a nucleic acid agent, such as an ASO, to the central nervous system including the brain, is required.

CITATION LIST

Patent Literature

Patent Literature 1: International Publication No. WO2017/053999

SUMMARY OF INVENTION

Technical Problem

An object of the present invention is to provide a nucleic acid agent that can be efficiently delivered to the nervous system, particularly to the central nervous system to which the BBB mechanism prevents drug delivery, and can produce an antisense effect on a target transcriptional product at the delivered site, and a composition comprising the same.

Solution to Problem

To solve the above-described problem, the present inventors studied diligently and found that a nucleic acid complex formed by annealing an ASO and a complementary strand of the ASO bound to e.g., tocopherol, cholesterol, or an analog thereof, and so on can be efficiently delivered to the central nervous system and exhibit a high antisense effect there. Based on these findings, the inventors have completed the present invention. The present invention thus encompasses the following aspects.

[1] A nucleic acid complex or a salt thereof comprising a first nucleic acid strand and a second nucleic acid strand, wherein:

the first nucleic acid strand comprises a base sequence capable of hybridizing to at least part of a target transcriptional product, and has an antisense effect on the target transcriptional product;

the second nucleic acid strand comprises a base sequence complementary to the first nucleic acid strand, and is bound to (1) tocopherol or an analog thereof, (2) cholesterol or an analog thereof, or (3) a substituted or unsubstituted $C_{1-30}$ alkyl group, a substituted or unsubstituted $C_{2-30}$ alkenyl group, or a substituted or unsubstituted $C_{1-30}$ alkoxy group; and the first nucleic acid strand is annealed to the second nucleic acid strand.

[2] The nucleic acid strand or a salt thereof, wherein the nucleic acid strand is bound to (1) tocopherol or an analog thereof, (2) cholesterol or an analog thereof, or (3) a substituted or unsubstituted $C_{1-30}$ alkyl group, a substituted or unsubstituted $C_{2-30}$ alkenyl group, or a substituted or unsubstituted $C_{1-30}$ alkoxy group; comprises a base sequence capable of hybridizing to at least part of a target transcriptional product, and has an antisense effect on the target transcriptional product.

[3] The nucleic acid complex, nucleic acid strand, or the salt thereof according to [1] or [2], wherein the tocopherol or the analog thereof is represented by the following Formula (I):

[Chem 1]

(I)

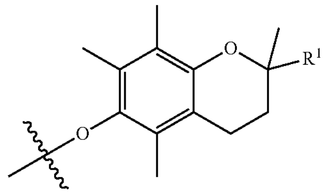

(wherein $R^1$ represents a substituted or unsubstituted $C_{1-30}$ alkyl group, or a substituted or unsubstituted $C_{2-30}$ alkenyl group.)

[4] The nucleic acid complex, nucleic acid strand, or the salt thereof according to any of [1] to [3], wherein the cholesterol or the analog thereof is represented by a Formula selected from the group consisting of the following Formulas (II), (V), (VI), and (VII):

[Chem 2]

(II)

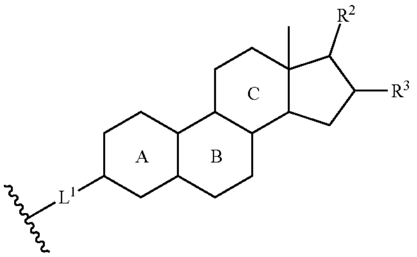

(wherein:

the ring A represents a substituted or unsubstituted cyclohexane, or a substituted or unsubstituted benzene;

the ring B represents a substituted or unsubstituted cyclohexene, a substituted or unsubstituted cyclohexane, or a substituted or unsubstituted cyclohexadiene;

the ring C represents a substituted or unsubstituted cyclohexene, or a substituted or unsubstituted cyclohexane;

$R^2$ represents a hydrogen atom, a substituted or unsubstituted $C_{1-30}$ alkyl group, a substituted or unsubstituted $C_{2-30}$ alkenyl group, a substituted or unsubstituted $C_{1-6}$ alkyl-carbonyl group, a substituted or unsubstituted $C_{1-6}$ alkyl-carbonyl-oxy group, or an oxo group;

$R^3$ represents a hydrogen atom;

$R^2$ and $R^3$ may together form a substituted or unsubstituted 1,6-dioxaspiro[4.5]decane ring, and $L^1$ represents —O—, —NH—,

[Chem 3]

(III)

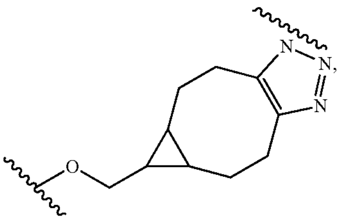

or

[Chem 4]

(IV)

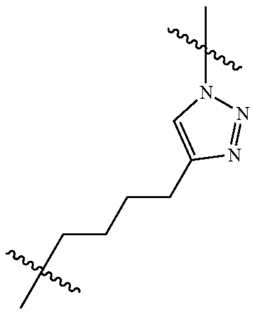

),

-continued

[Chem 5]

(V)

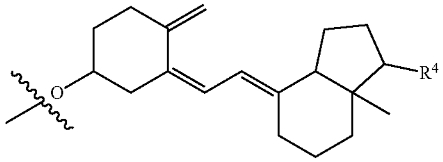

(wherein $R^4$ represents a substituted or unsubstituted $C_{1-30}$ alkyl group, or a substituted or unsubstituted $C_{2-30}$ alkenyl group),

[Chem 6]

(VI)

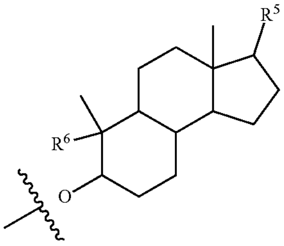

(wherein each of $R^5$ and $R^6$ independently represents a substituted or unsubstituted $C_{1-30}$ alkyl group, or a substituted or unsubstituted $C_{2-30}$ alkenyl group), and

[Chem 7]

(VII)

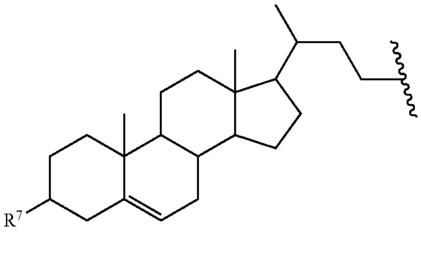

(wherein $R^7$ represents a hydroxy group, a substituted or unsubstituted $C_{1-30}$ alkyl-carbonyl-oxy group, or a substituted or unsubstituted $C_{1-30}$ alkenyl-carbonyl-oxy group.)

[5] The nucleic acid complex, nucleic acid strand, or the salt thereof according to [1] or [2], wherein the cholesterol or the analog thereof is represented by the following Formula (IIa):

[Chem 8]

(IIa)

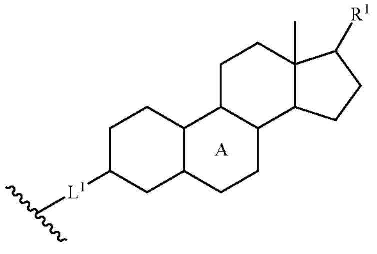

(wherein:

the ring A represents a substituted or unsubstituted cyclohexene, a substituted or unsubstituted cyclohexane, or a substituted or unsubstituted cyclohexadiene, $R^1$ represents a substituted or unsubstituted $C_{1-30}$ alkyl group, a substituted or unsubstituted $C_{2-30}$ alkenyl group, a substituted or unsubstituted $C_{1-6}$ alkyl-carbonyl group, a substituted or unsubstituted $C_{1-6}$ alkyl-carbonyl-oxy group, or an oxo group, and $L^1$ represents —O—, —NH—,

[Chem 9]

(III)

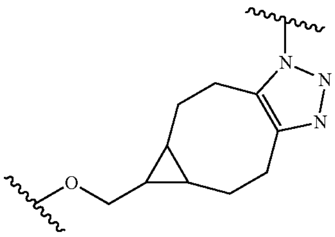

, or

[Chem 10]

(IV)

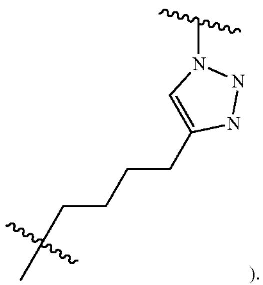

).

[6] The nucleic acid complex, nucleic acid strand, or the salt thereof according to [1] or [2], wherein the cholesterol or the analog thereof is represented by a Formula selected from the group consisting of the following Formulas (IIa-1), (IIa-2), (IIa-3), and (IIa-4):

[Chem 11]

(IIa-1)

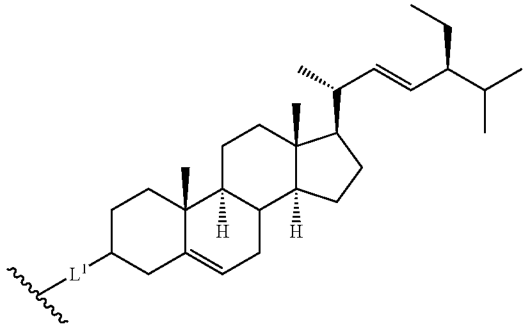

, (IIa-2)

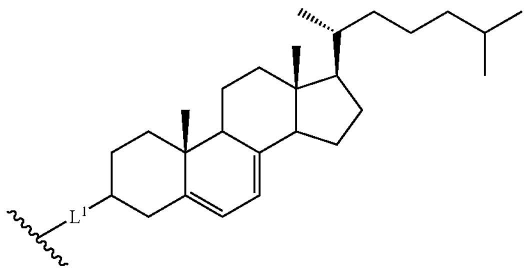

, (IIa-3)

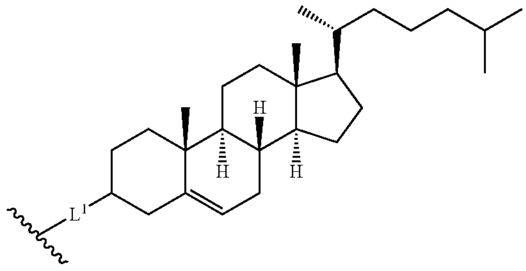

, (IIa-4)

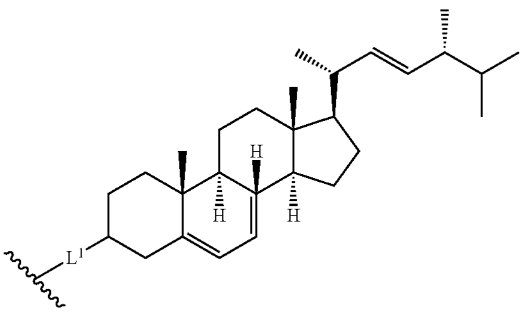

(wherein $L^1$ represents —O—, —NH—,

[Chem 12]

(III)

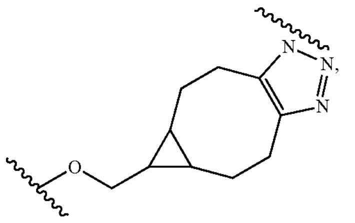

or

[Chem 13]

(IV)

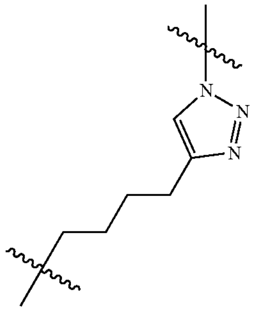

).

[7] The nucleic acid complex, nucleic acid strand, or the salt thereof according to any of [1] to [6] above, wherein the second nucleic acid strand is bound to:

(1) tocopherol or an analog thereof, (2) cholesterol or an analog thereof, or (3) a substituted or unsubstituted $C_{3-30}$ alkyl group, a substituted or unsubstituted $C_{2-30}$ alkenyl group, or a substituted or unsubstituted $C_{1-30}$ alkoxy group, via a linker represented by the following Formula (VIII):

[Chem 14]

(VIII)

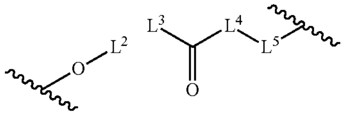

(wherein:

$L^2$ represents a substituted or unsubstituted $C_{1-12}$ alkylene group, a substituted or unsubstituted $C_{3-8}$ cycloalkylene group, $-(CH_2)_2-O-(CH_2)_2-O-(CH_2)_2-O-(CH_2)_3-$, or $CH(CH_2-OH)-CH_2-O-(CH_2)_2-O-(CH_2)_2-O-(CH_2)_2-O-(CH_2)_3-$;

$L^3$ represents —NH— or a bond;

$L^4$ represents a substituted or unsubstituted $C_{3-32}$ alkylene group, a substituted or unsubstituted $C_{3-8}$ cycloalkylene group, $-(CH_2)_2-[O-(CH_2)_2]_m-$, or a bond, wherein m represents an integer of 1 to 25; and $L^5$ represents —NH—(C═O)—, —(C═O)—, or a bond).

[8] The nucleic acid complex, nucleic acid strand, or the salt thereof according to any of [1] to [7], wherein the first nucleic acid strand comprises at least four contiguous deoxyribonucleosides.

[9] The nucleic acid complex, nucleic acid strand, or the salt thereof according to any of [1] to [8], wherein the first nucleic acid strand is a gapmer.

[10] The nucleic acid complex, nucleic acid strand, or the salt thereof according to [8] or [9], wherein the second nucleic acid strand comprises at least four contiguous ribonucleosides complementary to at least four contiguous deoxyribonucleosides in the first nucleic acid strand.

[11] The nucleic acid complex, nucleic acid strand, or the salt thereof according to any of [1] to [7], wherein the first nucleic acid strand is a mixmer.

[12] The nucleic acid complex, nucleic acid strand, or the salt thereof according to any of [1] to [11], wherein the first nucleic acid strand is from 13 to 20 bases in length.

[13] The nucleic acid complex, nucleic acid strand, or the salt thereof according to any of [1] to [12], wherein the second nucleic acid strand does not comprise a natural ribonucleoside.

[14] The nucleic acid complex, nucleic acid strand, or the salt thereof according to any of [1] to [13], wherein the nucleic acid portion in the second nucleic acid strand consists of deoxyribonucleosides and/or sugar-modified nucleosides linked by a modified or unmodified internucleoside bond.

[15] A composition for regulating expression or editing of a target transcriptional product in the central nervous system of a subject, comprising the nucleic acid complex, nucleic acid strand, or the salt thereof according to any of [1] to [14].

[16] The composition according to [15] for treating a central nervous system disease of a subject.

[17] The composition according to [16], wherein the central nervous system disease is an immune-mediated central nervous system disease.

[18] A composition for delivering a drug to the central nervous system of a subject comprising the nucleic acid complex, nucleic acid strand, or the salt thereof according to any of [1] to [14].

[19] The composition according to any of [15] to [18], wherein the central nervous system is selected from the group consisting of the cerebral cortex, basal ganglion, cerebral white matter, diencephalon, brainstem, cerebellum, and spinal cord.

[20] The composition according to any of [15] to [18], wherein the central nervous system is selected from the group consisting of the frontal lobe, temporal lobe, hippocampus, parahippocampal gyrus, parietal lobe, occipital lobe, striatum, globus pallidus, claustrum, thalamus, subthalamic nucleus, midbrain, substantia nigra, pons, medulla oblongata, cerebellar cortex, cerebellar nucleus, cervical spinal cord, thoracic spinal cord, and lumbar spinal cord.

[21] The composition according to any of [15] to [20] for intravenous administration or subcutaneous administration.

[22] The composition according to any of [15] to [21] comprising 5 mg/kg or more of the nucleic acid complex, nucleic acid strand, or the salt thereof in a single dose.

[23] The composition according to any of [15] to [22], wherein the nucleic acid complex, nucleic acid strand, or the salt thereof crosses the blood-brain barrier (BBB).

[24] The composition according to [17], wherein the immune-mediated central nervous system disease is a microglia-associated disease.

[25] The composition according to [24], wherein the microglia-associated disease is Alzheimer's disease, multiple sclerosis, ALS, or neuropathic pain.

[26] The composition according to any of [15] to [25] for regulating expression or editing of a target transcriptional product in microglia.

The present description encompasses the disclosures in Japanese Patent Application No. 2018-055372, which is the basis for the priority of the present application.

Advantageous Effects of Invention

The present invention can provide a nucleic acid agent that is efficiently delivered to the central nervous system and produces an antisense effect at the delivered site, and a composition comprising the same.

BRIEF DESCRIPTION OF DRAWINGS

FIG. 1*a* shows a nucleic acid complex in which tocopherol is bound to the 5' end of the second nucleic acid strand. FIG. 1*b* shows a nucleic acid complex in which cholesterol is bound to the 5' end of the second nucleic acid strand. FIG. 1*c* shows a nucleic acid complex in which tocopherol is bound to the 3' end of the second nucleic acid strand. FIG. 1*d* shows a nucleic acid complex in which cholesterol is bound to the 3' end of the second nucleic acid strand.

DESCRIPTION OF EMBODIMENTS

The first aspect of the present invention is a nucleic acid complex, and more preferably a blood-brain barrier crossing nucleic acid complex. This nucleic acid complex comprises a first nucleic acid strand and a second nucleic acid strand. The second nucleic acid strand is a nucleotide strand that comprises a base sequence complementary to the first nucleic acid strand. In the nucleic acid complex, the first nucleic acid strand is annealed to the second nucleic acid strand. In an embodiment, the second nucleic acid strand is bound to (1) tocopherol or an analog thereof, (2) cholesterol or an analog thereof, or (3) a substituted or unsubstituted $C_{1-0}$ alkyl group, a substituted or unsubstituted $C_{2-30}$ alkenyl group, or a substituted or unsubstituted $C_{1-30}$ alkoxy group (herein, the above (1) to (3) are also collectively referred to as "tocopherol, cholesterol, or an analog thereof, and so on").

Figure 1:
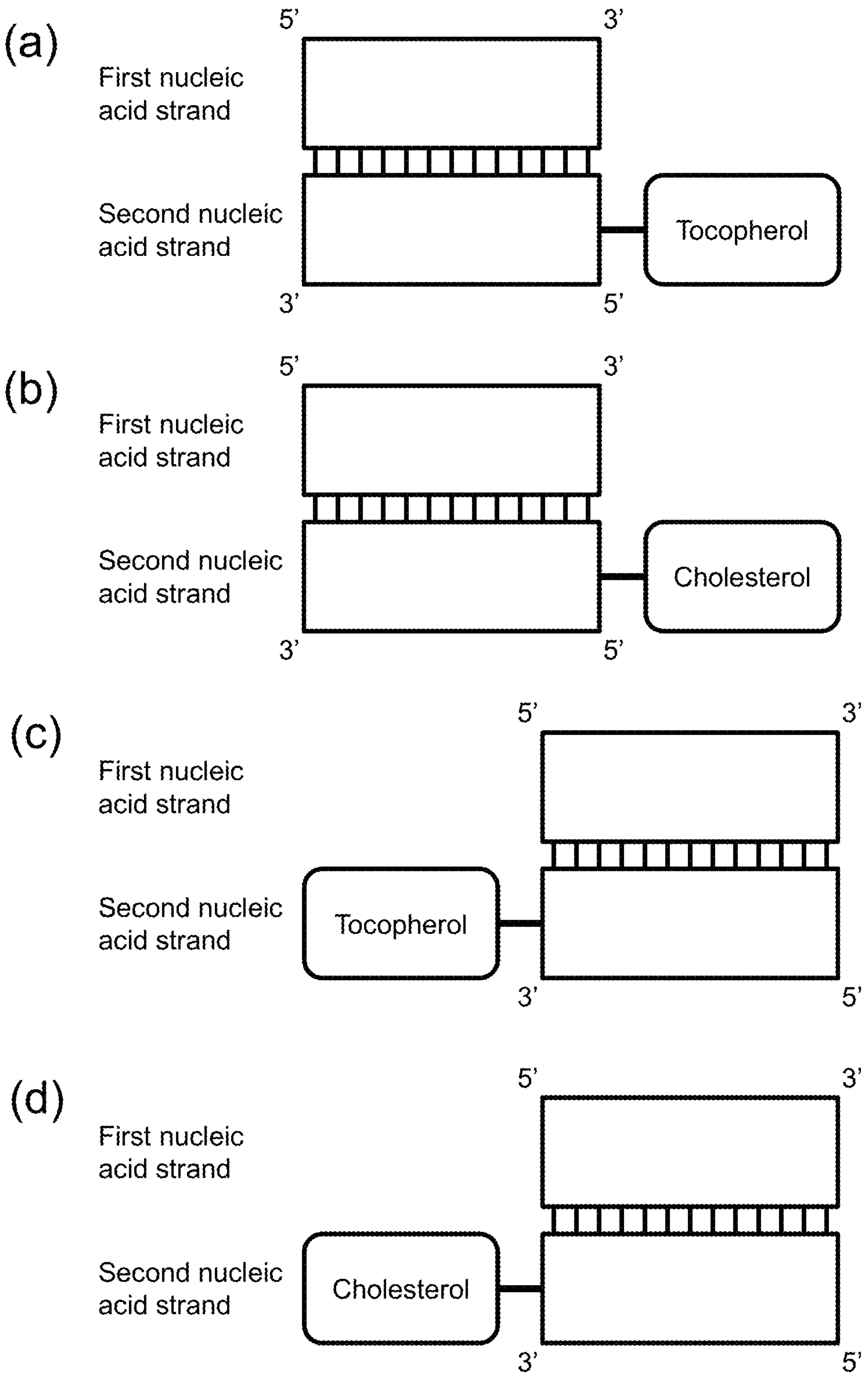
FIG. 1 is a schematic diagram showing examples of specific embodiments of the nucleic acid complex used in the present invention. This figure shows four modes in terms of a binding position of tocopherol or cholesterol in the second nucleic acid strand.

A representative schematic diagram of the nucleic acid complex is shown in FIG. 1. FIG. 1*a* shows a nucleic acid complex in which tocopherol is bound to the 5' end of the second nucleic acid strand. FIG. 1*b* shows a nucleic acid complex in which cholesterol is bound to the 5' end of the second nucleic acid strand. FIG. 1*c* shows a nucleic acid complex in which tocopherol is bound to the 3' end of the second nucleic acid strand. FIG. 1*d* shows a nucleic acid complex in which cholesterol is bound to the 3' end of the second nucleic acid strand. However, as described below, tocopherol, cholesterol, or an analog thereof, and so on may be bound to the 5' end, the 3' end, or both the ends of the second nucleic acid strand, or to a nucleotide inside the second nucleic acid strand.

In an embodiment, the first nucleic acid strand is a nucleotide strand comprising a base sequence capable of hybridizing to at least part of a target transcriptional product. In a certain embodiment, the first nucleic acid strand is a nucleotide strand having an antisense effect on a transcriptional product of a target gene, or a target transcriptional product.

In an embodiment, the present invention relates to a single-stranded nucleic acid strand that is bound to (1) tocopherol or an analog thereof, (2) cholesterol or an analog thereof, or (3) a substituted or unsubstituted $C_{1-30}$ alkyl group, a substituted or unsubstituted $C_{2-30}$ alkenyl group, or a substituted or unsubstituted $C_{1-30}$ alkoxy group. This nucleic acid strand corresponds to the first nucleic acid strand of the aforedescribed nucleic acid complex, which is a nucleotide strand comprising a base sequence capable of hybridizing to at least part of a target transcriptional product. In a certain embodiment, the nucleic acid strand is a nucleotide strand having an antisense effect on a transcriptional product of a target gene, or a target transcriptional product.

Definition of Terms

A "target transcriptional product" means herein any RNA that can be a target of a nucleic acid complex of the present invention, and is synthesized by a DNA-dependent RNA polymerase. In general, a transcriptional product of a target gene corresponds to the same. Specifically, the same may comprise mRNA transcribed from a target gene (such as mature mRNA, mRNA precursor, and mRNA without a base modification), and non-coding RNA (ncRNA) such as miRNA.

The "target gene" is not particularly limited herein, and examples thereof include a gene derived from an organism into which a nucleic acid complex of the present invention is introduced, such as a gene whose expression is increased in various diseases. Further, a target transcriptional product may comprise mRNA transcribed from the genomic DNA encoding a target gene, and further mRNA without a base modification, and an unprocessed mRNA precursor and so on. A "target transcriptional product" may comprise not only mRNA, but also non-coding RNA (ncRNA) such as miRNA. Further, a "transcriptional product" may be, in general, any RNA synthesized by a DNA-dependent RNA polymerase. In an embodiment, a "target transcriptional product" may comprise, for example, a scavenger receptor B1 (herein often denoted as "SR-B1 mRNA") and a metastasis associated lung adenocarcinoma transcript 1 (herein often denoted as "Malat1") non-coding RNAs. The base sequence of murine Malat1 non-coding RNA is shown in SEQ ID NO: 3, and the base sequence of human Malat1 non-coding RNA is shown in SEQ ID NO: 4. Also, the base sequence of murine SR-B1 mRNA is shown in SEQ ID NO: 5, and the base sequence of human SR-B1 mRNA is shown in SEQ ID NO: 6. Further, the base sequence of murine DMPK mRNA is shown in SEQ ID NO: 7, and the base sequence of human DMPK mRNA is shown in SEQ ID NO:8. In each of SEQ ID NO: 1 to 8, the base sequence of mRNA is replaced with the base sequence of DNA. Information on the base sequences of these genes and transcriptional products is available from public databases, such as the NCBI (U.S. National Center for Biotechnology Information) database.

An "antisense oligonucleotide (ASO)" or an "antisense nucleic acid" refers herein to a single-stranded oligonucleotide comprising a complementary base sequence that is capable of hybridizing to at least part, e.g., any target region, of a target transcriptional product, and can inhibit and regulate the expression of a transcriptional product of the target gene, or the level of the target transcriptional product through an antisense effect. In a nucleic acid complex of the present invention, the first nucleic acid strand functions as an ASO, and the target region thereof may comprise a 3'UTR, a 5'UTR, an exon, an intron, a coding region, a translation initiation region, a translation termination region, or any other nucleic acid region. The target region of a target transcriptional product may be at least 8 bases in length, for example, from 10 to 35 bases in length, from 12 to 25 bases in length, from 13 to 20 bases in length, from 14 to 19 bases in length, or from 15 to 18 bases in length.

Figure 2:
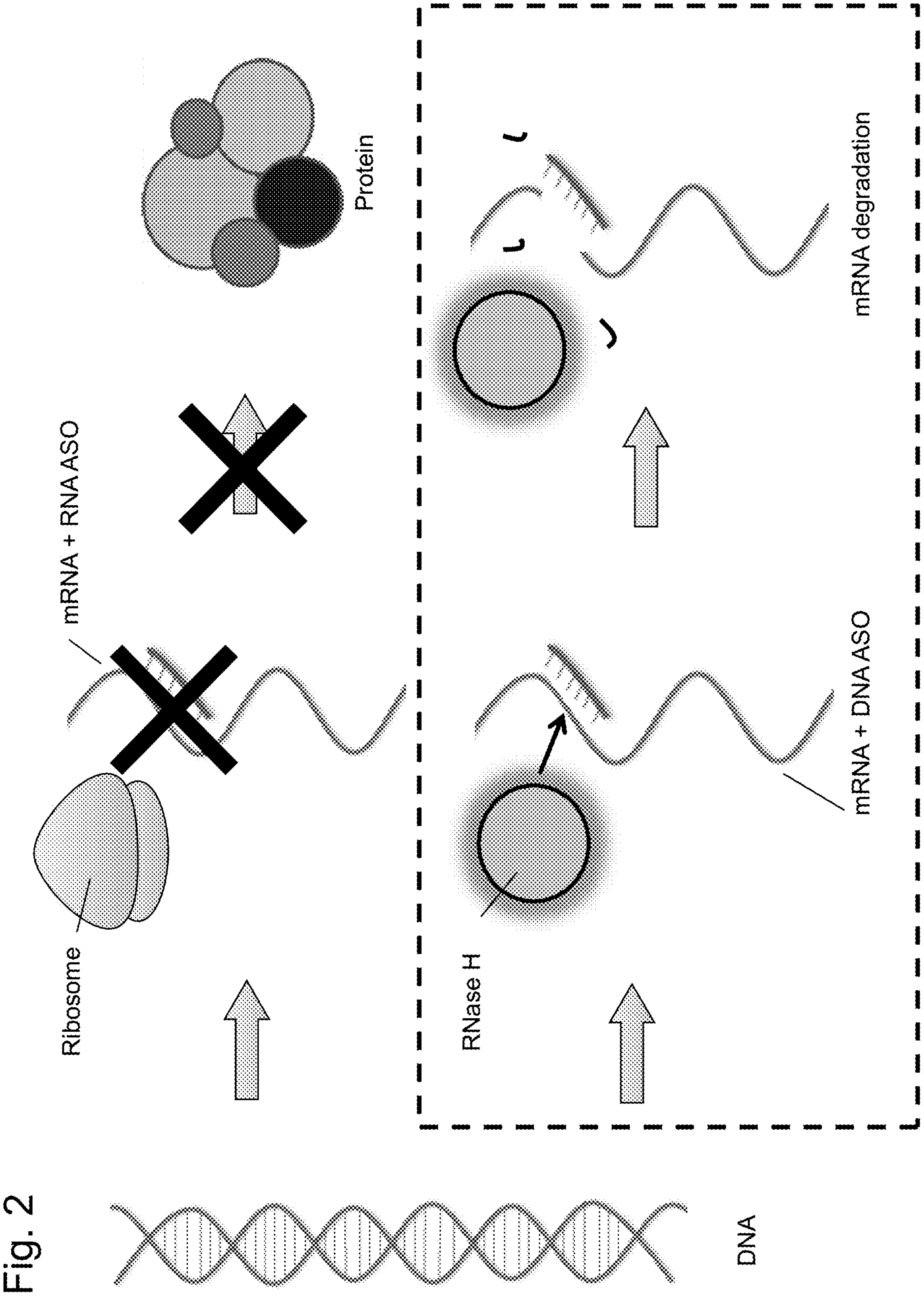
FIG. 2 is a diagram showing an example of a general mechanism of the antisense method. In the diagram "X" indicates a position of suppression or inhibition in the steps from expression of a gene to translation. The figure inside the dashed line is a schematic diagram in which a heteroduplex strand portion is recognized by RNase H and the mRNA of the target gene is degraded.

An "antisense effect" means an effect of regulating the expression or editing to be produced on a target transcriptional product by hybridization of an ASO to the target transcriptional product (e.g., RNA-sense strand). To "regulate the expression or editing of a target transcriptional product" means an effect of inhibiting or decreasing the expression of a target gene or the expression amount of a target transcriptional product (the "expression amount of a target transcriptional product" is herein often denoted as a "level of a target transcriptional product"), inhibiting translation, modifying a splicing function (such as exon skipping), or degrading a transcriptional product. For example, as illustrated in FIG. 2, regarding inhibition of translation, when an oligonucleotide (e.g., RNA) is introduced into a cell as an ASO, the ASO binds to mRNA or the like that is a transcriptional product of a target gene to form a partial double strand. This partial double strand serves as a cover to prevent translation by ribosomes, and as a result expression of a protein encoded by the target gene is inhibited at the translational level (FIG. 2, symbol X outside the dashed line). Meanwhile, when oligonucleotides comprising DNA are introduced into a cell as an ASO, a partial DNA-RNA heteroduplex strand is formed. As a result of this heteroduplex strand structure being recognized by RNase H, the mRNA of the target gene is degraded and expression of a protein encoded by the target gene inhibited at the expression level (FIG. 2, inside the dashed line). This is referred to as "RNase H dependent pathway". Furthermore, in a certain example, an antisense effect can be brought about by targeting an intron of a mRNA precursor. An antisense effect may be brought about by targeting a miRNA, and in this case the function of the miRNA is inhibited and the expression of the gene whose expression is normally regulated by the miRNA may be increased. In an embodiment, the expression regulation of a target transcriptional product may be a decrease in the amount of the target transcriptional product.

The term "nucleic acid" or "nucleic acid molecule" as used herein means a nucleoside or a nucleotide in the case of a monomer, an oligonucleotide in the case of an oligomer, and a polynucleotide in the case of a polymer.

A "nucleoside" generally refers to a molecule consisting of a combination of a base and a sugar. The sugar moiety of a nucleoside is usually, but without limitation, composed of a pentofuranosyl sugar, and specific examples thereof include ribose and deoxyribose. The base moiety (nucleobase) of a nucleoside is usually a heterocyclic base moiety. Examples thereof include, but not limited to, adenine, cytosine, guanine, thymine, uracil, and other modified nucleobases (modified bases).

A "nucleotide" refers to a molecule in which a phosphate group is covalently bonded to the sugar moiety of the nucleoside. In the case of a nucleotide comprising a pentofuranosyl sugar, a phosphate group is usually linked to the hydroxyl group at the 2', 3', or 5' position of the sugar.

An "oligonucleotide" means a linear oligomer formed by linking several to dozens of contiguous nucleotides through covalent bonds between hydroxyl groups in the sugar moiety and phosphate groups. A "polynucleotide" means a linear polymer formed by linking a larger number of nucleotides than in an oligonucleotide, namely dozens or more, and preferably hundreds or more nucleotides through the aforedescribed covalent bonds. Inside the structure of an oligonucleotide or a polynucleotide, a phosphate group is generally considered to form an internucleoside bond.

The term "nucleic acid strand" or mere "strand" as used herein means an oligonucleotide or a polynucleotide. A nucleic acid strand can be produced as a full-length strand, or a partial strand by a chemical synthesis method, for example, using an automated synthesizer, or by an enzymatic process by a polymerase, a ligase, or a restriction reaction. A nucleic acid strand may comprise a natural nucleotide and/or a non-natural nucleotide.

A "natural nucleoside" means herein a naturally occurring nucleoside. Examples thereof include, for example, a ribonucleoside consisting of ribose and a base such as adenine, cytosine, guanine, or uracil, and a deoxyribonucleoside consisting of deoxyribose and the aforedescribed base such as adenine, cytosine, guanine, or thymine. A ribonucleoside found in RNA, and a deoxyribonucleoside found in DNA may be respectively referred to as "DNA nucleoside" and "RNA nucleoside". Similarly, a "natural nucleotide" is a naturally occurring nucleotide that is a molecule in which a phosphate group is covalently bonded to the sugar moiety of a natural nucleoside. Examples thereof include a ribonucleotide which is known as a constituent of RNA, and in which a phosphate group is bound to a ribonucleoside, and a deoxyribonucleotide which is known as a constituent of DNA, and in which a phosphate group is bound to a deoxyribonucleoside.

A "non-natural nucleoside" refers herein to any nucleoside other than natural nucleosides. Examples thereof include a modified nucleoside, or a nucleoside mimic. A "modified nucleoside" means herein a nucleoside having a modified sugar moiety and/or a modified nucleobase. A nucleic acid strand comprising a non-natural oligonucleotide is in many cases more preferable than a natural type, because of such desirable characteristics as enhanced cellular uptake, enhanced affinity for a nucleic acid target, increased stability in the presence of a nuclease, or increased inhibitory activity.

A "mimic" refers herein to a functional group that replaces a sugar, a nucleobase, and/or an internucleoside bond. In general, a mimic is used in place of a sugar or a combination of sugar-internucleoside bond, and a nucleobase is maintained for hybridization to a selected target. A "nucleoside mimic" comprises a structure used for replacing a sugar, or replacing a sugar and a base, or replacing a bond and so on between monomeric subunits constituting an oligomeric compound, at one or more positions of an oligomeric compound. An "oligomeric compound" means a polymer of linked monomeric subunits capable of hybridizing to at least some region of a nucleic acid molecule. Example of a nucleoside mimic include morpholino, cyclohexenyl, cyclohexyl, tetrahydropyranyl, bicyclic or tricyclic sugar mimic, e.g., a nucleoside mimic having a non-furanose sugar unit.

Figure 3:
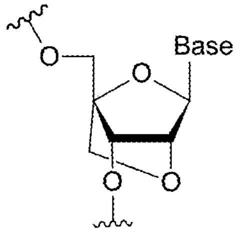
FIG. 3 is a diagram showing the structures of various bridged nucleic acids.
Figure 3:
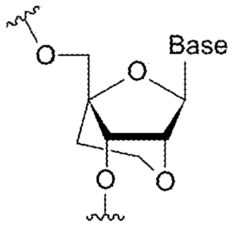
Figure 3:
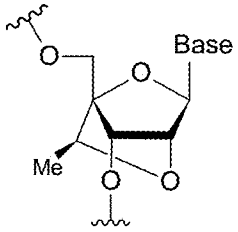
Figure 3:
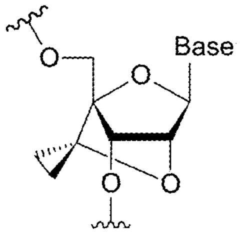
Figure 3:
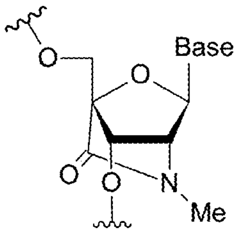
Figure 3:
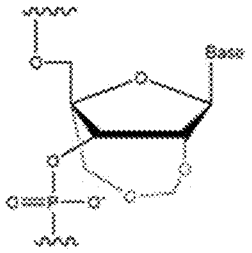
Figure 3:
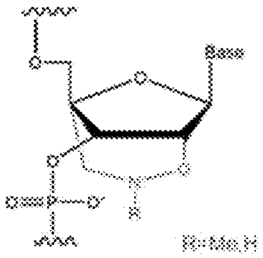

A "bicyclic nucleoside" means herein a modified nucleoside comprising a bicyclic sugar moiety. A nucleic acid comprising a bicyclic sugar moiety is generally referred to as bridged nucleic acid (BNA). A nucleoside comprising a bicyclic sugar moiety is herein sometimes referred to as "bridged nucleoside". Examples of a bridged nucleic acid are partly illustrated in FIG. 3.

A bicyclic sugar may be a sugar in which the carbon atom at the 2' position and the carbon atom at the 4' position are bridged via two or more atoms. Examples of a bicyclic sugar are publicly known to those skilled in the art. A subgroup of nucleic acid (BNA) comprising a bicyclic sugar may be described as having a carbon atom at the 2' position and a carbon atom at the 4' position bridged by 4'-$(CH_2)_p$—O-2', 4'-$(CH_2)_p$—$CH_2$-2', 4'-$(CH_2)_p$—S-2', 4'-$(CH_2)_p$—O $CH_2$O-2', or 4'-$(CH_2)_n$—N($R_3$)—O—$(CH_2)_m$-2' [wherein p, m, and n respectively represent integers of 1 to 4, 0 to 2, and 1 to 3; and $R_3$ represents a hydrogen atom, an alkyl group, an alkenyl group, a cycloalkyl group, an aryl group, an aralkyl group, an acyl group, a sulfonyl group, or a unit substituent (such as a fluorescent or chemiluminescent labeling molecule, a functional group having nucleic acid cleavage activity, and intracellular or intranuclear localization signal peptide)]. Further, in the BNA according to a specific embodiment, with respect to an $OR_2$ substituent on the carbon atom at the 3' position, and an $OR_1$ substituent on the carbon atom at the 5' position, $R_1$ and $R_2$ are typically a hydrogen atom, but they may be the same or different each other, and, further, a protecting group for a hydroxyl group for nucleic acid synthesis, an alkyl group, an alkenyl group, a cycloalkyl, an aryl group, an aralkyl group, an acyl group, a sulfonyl group, a silyl group, a phosphate group, a phosphate group protected by a protecting group for nucleic acid synthesis, or —P($R^4$)$R^5$ [wherein $R^4$ and $R^5$ may be the same or different each other, and respectively are a hydroxyl group, a hydroxyl group protected by a protecting group for nucleic acid synthesis, a mercapto group, a mercapto group protected by a protecting group for nucleic acid synthesis, an amino group, an alkoxy group having 1 to 5 carbon atoms, an alkylthio group having 1 to 5 carbon atoms, a cyanoalkoxy group having 1 to 6 carbon atoms, or an amino group substituted with an alkyl group having 1 to 5 carbon atoms]. Non-restrictive examples of such BNA include methyleneoxy (4'-$CH_2$—O-2') BNA (LNA (Locked Nucleic Acid®, also known as 2',4'-BNA), e.g., α-L-methyleneoxy (4'-$CH_2$—O-2') BNA, or β-D-methyleneoxy (4'-$CH_2$—O-2') BNA, ethyleneoxy (4'-$(CH_2)_2$—O-2') BNA (also known as ENA), β-D-thio (4'-$CH_2$—S-2') BNA, aminooxy (4'-$CH_2$—O—N($R_3$)-2') BNA, oxyamino (4'-$CH_2$—N($R_3$)—O-2') BNA (also known as 2',4'-$BNA^{NC}$), 2',4'-$BNA^{coc}$, 3'-amino-2',4'-BNA, 5'-methyl BNA, (4'-CH($CH_3$)—O-2') BNA (also known as cEt BNA), (4'-CH($CH_2OCH_3$)—O-2')BNA (also known as cMOE BNA), amide BNA (4'-C(O)—N(R)-2') BNA (R═H, Me) (also known as AmNA), 2'-0,4'-C-spirocyclopropylene bridged nucleic acid (also known as scpBNA), and other BNAs publicly known to those skilled in the art. A bicyclic nucleoside having a methyleneoxy (4'-$CH_2$—O-2') bridge is herein sometimes referred to as "LNA nucleoside".

A "non-natural nucleotide" refers herein to any nucleotide other than natural nucleotides and comprises a modified nucleotide and a nucleotide mimic. A "modified nucleotide" means herein a nucleotide having any one or more of a modified sugar moiety, a modified internucleoside bond, and a modified nucleobase.

Figure 4:
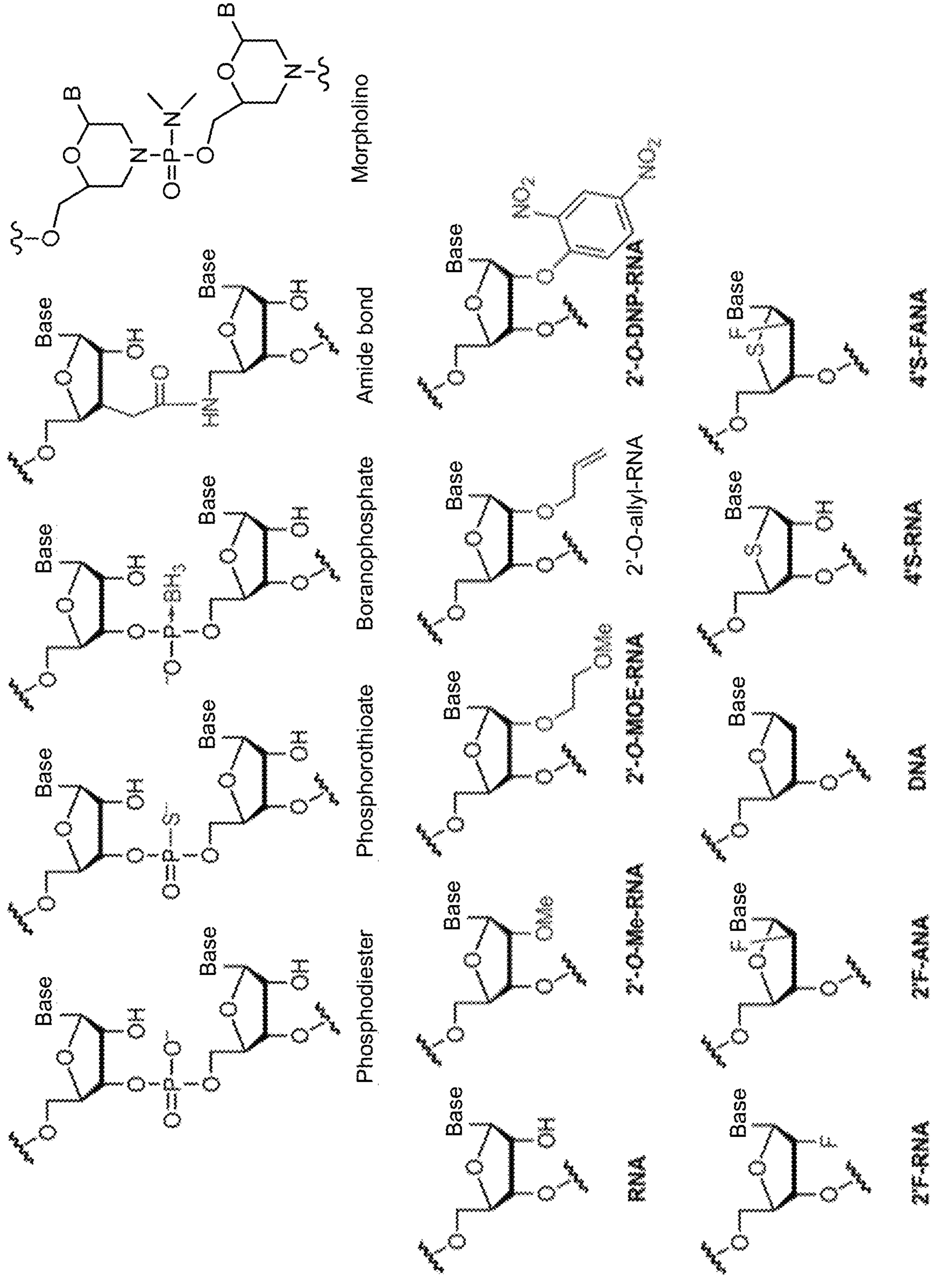
FIG. 4 is a diagram showing the structures of various natural nucleotides and non-natural nucleotides.

A "nucleotide mimic" comprises a structure used for replacing a nucleoside and a bond at one or more positions of an oligomeric compound. Example of a nucleotide mimic include a peptide nucleic acid, and a morpholino nucleic acid (a morpholino linked by —N(H)—C(═O)—O— or other non-phosphodiester bonds). A peptide nucleic acid (PNA) is a nucleotide mimic having a main chain in which N-(2-aminoethyl)glycine is linked by an amide bond in place of a sugar. An example of the structure of a morpholino nucleic acid is shown in FIG. 4. A nucleic acid strand comprising a non-natural oligonucleotide herein has in many cases such desirable characteristics as enhanced cellular uptake, enhanced affinity for a nucleic acid target, increased stability in the presence of a nuclease, or increased inhibitory activity. Therefore, it is more preferable than a natural nucleotide.

A "modified internucleoside bond" means herein an internucleoside bond having a substitution or any change from a naturally occurring internucleoside bond (i.e., phosphodiester bond). The modified internucleoside bond comprises a phosphorus-containing internucleoside bond comprising a phosphorus atom, and a phosphorus-free internucleoside bond not comprising a phosphorus atom. Examples of a typical phosphorus-containing internucleoside bond include, but not limited to, a phosphodiester bond, a phosphorothioate bond, a phosphorodithioate bond, a phosphotriester bond, an alkylphosphonate bond, an alkylthiophosphonate bond, a boranophosphate bond, and a phosphoramidate bond. A phosphorothioate bond is an internucleoside bond in which a non-bridging oxygen atom of a phosphodiester bond is substituted with a sulfur atom. A method for preparing a phosphorus-containing bond or a phosphorus-free bond is well known. A modified internucleoside bond should preferably be a bond whose nuclease resistance is higher than a naturally occurring internucleoside bond.

A "modified nucleobase" or a "modified base" means herein any nucleobases other than adenine, cytosine, guanine, thymine, and uracil. Examples of a modified nucleobase include, but not limited to, 5-methylcytosine, 5-fluorocytosine, 5-bromocytosine, 5-iodocytosine, N4-methylcytosine, N6-methyladenine, 8-bromoadenine, N2-methylguanine, and 8-bromoguanine. A preferable modified nucleobase is 5-methylcytosine. An "unmodified nucleobase" or an "unmodified base" is synonymous with a natural nucleobase, and means adenine (A) and guanine (G), which are purine bases, as well as thymine (T), cytosine (C), and uracil (U), which are pyrimidine bases.

The term "modified sugar" refers herein to a sugar having a substitution and/or any change from a natural sugar moiety (i.e., a sugar moiety found in DNA(2'-H) or RNA(2'-OH)). A nucleic acid strand may herein, in some cases, comprise one or more modified nucleosides including a modified sugar. A sugar-modified nucleoside can confer beneficial biological properties, such as an enhanced nuclease stability, an increased binding affinity, or the like to a nucleic acid strand. A nucleoside may comprise a chemically modified ribofuranose ring moiety. Examples of a chemically modified ribofuranose ring include, but not limited to, addition of a substituent (including 5' or 2' substituent), formation of a bicyclic nucleic acid (bridged nucleic acid, BNA) by forming a bridge between non-geminal ring atoms, substitution of a ribosyl ring oxygen atom with S, N(R), or C(R1)(R2) (wherein each of R, R1 and R2 independently represents H, a $C_1$ to $C_{12}$ alkyl, or a protective group), and a combination thereof. Herein, examples of a nucleoside having a modified sugar moiety include, but not limited to, a nucleoside having a substituent of 5'-vinyl, 5'-methyl(R or S), 4'-S, 2'-F (2'-fluoro group), 2'-$OCH_3$ (2'-OMe group, or 2'-O-methyl group), and 2'-O$(CH_2)_2OCH_3$. A substituent at the 2' position may be selected from allyl, amino, azide, thio, —O-allyl, —O—$C_1$-$C_{10}$ alkyl, —$OCF_3$, —$O(CH_2)_2SCH_3$, —$O(CH_2)_2$—O—N(Rm)(Rn), and —O—$CH_2$—C(=O)—N(Rm)(Rn), wherein each Rm and Rn is independently H or a substituted or unsubstituted $C_1$-$C_{10}$ alkyl. A "2'-modified sugar" means herein a furanosyl sugar modified at the 2' position.

A method for preparing a modified sugar is well known to those skilled in the art. In a nucleotide having a modified sugar moiety, the nucleobase moiety (natural one, modified one, or a combination thereof) may be maintained for hybridization with an appropriate nucleic acid target.

In general, modifications can be performed so that nucleotides in the same strand can independently undergo different modifications. In addition, to confer resistance to enzymatic cleavage, the same nucleotide may have a modified inter-nucleoside bond (e.g., phosphorothioate bond), and also have a modified sugar (e.g., 2'-O-methyl modified sugar, or bicyclic sugar). Further, the same nucleotide can have a modified nucleobase (e.g., 5-methylcytosine), and also have a modified sugar (e.g., 2'-O-methyl modified sugar, or bicyclic sugar).

The number, type, and position of a non-natural nucleotide in a nucleic acid strand can influence the antisense effect or the like provided by a nucleic acid complex of the present invention. Selection of a modification may vary depending on the sequence of a target gene or the like, but one skilled in the art can determine a suitable embodiment by referring to descriptions in literatures related to the antisense method (for example, WO 2007/143315, WO 2008/043753, and WO 2008/049085). Furthermore, when the antisense effect of the nucleic acid complex after the modification is measured, if the measurement value thus obtained is not significantly lower than the measurement value for the nucleic acid complex before the modification (for example, in a case where the measurement value obtained after the modification is 70% or more, 80% or more, or 90% or more with respect to the measurement value for the nucleic acid complex before the modification), relevant modifications can be evaluated.

The term "complementary" as used herein means a relationship in which nucleobases can form so-called Watson-Crick base pairs (natural type base pairs), or non-Watson-Crick base pairs (Hoogsteen type base pairs, or the like) via hydrogen bonds. In the present invention, it is not necessarily required that a first nucleic acid strand is completely complementary to at least part of a target transcriptional product (e.g., the transcriptional product of a target gene), but it is permissible if the base sequence has a complementarity of at least 70%, preferably at least 80%, and more preferably at least 90% (e.g., 95%, 96%, 97%, 98%, or 99% or more). Similarly, it is not necessarily required that the complementary region in the second nucleic acid strand is completely complementary to at least part of the first nucleic acid strand, but it is permissible if the base sequence has a complementarity of at least 70%, preferably at least 80%, and more preferably at least 90% (e.g., 95%, 96%, 97%, 98%, or 99% or more).

The term "blood-brain barrier (BBB)," as used herein means a mechanism that selects and restricts substances which transfer to the brain, and serves to protect the brain from harmful substances, as described above.

The term "central nervous system" as used herein means a tissue consisting of the brain and spinal cord, which constitutes together with the peripheral nervous system the nervous system. The brain comprises cerebrum (cerebral cortex, cerebral white matter, and basal ganglion), diencephalon (thalamus, and subthalamic nucleus), cerebellum (cerebellar cortex, and cerebellar nucleus), and brainstem (midbrain, substantia nigra, pons, and medulla oblongata). Meanwhile, spinal cord comprises cervical spinal cord, thoracic spinal cord, lumbar spinal cord, sacral spinal cord, and coccygeal spinal cord. Although the central nervous system herein may be any of these regions, it may be preferably the cerebral cortex (frontal lobe, temporal lobe, parietal lobe, or occipital lobe), cerebellum, striatum, globus pallidus, claustrum, hippocampus, parahippocampal gyms, brainstem, cervical spinal cord, thoracic spinal cord, or lumbar spinal cord.

A "salt thereof" means herein a salt of a nucleic acid complex of the present invention, which is a physiologically and pharmaceutically acceptable salt of a nucleic acid complex of the present invention, namely a salt that retains the desired biological activity of the nucleic acid complex, and does not have an undesired toxicological effect. Examples of such a salt include an alkali metal salt, such as a sodium salt, a potassium salt, and a lithium salt; an alkali earth metal salt, such as a calcium salt, and a magnesium salt; a metal salt, such as an aluminum salt, an iron salt, a zinc salt, a copper slat, a nickel salt, and a cobalt salt; an inorganic salt, such as an ammonium salt; an amine salt, such as a t-octylamine salt, a dibenzylamine salt, a morpholine salt, a glucosamine salt, a phenylglycine alkyl ester salt, a ethylenediamine salt, a guanidine salt, a diethylamine salt, a triethylamine salt, a dicyclohexylamine salt, a N,N'-dibenzylethylenediamine salt, a chloroprocaine salt, a procaine salt, a diethanolamine salt, a N-benzyl-phenethylamine salt, a piperazine salt, a tetramethylammonium salt, a tris(hydroxymethyl)aminomethane salt, a diolamine salt, and a meglumine salt; a hydrohalic acid salt, such as a hydrofluoric acid salt, a hydrochloric acid salt, a hydrobromic acid salt, and a hydroiodic acid salt; an inorganic acid salt, such as a nitrate, a perchlorate, a sulfate, and a phosphate; a lower alkane sulfonate, such as methanesulfonate, trifluoromethane-sulfonate, and ethanesulfonate; an aryl sulfonate, such as benzene sulfonate, and p-toluene sulfonate; an organic salt, such as an acetate, a malate, a fumarate, a succinate, a citrate, a tartrate, an oxalate, and a maleate; and an amino acid salt, such as a glycine salt, a lysine salt, an arginine salt, an ornithine salt, a glutamate, and an aspartate.

In a certain embodiment, a nucleic acid complex of the present invention includes any pharmaceutically acceptable salt of the nucleic acid complex, an ester of the nucleic acid complex, or a salt of the ester. Examples of a suitable pharmaceutically acceptable salt include, but not limited to, a sodium salt, a potassium salt, and a meglumine salt.

(Constitution of a First Nucleic Acid Strand and a Second Nucleic Acid Strand)

In one aspect, the present invention relates to a nucleic acid complex comprising a first nucleic acid strand and a second nucleic acid strand.

The first nucleic acid strand is a single-stranded oligonucleotide strand that comprises a base sequence capable of hybridizing to at least part of a target transcriptional product, and provides an antisense effect on the target transcriptional product.

The second nucleic acid strand is a single-stranded oligonucleotide strand comprising a base sequence complementary to the first nucleic acid strand. The second nucleic acid strand is bound to tocopherol, cholesterol, or an analog thereof, and so on. In a nucleic acid complex, the second nucleic acid strand is annealed to the first nucleic acid strand via hydrogen bonds of complementary base pairs.

In an embodiment, the present invention relates to a single-stranded nucleic acid strand bound to (1) tocopherol or an analog thereof, (2) cholesterol or an analog thereof, or (3) a substituted or unsubstituted $C_{1-30}$ alkyl group, a substituted or unsubstituted $C_{2-30}$ alkenyl group, or a substituted or unsubstituted $C_{1-30}$ alkoxy group. The constitution of the single-stranded nucleic acid is the same as the first nucleic acid strand except that it is bound to tocopherol, cholesterol, an analog thereof, and so on. The constitution of tocopherol, cholesterol, an analog thereof, and so on, and the form of its linkage with the nucleic acid strand are as described herein in connection with a nucleic acid complex.

The base lengths of the first nucleic acid strand and the second nucleic acid strand may be usually, but not particularly limited to, at least 8 bases in length, at least 9 bases in length, at least 10 bases in length, at least 11 bases in length, at least 12 bases in length, at least 13 bases in length, at least 14 bases in length, or at least 15 bases in length. Further, the base lengths of the first nucleic acid strand and the second nucleic acid strand may be 35 bases in length or less, 30 bases in length or less, 25 bases in length or less, 24 bases in length or less, 23 bases in length or less, 22 bases in length or less, 21 bases in length or less, 20 bases in length or less, 19 bases in length or less, 18 bases in length or less, 17 bases in length or less, or 16 bases in length or less. The first nucleic acid strand and the second nucleic acid strand may be about 100 bases in length, or from 10 to 35 bases in length, from 12 to 25 bases in length, from 13 to 20 bases in length, from 14 to 19 bases in length, or from 15 to 18 bases in length. The first nucleic acid strand and the second nucleic acid strand may be in the same length or different lengths (e.g., either one may be shorter or longer by 1 to 3 bases). The double-stranded structure formed by the first nucleic acid strand and the second nucleic acid strand may comprise a bulge. The length may be selected especially according to the balance between the strength of the antisense effect and the specificity of the nucleic acid strand with respect to a target, among other factors such as, for example, cost, or synthesis yield.

The internucleoside bond in the first nucleic acid strand and the second nucleic acid strand may be a naturally occurring internucleoside bond and/or a modified internucleoside bond. Without limitation, at least one, at least two, or at least three internucleoside bonds from the end (5' end, 3' end or both the ends) of the first nucleic acid strand and/or the second nucleic acid strand are preferably modified internucleoside bonds. In this regard, for example, two internucleoside bonds from the end of a nucleic acid strand refers to an internucleoside bond closest to the end of the nucleic acid strand, and an internucleoside bond positioned next thereto on the opposite side to the end of the nucleic acid strand. Modified internucleoside bonds in the terminal region of a nucleic acid strand are preferred because they can reduce or inhibit undesired degradation of the nucleic acid strand. In an embodiment, all internucleoside bonds of the first nucleic acid strand and/or the second nucleic acid strand may be modified internucleoside bonds. The modified internucleoside bond may be a phosphorothioate bond.

At least one (e.g., three) internucleoside bond from the 3' end of the second nucleic acid strand may be a modified internucleoside bond, such as a phosphorothioate bond having high RNase resistance. It is preferable that an internucleoside bond such as a phosphorothioate modification is comprised at the 3' end of the second nucleic acid strand, because the gene inhibition activity of the double-stranded nucleic acid complex is enhanced.

At the 5' end and the 3' end of the second nucleic acid strand, internucleoside bonds for 2 to 6 bases at the end unbound to tocopherol, cholesterol, or an analog thereof, and so on may be also modified internucleoside bonds (e.g., phosphorothioate bonds).

At least one (e.g., three) nucleoside from the 3' end of the second nucleic acid strand may be, for example, a modified nucleoside, such as 2'F-RNA, and 2'-OMe, which have high RNase resistance. It is preferable that a modified nucleoside such as 2'F-RNA, and 2'-OMe is comprised at the 3' end of the second nucleic acid strand, because the gene inhibition activity of the double-stranded nucleic acid complex is enhanced.

At the 5' end and the 3' end of the second nucleic acid strand, one to five nucleosides at the end unbound to tocopherol, cholesterol, or an analog thereof, and so on may be, for example, modified nucleosides such as 2'F-RNA having high RNase resistance.

A nucleoside in the first nucleic acid strand and the second nucleic acid strand may be a natural nucleoside (deoxyribonucleoside, ribonucleoside, or both) and/or a non-natural nucleoside.

Since the base sequence of the first nucleic acid strand is herein complementary to at least part of the base sequence of a target transcriptional product it can hybridize (or anneal) to the target transcriptional product. The complementarity of a base sequence can be determined using a BLAST program or the like. One skilled in the art can easily determine the conditions (temperature, salt concentration, etc.) under which the two strands can be hybridized, taking into account the complementarity between the strands. Further, one skilled in the art can easily design an antisense nucleic acid that is complementary to the target transcriptional product based on, for example, information on the base sequence of a target gene.

Hybridization conditions may be a variety of stringent conditions, such as a low-stringent condition and a high-stringent condition. A low-stringent condition may be a condition with a relatively low temperature, and a high salt concentration, for example, 30° C., 2×SSC, and 0.1% SDS. A high-stringent condition may be a condition with a relatively high temperature, and a low salt concentration, for example, 65° C., 0.1×SSC, and 0.1% SDS. The stringency of hybridization can be adjusted by varying the conditions, such as temperature and salt concentration. Here, 1×SSC contains 150 mM of sodium chloride and 15 mM of sodium citrate.

The first nucleic acid strand may comprise at least four, at least five, at least six, or at least seven contiguous nucleosides that are recognized by RNase H when hybridized to a target transcriptional product. Ordinarily, it can be a region comprising contiguous nucleosides of from 4 to 20 bases, from 5 to 16 bases, or from 6 to 12 bases. As a nucleoside recognizable by RNase H, for example, a natural deoxyribonucleoside can be used. A suitable nucleoside comprising a modified deoxyribonucleoside and other bases are well known in the art. It is also known that a nucleoside having a hydroxy group at the 2' position, such as a ribonucleoside, is unsuitable as the nucleoside. The suitability of a nucleoside for use in the region comprising "at least four contiguous nucleosides" can be easily determined. In an embodiment, the first nucleic acid strand may comprise at least four contiguous deoxyribonucleosides.

In an embodiment, the full length of the first nucleic acid strand is not constituted solely by natural ribonucleosides. In the first nucleic acid strand, natural ribonucleosides should preferably be less than half of the full length, or should not be contained.

In an embodiment, the second nucleic acid strand may comprise at least four contiguous ribonucleosides complementary to the above-described at least four contiguous nucleosides (e.g., deoxyribonucleosides) in the first nucleic acid strand. This is for the purpose that the second nucleic acid strand forms a partial DNA-RNA heteroduplex strand with the first nucleic acid strand, which can then be recognized and cleaved by RNase H. The at least four contiguous ribonucleosides in the second nucleic acid strand are preferably linked by naturally occurring internucleoside bonds, namely phosphodiester bonds.

In the second nucleic acid strand, all the nucleosides may be composed of ribonucleosides and/or modified nucleosides. All the nucleosides in the second nucleic acid strand may be composed of deoxyribonucleosides and/or modified nucleosides, or the second nucleic acid strand may not comprise a ribonucleoside.

The first nucleic acid strand and/or the second nucleic acid strand constituting a nucleic acid complex of the present invention may be a gapmer. The "gapmer" means herein a single-stranded nucleic acid consisting of a central region (DNA gap region), and a 5' wing region and a 3' wing region located respectively on the 5' end side and the 3' end side of the central region. The central region in a gapmer comprises at least four contiguous deoxyribonucleosides, and the 5' wing region and the 3' wing region comprise a non-natural nucleoside. When the non-natural nucleoside constituting a 5' wing region and a 3' wing region comprise a bridged nucleoside, or consist thereof, the gapmer is especially referred to as "BNA/DNA gapmer". When the non-natural nucleoside constituting a 5' wing region and a 3' wing region comprise a peptide nucleic acid or consist thereof, the gapmer is especially referred to as "peptide nucleic acid gapmer". When the non-natural nucleoside constituting a 5' wing region and a 3' wing region comprise a peptide nucleic acid, or consist thereof, the gapmer is especially referred to as "morpholino nucleic acid gapmer". The number of bridged nucleoside comprised in the 5' wing region or the 3' wing region may be two or three. The bridged nucleoside comprised in the 5' wing region and the 3' wing region may exist contiguously or noncontiguously in the 5' wing region and the 3' wing region. A bridged nucleoside may further comprise a modified nucleobase (e.g., 5-methylcytosine). When the bridged nucleoside is an LNA nucleoside, the gapmer is referred to as "LNA/DNA gapmer". Each of the base length of the 5' wing region and the 3' wing region may be independently at least 2 bases in length, e.g., from 2 to 10 bases in length, from 2 to 7 bases in length, or from 3 to 5 bases in length. The 5' wing region and the 3' wing region may comprise at least one kind of non-natural nucleoside, and may further comprise a natural nucleoside.

The first nucleic acid strand and/or the second nucleic acid strand constituting the gapmer may consist of bridged nucleosides from 2 to 7 bases in length or from 3 to 5 bases in length, ribonucleosides or deoxyribonucleosides from 4 to 15 bases in length, or from 8 to 12 bases in length, and bridged nucleosides from 2 to 7 bases in length, or from 3 to 5 bases in length from the 5' end in this order.

The first nucleic acid strand and/or the second nucleic acid strand constituting a nucleic acid complex of the present invention may be a mixmer. A "mixmer" means herein a nucleic acid strand which alternatingly comprises natural nucleosides and non-natural nucleosides having periodic, or random segment lengths, and does not comprise four or more contiguous deoxyribonucleosides, or ribonucleosides. Among mixmers, a mixmer in which the non-natural nucleoside is a bridged nucleoside, and the natural nucleoside is a deoxyribonucleoside, is specifically called "BNA/DNA mixmer". Among mixmers, a mixmer in which the non-natural nucleoside is a peptide nucleic acid, and the natural nucleoside is a deoxyribonucleoside, is specifically called "peptide nucleic acid/DNA mixmer". Among mixmers, a mixmer in which the non-natural nucleoside is a morpholino nucleic acid, and the natural nucleoside is a deoxyribonucleoside, is specifically called "morpholino nucleic acid/DNA mixmer". A mixmer is not limited to comprise only two kinds of nucleosides. A mixmer may comprise any number of kinds of nucleosides, irrespective of a natural or modified nucleoside, or a nucleoside mimic. For example, it may comprise one or two contiguous deoxyribonucleosides separated by a bridged nucleoside (e.g., LNA nucleoside). A bridged nucleoside may further comprise a modified nucleobase (e.g., 5-methylcytosine).

At least one, at least two, at least three, or at least four nucleosides from an end (5' end, 3' end, or both the ends) of the second nucleic acid strand may be modified nucleosides. The modified nucleoside may comprise a modified sugar and/or a modified nucleobase. The modified sugar may be a 2'-modified sugar (e.g., a sugar comprising a 2'-O-methyl group). The modified nucleobase may be 5-methylcytosine.

The second nucleic acid strand may be composed of modified nucleosides (e.g., modified nucleosides comprising a 2'-modified sugar) from 2 to 7 bases in length, or from 3 to 5 bases in length, ribonucleosides or deoxyribonucleosides from 4 to 15 bases in length, or from 8 to 12 bases in length (optionally linked by a modified internucleoside bond), and modified nucleosides (e.g., a modified nucleoside comprising a 2'-modified sugar) from 2 to 7 bases in length or from 3 to 5 bases in length from the 5' end in this order. In this case, the first nucleic acid strand may be a gapmer.

The first nucleic acid strand and the second nucleic acid strand, as a whole or in part, may comprise a nucleoside mimic or a nucleotide mimic. A nucleotide mimic may be a peptide nucleic acid and/or a morpholino nucleic acid. The first nucleic acid strand may comprise at least one modified nucleoside. The modified nucleoside may comprise a 2'-modified sugar. The 2'-modified sugar may be a sugar comprising a 2'-O-methyl group.

The first nucleic acid strand and the second nucleic acid strand may comprise any combination of the modified internucleoside bond and the modified nucleoside described above.

The second nucleic acid strand is bound to (1) tocopherol or an analog thereof, (2) cholesterol or an analog thereof, or (3) a substituted or unsubstituted $C_{1-30}$ alkyl group, a substituted or unsubstituted $C_{2-30}$ alkenyl group, or a substituted or unsubstituted $C_{1-30}$ alkoxy group. Those skilled in the art can produce tocopherol, cholesterol, or an analog thereof, and so on using a publicly know method.

An "analog" herein refers to a compound having a similar structure and property, having the same or a similar basic backbone. An analog comprises, for example, a biosynthetic intermediate, and a metabolite. Those skilled in the art can determine whether a compound is an analog of another compound.

A tocopherol may be selected from the group consisting of α-tocopherol, β-tocopherol, γ-tocopherol, and δ-tocopherol. Examples of an analog of tocopherol comprise various unsaturated analogs of tocopherol, such as α-tocotrienol, β-tocotrienol, γ-tocotrienol, and δ-tocotrienol. Preferably, tocopherol is α-tocopherol.

An analog of cholesterol refers to various cholesterol metabolites and analogs which are alcohols having a sterol backbone. Examples thereof include, but not limited to, cholestanol, lanosterol, cerebrosterol, dehydrocholesterol, and coprostanol.

The second nucleic acid strand bound to tocopherol or an analog thereof may have a group represented by the following Formula (I).

[Chem 15]

(I)

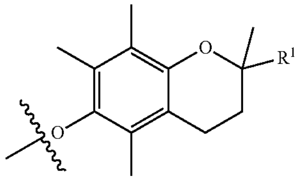

[wherein $R^1$ is a substituted or unsubstituted $C_{1-30}$ alkyl group (e.g., methyl, or 4,8,12-trimethyltridecyl), or a substituted or unsubstituted $C_{2-30}$ alkenyl group (e.g., 4,8,12-trimethyl-3,7,11-tridecatrien-1-yl) (wherein the substitution is preferably done with a halogen atom)].

The second nucleic acid strand bound to cholesterol or an analog thereof may have a group selected from the group consisting of the following Formulas (II), (V), (VI), and (VII):

[Chem 16]

(II)

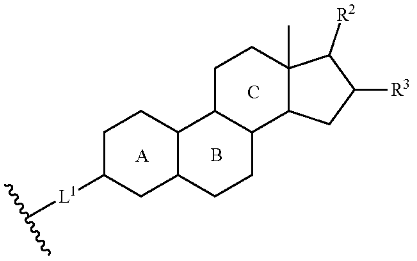

(wherein the ring A represents a substituted or unsubstituted cyclohexane, or a substituted or unsubstituted benzene; the ring B represents a substituted or unsubstituted cyclohexene, a substituted or unsubstituted cyclohexane, or a substituted or unsubstituted cyclohexadiene; the ring C represents a substituted or unsubstituted cyclohexene, or a substituted or unsubstituted cyclohexane; $R^2$ represents a hydrogen atom, a substituted or unsubstituted $C_{1-30}$ alkyl group (e.g., ethyl, isopropyl, 1-methylpropyl, 1,5-dimethylhexyl, 4-ethyl-1,5-dimethylhexyl), a substituted or unsubstituted $C_{2-30}$ alkenyl group (e.g., 1,5-dimethyl-4-hexen-1-yl, 1,4,5-trimethyl-2-hexen-1-yl, 4-(ethyl-1,5-dimethyl-2-hexen-1-yl), a substituted or unsubstituted $C_{1-6}$ alkyl-carbonyl group (e.g., 1-oxoethyl), a substituted or unsubstituted $C_{1-6}$ alkyl-carbonyloxy group (e.g., (1-oxoheptyl)oxy), or an oxo group; $R^3$ represents a hydrogen atom; and $R^2$ and $R^3$ may together form a substituted or unsubstituted 1,6-dioxaspiro[4.5]decane ring).

In the Formula, $L^1$ represents —O—, —NH—,

[Chem 17]

(III)

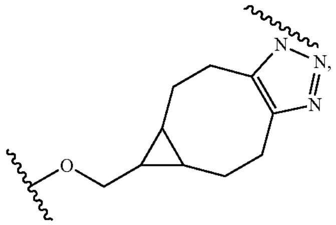

or

[Chem 18]

(IV)

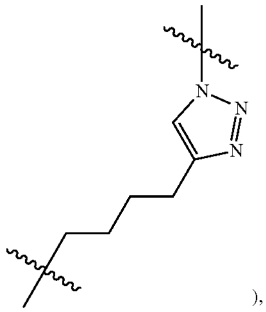

),

[Chem 19]

(V)

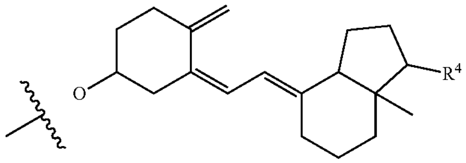

(wherein $R^4$ represents a substituted or unsubstituted $C_{3-30}$ alkyl group (e.g., 1,5-dimethylhexyl), or a substituted or unsubstituted $C_{2-30}$ alkenyl group);

[Chem 20]

(VI)

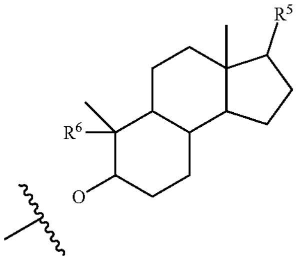

(wherein each of $R^5$ and $R^6$ independently represents a substituted or unsubstituted $C_{1-30}$ alkyl group (e.g., butyl, or 1,5-dimethylhexyl), or a substituted or unsubstituted $C_{2-30}$ alkenyl group); and

[Chem 21]

(VII)

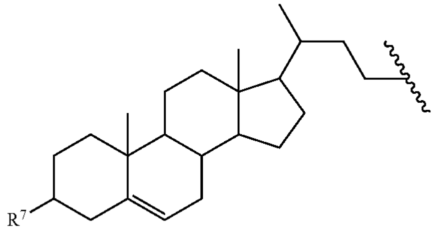

(wherein $R^7$ represents a hydroxy group, a substituted or unsubstituted $C_{1-30}$ alkyl-carbonyl-oxy group (e.g., (1-oxododecyl)oxy), or a substituted or unsubstituted $C_{1-30}$ alkenyl-carbonyl-oxy group (e.g., (1-oxo-9-octadecenyl)oxy). In the group selected from the group consisting of (II), (V), (VI), and (VII) above, the substitution is preferably done with a halogen atom (e.g., a fluorine atom), a $C_{1-3}$ alkyl group (e.g., methyl), a hydroxy group, a $C_{1-6}$ alkyl-carbonyl group (e.g., 1-oxo-2-methylpropyl), a carbamoyl group which is mono- or di-substituted with phenyl groups substituted with one to five $C_{1-3}$ alkyl groups substituted with one to three halogen atoms (e.g., [3,5-bis(trifluoromethyl) benzoyl]amino), or a $C_{1-6}$ alkyl-carbonyl group (e.g., 2-methyl-1-oxopropyl).

In an embodiment, the second nucleic acid strand is bound to a substituted or unsubstituted $C_{1-30}$ alkyl group (e.g., heptadecyl, 16-methylheptadecyl, or henicosyl), a substituted or unsubstituted $C_{2-30}$ alkenyl group (e.g., 2,6-dimethyl-1,3,5,7-octatetraen-1-yl, 8-heptadecen-1-yl, 8,11-heptadecadien-1-yl, or 8,11,14-heptadecatrien-1-yl), or a substituted or unsubstituted $C_{1-30}$ alkoxy group (e.g., henicosoxy) (wherein the substitution is preferably done with a halogen atom, or a cyclohexenyl group substituted with one to five $C_{1-3}$ alkyl groups (e.g., 2,6,6-trimethyl-1-cyclohexen-1-yl)).

In an embodiment, the second nucleic acid strand bound to tocopherol or an analog thereof may have a group represented by the following Formula (IIa):

[Chem 22]

(IIa)

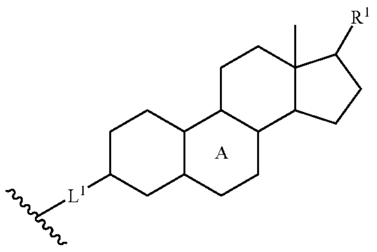

(wherein:

the ring A represents a substituted or unsubstituted cyclohexene, a substituted or unsubstituted cyclohexane, or a substituted or unsubstituted cyclohexadiene;

$R^1$ represents a substituted or unsubstituted $C_{1-30}$ alkyl group (e.g., a $C_{2-20}$, $C_{4-16}$, $C_{6-12}$, or $C_{8-10}$ alkyl group), a substituted or unsubstituted $C_{2-30}$ alkenyl group (e.g., a $C_{2-20}$, $C_{4-16}$, $C_{6-12}$, or $C_{8-10}$ alkenyl group), a substituted or unsubstituted $C_{1-6}$ alkyl-carbonyl group, a substituted or unsubstituted $C_{1-6}$ alkyl-carbonyl-oxy group, or an oxo group; and $L^1$ represents —O—, —NH—,

[Chem 23]

(III)

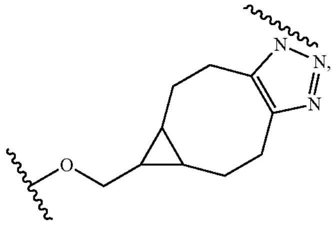

or

[Chem 24]

(IV)

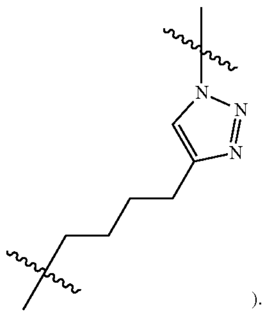

).

In an embodiment, the second nucleic acid strand bound to tocopherol or an analog thereof may have a group represented by the following Formulas (IIa-1), (IIa-2), (IIa-3), and (IIa-4):

[Chem 25]

(IIa-1)

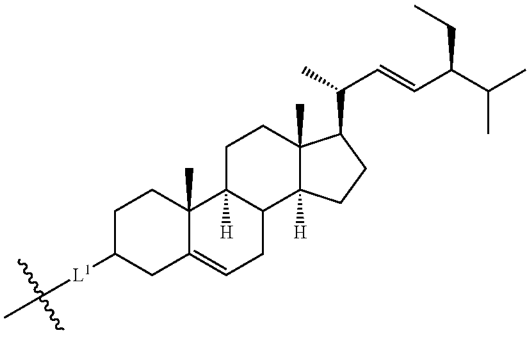

(IIa-2)

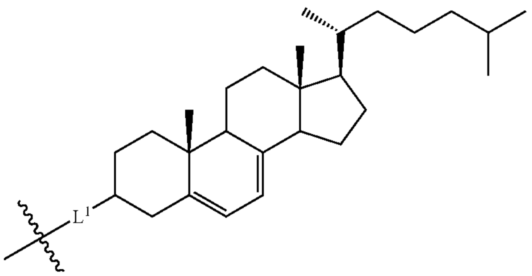

-continued (IIa-3)

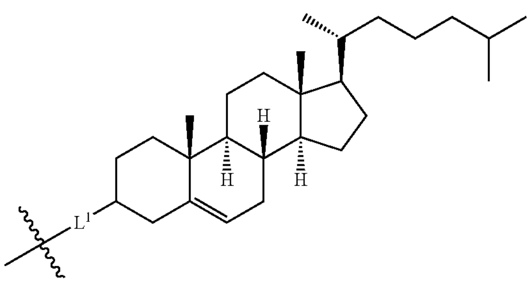

(IIa-4)

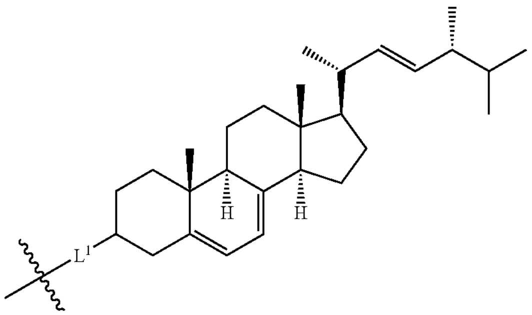

(wherein $L^1$ represents —O—, —NH—,

[Chem 26]

(III)

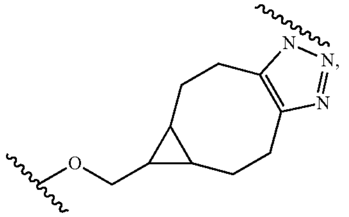

or

[Chem 27]

(IV)

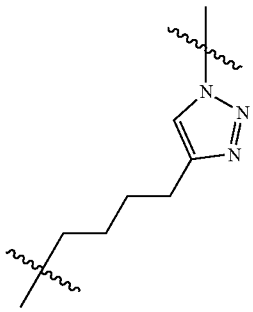

).

In an embodiment, the second nucleic acid strand bound to tocopherol or an analog thereof does not have a group represented by the following Formula (IIa-3).

[Chem 28]

(IIa-3)

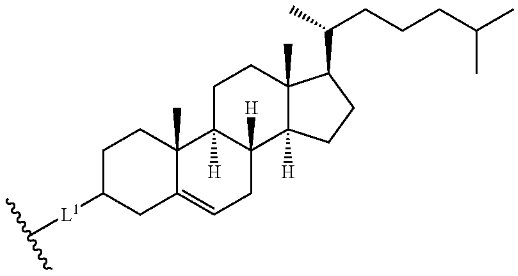

Tocopherol, cholesterol, or an analog thereof, and so on may be linked to the 5' end, the 3' end, or both the ends of the second nucleic acid strand. Alternatively, tocopherol, cholesterol, or an analog thereof, and so on may be linked to a nucleotide inside the second nucleic acid strand. For example, cholesterol can be bound to the 5' end of the second nucleic acid strand. In other embodiments, the second nucleic acid strand may comprise two or more of tocopherol, cholesterol, and an analog, and so on, which may be bound to the second nucleic acid strand at a plurality of positions, or bound to the second nucleic acid strand as a group at a single position. Tocopherol, cholesterol, or an analog thereof, and so on may be linked one each to the 5' end and the 3' end of the second nucleic acid strand. Cholesterol, or an analog thereof may be linked one each to the 5' end and the 3' end of the second nucleic acid strand.

The binding between the second nucleic acid strand and tocopherol, cholesterol, or an analog thereof, and so on may be either a direct binding or an indirect binding. The direct binding refers to that two molecules are bound. The indirect binding refers to that the two molecules to be bound are bound via another substance.

In an embodiment, the binding between the second nucleic acid strand and tocopherol, cholesterol, and/or an analog thereof, and so on may be to a nucleotide at the 5' end, the 3' end of the second nucleic acid strand or inside the second nucleic acid strand via a phosphate ester bond or a phosphorothioate bond.

In an embodiment, the binding is to the 5' end of the second nucleic acid strand via a phosphate ester bond or a phosphorothioate bond.

In an embodiment, the binding is to the 5' end of the second nucleic acid strand via a phosphate ester bond.

When the second nucleic acid strand and tocopherol, cholesterol, or an analog, etc. thereof are indirectly bound, they may be bound via a linking group (herein frequently referred to as a "linker"). A linker may be bound to a nucleotide at the 5' end, the 3' end of the second nucleic acid strand or inside the second nucleic acid strand via a phosphate ester bond or a phosphorothioate bond.

In an embodiment, the linker is bound to the 5' end of the second nucleic acid strand via a phosphate ester bond or a phosphorothioate bond.

In an embodiment, the linker is bound to the 5' end of the second nucleic acid strand via a phosphate ester bond.

As a specific example of the linker, there is a linker represented by the following Formula (VIII):

[Chem 29]

(VIII)

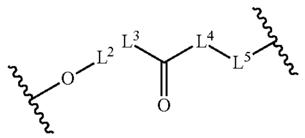

(wherein $L^2$ represents a substituted or unsubstituted $C_{1-12}$ alkylene group (e.g., propylene, hexylene, or dodecylene), a substituted or unsubstituted $C_{3-8}$ cycloalkylene group (e.g., cyclohexylene), $—(CH_2)_2—O—(CH_2)_2—O—(CH_2)_2—O—(CH_2)_3—$ or $CH(CH_2—OH)—CH_2—O—(CH_2)_2—O—(CH_2)_2—O—(CH_2)_2—O—(CH_2)_3—$; $L^3$ represents —NH— or a bond; and $L^4$ represents a substituted or unsubstituted $C_{1-12}$ alkylene group (e.g., ethylene, pentylene, heptylene, or undecylene), a substituted or unsubstituted $C_{3-8}$ cycloalkylene group (e.g., cyclohexylene), $—(CH_2)_2—[O—(CH_2)_2]_m—$, or a bond, wherein m represents an integer of 1 to 25; and $L^5$ represents —NH—(C═O)—, —(C═O)—, or a bond (wherein the substitution is preferably done with a halogen atom).

When the second nucleic acid strand and tocopherol, cholesterol, or an analog thereof, and so on are indirectly bounded, they may be bound via a cleavable linker. A "cleavable linker" refers to a linking group that can be cleaved under physiological conditions, for example, in a cell or in an animal body (e.g., in a human body). A cleavable linker may be selectively cleaved by an endogenous enzyme, such as a nuclease, and a peptidase, under acidic conditions, in a reductive environment, etc. Specific examples thereof include an amide bond, an ester bond, a phosphate ester bond, either or both ester bonds of a phosphodiester bond, a carbamate bond, and a disulfide bond, as well as a nucleotide linker such as a natural DNA linker.

Conversely, when the second nucleic acid strand and tocopherol, cholesterol, or an analog thereof, and so on are indirectly bound, they may also be bound via an uncleavable linker. An "uncleavable linker" refers to a linking group that is not cleavable under physiological conditions. Examples of such an uncleavable linker include a phosphorothioate bond, and a linker consisting of modified or unmodified deoxyribonucleosides, or modified or unmodified ribonucleosides linked by a phosphorothioate bond.

Although there is no particular restriction on the strand length of a cleavable linker, or an uncleavable linker in the case of a nucleic acid such as DNA, or an oligonucleotide, it is usually from 1 to 20 bases in length, from 1 to 10 bases in length, or from 1 to 6 bases in length.

In a certain embodiment, in a case where a nucleic acid complex of the present invention comprises optical isomers, stereoisomers, regioisomers, or rotational isomers, these may also be comprised as a nucleic acid complex of the present invention, and each may be obtained as an isolated product by a publicly known synthesis method and a separation method. For example, if optical isomers are present in a nucleic acid complex of the present invention, the optical isomers separated from the compound are also encompassed in the nucleic acid complex of the present invention.

In a certain embodiment, a nucleic acid complex of the present invention comprises a prodrug and a pharmaceutically acceptable salt of the prodrug. A prodrug of a nucleic acid complex of the present invention and a pharmaceutically acceptable salt of the prodrug refer to compounds that are converted to a nucleic acid complex of the present invention by a reaction with an enzyme, gastric acid, or the like under physiological conditions in vivo, namely compounds that are changed to a nucleic acid complex of the present invention by enzymatically causing oxidation, reduction, or hydrolysis, or compounds that are changed to a nucleic acid complex of the present invention by hydrolysis caused by gastric acid, or the like. In a certain embodiment, a prodrug of a nucleic acid complex comprises one or more of tocopherol, cholesterol, or an analog thereof, and so on bound to the first nucleic acid strand or the second nucleic acid strand.

With respect to a nucleic acid complex of the present invention, an antisense effect of the first nucleic acid strand on a target transcriptional product can be measured by a method publicly known in the field. For example, it can be measured by using a publicly known technique, such as northern blotting, quantitative PCR, or western blotting, after introducing a nucleic acid complex into cells or the like. Specifically, it may be performed by examining a decrease in the expression amount of a target gene or the level of a target transcriptional product in cells (e.g., the amount of RNA such as the amount of mRNA or the amount of microRNA, the amount of cDNA, or the amount of a protein) by an antisense effect, using the aforedescribed publicly known technique.

Measurement of the antisense effect of a nucleic acid complex of the present invention in the central nervous system, and judgement of crossing through the blood-brain barrier can also be performed by a method publicly known in the art. For example, but without limitation, such judgment is possible by measuring whether the expression amount of a target gene or the level of a target transcriptional product in the central nervous system is inhibited or not after several days to several months (e.g., after 2 to 7 days, or 1 month) from administration of a nucleic acid complex of the present invention to a subject (e.g., mouse). As for the judgment criteria, in a case where a measurement value for the expression amount of a target gene or the level of a target transcriptional product is decreased by at least 5%, at least 10%, at least 15%, at least 20%, at least 25%, at least 30%, or at least 40% compared with a measurement value for a negative control (e.g., vehicle administration), it may be judged that the nucleic acid complex of the present invention has crossed the blood-brain barrier, and exerted the antisense effect on the central nervous system. Further, the judgement on crossing through the blood-brain barrier can also be made by measuring the abundance (concentration) of a nucleic acid complex of the present invention in the central nervous system after several days to several months (e.g., after 2 to 7 days, or 1 month) from administration of a nucleic acid complex of the present invention to a subject (e.g., mouse).

Exemplary embodiments of a nucleic acid complex of the present invention are described above, however a nucleic acid complex of the present invention is not limited to the above exemplary embodiments. Further, one skilled in the art can produce a first nucleic acid strand and a second nucleic acid strand constituting various embodiments of the nucleic acid complex of the present invention by appropriately selecting a publicly known method. For example, a nucleic acid molecule of the present invention can be produced by designing each nucleic acid molecule based on the information on the base sequence of a target transcriptional product (e.g., the base sequence of a target gene), synthesizing the nucleic acid using a commercially available automatic nucleic acid synthesizer, such as the products of GE Healthcare, Thermo Fisher Scientific, and Beckman Coulter, and then purifying the obtained oligonucleotides using a reversed phase column, or the like.

The second nucleic acid strand may further comprise at least one functional moiety bound to the polynucleotide. There is no particular restriction on the structure of a "functional moiety" in a specific embodiment insofar as the functional moiety imparts a desired function to a nucleic acid complex and/or the strand to which the functional moiety is bound. Examples of the desired function include a labeling function, and a purifying function. Examples of a moiety that provides a labeling function include compounds such as a fluorescent protein, and luciferase. Examples of a moiety that provides a purifying function include compounds such as biotin, avidin, His-tag peptide, GST-tag peptide, and FLAG-tag peptide. The binding position and the type of binding of the functional moiety in the second nucleic acid strand are as described above in connection with the binding of tocopherol, cholesterol, or an analog thereof, and so on to the second nucleic acid strand.

In an embodiment, a nucleic acid complex to which a functional moiety is bound can be produced by using a nucleic acid species to which a functional moiety has been bound in advance, and performing the synthesis, purification, and annealing as described above. For example, the second nucleic acid strand can be produced by performing the above synthesis and purification using a nucleic acid species to which tocopherol, cholesterol, or an analog thereof, and so on has been bound in advance.

In an embodiment, tocopherol, cholesterol, or an analog thereof, and so on can be bound by a publicly known method to a second nucleic acid strand produced by performing the above synthesis and purification. The method for linking a functional moiety to a nucleic acid is well known in the art. Nucleic acids produced by this method are mixed in an appropriate buffer solution, denatured in a range of about 90° C. to 98° C. for several minutes (e.g., for 5 min), and then the nucleic acids are annealed in a range of about 30° C. to 70° C. for about 1 to 8 hours to prepare one nucleic acid complex of the present invention. Alternatively, a nucleic acid strand is available by ordering from various manufacturers (e.g., GeneDesign Inc.), by specifying the base sequence, and the modified position and type. The above annealing step can be performed by leaving the solution at room temperature (about 10° C. to about 35° C.) for about 5 to 60 min.

The first nucleic acid strand and the second nucleic acid strand are each dissolved in a buffer solution (e.g., phosphate-buffered saline) or in water in a range of about 70° C. to 98° C., and the obtained two solutions are mixed. The mixed liquid may be kept in a range of about 70° C. to 98° C. for several minutes (e.g., 5 min), and then in a range of about 30° C. to 70° C. (or 30° C. to 50° C.) for about 1 to 8 hours to prepare a nucleic acid complex of some embodiments of the present invention. The first nucleic acid strand and the second nucleic acid strand may be each dissolved in a buffer solution (e.g., phosphate-buffered saline) or water at room temperature (about 10° C. to about 35° C.).

However, the conditions (time and temperature) for annealing at the time of preparing a nucleic acid complex are not limited to the aforedescribed conditions. Conditions suitable for promoting the annealing of a nucleic acid strand are well known in the art.

(Effect of Nucleic Acid Complex)

The nucleic acid complex of the present invention can inhibit the effect of a target miRNA in the central nervous system of a subject. Specific examples include a nucleic acid complex, in which a first nucleic acid strand comprises a base sequence capable of hybridizing to at least part of a target miRNA and has an antisense effect on the target miRNA; and a second nucleic acid strand comprises a base sequence complementary to the first nucleic acid strand, and is bound to tocopherol, cholesterol, or an analog thereof, and so on; and further the first nucleic acid strand is annealed to the second nucleic acid strand. By inhibiting the effect of the target miRNA by this nucleic acid complex, the expression of a gene that is normally downregulated by the target miRNA can be upregulated.

The nucleic acid complex of the present invention can regulate expression or editing of a target RNA in the central nervous system of a subject. Specific examples include a nucleic acid complex, in which a first nucleic acid strand comprises a base sequence capable of hybridizing to at least part of a target RNA, and has an antisense effect on the target RNA; and a second nucleic acid strand comprises a base sequence complementary to the first nucleic acid strand, and is bound to tocopherol, cholesterol, or an analog thereof, and so on, while the first nucleic acid strand is annealed to the second nucleic acid strand. Here, "expression regulation of a target RNA" includes, for example, up-regulation and down-regulation of the expression amount. Further, "regulation of editing of a target RNA" includes regulation of splicing by RNA editing, e.g., exon skipping and exon inclusion. The target RNA may be a viral or bacterial RNA, or a toxic RNA (Toxic RNA).

The nucleic acid complex of the present invention can inhibit the translation of a target mRNA in the central nervous system of a subject. Specific examples include a nucleic acid complex, in which a first nucleic acid strand comprises a base sequence capable of hybridizing to at least part of a target mRNA, and has an antisense effect on the target mRNA; and a second nucleic acid strand comprises a base sequence complementary to the first nucleic acid strand, and is bound to tocopherol, cholesterol, or an analog thereof, and so on, while the first nucleic acid strand is annealed to the second nucleic acid strand. This nucleic acid complex causes a steric block to inhibit the translation of mRNA by binding of the first nucleic acid strand to the target mRNA.

The nucleic acid complex of the present invention can be effectively used, but without limitation, in the regulation of expression or editing of a target transcriptional product in the microglia in the central nervous system.

<Composition>

The second aspect of the present invention is a composition. The composition of the present invention comprises the nucleic acid complex of the first aspect, or a single-stranded nucleic acid strand as an active ingredient and/or a drug delivering molecule. The nucleic acid complex of the first aspect, or a single-stranded nucleic acid strand can cross the BBB and regulate the expression amount of a target transcriptional product in the central nervous system by an antisense effect (e.g., the expression amount is decreased). Therefore, the composition of the present invention may be a composition or a pharmaceutical composition that delivers a nucleic acid complex for treating a subject by administering to the subject. The composition of the present invention may be effectively used, without limitation thereto, in regulating the expression or editing of a target transcriptional product in the microglia in the central nervous system.

Further, an embodiment of the present invention relates to a therapeutic method for treating each central nervous system disease by administering a composition comprising a nucleic acid complex.

(Formulation)

The composition herein can be formulated by a publicly known method. For example, the present composition can be used perorally or parenterally in a form of capsule, tablet, pill, liquid formulation, dispersant, granule, microgranule, film-coated tablet, pellet, lozenge, sublingual formulation, peptizer, buccal tablet, paste, syrup, suspension, elixir, emulsion, coating formulation, ointment, plaster, cataplasm, transdermal patch, lotion, inhalant, aerosol, eye drop, injection, or suppository.

In formulating these formulations, a pharmaceutically acceptable carrier or solvent, or a carrier or solvent acceptable as a food and beverage may be incorporated as appropriate. Specific examples of such a carrier or solvent include sterile water, physiological saline, vegetable oil, base, emulsifier, suspending agent, surfactant, pH adjuster, stabilizer, flavor, perfume, excipient, vehicle, preservative, binder, diluent, isotonizing agent, sedatives, bulking agent, disintegrating agent, buffer, coating agent, lubricant, colorant, sweetening agent, thickener, flavoring substance, dissolution aid, and other additives.

(Administration Mode, Dosage)

There is no particular restriction herein on a preferable administration mode of the composition. For example, it may be peroral administration or parenteral administration. Specific examples of parenteral administration include intravenous administration, intraarterial administration, intraperitoneal administration, subcutaneous administration, intradermal administration, tracheal/bronchial administration, rectal administration, and intramuscular administration, as well as administration by blood transfusion. Administration by intramuscular injection, intravenous infusion, or implanted continuous subcutaneous administration is also possible. Since self-injection by a patient is possible in the case of subcutaneous administration, it is convenient. In the case of intravenous administration, the amount of a nucleic acid complex contained in a single dose of the composition, namely the single dose of a nucleic acid complex may be, for example, 0.001 mg/kg or more, 0.005 mg/kg or more, 0.01 mg/kg or more, 0.25 mg/kg or more, 0.5 mg/kg or more, 1 mg/kg or more, 2.5 mg/kg or more, 5 mg/kg or more, 10 mg/kg or more, 20 mg/kg or more, 30 mg/kg or more, 40 mg/kg or more, 50 mg/kg or more, 75 mg/kg or more, 100 mg/kg or more, 150 mg/kg or more, 200 mg/kg or more, 300 mg/kg or more, 400 mg/kg or more, or 500 mg/kg or more. For example, any amount within the range of 0.001 mg/kg to 500 mg/kg (e.g., 0.001 mg/kg, 0.01 mg/kg, 0.1 mg/kg, 1 mg/kg, 5 mg/kg, 10 mg/kg, 50 mg/kg, 100 mg/kg, or 200 mg/kg) can be selected as appropriate.

(Subject, Application Subject)

A "subject" herein refers to a subject to which the composition of the present invention is applied. The subject includes an individual as well as an organ, a tissue, and a cell. In a case where the subject is an individual, the composition of the present invention may be applied to any animals, including humans. Subjects other than humans may include, for example, various domestic animals, poultry, pets, and laboratory animals. The subject may be an individual that needs reduction in the expression amount of a target transcriptional product in the central nervous system, or an individual that needs a treatment for a central nervous system disease.

The composition of the present invention can reduce the expression amount of the target transcriptional product in the central nervous system due to a BBB crossing effect and an antisense effect of the nucleic acid complex of the first aspect, or a single-stranded nucleic acid strand that are contained therein.

When the composition of the present invention is applied for treating a central nervous system disease, the disease to be treated is preferably a central nervous system disease related to increase or decrease in the gene expression, especially a disease related to increase in a target transcriptional product, or the expression of a target gene (e.g., tumor). Examples thereof include, but not limited to, brain tumor, Alzheimer's disease, Parkinson's disease, amyotrophic lateral sclerosis, multiple sclerosis, and Huntington's disease.

In an embodiment, the composition of the present invention is applied for treating an immune-mediated central nervous system disease. Examples of an immune-mediated central nervous system disease include a microglia-associated disease, and examples of a microglia-associated disease include Alzheimer's disease, multiple sclerosis, ALS, and neuropathic pains.

Although there is no particular restriction on the delivery site of a composition of the present invention, more specifically the delivery site of an active ingredient contained in the composition, when it is delivered to an appropriate site depending on each disease, more effective results can be obtained. To give a specific example, in the treatment of Alzheimer's disease, drug delivery to the hippocampus and/or the parietal lobe may be effective. Further, in the treatment of frontotemporal dementia (FTD) (including frontotemporal lobar degeneration (FTLD), semantic dementia (SD), and progressive nonfluent aphasia (PNFA)), or Pick's disease, drug delivery to the frontal lobe, temporal lobe and/or substantia nigra may be effective. Further, in the treatment of Parkinson's disease dementia, drug delivery to the occipital lobe, substantia nigra and/or striatum may be effective. In the treatment of Parkinson's disease, drug delivery to the substantia nigra and/or striatum may be effective. In the treatment of corticobasal degeneration (CBD), drug delivery to the frontal lobe, parietal lobe, basal ganglion, and/or substantia nigra may be effective. In the treatment of progressive supranuclear paralysis (PSP), drug delivery to the frontal lobe, basal ganglion and/or substantia nigra may be effective. In the treatment of amyotrophic lateral sclerosis, drug delivery to the frontal lobe, parietal lobe, basal ganglion and/or substantia nigra may be effective. In the treatment of spinocerebellar degeneration (SCD) SCA type 1 to SCA type 34, drug delivery to the brainstem and/or cerebellum may be effective. In the treatment of dentatorubral-pallidoluysian atrophy (DRPLA), drug delivery to the basal ganglion, brainstem and/or cerebellum may be effective. In the treatment of spinal and bulbar muscular atrophy (SBMA), drug delivery to the brainstem and/or spinal cord may be effective. In the treatment of Friedreich's ataxia (FA), drug delivery to the brainstem and/or cerebellum may be effective. In the treatment of Huntington's disease, drug delivery to the striatum, frontal lobe, parietal lobe and/or basal ganglion may be effective. In the treatment of prion diseases (including mad cow disease and GSS), drug delivery to the cerebral cortex, cerebral white matter, basal ganglion and/or substantia nigra may be effective. In the treatment of white matter encephalopathy, drug delivery to the cerebral white matter may be effective. In the treatment of encephalitis (including viral, bacterial, fungal, and tuberculous encephalitis), and meningitis (including viral, bacterium, fungal, and tuberculous meningitis), drug delivery to the entire brain may be effective. In the treatment of metabolic encephalopathy, toxic encephalopathy, and trophopathic encephalopathy, drug delivery to the entire brain may be effective. In the treatment of white matter encephalopathy, drug delivery to the cerebral white matter may be effective. In the treatment of cerebral infarction, cerebral hemorrhage, subarachnoid hemorrhage, moyamoya disease, and cerebral anoxia, drug delivery to the entire brain may be effective. In the treatment of white matter encephalopathy, drug delivery to the cerebral white matter may be effective. In the treatment of diffuse axonal injury, drug delivery to the cerebral white matter may be effective. In the treatment of head trauma, drug delivery to the entire brain may be effective. In the treatment of multiple sclerosis (MS), and neuromyelitis optica (NMO), drug delivery to the cerebral white matter, cerebral cortex, optic nerve and/or spinal cord may be effective. In the treatment of myotonic dystrophy (DM1, DM2), drug delivery to the skeletal muscle, cardiac muscle, cerebral cortex, and/or cerebral white matter may be effective. In the treatment of hereditary spastic paraparesis (HSP), drug delivery to the parietal lobe and/or spinal cord may be effective. In the treatment of Fukuyama type muscular dystrophy, drug delivery to the skeletal muscle, cerebral cortex and/or cerebral white matter may be effective. In the treatment of dementia with Lewy bodies (DLB), drug delivery to the substantia nigra, striatum, occipital lobe, frontal lobe and/or parietal lobe may be effective. In the treatment of multiple system atrophy (MSA), drug delivery to the striatum, basal ganglion, cerebellum, substantia nigra, frontal lobe and/or temporal lobe may be effective. In the treatment of Alexander's disease, drug delivery to the cerebral white matter may be effective. In the treatment of CADASIL or CARASIL, drug delivery to the cerebral white matter may be effective.

When a composition is applied by administration or ingestion, the administration amount or the ingestion amount may be appropriately selected according to the age (such as age in months and age in weeks), body weight, symptoms and health conditions of a subject, the type of the composition (such as medicine, food and beverage), or the like. The effective ingestion amount of the composition of the present invention for a subject in terms of the content of the nucleic acid complex may be from 0.00001 mg/kg/day to 10000 mg/kg/day, or from 0.001 mg/kg/day to 100 mg/kg/day. The composition may be applied by a single administration, or multiple administrations. In the case of multiple administrations, it may be administered daily or at appropriate time intervals (e.g., at intervals of 1 day, 2 days, 3 days, 1 week, 2 weeks, or 1 month), for example, for 2 to 20 times. A single dosage of the nucleic acid complex described above may be, for example, 0.001 mg/kg or more, 0.005 mg/kg or more, 0.01 mg/kg or more, 0.25 mg/kg or more, 0.5 mg/kg or more, 1 mg/kg or more, 2.5 mg/kg or more, 0.5 mg/kg or more, 1.0 mg/kg or more, 2.0 mg/kg or more, 3.0 mg/kg or more, 4.0 mg/kg or more, 5 mg/kg or more, 10 mg/kg or more, 20 mg/kg or more, 30 mg/kg or more, 40 mg/kg or more, 50 mg/kg or more, 75 mg/kg or more, 100 mg/kg or more, 150 mg/kg or more, 200 mg/kg or more, 300 mg/kg or more, 400 mg/kg or more, or 500 mg/kg or more. For example, any amount within a range from 0.001 mg/kg to 500 mg/kg (e.g., 0.001 mg/kg, 0.01 mg/kg, 0.1 mg/kg, 1 mg/kg, 5 mg/kg, 10 mg/kg, 50 mg/kg, 100 mg/kg, or 200 mg/kg) may be appropriately selected.

The nucleic acid complex of the present invention may be administered four times at a frequency of twice a week at a dose of from 0.01 to 10 mg/kg (e.g., about 6.25 mg/kg). Further, the nucleic acid complex may be administered two to four times at a frequency of once to twice a week, for example, administered twice at a frequency of twice a week, at a dose of from 0.05 to 30 mg/kg (e.g., about 25 mg/kg). By adopting such a dosing regimen (divided administration), the toxicity can be lowered and the load on a subject can be reduced compared to a single administration of a higher dose.

Although there is a limit (upper limit) on the amount crossing the BBB, or the amount crossing the BNB by a single administration of a nucleic acid complex, in the case of repeated administrations, the inhibitory effect is considered to be produced additively in cells. That is, at a higher dose beyond the BBB crossing limit or the BNB crossing limit (e.g., 25 mg/kg or higher), enhancement of the effectiveness is reduced when the amount of a single administration is increased, however the effectiveness is considered to be enhanced by performing repeated administrations at an administration interval of certain extent (e.g., more than half a day).

(Drug Delivery)

The composition of the present invention can deliver a specific drug to the nervous system, especially to the central nervous system, by binding the drug to the first nucleic acid strand and/or the second nucleic acid strand, utilizing the fact that a nucleic acid complex of the first aspect or a single-stranded nucleic acid strand, which is contained as an active ingredient, can cross the BBB to be delivered efficiently to the central nervous system. There is no particular restriction on the drug to be delivered to the nervous system, and examples thereof include a peptide, a protein, and a nucleic acid drug as well as other organic compounds, such as an antitumor drug, a hormonal drug, an antibiotic, an antiviral drug, and an anti-inflammatory drug. The drug is preferably a small molecule drug. The meaning of a "small molecule drug" is well understood in the art. A small molecule drug typically refers to a drug having a molecular weight of less than 1,000 Da. The drug may be also a lipophilic drug. Examples of a nucleic acid drug includes, but not particularly limited to, ASO, antagomiR, splice-switching oligonucleotide, aptamer, single-stranded siRNA, microRNA, and pre-microRNA. The binding position and the type of binding of a drug in the second nucleic acid strand are as described above in connection with the binding of tocopherol, cholesterol, or an analog thereof, and so on to the second nucleic acid strand.

The composition of the present invention can be highly efficiently delivered to the central nervous system to effectively modify or inhibit the expression of a target gene, or the level of a target transcriptional product, as disclosed in the following Examples. Consequently, provided is a method of decreasing the expression amount of a target transcriptional product in the central nervous system of a subject, comprising administering a composition comprising the above nucleic acid complex to a subject. This method may be a method for treating a central nervous system disease of a subject. Further provided is a method of delivering a drug to the central nervous system of a subject, comprising administering a composition comprising the above nucleic acid complex to a subject.

EXAMPLES

The invention is further described in detail by way of the following Reference Examples and Examples, provided that these do not restrict the present invention, and may be modified without departing from the scope of the present invention.

In the following Examples, "room temperature" usually indicates about 10° C. to about 35° C. The ratio indicated with respect to a mixed solvent is a volume ratio unless otherwise specified. A percentage (%) indicates % by weight unless otherwise specified.

Elution in the column chromatography in Examples was performed under observation by TLC (Thin Layer Chromatography), unless otherwise specified. For TLC observation, 60 $F_{254}$ (manufactured by Merck) was used as a TLC plate, and as a developing solvent, the solvent used as an eluting solvent for column chromatography was used. For detection, a UV detector was employed. In preparative HPLC (high performance liquid chromatography) when denoted with C18, an octadecyl-bound silica gel was used. The ratio indicated with respect to an eluting solvent is a volume ratio unless otherwise specified.

For the analysis of $^1$H NMR, an ACD/SpecManager (producte name) software, or the like was used. A proton peak of a hydroxy group, an amino group, or the like is sometimes not described when the peak is very shallow.

The meanings of the abbreviations used in Examples are as follow.

M: Molar concentration
N: Normality
$CDCl_3$: Deuterated chloroform
DMSO-$d_6$: Deuterated dimethyl sulfoxide
$^1$H NMR: Proton nuclear magnetic resonance
LC/MS: Liquid chromatography-mass spectrometer
DIPEA: N,N-Diisopropylethylamine
DMAP: 4-Dimethylaminopyridine
DMF: Dimethylformamide
DMSO: Dimethyl sulfoxide
HATU: O-(7-Azabenzotriazol-1-yl)-N,N,N',N'-tetramethyluronium hexafluorophosphate
NMP: N-Methyl-2-pyrrolidone
PBS: Phosphate-buffered saline
TEA: Triethylamine
TEAA: Triethylamine acetate
THF: Tetrahydrofuran The structures of oligonucleotides used in the following Examples are summarized in Table 1. Among the oligonucleotides used in Examples, ASO (Malat1), Y61-cRNA (Malat1), Y62-cRNA (Malat1), Y63-cRNA (Malat1), Y64-cRNA (Malat1), Y59-cRNA (Malat1), Y60-cRNA (Malat1), and Chol-cRNA (Malat1) were synthesized by GeneDesign Inc. (Osaka, Japan).

TABLE 1

| Double strand No. | Double-stranded nucleic acid agent name | Oligonucleotide name | 5'-Modification | Sequence (from 5' to 3') | SEQ ID NO: |
|---|---|---|---|---|---|
| n/a | n/a | ASO (Malat1) | | C*T*A*g*t*t*c*a*c*t*g*a*a*T*G*C | 1 |
| n/a | n/a | Chol-cRNA (Malat1) | Chol- | g*c*a*UUCAGUGAAC*u*a*g | 2 |
| n/a | n/a | Y61-cRNA (Malat1) | Y61- | g*c*a*UUCAGUGAAC*u*a*g | 2 |
| n/a | n/a | Y62-cRNA (Malat1) | Y62- | g*c*a*UUCAGUGAAC*u*a*g | 2 |
| n/a | n/a | Y63-cRNA (Malat1) | Y63- | g*c*a*UUCAGUGAAC*u*a*g | 2 |
| n/a | n/a | Y64-cRNA (Malat1) | Y64- | g*c*a*UUCAGUGAAC*u*a*g | 2 |
| 1 | Y1-HDO | ASO (Malat1)<br>Y1-cRNA (Malat1) | <br>Y1- | C*T*A*g*t*t*c*a*c*t*g*a*a*T*G*C<br>g*c*a*UUCAGUGAAC*u*a*g | 1<br>2 |
| 3 | Y3-HDO | ASO (Malat1)<br>Y3-cRNA (Malat1) | <br>Y3- | C*T*A*g*t*t*c*a*c*t*g*a*a*T*G*C<br>g*c*a*UUCAGUGAAC*u*a*g | 1<br>2 |
| 4 | Y4-HDO | ASO (Malat1)<br>Y4-cRNA (Malat1) | <br>Y4- | C*T*A*g*t*t*c*a*c*t*g*a*a*T*G*C<br>g*c*a*UUCAGUGAAC*u*a*g | 1<br>2 |
| 5 | Y5-HDO | ASO (Malat1)<br>Y5-cRNA (Malat1) | <br>Y5- | C*T*A*g*t*t*c*a*c*t*g*a*a*T*G*C<br>g*c*a*UUCAGUGAAC*u*a*g | 1<br>2 |
| 6 | Y6-HDO | ASO (Malat1)<br>Y6-cRNA (Malat1) | <br>Y6- | C*T*A*g*t*t*c*a*c*t*g*a*a*T*G*C<br>g*c*a*UUCAGUGAAC*u*a*g | 1<br>2 |
| 7 | Y7-HDO | ASO (Malat1)<br>Y7-cRNA (Malat1) | <br>Y7- | C*T*A*g*t*t*c*a*c*t*g*a*a*T*G*C<br>g*c*a*UUCAGUGAAC*u*a*g | 1<br>2 |
| 8 | Y8-HDO | ASO (Malat1)<br>Y8-cRNA (Malat1) | <br>Y8- | C*T*A*g*t*t*c*a*c*t*g*a*a*T*G*C<br>g*c*a*UUCAGUGAAC*u*a*g | 1<br>2 |
| 9 | Y9-HDO | ASO (Malat1)<br>Y9-cRNA (Malat1) | <br>Y9- | C*T*A*g*t*t*c*a*c*t*g*a*a*T*G*C<br>g*c*a*UUCAGUGAAC*u*a*g | 1<br>2 |
| 10 | Y10-HDO | ASO (Malat1)<br>Y10-cRNA (Malat1) | <br>Y10- | C*T*A*g*t*t*c*a*c*t*g*a*a*T*G*C<br>g*c*a*UUCAGUGAAC*u*a*g | 1<br>2 |
| 11 | Y11-HDO | ASO (Malat1)<br>Y11-cRNA (Malat1) | <br>Y11- | C*T*A*g*t*t*c*a*c*t*g*a*a*T*G*C<br>g*c*a*UUCAGUGAAC*u*a*g | 1<br>2 |
| 12 | Y12-HDO | ASO (Malat1)<br>Y12-cRNA (Malat1) | <br>Y12- | C*T*A*g*t*t*c*a*c*t*g*a*a*T*G*C<br>g*c*a*UUCAGUGAAC*u*a*g | 1<br>2 |
| 13 | Y13-HDO | ASO (Malat1)<br>Y13-cRNA (Malat1) | <br>Y13- | C*T*A*g*t*t*c*a*c*t*g*a*a*T*G*C<br>g*c*a*UUCAGUGAAC*u*a*g | 1<br>2 |

TABLE 1-continued

| Double strand No. | Double-stranded nucleic acid agent name | Oligonucleotide name | 5'-Modification | Sequence (from 5' to 3') | SEQ ID NO: |
|---|---|---|---|---|---|
| 14 | Y14-HDO | ASO (Malat1) | | C*T*A*g*t*t*c*a*c*t*g*a*a*T*G*C | 1 |
| | | Y14-cRNA (Malat1) | Y14- | g*c*a*UUCAGUGAAC*u*a*g | 2 |
| 15 | Y15-HDO | ASO (Malat1) | | C*T*A*g*t*t*c*a*c*t*g*a*a*T*G*C | 1 |
| | | Y15-cRNA (Malat1) | Y15- | g*c*a*UUCAGUGAAC*u*a*g | 2 |
| 16 | Y16-HDO | ASO (Malat1) | | C*T*A*g*t*t*c*a*c*t*g*a*a*T*G*C | 1 |
| | | Y16-cRNA (Malat1) | Y16- | g*c*a*UUCAGUGAAC*u*a*g | 2 |
| 17 | Y17-HDO | ASO (Malat1) | | C*T*A*g*t*t*c*a*c*t*g*a*a*T*G*C | 1 |
| | | Y17-cRNA (Malat1) | Y17- | g*c*a*UUCAGUGAAC*u*a*g | 2 |
| 18 | Y18-HDO | ASO (Malat1) | | C*T*A*g*t*t*c*a*c*t*g*a*a*T*G*C | 1 |
| | | Y18-cRNA (Malat1) | Y18- | g*c*a*UUCAGUGAAC*u*a*g | 2 |
| 19 | Y19-HDO | ASO (Malat1) | | C*T*A*g*t*t*c*a*c*t*g*a*a*T*G*C | 1 |
| | | Y19-cRNA (Malat1) | Y19- | g*c*a*UUCAGUGAAC*u*a*g | 2 |
| 20 | Y20-HDO | ASO (Malat1) | | C*T*A*g*t*t*c*a*c*t*g*a*a*T*G*C | 1 |
| | | Y20-cRNA (Malat1) | Y20- | g*c*a*UUCAGUGAAC*u*a*g | 2 |
| 59 | Y59-HDO | ASO (Malat1) | | C*T*A*g*t*t*c*a*c*t*g*a*a*T*G*C | 1 |
| | | Y59-cRNA (Malat1) | Y59- | g*c*a*UUCAGUGAAC*u*a*g | 2 |
| 60 | Y60-HDO | ASO (Malat1) | | C*T*A*g*t*t*c*a*c*t*g*a*a*T*G*C | 1 |
| | | Y60-cRNA (Malat1) | Y60- | g*c*a*UUCAGUGAAC*u*a*g | 2 |
| 21 | Y21-HDO | ASO (Malat1) | | C*T*A*g*t*t*c*a*c*t*g*a*a*T*G*C | 1 |
| | | Y21-cRNA (Malat1) | Y21- | g*c*a*UUCAGUGAAC*u*a*g | 2 |
| 22 | Y22-HDO | ASO (Malat1) | | C*T*A*g*t*t*c*a*c*t*g*a*a*T*G*C | 1 |
| | | Y22-cRNA (Malat1) | Y22- | g*c*a*UUCAGUGAAC*u*a*g | 2 |
| 23 | Y23-HDO | ASO (Malat1) | | C*T*A*g*t*t*c*a*c*t*g*a*a*T*G*C | 1 |
| | | Y23-cRNA (Malat1) | Y23- | g*c*a*UUCAGUGAAC*u*a*g | 2 |
| 24 | Y24-HDO | ASO (Malat1) | | C*T*A*g*t*t*c*a*c*t*g*a*a*T*G*C | 1 |
| | | Y24-cRNA (Malat1) | Y24- | g*c*a*UUCAGUGAAC*u*a*g | 2 |
| 25 | Y25-HDO | ASO (Malat1) | | C*T*A*g*t*t*c*a*c*t*g*a*a*T*G*C | 1 |
| | | Y25-cRNA (Malat1) | Y25- | g*c*a*UUCAGUGAAC*u*a*g | 2 |
| 26 | Y26-HDO | ASO (Malat1) | | C*T*A*g*t*t*c*a*c*t*g*a*a*T*G*C | 1 |
| | | Y26-cRNA (Malat1) | Y26- | g*c*a*UUCAGUGAAC*u*a*g | 2 |
| 27 | Y27-HDO | ASO (Malat1) | | C*T*A*g*t*t*c*a*c*t*g*a*a*T*G*C | 1 |
| | | Y27-cRNA (Malat1) | Y27- | g*c*a*UUCAGUGAAC*u*a*g | 2 |
| 28 | Y28-HDO | ASO (Malat1) | | C*T*A*g*t*t*c*a*c*t*g*a*a*T*G*C | 1 |
| | | Y28-cRNA (Malat1) | Y28- | g*c*a*UUCAGUGAAC*u*a*g | 2 |
| 29 | Y29-HDO | ASO (Malat1) | | C*T*A*g*t*t*c*a*c*t*g*a*a*T*G*C | 1 |
| | | Y29-cRNA (Malat1) | Y29- | g*c*a*UUCAGUGAAC*u*a*g | 2 |
| 30 | Y30-HDO | ASO (Malat1) | | C*T*A*g*t*t*c*a*c*t*g*a*a*T*G*C | 1 |
| | | Y30-cRNA (Malat1) | Y30- | g*c*a*UUCAGUGAAC*u*a*g | 2 |
| 31 | Y31-HDO | ASO (Malat1) | | C*T*A*g*t*t*c*a*c*t*g*a*a*T*G*C | 1 |
| | | Y31-cRNA (Malat1) | Y31- | g*c*a*UUCAGUGAAC*u*a*g | 2 |
| 32 | Y32-HDO | ASO (Malat1) | | C*T*A*g*t*t*c*a*c*t*g*a*a*T*G*C | 1 |
| | | Y32-cRNA (Malat1) | Y32- | g*c*a*UUCAGUGAAC*u*a*g | 2 |
| 33 | Y33-HDO | ASO (Malat1) | | C*T*A*g*t*t*c*a*c*t*g*a*a*T*G*C | 1 |
| | | Y33-cRNA (Malat1) | Y33- | g*c*a*UUCAGUGAAC*u*a*g | 2 |
| 34 | Y34-HDO | ASO (Malat1) | | C*T*A*g*t*t*c*a*c*t*g*a*a*T*G*C | 1 |
| | | Y34-cRNA (Malat1) | Y34- | g*c*a*UUCAGUGAAC*u*a*g | 2 |
| 35 | Y35-HDO | ASO (Malat1) | | C*T*A*g*t*t*c*a*c*t*g*a*a*T*G*C | 1 |
| | | Y35-cRNA (Malat1) | Y35- | g*c*a*UUCAGUGAAC*u*a*g | 2 |
| 36 | Y36-HDO | ASO (Malat1) | | C*T*A*g*t*t*c*a*c*t*g*a*a*T*G*C | 1 |
| | | Y36-cRNA (Malat1) | Y36- | g*c*a*UUCAGUGAAC*u*a*g | 2 |

TABLE 1-continued

| Double strand No. | Double-stranded nucleic acid agent name | Oligonucleotide name | 5'-Modification | Sequence (from 5' to 3') | SEQ ID NO: |
|---|---|---|---|---|---|
| 37 | Y37-HDO | ASO (Malat1) | | C*T*A*g*t*t*c*a*c*t*g*a*a*T*G*C | 1 |
| | | Y37-cRNA (Malat1) | Y37- | g*c*a*UUCAGUGAAC*u*a*g | 2 |
| 38 | Y38-HDO | ASO (Malat1) | | C*T*A*g*t*t*c*a*c*t*g*a*a*T*G*C | 1 |
| | | Y38-cRNA (Malat1) | Y38- | g*c*a*UUCAGUGAAC*u*a*g | 2 |
| 39 | Y39-HDO | ASO (Malat1) | | C*T*A*g*t*t*c*a*c*t*g*a*a*T*G*C | 1 |
| | | Y39-cRNA (Malat1) | Y39- | g*c*a*UUCAGUGAAC*u*a*g | 2 |
| 40 | Y40-HDO | ASO (Malat1) | | C*T*A*g*t*t*c*a*c*t*g*a*a*T*G*C | 1 |
| | | Y40-cRNA (Malat1) | Y40- | g*c*a*UUCAGUGAAC*u*a*g | 2 |
| 41 | Y41-HDO | ASO (Malat1) | | C*T*A*g*t*t*c*a*c*t*g*a*a*T*G*C | 1 |
| | | Y41-cRNA (Malat1) | Y41- | g*c*a*UUCAGUGAAC*u*a*g | 2 |
| 42 | Y42-HDO | ASO (Malat1) | | C*T*A*g*t*t*c*a*c*t*g*a*a*T*G*C | 1 |
| | | Y42-cRNA (Malat1) | Y42- | g*c*a*UUCAGUGAAC*u*a*g | 2 |
| 43 | Y43-HDO | ASO (Malat1) | | C*T*A*g*t*t*c*a*c*t*g*a*a*T*G*C | 1 |
| | | Y43-cRNA (Malat1) | Y43- | g*c*a*UUCAGUGAAC*u*a*g | 2 |
| 44 | Y44-HDO | ASO (Malat1) | | C*T*A*g*t*t*c*a*c*t*g*a*a*T*G*C | 1 |
| | | Y44-cRNA (Malat1) | Y44- | g*c*a*UUCAGUGAAC*u*a*g | 2 |
| 45 | Y45-HDO | ASO (Malat1) | | C*T*A*g*t*t*c*a*c*t*g*a*a*T*G*C | 1 |
| | | Y45-cRNA (Malat1) | Y45- | g*c*a*UUCAGUGAAC*u*a*g | 2 |
| 46 | Y46-HDO | ASO (Malat1) | | C*T*A*g*t*t*c*a*c*t*g*a*a*T*G*C | 1 |
| | | Y46-cRNA (Malat1) | Y46- | g*c*a*UUCAGUGAAC*u*a*g | 2 |
| 47 | Y47-HDO | ASO (Malat1) | | C*T*A*g*t*t*c*a*c*t*g*a*a*T*G*C | 1 |
| | | Y47-cRNA (Malat1) | Y47- | g*c*a*UUCAGUGAAC*u*a*g | 2 |
| 48 | Y48-HDO | ASO (Malat1) | | C*T*A*g*t*t*c*a*c*t*g*a*a*T*G*C | 1 |
| | | Y48-cRNA (Malat1) | Y48- | g*c*a*UUCAGUGAAC*u*a*g | 2 |
| 49 | Y49-HDO | ASO (Malat1) | | C*T*A*g*t*t*c*a*c*t*g*a*a*T*G*C | 1 |
| | | Y49-cRNA (Malat1) | Y49- | g*c*a*UUCAGUGAAC*u*a*g | 2 |
| 50 | Y50-HDO | ASO (Malat1) | | C*T*A*g*t*t*c*a*c*t*g*a*a*T*G*C | 1 |
| | | Y50-cRNA (Malat1) | Y50- | g*c*a*UUCAGUGAAC*u*a*g | 2 |
| 51 | Y51-HDO | ASO (Malat1) | | C*T*A*g*t*t*c*a*c*t*g*a*a*T*G*C | 1 |
| | | Y51-cRNA (Malat1) | Y51- | g*c*a*UUCAGUGAAC*u*a*g | 2 |
| 52 | Y52HDO | ASO (Malat1) | | C*T*A*g*t*t*c*a*c*t*g*a*a*T*G*C | 1 |
| | | Y52-cRNA (Malat1) | Y52- | g*c*a*UUCAGUGAAC*u*a*g | 2 |
| 53 | Y53-HDO | ASO (Malat1) | | C*T*A*g*t*t*c*a*c*t*g*a*a*T*G*C | 1 |
| | | Y53-cRNA (Malat1) | Y53- | g*c*a*UUCAGUGAAC*u*a*g | 2 |
| 54 | Y54-HDO | ASO (Malat1) | | C*T*A*g*t*t*c*a*c*t*g*a*a*T*G*C | 1 |
| | | Y54-cRNA (Malat1) | Y54- | g*c*a*UUCAGUGAAC*u*a*g | 2 |
| 55 | Y55-HDO | ASO (Malat1) | | C*T*A*g*t*t*c*a*c*t*g*a*a*T*G*C | 1 |
| | | Y55-cRNA (Malat1) | Y55- | g*c*a*UUCAGUGAAC*u*a*g | 2 |
| 57 | Y57-HDO | ASO (Malat1) | | C*T*A*g*t*t*c*a*c*t*g*a*a*T*G*C | 1 |
| | | Y57-cRNA (Malat1) | Y57- | g*c*a*UUCAGUGAAC*u*a*g | 2 |
| 58 | Chol-HDO | ASO (Malat1) | | C*T*A*g*t*t*c*a*c*t*g*a*a*T*G*C | 1 |
| | | Chol-cRNA (Malat1) | Chol- | g*c*a*UUCAGUGAAC*u*a*g | 2 |

Upper case/Underlined: LNA(C = 5-Methyl cytosine LNA),
Lower case, DNA,
Upper case: RNA,
Lower case/Underlined: 2'-OMe RNA,
*Phosphorothioate bond The 5' end structure of the oligonucleotide Y61-cRNA (Malat1) shown in Table 1 is shown below. In the following Formula, the indication "oligo" represents an oligonucleotide.

[Chem. 30]

Y61-

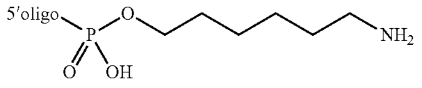

The 5' end structure of the oligonucleotide Y62-cRNA (Malat1) shown in Table 1 is shown below. In the following Formula, the indication "oligo" represents an oligonucleotide.

[Chem. 31]

Y62-

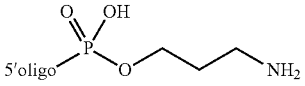

The 5' end structure of the oligonucleotide Y63-cRNA (Malat1) shown in Table 1 is shown below. In the following Formula, the indication "oligo" represents an oligonucleotide.

[Chem. 32]

Y63-

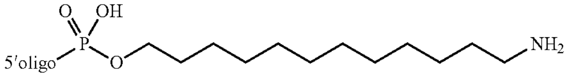

The 5' end structure of the oligonucleotide Y64-cRNA (Malat1) shown in Table 1 is shown below. In the following Formula, the indication "oligo" represents an oligonucleotide.

[Chem 33]

Y64-

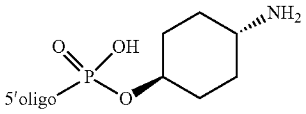

The 5' end structure of the oligonucleotide Y1-cRNA (Malat1) shown in Table 1 is shown below. In the following Formula, the indication "oligo" represents an oligonucleotide.

[Chem. 34]

Y1-

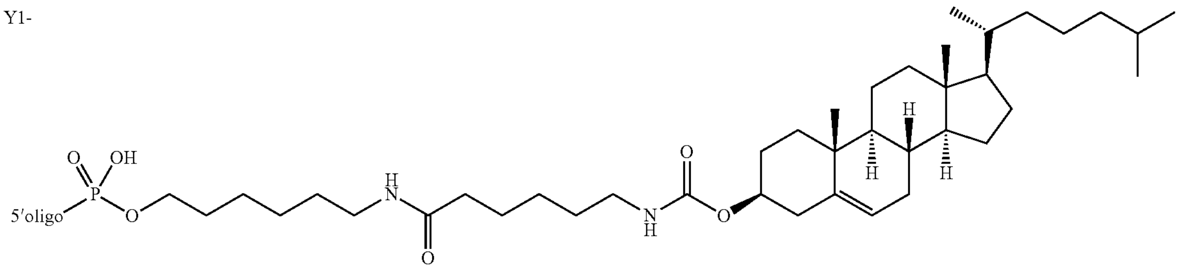

The 5' end structure of the oligonucleotide Y3-cRNA (Malat1) shown in Table 1 is shown below. In the following Formula, the indication "oligo" represents an oligonucleotide.

[Chem. 35]

Y3-

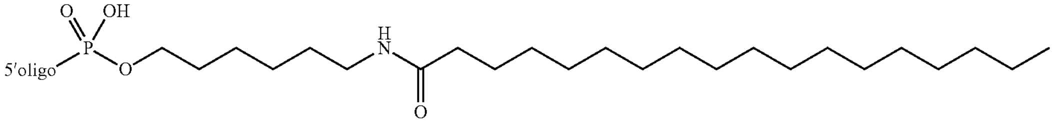

The 5' end structure of the oligonucleotide Y4-cRNA (Malat1) shown in Table 1 is shown below. In the following Formula, the indication "oligo" represents an oligonucleotide.

[Chem 36]

Y4-

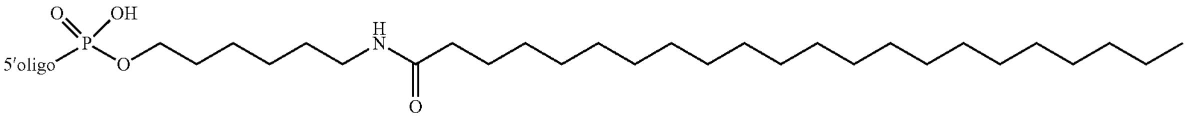

The 5' end structure of the oligonucleotide Y5-cRNA (Malat1) shown in Table 1 is shown below. In the following Formula, the indication "oligo" represents an oligonucleotide.

[Chem. 37]

Y5-

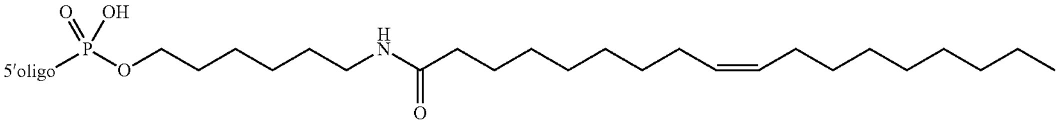

The 5' end structure of the oligonucleotide Y6-cRNA (Malat1) shown in Table 1 is shown below. In the following Formula, the indication "oligo" represents an oligonucleotide.

[Chem. 38]

Y6-

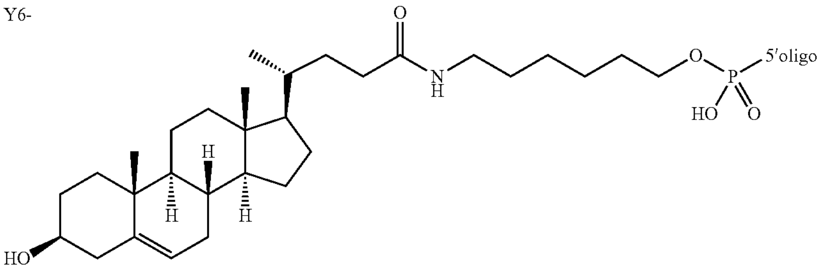

The 5' end structure of the oligonucleotide Y7-cRNA (Malat1) shown in Table 1 is shown below. In the following Formula, the indication "oligo" represents an oligonucleotide.

[Chem 39]

Y7-

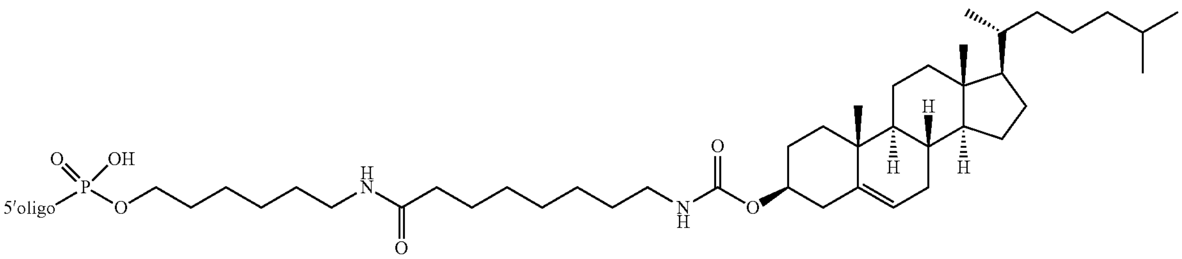

The 5' end structure of the oligonucleotide Y8-cRNA (Malat1) shown in Table 1 is shown below. In the following Formula, the indication "oligo" represents an oligonucleotide.

[Chem. 40]

Y8-

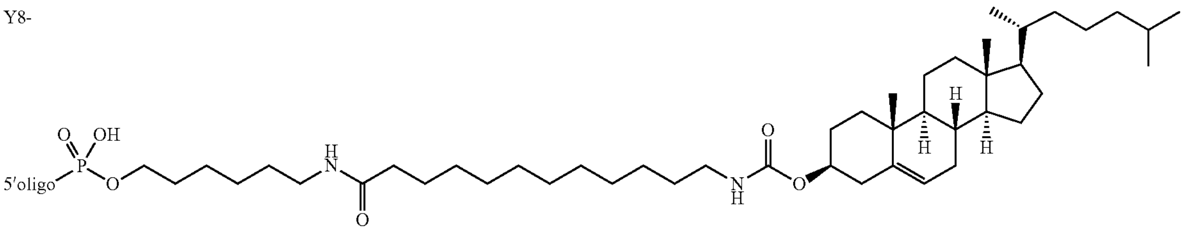

The 5' end structure of the oligonucleotide Y9-cRNA (Malat1) shown in Table 1 is shown below. In the following Formula, the indication "oligo" represents an oligonucleotide.

[Chem 41]

Y9-

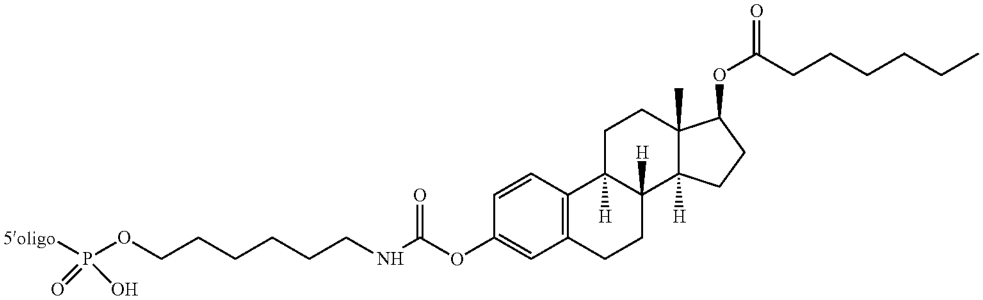

The 5' end structure of the oligonucleotide Y10-cRNA (Malat1) shown in Table 1 is shown below. In the following Formula, the indication "oligo" represents an oligonucleotide.

[Chem 42]

Y10-

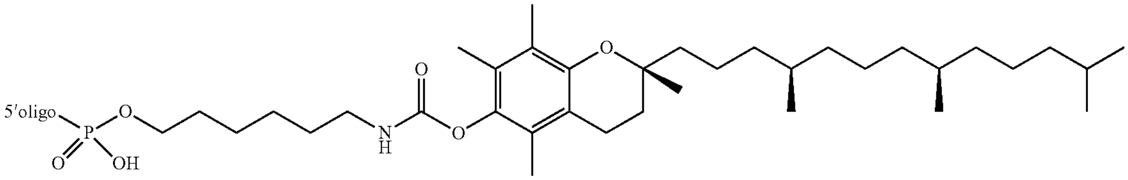

The 5' end structure of the oligonucleotide Y11-cRNA (Malat1) shown in Table 1 is shown below. In the following Formula, the indication "oligo" represents an oligonucleotide.

[Chem 43]

Y11-

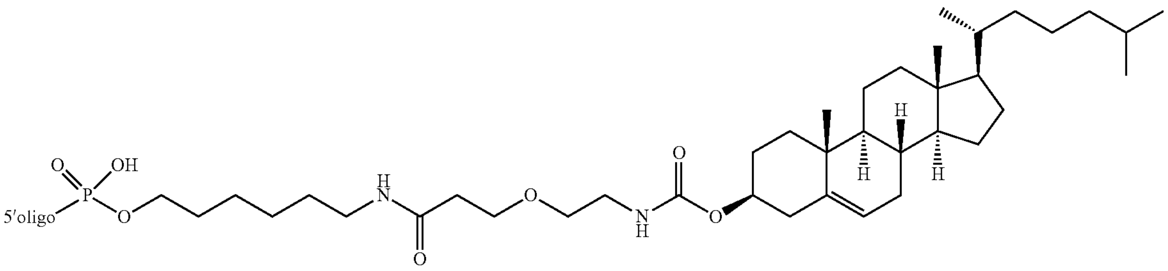

The 5' end structure of the oligonucleotide Y12-cRNA (Malat1) shown in Table 1 is shown below. In the following Formula, the indication "oligo" represents an oligonucleotide.

[Chem 44]

Y12-

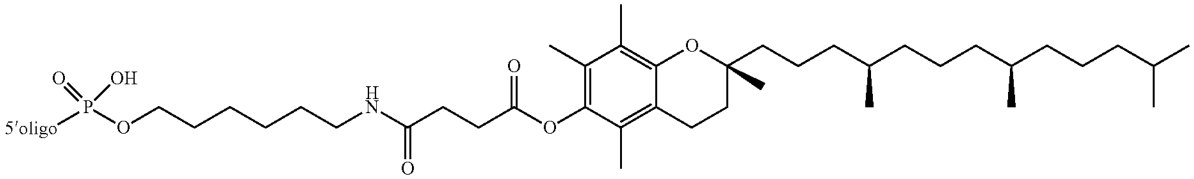

The 5' end structure of the oligonucleotide Y13-cRNA (Malat1) shown in Table 1 is shown below. In the following Formula, the indication "oligo" represents an oligonucleotide.

[Chem 45]

Y13-

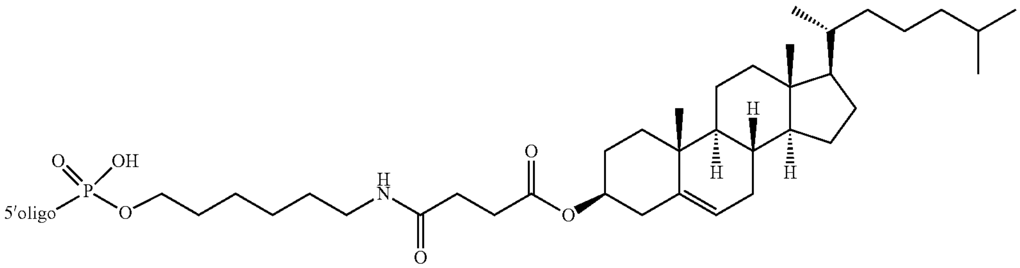

The 5' end structure of the oligonucleotide Y14-cRNA (Malat1) shown in Table 1 is shown below. In the following Formula, the indication "oligo" represents an oligonucleotide.

[Chem 46]
Y14-
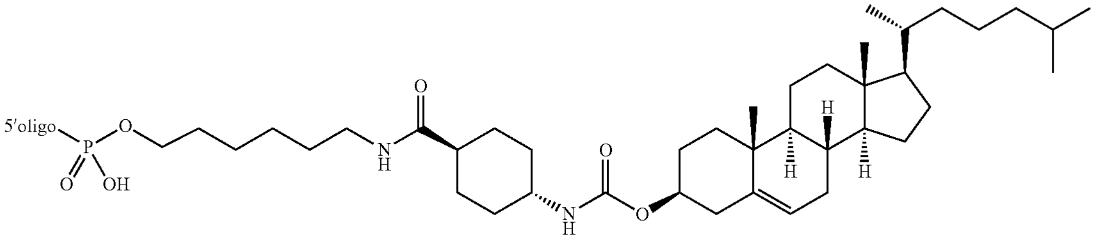
The 5' end structure of the oligonucleotide Y15-cRNA (Malat1) shown in Table 1 is shown below. In the following Formula, the indication "oligo" represents an oligonucleotide.
[Chem 47]
Y15-
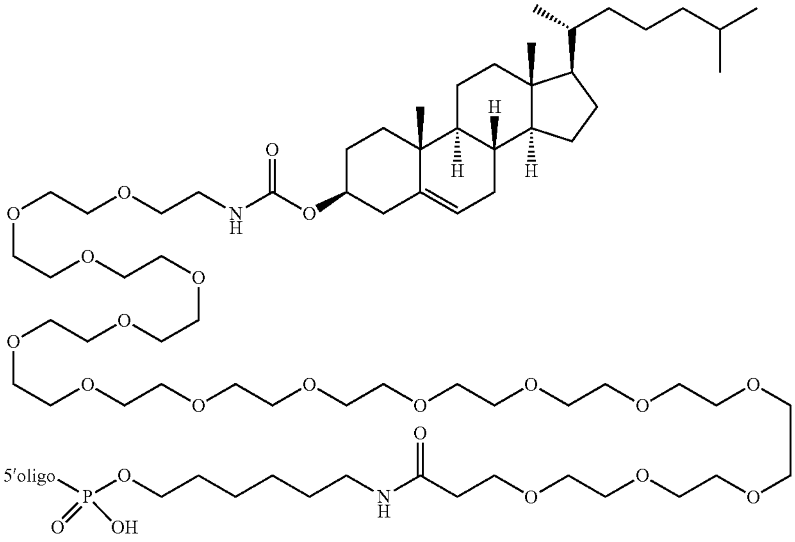
The 5' end structure of the oligonucleotide Y16-cRNA (Malat1) shown in Table 1 is shown below. In the following Formula, the indication "oligo" represents an oligonucleotide.
[Chem 48]
Y16-
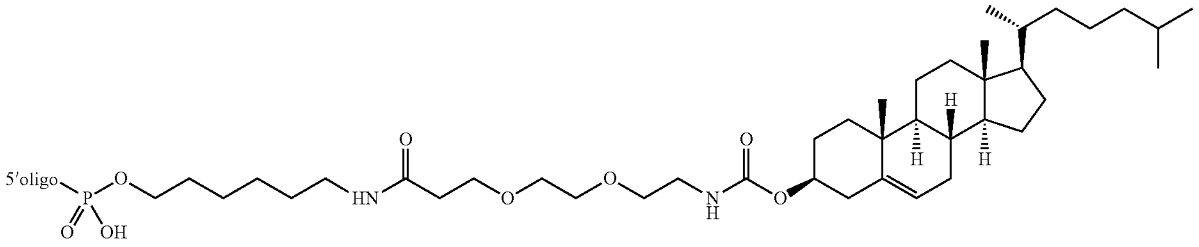

The 5' end structure of the oligonucleotide Y17-cRNA (Malat1) shown in Table 1 is shown below. In the following Formula, the indication "oligo" represents an oligonucleotide.

[Chem 49]

Y17-

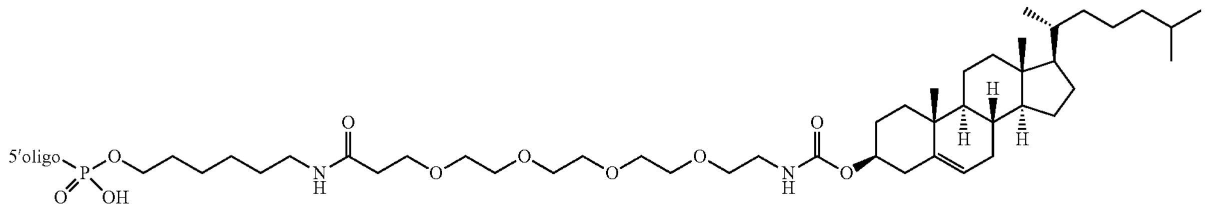

The 5' end structure of the oligonucleotide Y18-cRNA (Malat1) shown in Table 1 is shown below. In the following Formula, the indication "oligo" represents an oligonucleotide.

[Chem 50]

Y18-

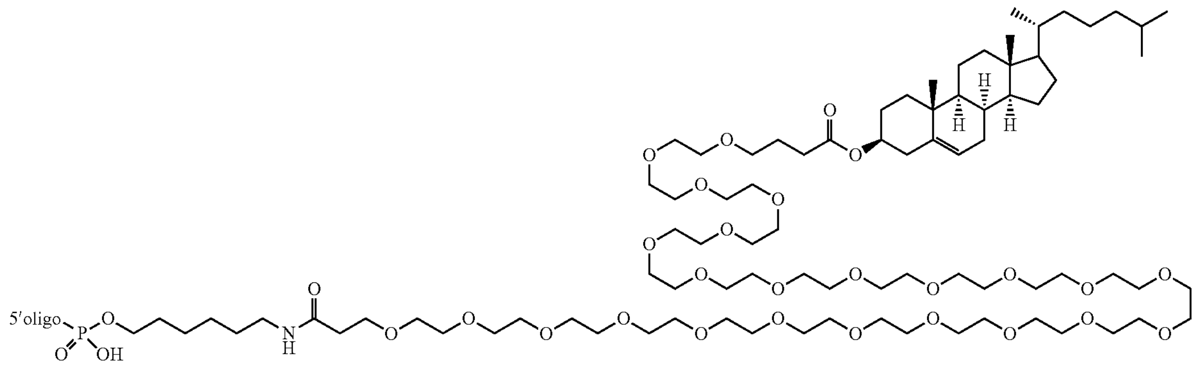

The 5' end structure of the oligonucleotide Y19-cRNA (Malat1) shown in Table 1 is shown below. In the following Formula, the indication "oligo" represents an oligonucleotide.

[Chem 51]

Y19-

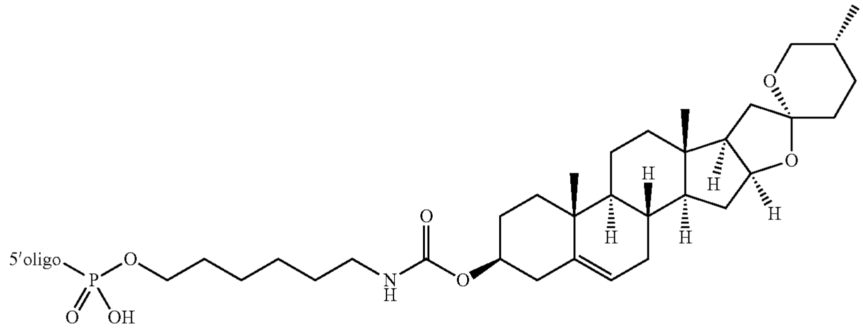

The 5' end structure of the oligonucleotide Y20-cRNA (Malat1) shown in Table 1 is shown below. In the following Formula, the indication "oligo" represents an oligonucleotide.

[Chem 52]

Y20-

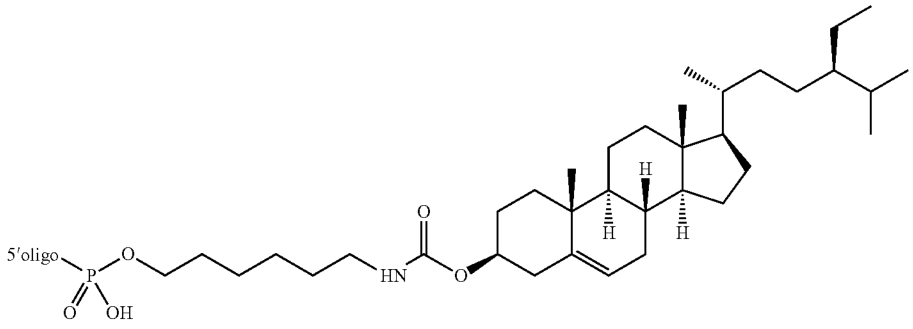

The 5' end structure of the oligonucleotide Y59-cRNA (Malat1) shown in Table 1 is shown below. In the following Formula, the indication "oligo" represents an oligonucleotide.

[Chem 53]

Y59-

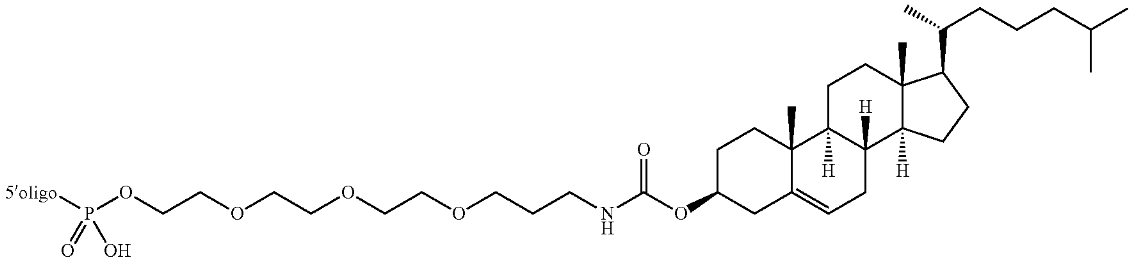

The 5' end structure of the oligonucleotide Y60-cRNA (Malat1) shown in Table 1 is shown below. In the following Formula, the indication "oligo" represents an oligonucleotide.

[Chem 54]

Y60-

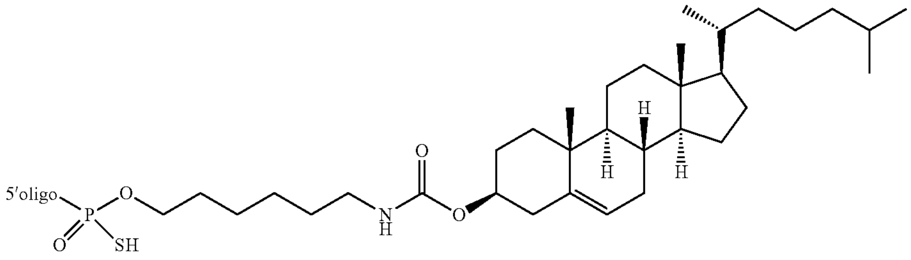

The 5' end structure of the oligonucleotide Y21-cRNA (Malat1) shown in Table 1 is shown below. In the following Formula, the indication "oligo" represents an oligonucleotide.

[Chem 55]

Y21-

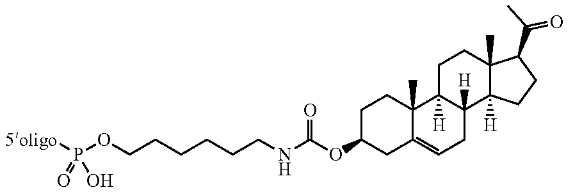

The 5' end structure of the oligonucleotide Y22-cRNA (Malat1) shown in Table 1 is shown below. In the following Formula, the indication "oligo" represents an oligonucleotide.

[Chem 56]

Y22-

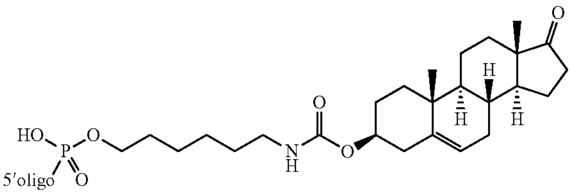

The 5' end structure of the oligonucleotide Y23-cRNA (Malat1) shown in Table 1 is shown below. In the following Formula, the indication "oligo" represents an oligonucleotide.

[Chem 57]

Y23-

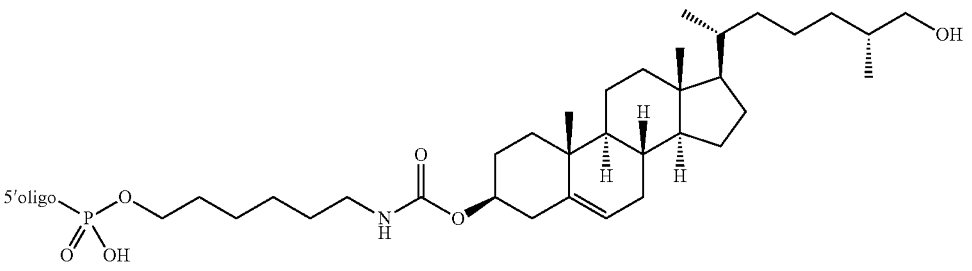

The 5' end structure of the oligonucleotide Y24-cRNA (Malat1) shown in Table 1 is shown below. In the following Formula, the indication "oligo" represents an oligonucleotide.

[Chem 58]

Y24-

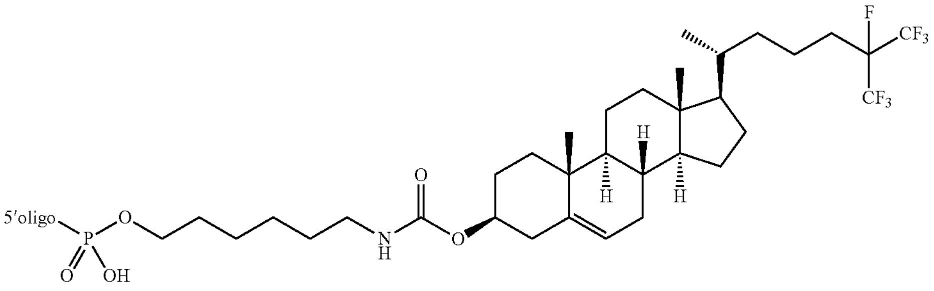

The 5' end structure of the oligonucleotide Y25-cRNA (Malat1) shown in Table 1 is shown below. In the following Formula, the indication "oligo" represents an oligonucleotide.

[Chem 59]
Y25-
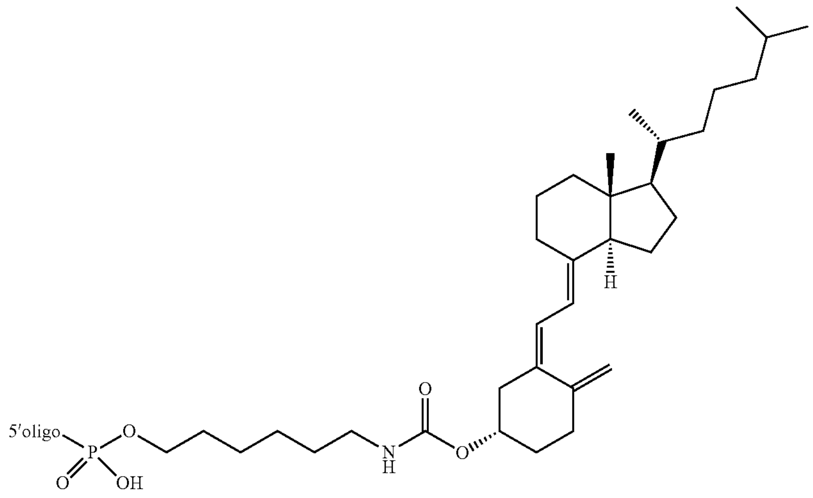
The 5' end structure of the oligonucleotide Y26-cRNA (Malat1) shown in Table 1 is shown below. In the following Formula, the indication "oligo" represents an oligonucleotide.
[Chem 60]
Y26-
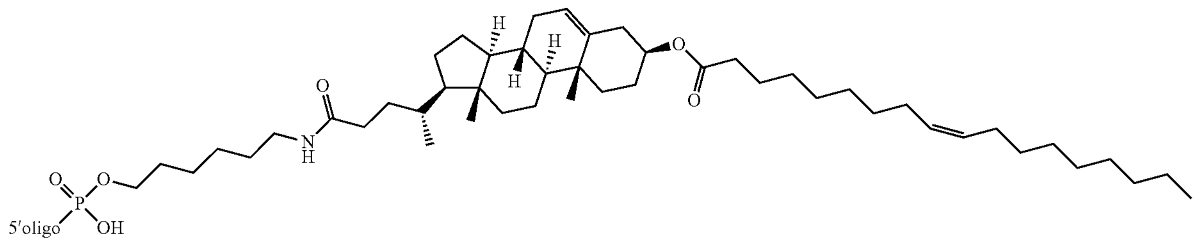
The 5' end structure of the oligonucleotide Y27-cRNA (Malat1) shown in Table 1 is shown below. In the following Formula, the indication "oligo" represents an oligonucleotide.
[Chem 61]
Y27-
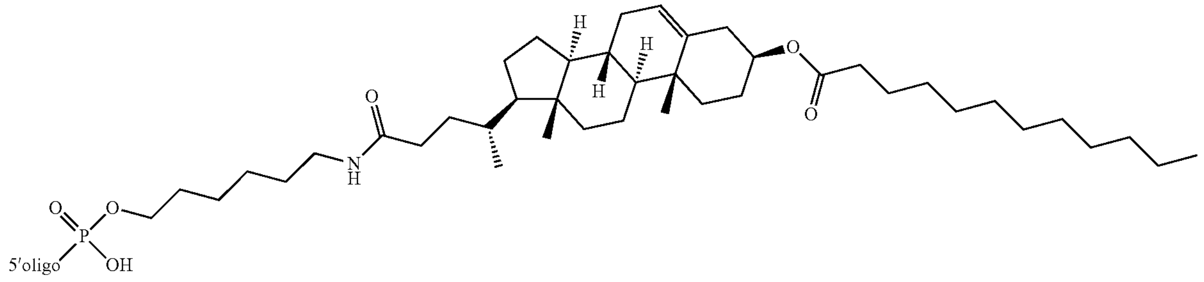

The 5' end structure of the oligonucleotide Y28-cRNA (Malat1) shown in Table 1 is shown below. In the following Formula, the indication "oligo" represents an oligonucleotide.

[Chem 62]

Y28-

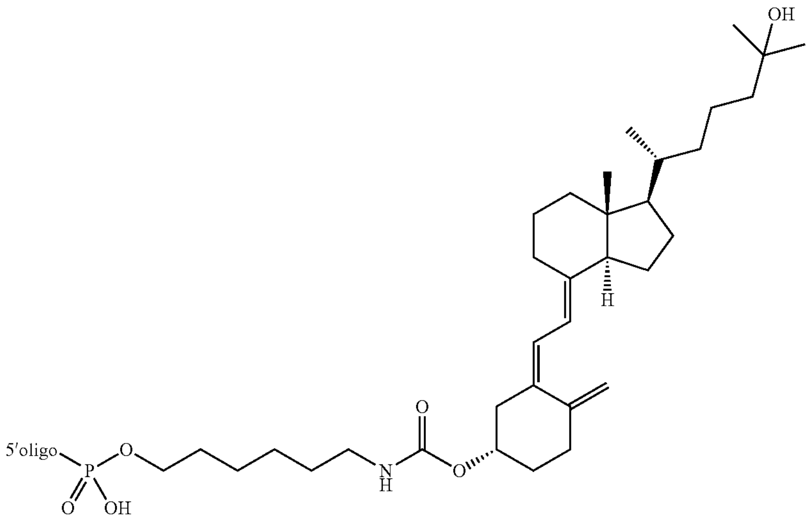

The 5' end structure of the oligonucleotide Y29-cRNA (Malat1) shown in Table 1 is shown below. In the following Formula, the indication "oligo" represents an oligonucleotide.

[Chem 63]

Y29-

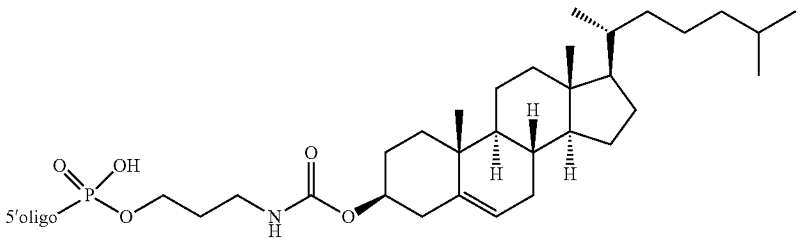

The 5' end structure of the oligonucleotide Y30-cRNA (Malat1) shown in Table 1 is shown below. In the following Formula, the indication "oligo" represents an oligonucleotide.

[Chem 64]
Y30-
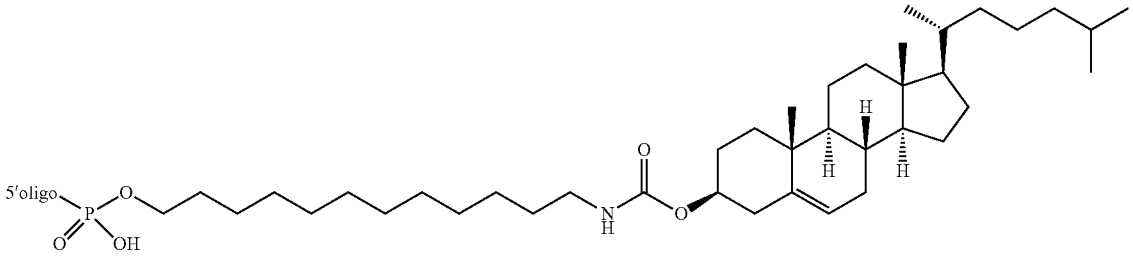
The 5' end structure of the oligonucleotide Y31-cRNA (Malat1) shown in Table 1 is shown below. In the following Formula, the indication "oligo" represents an oligonucleotide.
[Chem 65]
Y31-
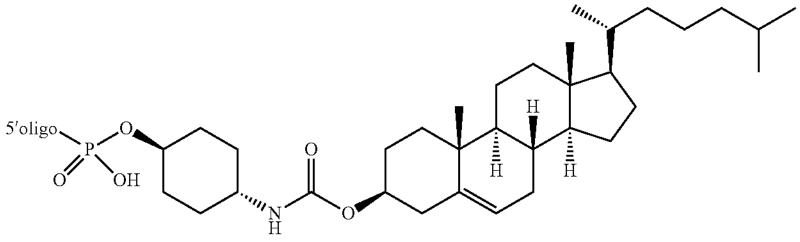
The 5' end structure of the oligonucleotide Y32-cRNA (Malat1) shown in Table 1 is shown below. In the following Formula, the indication "oligo" represents an oligonucleotide.
[Chem 66]
Y32-
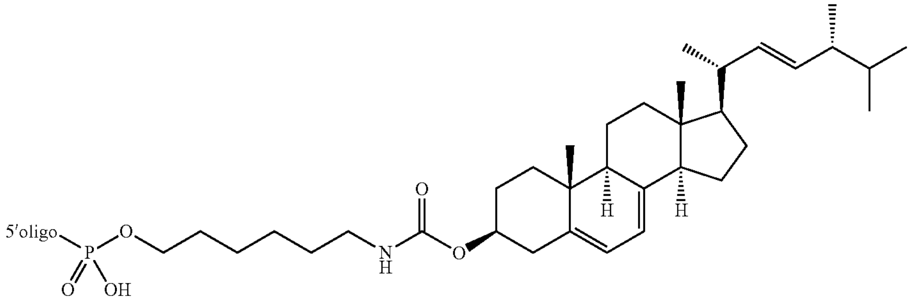

The 5' end structure of the oligonucleotide Y33-cRNA (Malat1) shown in Table 1 is shown below. In the following Formula, the indication "oligo" represents an oligonucleotide.

[Chem 67]

Y33-

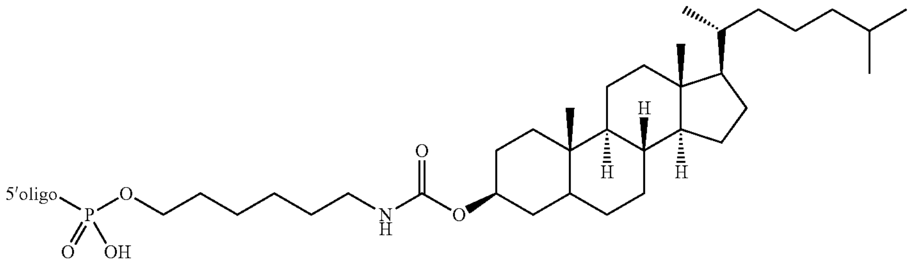

The 5' end structure of the oligonucleotide Y34-cRNA (Malat1) shown in Table 1 is shown below. In the following Formula, the indication "oligo" represents an oligonucleotide.

[Chem 68]

Y34-

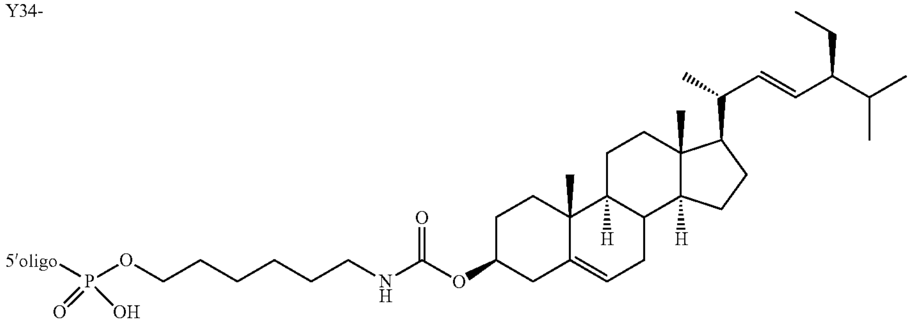

The 5' end structure of the oligonucleotide Y35-cRNA (Malat1) shown in Table 1 is shown below. In the following Formula, the indication "oligo" represents an oligonucleotide.

[Chem 69]

Y35-

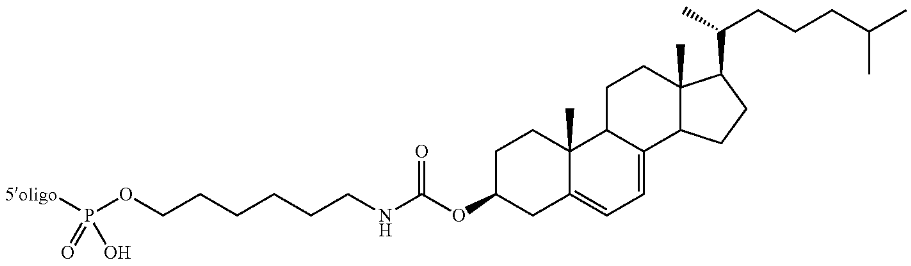

The 5' end structure of the oligonucleotide Y36-cRNA (Malat1) shown in Table 1 is shown below. In the following Formula, the indication "oligo" represents an oligonucleotide.

[Chem 70]

Y36-

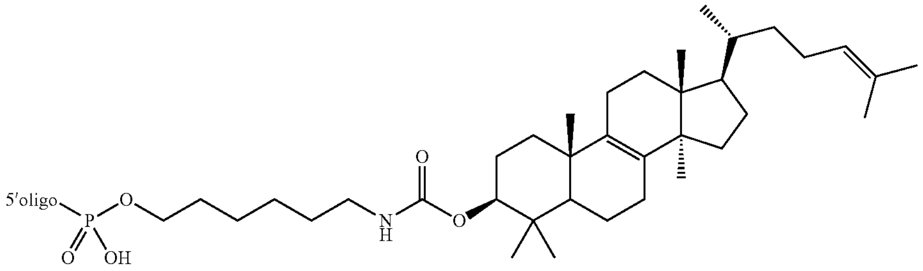

The 5' end structure of the oligonucleotide Y37-cRNA (Malat1) shown in Table 1 is shown below. In the following Formula, the indication "oligo" represents an oligonucleotide.

[Chem 71]

Y37-

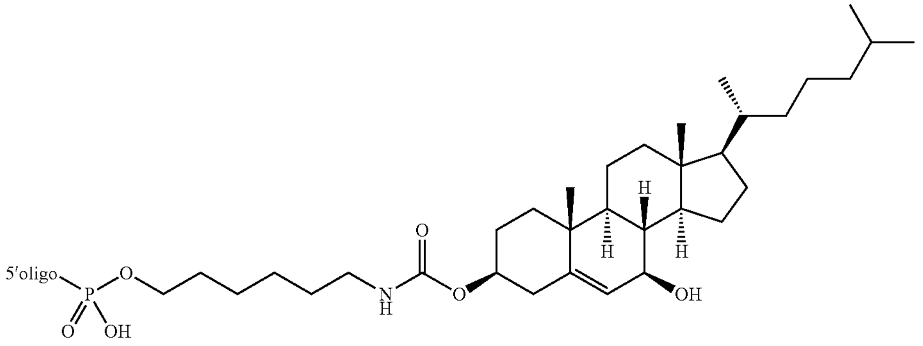

The 5' end structure of the oligonucleotide Y38-cRNA (Malat1) shown in Table 1 is shown below. In the following Formula, the indication "oligo" represents an oligonucleotide.

[Chem 72]

Y38-

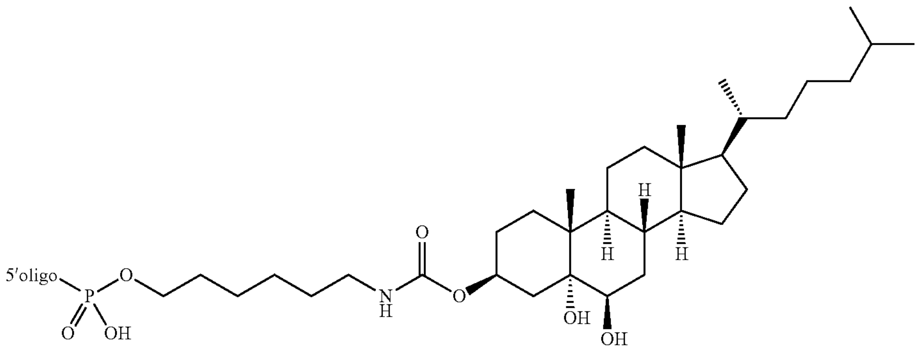

The 5' end structure of the oligonucleotide Y39-cRNA (Malat1) shown in Table 1 is shown below. In the following Formula, the indication "oligo" represents an oligonucleotide.

[Chem 73]

Y39-

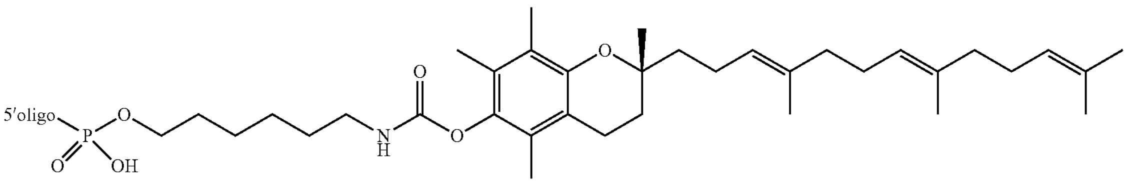

The 5' end structure of the oligonucleotide Y40-cRNA (Malat1) shown in Table 1 is shown below. In the following Formula, the indication "oligo" represents an oligonucleotide.

[Chem 74]

Y40-

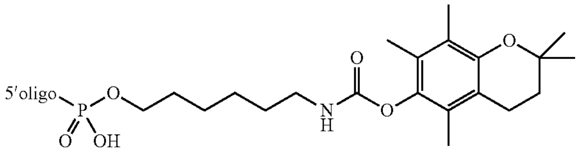

The 5' end structure of the oligonucleotide Y41-cRNA (Malat1) shown in Table 1 is shown below. In the following Formula, the indication "oligo" represents an oligonucleotide.

[Chem 75]

Y41-

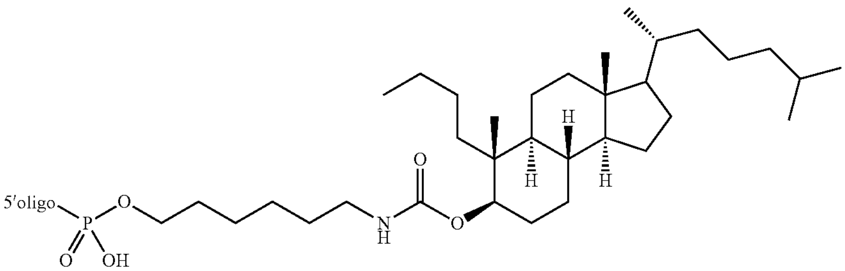

The 5' end structure of the oligonucleotide Y42-cRNA (Malat1) shown in Table 1 is shown below. In the following Formula, the indication "oligo" represents an oligonucleotide.

[Chem 76]

Y42-

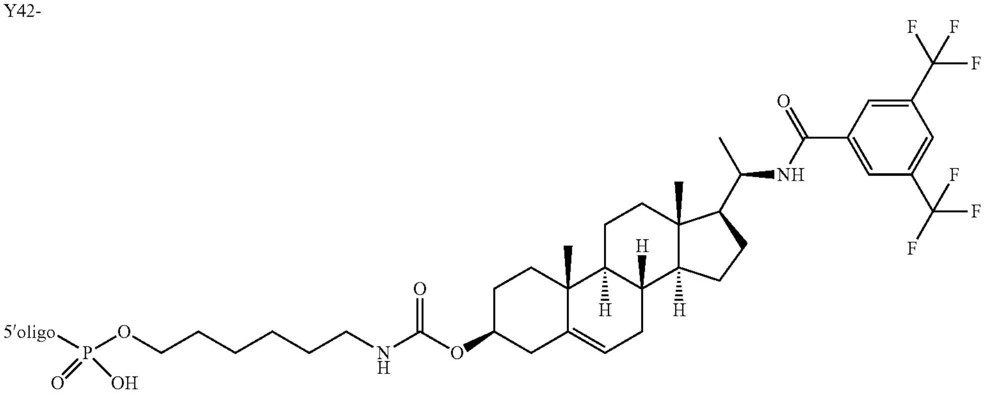

The 5' end structure of the oligonucleotide Y43-cRNA (Malat1) shown in Table 1 is shown below. In the following Formula, the indication "oligo" represents an oligonucleotide.

[Chem 77]

Y43-

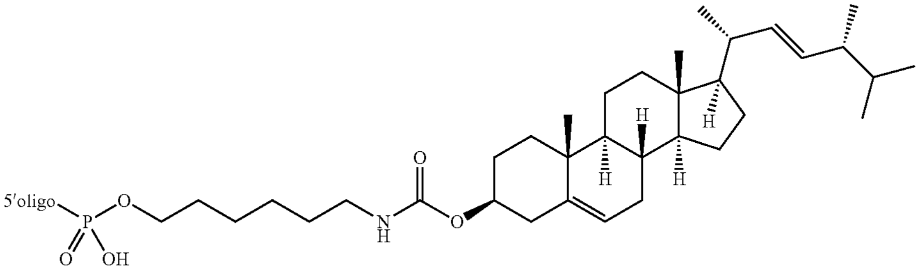

The 5' end structure of the oligonucleotide Y44-cRNA (Malat1) shown in Table 1 is shown below. In the following Formula, the indication "oligo" represents an oligonucleotide.

[Chem 78]

Y44-

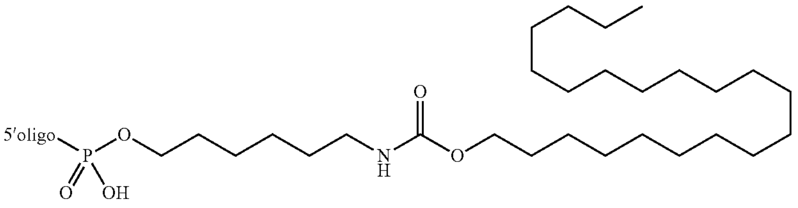

The 5' end structure of the oligonucleotide Y45-cRNA (Malat1) shown in Table 1 is shown below. In the following Formula, the indication "oligo" represents an oligonucleotide.

[Chem 79]

Y45-

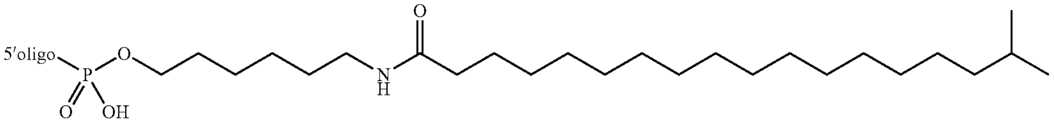

The 5' end structure of the oligonucleotide Y46-cRNA (Malat1) shown in Table 1 is shown below. In the following Formula, the indication "oligo" represents an oligonucleotide.

[Chem 80]

Y46-

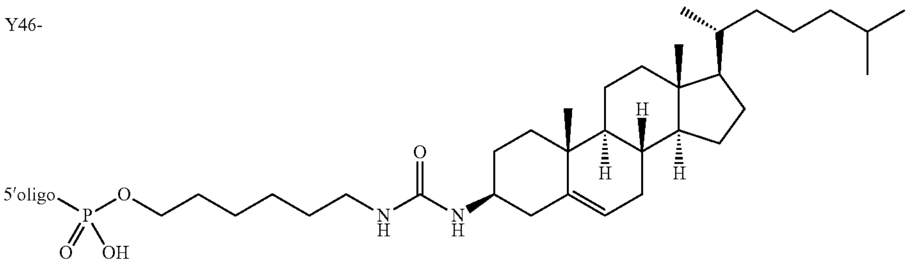

The 5' end structure of the oligonucleotide Y47-cRNA (Malat1) shown in Table 1 is shown below. In the following Formula, the indication "oligo" represents an oligonucleotide.

[Chem 81]

Y47-

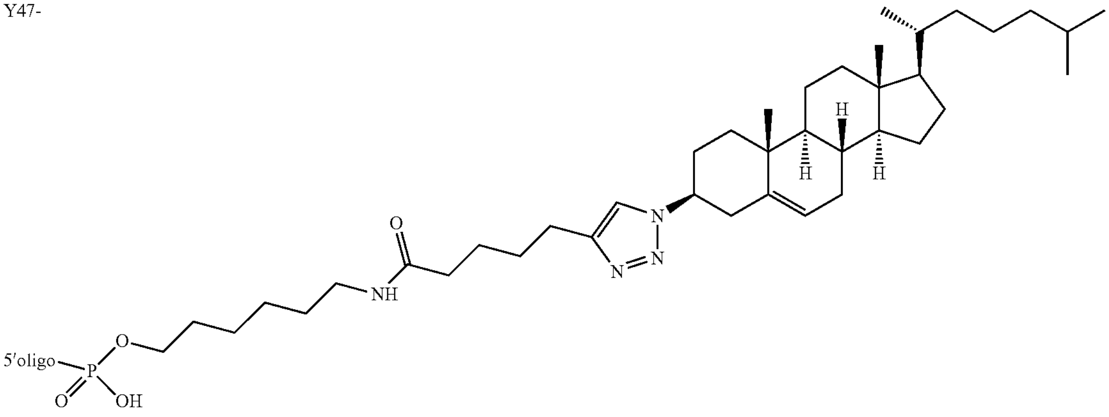

The 5' end structure of the oligonucleotide Y48-cRNA (Malat1) shown in Table 1 is shown below. In the following Formula, the indication "oligo" represents an oligonucleotide.

[Chem 82]

Y48-

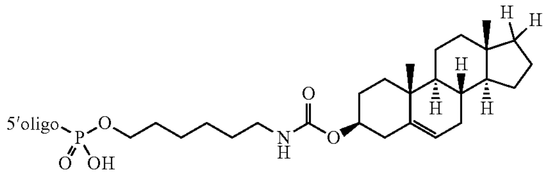

The 5' end structure of the oligonucleotide Y49-cRNA (Malat1) shown in Table 1 is shown below. In the following Formula, the indication "oligo" represents an oligonucleotide.

[Chem 83]

Y49-

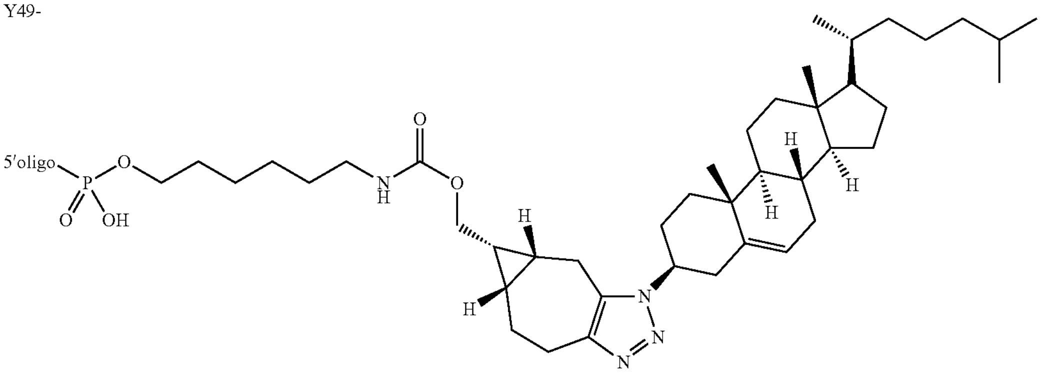

The 5' end structure of the oligonucleotide Y50-cRNA (Malat1) shown in Table 1 is shown below. In the following Formula, the indication "oligo" represents an oligonucleotide.

[Chem 84]

Y50-

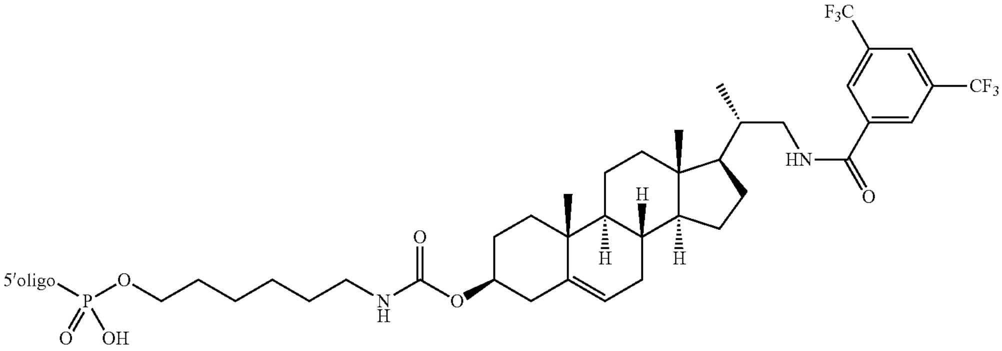

The 5' end structure of the oligonucleotide Y51-cRNA (Malat1) shown in Table 1 is shown below. In the following Formula, the indication "oligo" represents an oligonucleotide.

[Chem 85]

Y51-

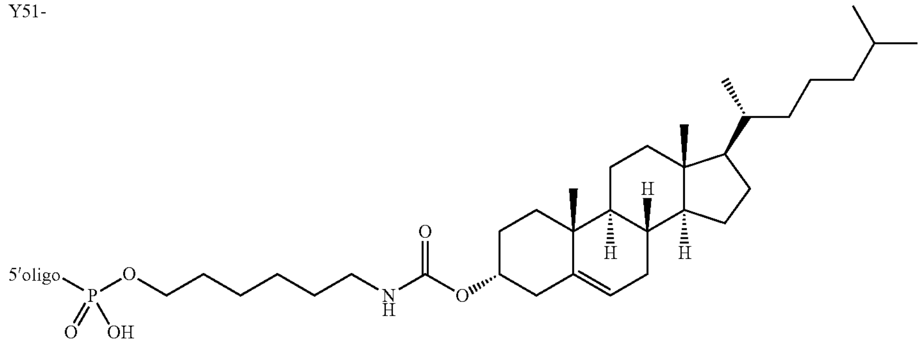

The 5' end structure of the oligonucleotide Y52-cRNA (Malat1) shown in Table 1 is shown below. In the following Formula, the indication "oligo" represents an oligonucleotide.

[Chem 86]

Y52-

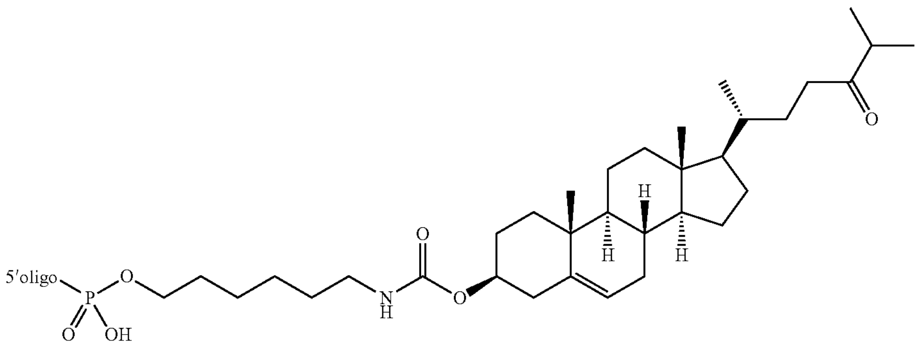

The 5' end structure of the oligonucleotide Y53-cRNA (Malat1) shown in Table 1 is shown below. In the following Formula, the indication "oligo" represents an oligonucleotide.

[Chem 87]

Y53-

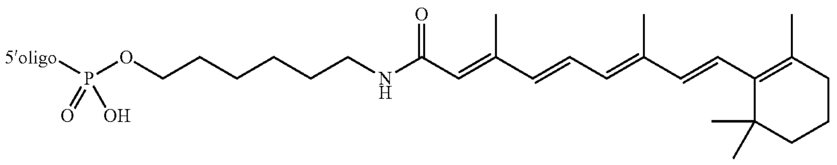

The 5' end structure of the oligonucleotide Y54-cRNA (Malat1) shown in Table 1 is shown below. In the following Formula, the indication "oligo" represents an oligonucleotide.

[Chem 88]

Y54-

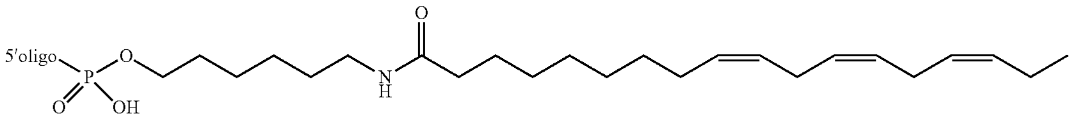

The 5' end structure of the oligonucleotide Y55-cRNA (Malat1) shown in Table 1 is shown below. In the following Formula, the indication "oligo" represents an oligonucleotide.

[Chem 89]

Y55-

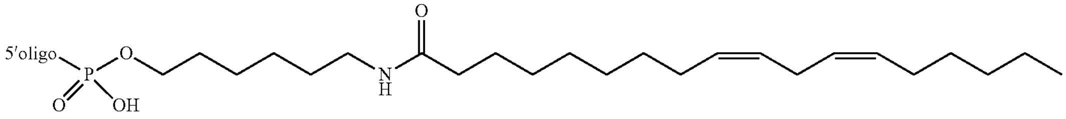

The 5' end structure of the oligonucleotide Y57-cRNA (Malat1) shown in Table 1 is shown below. In the following Formula, the indication "oligo" represents an oligonucleotide.

[Chem 90]

Y57-

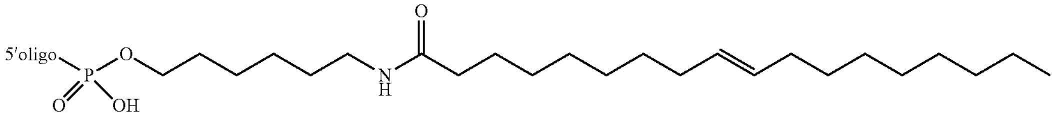

The 5' end structure of the oligonucleotide Chol-cRNA (Malat1) shown in Table 1 is shown below. In the following Formula, the indication "oligo" represents an oligonucleotide.

[Chem 91]

Chol-

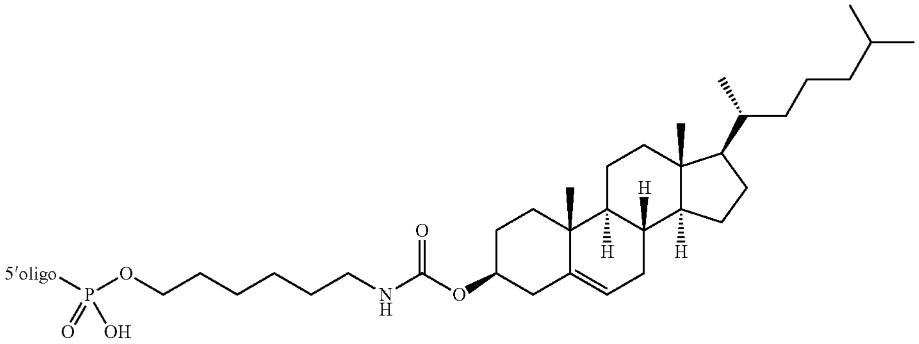

Reference Example 1

Synthesis of IY1

Trimethylsilyl chloride (569 μL) was added to a pyridine solution (5567 μL) of 6-aminohexanoic acid (146 mg) at 0° C. The reaction mixture was stirred at room temperature in a nitrogen atmosphere for 30 min. Cholesteryl chloroformate (500 mg) was added at 0° C., and the reaction mixture was stirred in a nitrogen atmosphere at room temperature for 30 min. The reaction mixture was neutralized by adding a 1 N hydrochloric acid aqueous solution at 0° C. and extracted with ethyl acetate. The organic layer was separated, washed with water, and then with saturated saline solution, dried over magnesium sulfate, and concentrated to dryness. The resulting solid was washed with diisopropyl ether to yield 200 mg of the title compound.

The compounds of Reference Examples 7, 8, 14 and 15 were produced by the same method as in Reference Example 1.

The chemical structural formulas and the NMR data for the compounds of Reference Examples 1, 7, 8, 14, and 15 are shown in the following Table 2.

TABLE 2

| Reference Example | Compound name | Structural formula | NMR data |
|---|---|---|---|
| 1 | IY1 | 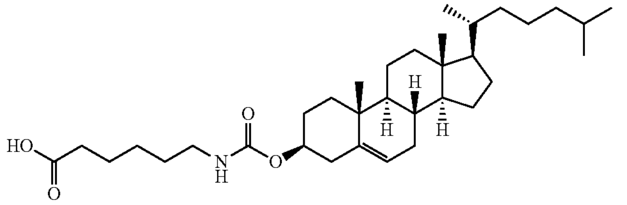 | 1H NMR (400 MHz, $CDCl_3$) δ 0.67 (3H, s), 0.86 (6H, dd, J = 6.6, 2.0 Hz), 0.90-1.58 (31H, m), 1.62-1.71 (2H, m), 1.77-1.91 (3H, m), 1.92-2.05 (2H, m), 2.36 (4H, t, J = 7.5 Hz), 3.07-3.22 (2H, m), 4.39-4.56 (1H, m), 4.63 (1H, brs), 5.34-5.41 (1H, m). |
| 7 | IY7 | 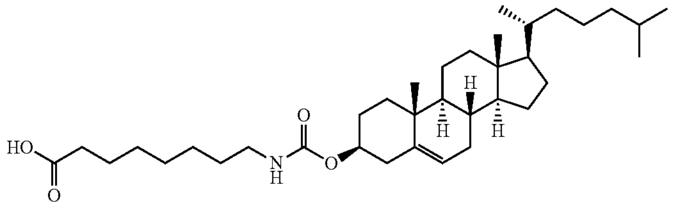 | 1H NMR (300 MHz, $CDCl_3$) δ 0.67 (3H, s), 0.83-0.93 (9H, m), 0.98-1.68 (34H, m), 1.74-2.08 (5H, m), 2.25-2.44 (4H, m), 2.98-3.29 (2H, m), 4.35-4.71 (2H, m), 5.37 (1H, d, J = 5.1 Hz). |
| 8 | IY8 | 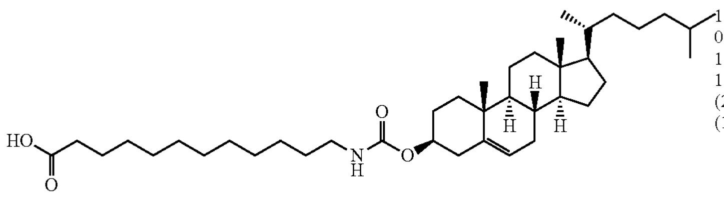 | 1H NMR (300 MHz, $CDCl_3$) δ 0.67 (3H, s), 0.84-0.93 (9H, m), 0.99-1.21 (12H, m), 1.26-1.40 (17H, m), 1.41-1.68 (12H, m), 1.72-2.10 (6H, m), 2.16-2.44 (4H, m), 3.15 (2H, q, J = 6.6 Hz), 4.37-4.68 (2H, m), 5.37 (1H, d, J = 5.1 Hz). |
| 14 | IY14 | 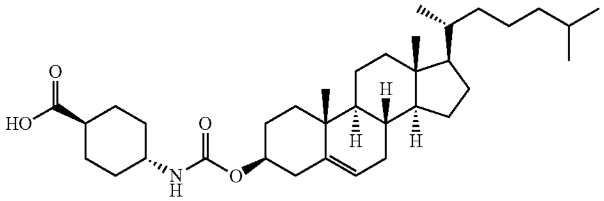 | 1H NMR (300 MHz. DMSO-d6) δ 0.65 (3H, s), 0.80-0.90 (9H, m), 0.96 (16H, s), 1.32 (12H, d, J = 9.0 Hz), 1.82 (9H, d, J = 13.8 Hz), 2.05-2.35 (3H, m), 3.19 (1H, dd, J = 7.5, 4.0 Hz), 4.10-4.43 (1H, m), 5.34 (1H, brs), 7.01 (1H, d, J = 7.6 Hz), 12.04 (1H, brs). |
| 15 | IY15 | 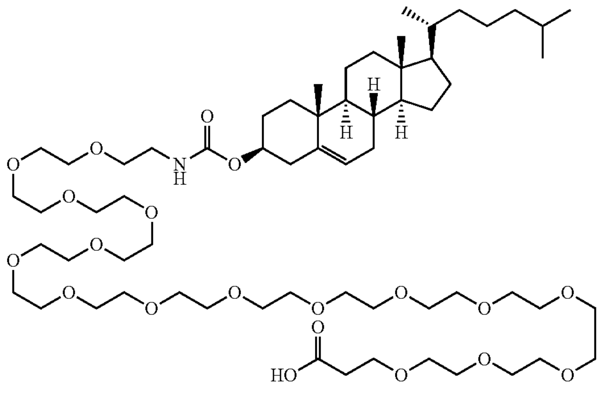 | 1H NMR (300 MHz, $CDCl_3$) δ 0.68 (3H, s), 0.78-1.67 (34H, m), 1.73-2.07 (6H, m), 2.17-2.46 (3H, m), 2.60 (2H, t, J = 6.0 Hz), 3.24-3.49 (3H, m), 3.50-3.72 (59H, m), 3.78 (2H, t, J = 6.0 Hz), 4.37-4.63 (1H, m), 5.22 (1H, t, J = 5.7 Hz), 5.37 (1H, d, J = 5.3 Hz). |

Reference Example 9

Synthesis of IY9

Nitrophenyl carbonochloridate (210 mg) was added at 0° C. into a THF solution (5 mL) of estradiol enanthate (200 mg) and pyridine (535 μL). The reaction mixture was allowed to react at room temperature for 3 hours. The precipitates were removed by celite filtration and the filtrate was washed with diisopropyl ether. The filtrate was concentrated under reduced pressure and the residue was purified by silica gel column chromatography (ethyl acetate/hexane) to yield 80 mg of the title compound.

The compounds of Reference Examples 10, 36, 39, and 40 were produced by the same method as in Reference Example 9.

The chemical structural formulas and the NMR data for the compounds of Reference Examples 9, 10, 36, 39 and 40 are shown in the following Table 3.

TABLE 3
| Reference Example | Compound name | Structural formula | NMR data |
|---|---|---|---|
| 9 | IY9 | 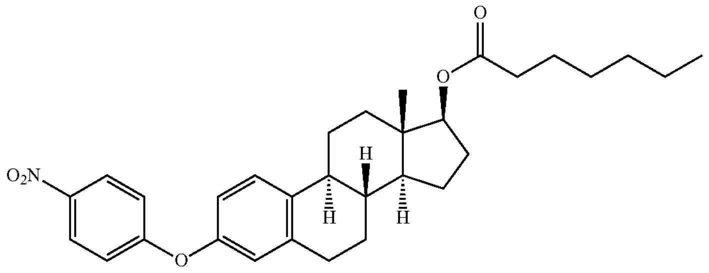 | 1H NMR (300 MHz, $CDCl_3$) δ 0.78-0.98 (6H, m), 1.19-1.99 (18H, m), 2.13-2.44 (5H, m), 2.81-3.01 (2H, m), 4.71 (1H, dd, J = 9.1, 7.6 Hz), 6.95-7.07 (2H, m), 7.33 (1H, d, J = 8.6 Hz), 7.43-7.53 (2H, m), 8.27-8.36 (2H, m). |
| 10 | IY10 | 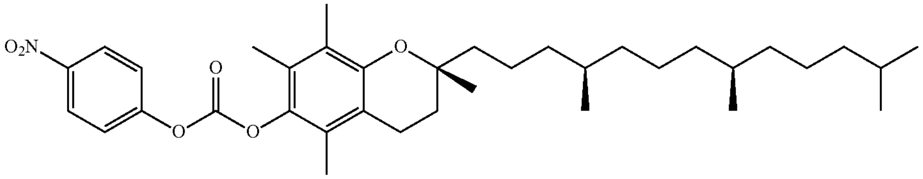 [SMILES: Cc1c(C)c2c(c(C)c1OC(=O)Oc1ccc([N+](=O)[O-])cc1)CC[C@@](C)(CCC[C@H](C)CCC[C@H](C)CCCC(C)C)O2] | 1H NMR (300 MHz, $CDCl_3$) δ 0.68-0.96 (15H, m), 0.98-1.95 (23H, m), 2.04-2.23 (9H, m), 2.62 (2H, t, J = 6.6 Hz), 7.48 (2H, d, J = 8.5 Hz), 8.31 (2H, d, J = 8.9 Hz), |
| 36 | IY36 | 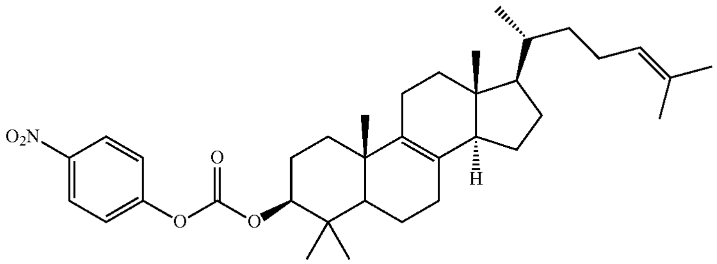 [SMILES: CC(C)=CCC[C@@H](C)[C@H]1CC[C@H]2C3=C(CC[C@]12C)[C@@]1(C)CC[C@H](OC(=O)Oc2ccc([N+](=O)[O-])cc2)C(C)(C)C1CC3] | 1H NMR (300 MHz, $CDCl_3$) δ 0.69 (3H, s), 0.80-1.53 (27H, m), 1.57-2.19 (17H, m), 4.48 (1H, dd, J = 11.5, 4.5 Hz), 5.10 (1H, brs), 7.39 (2H, d, J = 8.7 Hz), 8.28 (2H, d, J = 8.9 Hz). |
| 39 | IY39 | 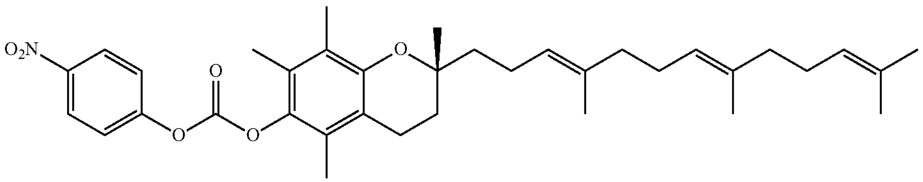 [SMILES: CC(C)=CCC/C(C)=C/CC/C(C)=C/CC[C@]1(C)CCc2c(C)c(OC(=O)Oc3ccc([N+](=O)[O-])cc3)c(C)c(C)c2O1] | 1H NMR (300 MHz, $CDCl_3$) δ 1.27 (3H, s), 1.49-2.25 (35H, m), 2.63 (2H, t, J = 6.7 Hz), 5.10 (3H, brs), 7.48 (2H, d, J = 8.9 Hz), 8.31 (2H, d, J = 8.9 Hz). |

TABLE 3-continued
| Reference Example | Compound name | Structural formula | NMR data |
|---|---|---|---|
| 40 | IY40 | 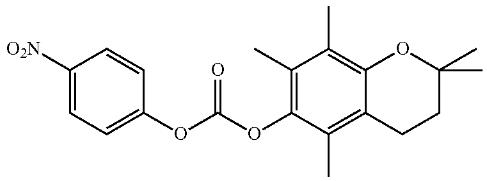 [SMILES: Cc1c(C)c2c(c(C)c1OC(=O)Oc1ccc([N+](=O)[O-])cc1)CCC(C)(C)O2] | 1H NMR (300 MHz, $CDCl_3$) δ 1.31 (6H, s), 1.81 (2H, t, J = 6.9 Hz), 2.12 (6H, s), 2.16 (3H, s), 2.64 (2H, t, J = 6.8 Hz), 7.48 (2H, d, J = 9.2 Hz), 8.31 (2H, d, J = 9.4 Hz). |

Reference Example 11

Synthesis of IY11

A) Synthesis of IY11-1

The title compound was produced in the same manner as in Reference Example 1 using cholesteryl chloroformate (300 mg) and 3-(2-aminoethoxy)propanoic acid (89 mg). This compound was used without purification in the next step.

B) Synthesis of IY11

Bis(pentafluorophenyl) carbonate (528 mg) was added to a tetrahydrofuran solution (6700 μL) of the IY11-1 obtained in step A, and the reaction mixture was stirred at room temperature in a nitrogen atmosphere for 1 hour. The reaction mixture was added to water at room temperature and extracted with ethyl acetate. The extract was washed with water and with a saturated saline solution, and dried with magnesium sulfate. The solvent was distilled off under reduced pressure, then the residue was purified by silica gel column chromatography (ethyl acetate/hexane) to yield 127 mg of the title compound.

IY16-1 of Reference Example 16 and IY17-1 of Reference Example 17 were produced in the same manner as in step A) of Reference Example 11. IY16 of Reference Example 16 and IY17 of Reference Example 17 were produced in the same manner as in step B) of Reference Example 11.

The chemical structural formulas and the NMR data for IY11-1, IY11, IY16-1, IY16, IY17-1, and IY17 are shown in the following Table 4.

TABLE 4
| Reference Example | Compound name | Structural formula | NMR data |
|---|---|---|---|
| 11 | IY11-1 | 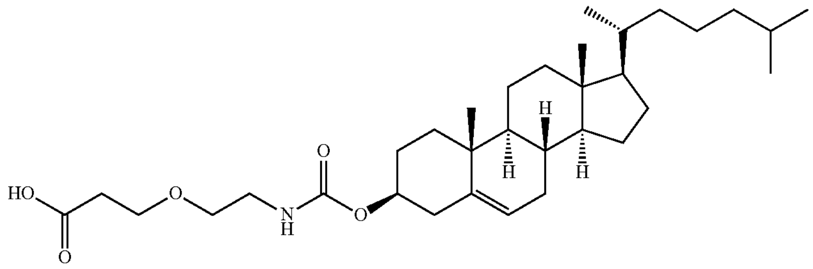 | 1H NMR (300 MHz, $CDCl_3$) δ 0.68 (3H, s), 0.84-0.93 (9H, m), 0.93-1.21 (13H, m), 1.23-1.64 (11H, m), 1.77-2.11 (5H, m), 2.17-2.40 (2H, m), 2.93 (2H, t, J = 6.0 Hz), 3.38 (2H, q, J = 5.1 Hz), 3.52-3.63 (2H, m), 3.85 (2H, t, J = 6.0 Hz), 4.49 (1H, d, J = 4.5 Hz), 5.04 (1H, brs), 5.36 (1H, d, J = 5.3 Hz). |
| 11 | IY11 | 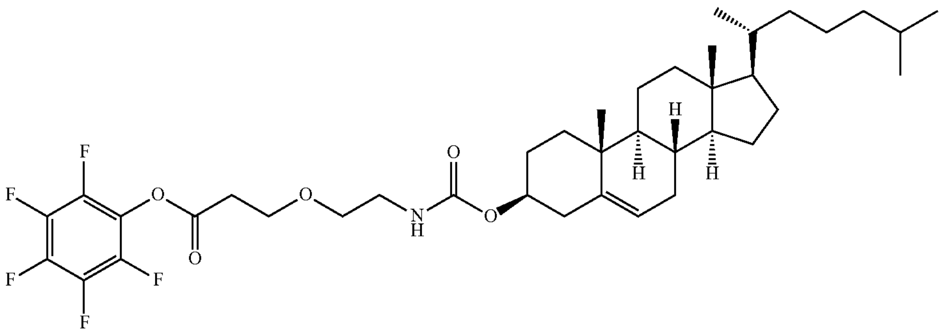 | 1H NMR (300 MHz, $CDCl_3$) δ 0.68 (3H, s), 0.86 (6H, dd, J = 6.7, 1.2 Hz), 0.91 (3H, d, J = 6.6 Hz), 0.98-1.29 (13H, m), 1.30-1.63 (10H, m), 1.76-2.05 (5H, m), 2.17-2.40 (2H, m), 2.93 (2H, t, J = 6.0 Hz), 3.38 (2H, q, J = 5.1 Hz), 3.49-3.65 (2H, m), 3.85 (2H, t, J = 6.0 Hz), 4.49 (1H, d, J = 4.5 Hz), 5.04 (1H, brs), 5.36 (1H, d, J = 5.3 Hz). |
| 16 | IY16-1 | 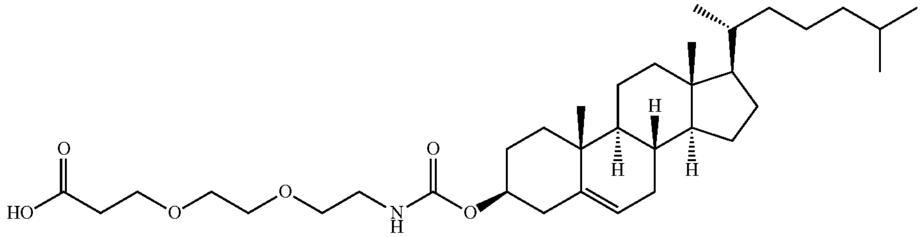 | |

TABLE 4-continued
| Reference Example | Compound name | Structural formula | NMR data |
|---|---|---|---|
| 16 | IY16 | 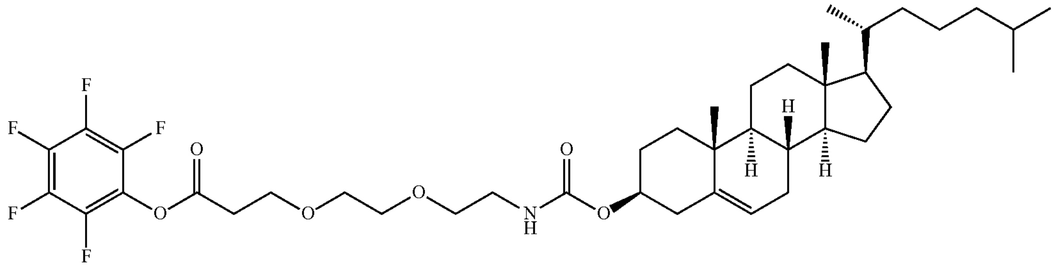 | |
| 17 | IY17-1 | 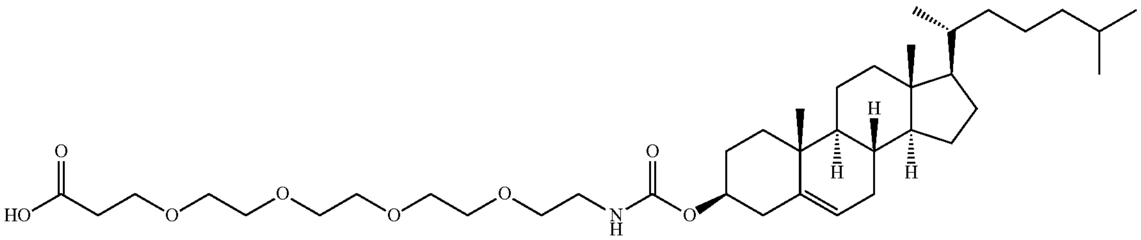 | |
| 17 | IY17 | 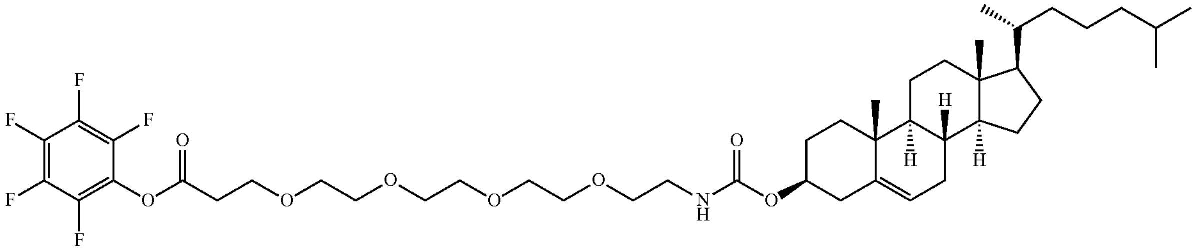 | 1H NMR (300 MHz, $CDCl_3$) δ 0.67 (3H, s), 0.80-1.68 (33H, m), 1.76-2.09 (5H, m), 2.19-2.44 (2H, m), 2.95 (2H, t, J = 6.3 Hz), 3.30-3.41 (2H, m), 3.51-3.57 (2H, m), 3.59-3.70 (12H, m), 3.88 (2H, t, J = 6.2 Hz), 4.49 (1H, t, J = 11.0 Hz), 5.16 (1H, brs), 5.37 (1H, d, J = 5.2 Hz). |

Reference Example 18

Synthesis of IY18

[Chem 92]

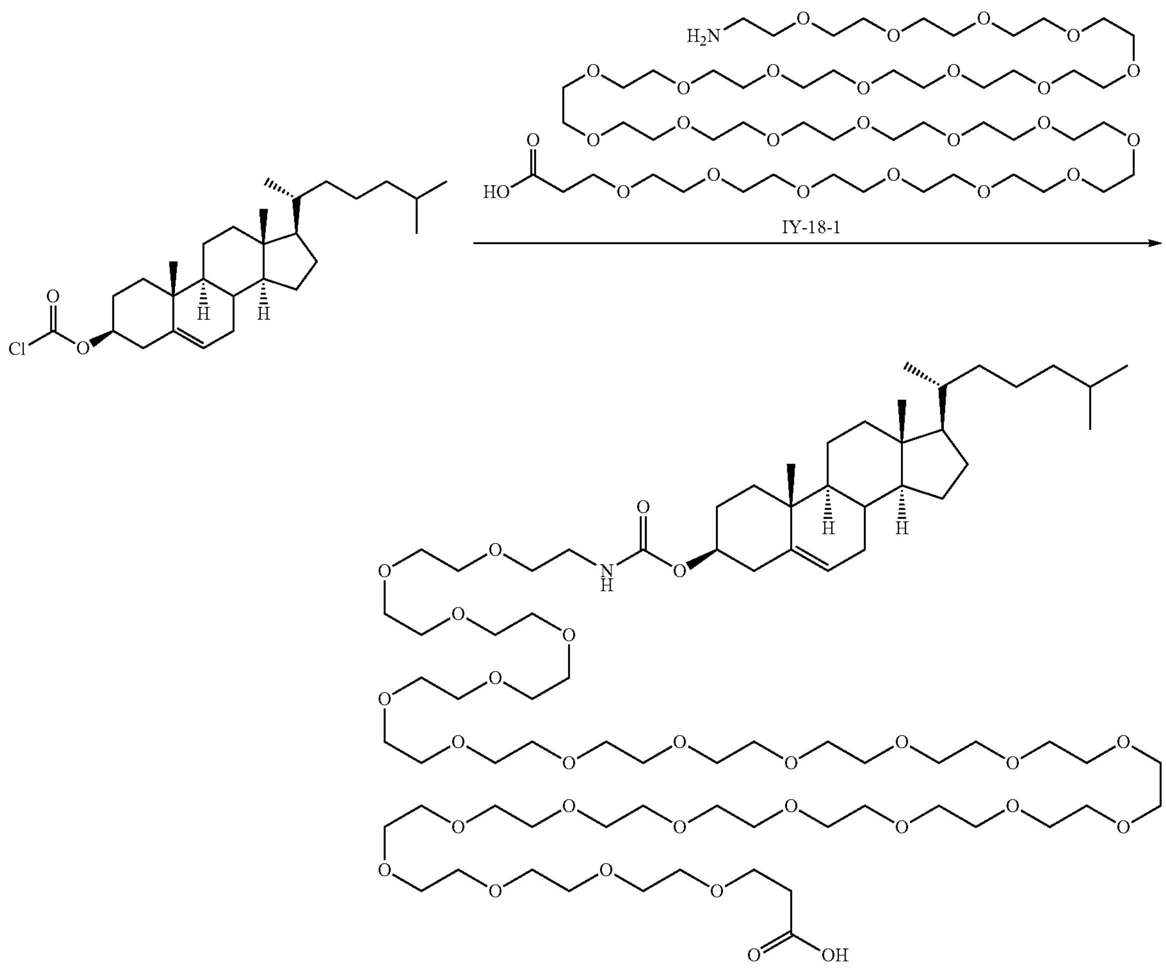

IY-18

A sodium hydroxide aqueous solution (0.1 N, 2.4 mL) of IY18-1 (138 mg) was added to a THF solution (3 mL) of cholesteryl chloroformate (49.1 mg) with cooling on ice, and the mixture was stirred at room temperature for 5 hours. The reaction solution was made acidic with 1 N hydrochloric acid, and the reaction mixture was extracted with THF/ethyl acetate (1:1). The organic layer was dried with magnesium sulfate and concentrated to dryness to yield 151 mg of the title compound.

The NMR results of the obtained compound are as follows.

$^1$H NMR (300 MHz, $CDCl_3$) δ 0.68 (3H, s), 0.80-1.69 (37H, m), 1.73-2.07 (6H, m), 2.18-2.71 (11H, m), 3.27-3.46 (3H, m), 3.47-3.73 (80H, m), 3.78 (2H, t, J=6.1 Hz), 4.39-4.66 (1H, m), 5.24 (1H, brs), 5.37 (1H, d, J=5.4 Hz), 6.98 (1H, s).

Reference Example 19

Synthesis of IY19

A mixture of diosgenin (445 mg), bis(2,5-dioxopyrrolidin-1-yl) carbonate (1650 mg), triethylamine (2.244 mL), and acetonitrile (10 mL) was allowed to react for 3 hours under sonication. The reaction mixture was diluted with a saturated sodium hydrogen carbonate solution, and then extracted with a mixture solvent of ethyl acetate and diethyl ether. The extract was washed with water and a saturated saline solution, and dried with magnesium sulfate. The solvent was distilled off under reduced pressure, and the residue was purified by silica gel column chromatography (ethyl acetate/hexane) to yield 55 mg of the title compound.

The compounds of Reference Examples 20, 21, 22, 24, 25, 28, 29, 32, 33, 34, 35, 43, 44, 48, 51, and 52 were produced in the same manner as in Reference Example 19.

The chemical structural formulas and the NMR data for the compounds of Reference Examples 19, 20, 21, 22, 24, 25, 28, 29, 32, 33, 34, 35, 43, 44, 48, 51, and 52 are shown in the following Table 5.

TABLE 5

| Reference Example | Compound name | Structural formula | NMR data |
|---|---|---|---|
| 19 | IY19 | 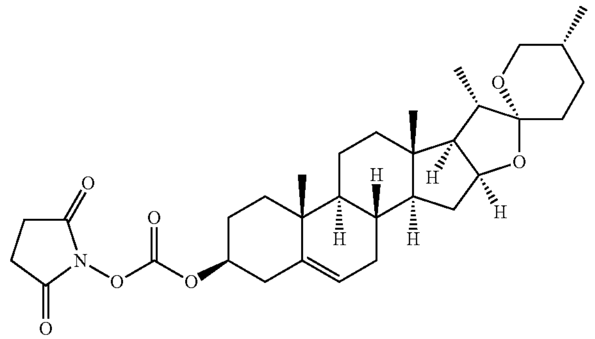 | 1H NMR (300 MHz, $CDCl_3$) δ 0.67-0.85 (6H, m), 0.90-1.21 (11H, m), 1.36-1.54 (4H, m), 1.58-2.03 (12H, m), 2.25-2.60 (2H, m), 2.71-2.94 (4H, m), 3.20-3.57 (2H, m), 3.84-4.01 (1H, m), 4.27-4.49 (1H, m), 4.58 (1H, s), 5.42 (1H, d, J = 5.3 Hz). |
| 20 | IY20 | 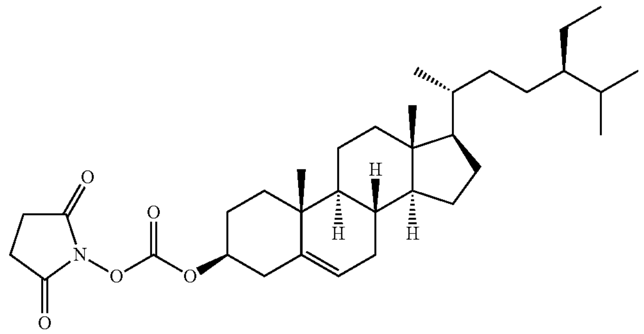 | 1H NMR (300 MHz, $CDCl_3$) δ 0.68 (3H, s), 0.73-1.49 (34H, m), 1.57-2.12 (8H, m), 2.49 (2H, d, J = 7.3 Hz), 2.83 (4H, s), 4.62 (1H, brs), 5.43 (1H, brs). |
| 21 | IY21 | 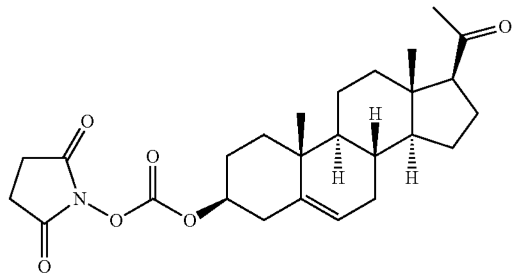 | 1H NMR (300 MHz, $CDCl_3$) δ 0.64 (3H, s), 1.03 (4H, s), 1.08-2.28 (19H, m), 2.41-2.61 (3H, m), 2.84 (4H, s), 4.50-4.69 (1H, m, J = 5.5 Hz), 5.43 (1H, brs). |
| 22 | IY22 | 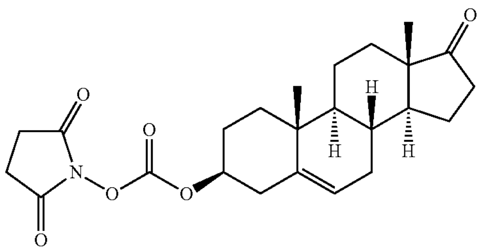 | 1H NMR (300 MHz, $CDCl_3$) δ 0.89 (3H, s), 1.14-2.58 (22H, m), 2.84 (4H, s), 4.60 (1H, d, J = 5.7 Hz), 5.45 (1H, brs). |

TABLE 5-continued
| Reference Example | Compound name | Structural formula | NMR data |
|---|---|---|---|
| 24 | IY24 | 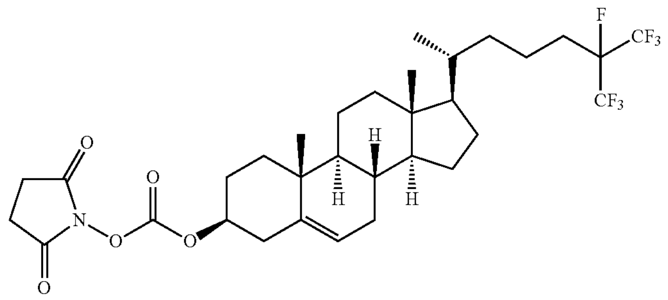 | 1H NMR (300 MHz, CDCl3) δ 0.69 (3H, s), 0.78-2.11 (31H, m), 2.49 (2H, d, J = 8.1 Hz), 2.83 (4H, s), 4.52-4.75 (1H, m), 5.42 (1H, d, J = 5.8 Hz). |
| 25 | IY25 | 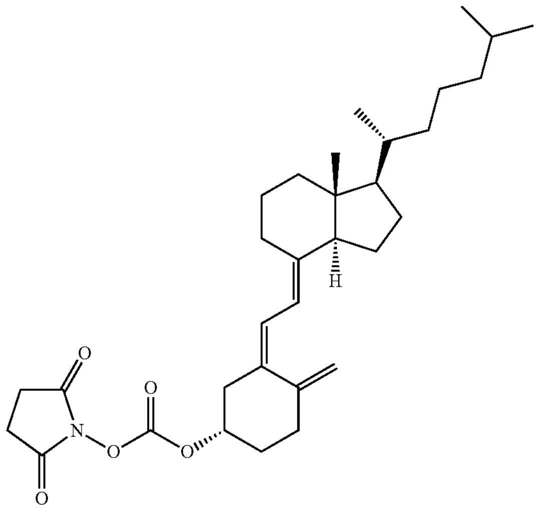 [SMILES: C=C1CC[C@H](OC(=O)ON2C(=O)CCC2=O)C/C1=C/C=C1\CCC[C@]2(C)[C@@H]([C@H](C)CCCC(C)C)CC[C@@H]12] | 1H NMR (300 MHz, $CDCl_3$) δ 0.54 (3H, s), 0.79-0.96 (9H, m), 0.98-1.53 (14H, m), 1.61-2.73 (11H , m), 2.75-2.92 (5H, m), 4.87 (1H, d, J = 2.3 Hz), 4.91-5.03 (1H, m), 5.09 (1H, d, J = 2.3 Hz), 6.02 (1H, d, J = 11.5 Hz), 6.26 (1H, d, J = 11.5 Hz) |
| 28 | IY28 | 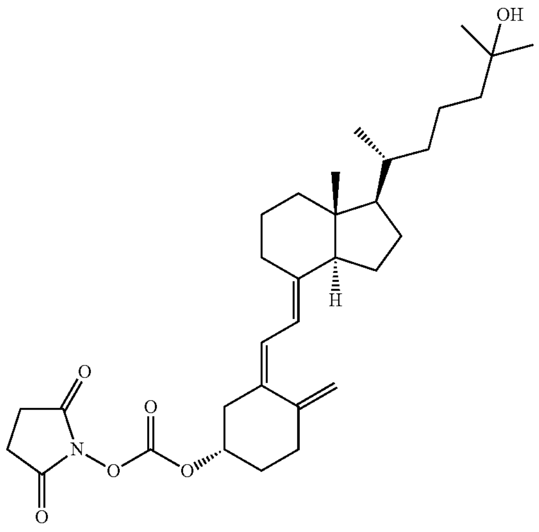 [SMILES: C=C1CC[C@H](OC(=O)ON2C(=O)CCC2=O)C/C1=C/C=C1\CCC[C@]2(C)[C@@H]([C@H](C)CCCC(C)(C)O)CC[C@@H]12] | 1H NMR (300 MHz, $CDCl_3$) δ 0.54 (3H, s), 0.94 (3H, d, J = 6.4 Hz), 1.01-2.04 (25H, m), 2.15-2.59 (3H, m), 2.62-2.73 (1H. m), 2.81 (6H, s), 3.41 (1H, brs), 4.87 (1H, d, J = 2.3 Hz), 4.90-5.04 (1H, m), 5.09 (1H, d, J = 2.1 Hz), 6.02 (1H, d, J = 11.3 Hz), 6.26 (1H, d, J = 11.3 Hz). |

TABLE 5-continued
| Reference Example | Compound name | Structural formula | NMR data |
|---|---|---|---|
| 29 | IY29 | 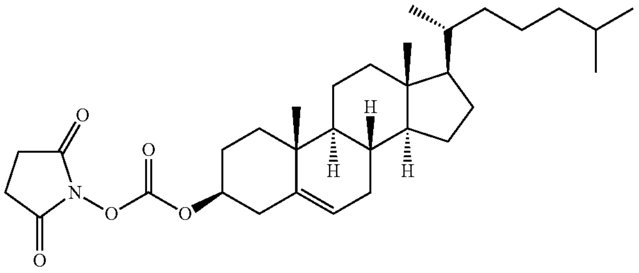 | 1H NMR (300 MHz, CHLOROFORM-d) δ ppm 0.68 (s, 3 H) 0.79-1.51 (m, 31 H) 1.58-2.12 (m, 7 H) 2.48 (d, J = 8.29 Hz, 2 H) 2.84 (s, 4 H) 4.51-4.68 (m, 1 H) 5.42 (d, J = 5.09 Hz, 1 H) |
| 32 | IY32 | 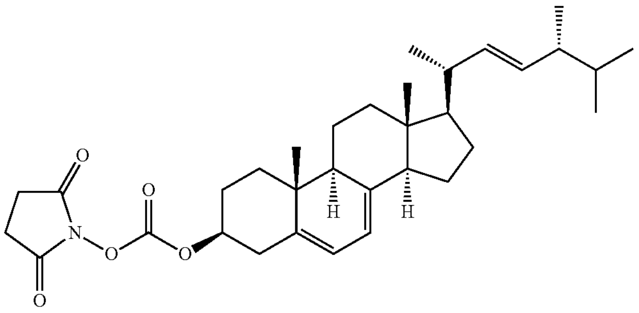 | 1H NMR (300 MHz, $CDCl_3$) δ 0.63 (3H, s), 0.83 (6H, dd, J = 6.7, 4.6 Hz), 0.88-0.99 (6H, m), 1.04 (3H, d, J = 6.6 Hz), 1.16-1.50 (6H, m), 1.58-2.21 (12H, m), 2.44-2.59 (1H, m), 2.61-2.73 (1H, m), 2.84 (4H, s), 4.60-4.83 (1H, m), 5.07-5.31 (2H, m), 5.34-5.46 (1H, m), 5.61 (1H, dd, J = 5.7, 2.3 Hz). |
| 33 | IY33 | 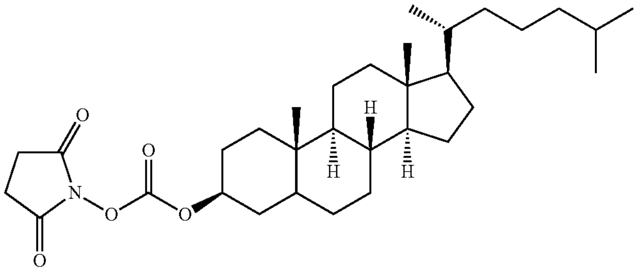 | 1H NMR (300 MHz, $CDCl_3$) δ 0.65 (3H, s), 0.78-0.94 (12H, m), 0.96-1.51 (22H, m), 1.60-2.14 (9H, m), 2.83 (4H, s), 4.52-4.81 (1H, m). |
| 34 | IY34 | 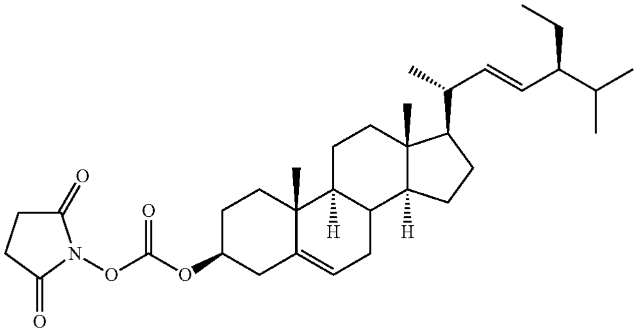 | 1H NMR (300 MHz, $CDCl_3$) δ 0.70 (3H, s), 0.75-0.89 (9H, m), 0.92-2.12 (29H, m), 2.48 (2H, d, J = 7.7 Hz), 2.83 (3H, s), 4.51-4.69 (1H, m), 4.95-5.08 (1H, m), 5.09-5.22 (1H, m, J = 8.5 Hz), 5.09-5.22 (1H, m), 5.42 (1H, d, J = 5.1 Hz). |
| 35 | IY35 | 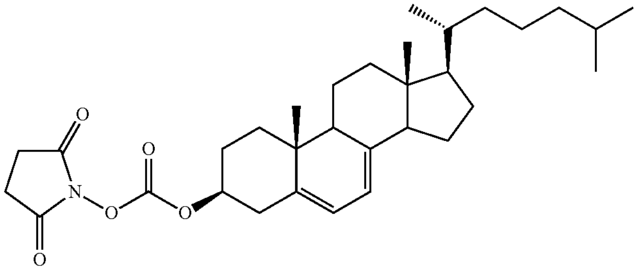 [SMILES: CC(C)CCC[C@@H](C)[C@H]1CCC2C3=CC=C4C[C@@H](OC(=O)ON5C(=O)CCC5=O)CC[C@]4(C)C3CC[C@@]21C] | 1H NMR (300 MHz, $CDCl_3$) δ 0.62 (3H, s), 0.76-1.52 (25H, m), 1.58-2.18 (10H, m), 2.42-2.74 (2H, m), 2.84 (4H, s), 4.58-4.80 (1H, m), 5.40 (1H, brs), 5.61 (1H, brs). |

TABLE 5-continued
| Reference Example | Compound name | Structural formula | NMR data |
|---|---|---|---|
| 43 | IY43 | 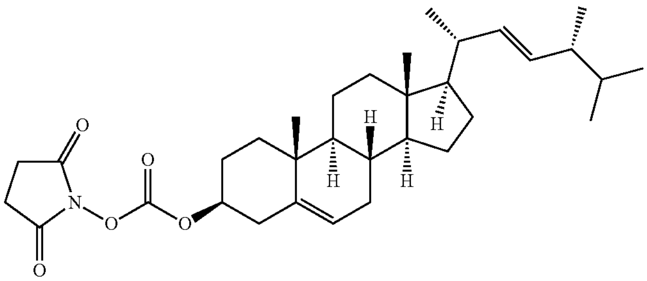 | 1H NMR (300 MHz, $CDCl_3$) δ 0.69 (3H, s), 0.76-2.13 (36H, m), 2.48 (2H, d, J = 7.9 Hz), 2.83 (4H, s), 4.41-4.73 (1H, m), 5.03-5.31 (2H, m), 5.41 (1H, d, J = 4.9 Hz). |
| 44 | IY44 | 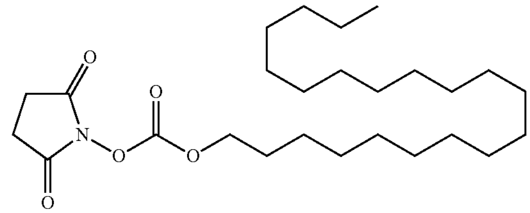 [SMILES: CCCCCCCCCCCCCCCCCCCCCOC(=O)ON1C(=O)CCC1=O] | 1H NMR (300 MHz, CDCl3) δ 0.88 (3H, t, J = 5.7 Hz), 1.18-1.45 (36H, m), 1.75 (2H, quin, J = 5.7 Hz), 2.84 (4H, s), 4.32 (2H, t, J = 6.8 Hz). |
| 48 | IY48 | 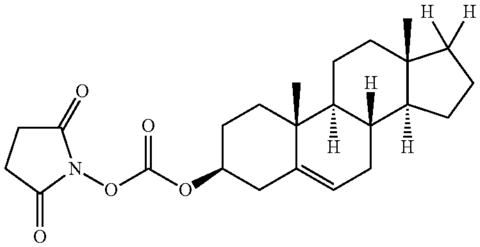 | 1H NMR (300 MHz, CDCl3) δ 0.72 (3H, s), 0.82-1.06 (5H, m), 1.07-1.28 (4H, m), 1.31-1.83 (10H, m), 1.88-2.11 (3H, m), 2.49 (2H, d, J = 8.3 Hz), 2.83 (4H, s), 4.50-4.74 (1H, m), 5.42 (1H, d, J = 4.7 Hz). |
| 51 | IY51 | 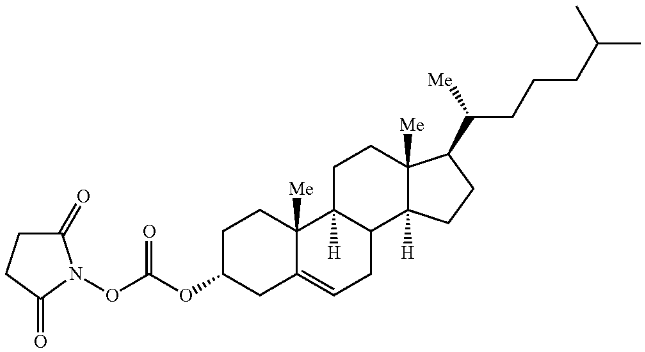 | 1H NMR (300 MHz, CDCl3) δ 0.68 (3H, s), 0.78-2.13 (38H, m), 2.29-2.46 (1H, m), 2.49-2.65 (1H, m), 2.82 (4H, s), 5.01 (1H, brs), 5.38 (1H, brs). |
| 52 | IY52 | 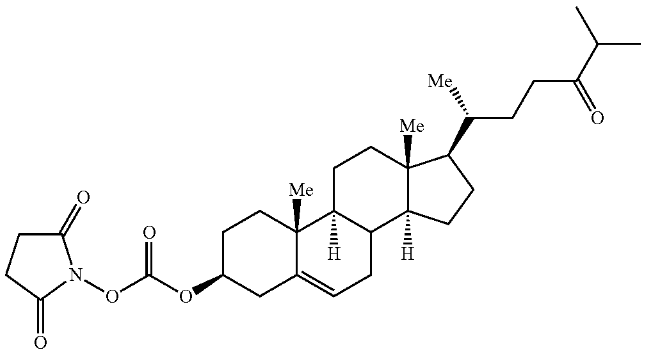 | 1H NMR (300 MHz, CDCl3) δ 0.68 (3H, s), 0.92 (3H, d, J = 6.4 Hz), 1.03 (3H, s), 1.09 (6H, d, J = 7.0 Hz), 1.11-2.71 (26H, m), 2.84 (4H, s), 4.65 (1H, brs), 5.43 (1H, brs). |

Reference Example 23

Synthesis of IY-23

[Chem 93]

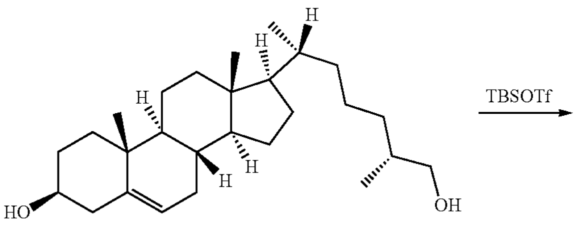

IY23-1

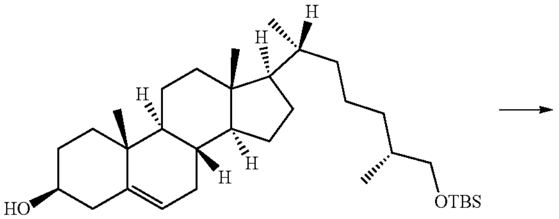

IY23-2

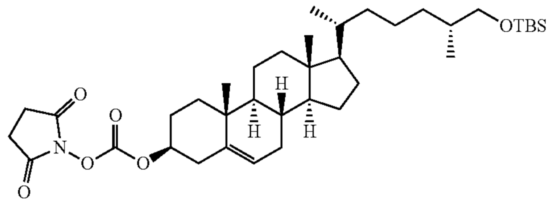

IY23

A) Synthesis of IY23-2

Imidazole (152 mg) and DMAP (91 mg) were added to a dichloromethane solution (10 mL) of IY23-1 (300 mg) at room temperature and the mixture was stirred for 15 min. Thereto tert-butyldimethylsilyl trifluoromethanesulfonate (0.34 mL) was added and the mixture was stirred at room temperature for 16 hours. Water was added to the reaction mixture, extraction was performed with ethyl acetate. The organic layers were combined, washed with water and with a saturated saline solution, and then dried over anhydrous sodium sulfate. The solvent was distilled off under reduced pressure and the residue was purified by silica gel column chromatography (ethyl acetate/hexane) to yield 150 mg of the title compound.

The NMR results of the obtained compound are as follows.

$^1$H NMR (400 MHz, $CDCl_3$) δ −0.01 (6H, s), 0.67 (3H, s), 0.66-0.96 (15H, m), 0.91-1.14 (9H, m), 1.11-1.40 (8H, m), 1.42 (2H, dd, J=8.0, 4.6 Hz), 1.44-1.53 (6H, m), 1.77-1.89 (3H, m), 1.91-2.05 (2H, m), 2.17-2.33 (2H, m), 3.34 (1H, dd, J=9.7, 6.8 Hz), 3.42 (1H, dd, J=9.6, 6.0 Hz), 3.47-3.57 (1H, m), 5.34 (1H, d, J=4.8 Hz).

B) Synthesis of IY23

The title compound was obtained in the same manner as in Reference Example 19 using the IY23-1 obtained in Step A.

The NMR results of the obtained compound are as follows.

$^1$H NMR (300 MHz, $CDCl_3$) δ 0.04 (s, 6H) 0.68 (s, 3H) 0.77-1.63 (m, 38H) 1.67-2.18 (m, 6H) 2.48 (d, J=7.54 Hz, 2H) 2.83 (s, 4H) 3.28-3.51 (m, 2H) 4.51-4.70 (m, 1H) 5.42 (d, J=4.14 Hz, 1H)

Reference Example 27

Synthesis of IY27

[Chem 94]

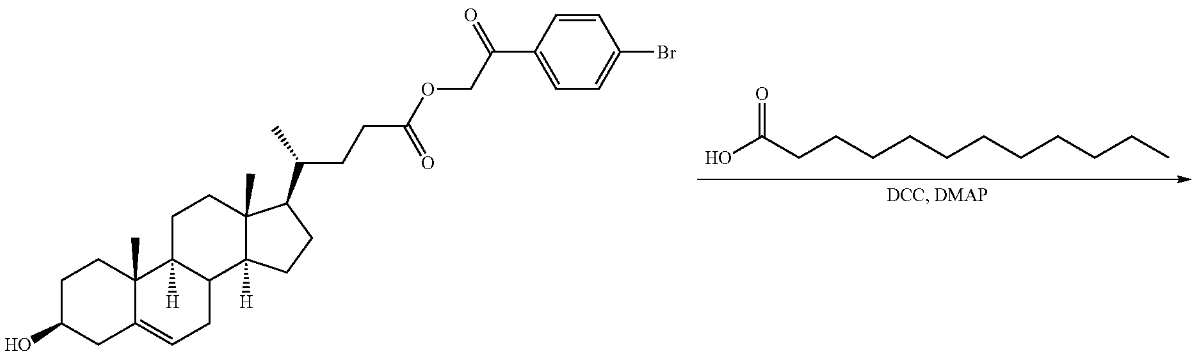

IY27-1

-continued

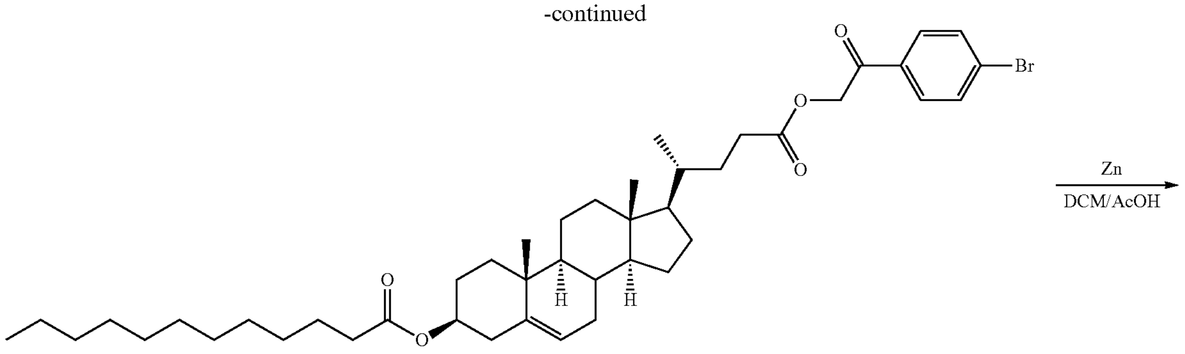

IY27-2

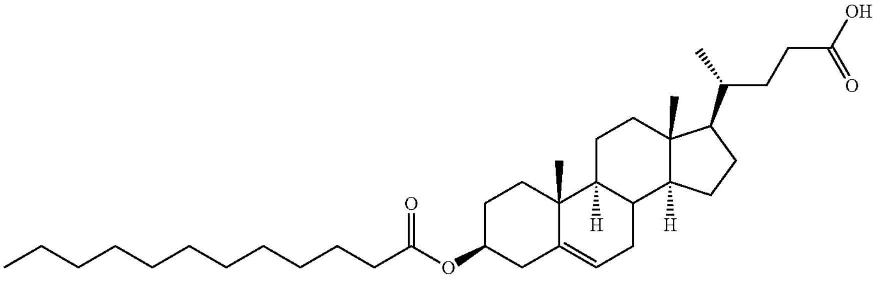

IY27

A) Synthesis of IY27-2

Dicyclohexylcarbodiimide (226 mg), IY27-1 (250 mg), and DMAP (26.7 mg) were added to a dichloromethane solution (15 mL) of lauric acid (148 mg) and the mixture was stirred at room temperature for 16 hours. The reaction solution was diluted with dichloromethane (50 mL) and the organic layer was washed with water and with a saturated saline solution, and then dried with anhydrous sodium sulfate. The solvent was distilled off under reduced pressure, and the residue was purified by silica gel column chromatography (ethyl acetate/hexane) to yield 230 mg of the title compound.

The NMR results of the obtained compound are as follows.

$^1$H NMR (400 MHz, $CDCl_3$) δ 0.68 (3H, s), 0.87 (3H, t, J=5.5 Hz), 0.95 (3H, d, J=6.1 Hz), 1.01 (3H, s), 1.05-1.18 (3H, m), 1.25 (16H, s), 1.36-1.65 (14H, m), 1.80-1.89 (4H, m), 1.91-2.04 (2H, m), 2.21-2.33 (4H, m), 2.34-2.45 (1H, m), 2.46-2.59 (1H, m), 4.55-4.65 (1H, m), 5.27 (2H, s), 5.36 (1H, d, J=2.8 Hz), 7.62 (2H, d, J=8.4 Hz), 7.77 (2H, d, J=8.5 Hz).

B) Synthesis of IY27

Acetic acid (10 mL) and zinc powder (113 mg) were added to a dichloromethane solution (10 mL) of the IY27-2 (180 mg) obtained in step A and the mixture was stirred at room temperature for 16 hours. The reaction mixture was filtered with celite and the filtrate was concentrated under reduced pressure. The concentrate was purified by silica gel column chromatography (ethyl acetate/hexane) to yield 100 mg of the title compound.

The NMR results of the obtained compound are as follows.

$^1$H NMR (400 MHz, $CDCl_3$) δ 0.67 (3H, s), 0.86 (3H, d, J=6.9 Hz), 0.93 (3H, d, J=6.3 Hz), 1.01 (3H, s), 1.06-1.19 (3H, m), 1.24 (14H, s), 1.36-1.65 (14H, m), 1.80-1.88 (5H, m), 1.91-2.02 (2H, m), 2.27 (7H, dt, J=15.1, 7.3 Hz), 4.53-4.67 (1H, m), 5.36 (1H, d, J=5.8 Hz).

Reference Example 37

Synthesis of IY37

[Chem 95]

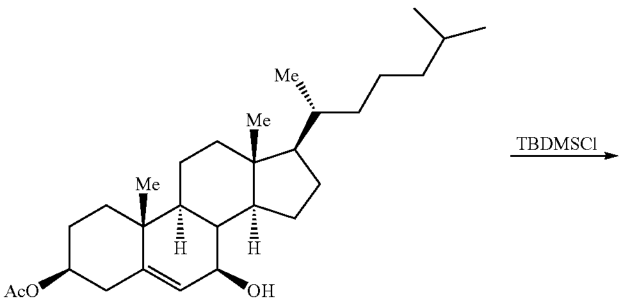

IY37-1

-continued

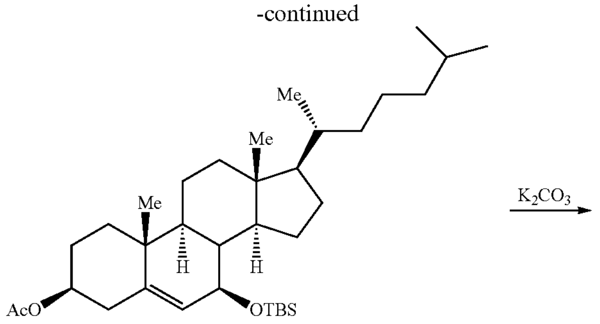

IY37-2

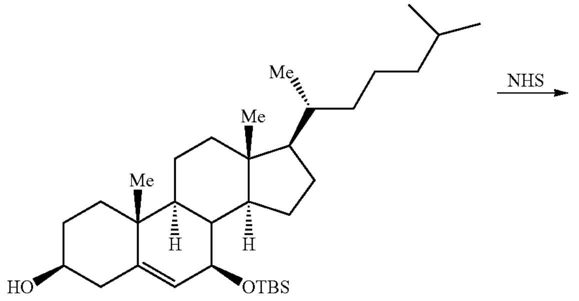

IY37-3

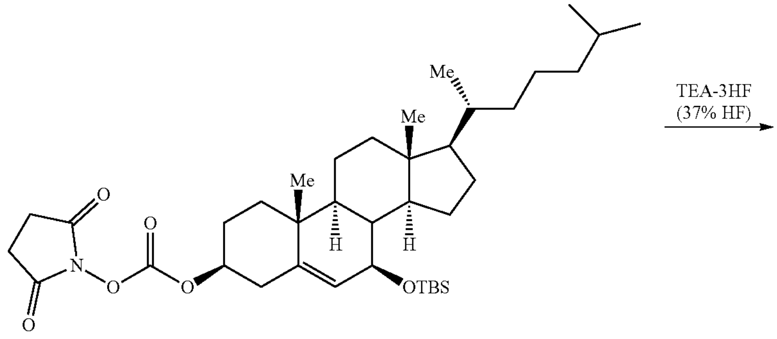

IY37-4

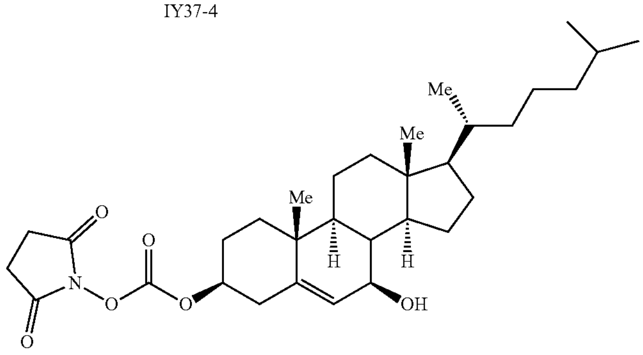

IY37

A) Synthesis of IY37-2

Imidazole (460 mg) and DMAP (275 mg) were added to a DMF solution (10 mL) of IY37-1 (1.0 g) at room temperature and the mixture was stirred for 15 min. Thereto tert-butyldimethylsilyl trifluoromethanesulfonate (1.03 mL) was added and the mixture was stirred at room temperature for 16 hours. Water was added to the reaction mixture and extraction was performed with ethyl acetate. The organic layers were combined, washed with water and a saturated saline solution, and dried with anhydrous sodium sulfate. The solvent was distilled off under reduced pressure and the residue was purified by silica gel column chromatography (ethyl acetate/hexane) to yield 1 g of the title compound.

The NMR results of the obtained compound are as follows.

$^1$H NMR (400 MHz, $CDCl_3$) δ 0.04 (6H, d, J=4.6 Hz), δ 0.66 (3H, s), 0.81-0.93 (17H, m), 0.95-1.17 (12H, m), 1.22-1.39 (6H, m), 1.39-1.54 (4H, m), 1.71-1.91 (5H, m), 1.94-2.06 (4H, m), 2.31 (2H, q, J=7.5 Hz), 3.93 (1H, d, J=7.9 Hz), 4.54-4.66 (1H, m), 5.29 (1H, s).

B) Synthesis of IY37-3

An sodium hydroxide aqueous solution (10%, 2.86 mL) was added to an ethanol (4 mL) and dichloromethane (2 mL) solution of the IY37-2 (1 g) obtained in step A, and the mixture was stirred at room temperature for 3 hours. The solvent was distilled off under reduced pressure, and ethyl acetate was added to the residue, which was then washed with water and a saturated saline solution, and dried with anhydrous sodium sulfate. The solvent was distilled off under reduced pressure to yield 800 mg of the title compound.

The NMR results of the obtained compound are as follows.

$^1$H NMR (400 MHz, $CDCl_3$) δ −0.04-0.09 (6H, m), 0.66 (3H, s), 0.82-0.93 (18H, m), 0.94-1.16 (12H, m), 1.24 (1H, d, J=7.3 Hz), 1.28-1.41 (4H, m), 1.52 (6H, d, J=32.7 Hz), 1.73-1.86 (4H, m), 1.95-2.05 (1H, m), 2.24 (2H, d, J=10.9 Hz), 3.47-3.58 (1H, m), 3.93 (1H, d, J=7.6 Hz), 5.26 (1H, s).

C) Synthesis of IY37-4

Triethylamine (3.26 mL) and bis(2,5-dioxopyrrolidin-1-yl) carbonate (2.38 g) were added to an acetonitrile (4 mL) and dichloromethane (4 mL) solution of the IY37-3 (800 mg) obtained in step B, and the mixture was stirred at 45° C. for 16 hours. The reaction mixture was filtered with celite and a 5% citric acid solution was added to the filtrate and extraction was performed with ethyl acetate. The organic layer was washed with water and a saturated saline solution, and dried with anhydrous sodium sulfate. The residue was purified by silica gel column chromatography (ethyl acetate/hexane) to yield 800 mg of the title compound.

The NMR results of the obtained compound are as follows.

$^1$H NMR (400 MHz, $CDCl_3$) δ 0.05 (6H, d, J=4.6 Hz), 0.66 (3H, s), 0.84-0.92 (17H, m), 0.95-1.16 (12H, m), 1.21-1.37 (6H, m), 1.40-1.55 (3H, m), 1.70-1.82 (3H, m), 1.89 (1H, d, J=13.8 Hz), 1.95-2.06 (3H, m), 2.47 (2H, d, J=7.8 Hz), 2.82 (4H, s), 3.92 (1H, d, J=7.5 Hz), 4.53-4.67 (1H, m), 5.31 (1H, d, J=15.7 Hz).

D) Synthesis of IY37

Triethylamine trihydrofluoride (2.64 mL) was added at 0° C. to a THF (8 mL) solution of the IY37-4 (800 mg) obtained in step C, and the mixture was stirred at room temperature for 16 hours. Water was added to the reaction mixture, and extraction was performed with ethyl acetate. The organic layers were combined, washed with water and a saturated saline solution, and dried with anhydrous sodium sulfate. The residue was purified by silica gel column chromatography (ethyl acetate/hexane) to yield 110 mg of the title compound.

The NMR results of the obtained compound are as follows.

$^1$H NMR (400 MHz, $CDCl_3$) δ 0.68 (3H, s), 0.86 (6H, d, J=5.0 Hz), 0.91 (3H, d, J=6.2 Hz), 0.98-1.17 (11H, m), 1.22-1.43 (8H, m), 1.41-1.53 (3H, m), 1.70-1.83 (2H, m), 1.84-1.96 (2H, m), 2.04 (2H, s), 2.51 (2H, t, J=9.1 Hz), 2.83 (4H, s), 3.85 (1H, s), 4.55-4.69 (1H, m), 5.35 (1H, s).

Reference Example 38

Synthesis of IY38

[Chem 96]

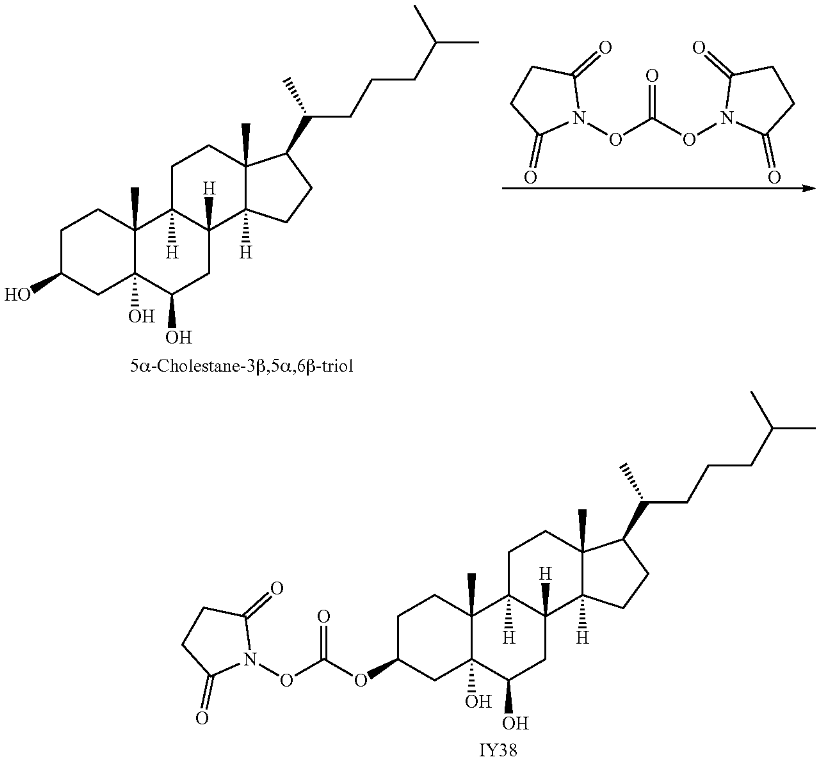

5α-Cholestane-3β,5α,6β-triol

IY38

The title compound was synthesized using 5α-cholestan-3β,5α,6β-triol in the same manner as step C in Reference Example 37.

The NMR results of the obtained compound are as follows.

$^1$H NMR (400 MHz, DMSO-d6) δ 0.63 (3H, s), 0.86 (8H, dd, J=16.0, 5.6 Hz), 0.94-1.38 (21H, m), 1.44-1.69 (6H, m), 1.71-1.81 (1H, m), 1.82-1.97 (2H, m), 2.15 (1H, t, J=12.0 Hz), 2.80 (4H, s), 3.38 (1H, s), 4.13 (1H, s), 4.64 (1H, d, J=4.0 Hz), 5.03-5.14 (1H, m).

Reference Example 41

Synthesis of IY41

[Chem 97]

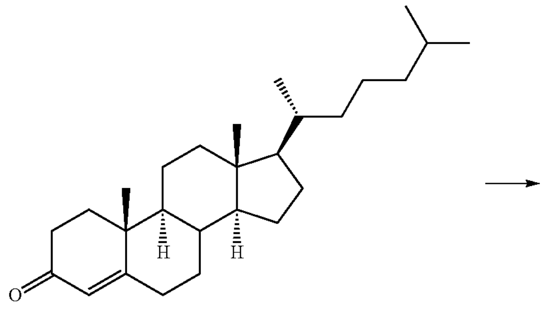

IY41-1

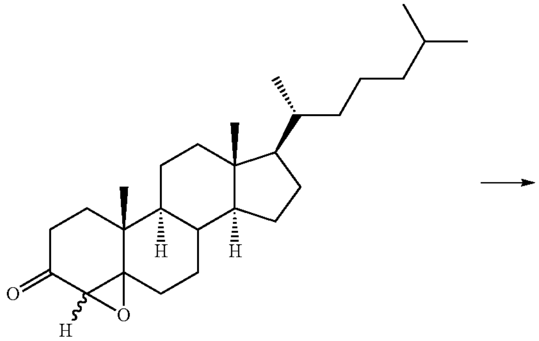

IY41-2

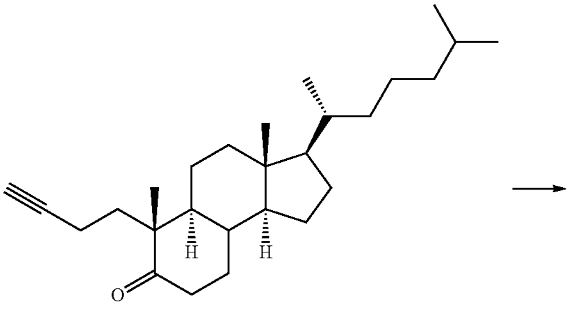

IY41-3

-continued

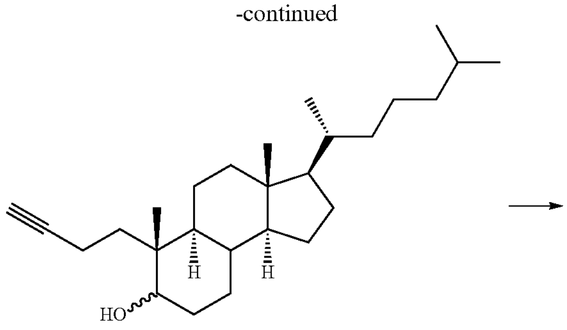

IY41-4

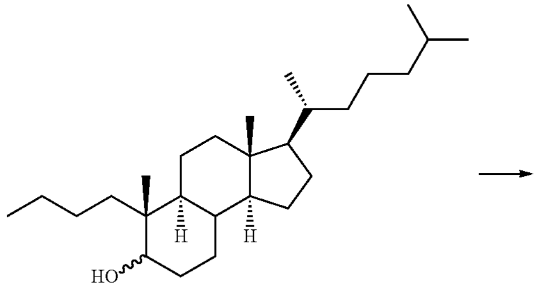

IY41-5

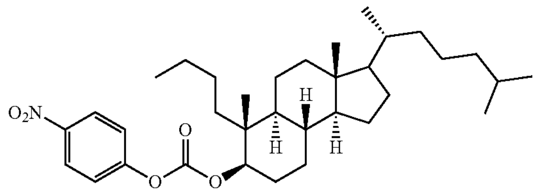

IY41

A) Synthesis of IY41-2

An 8 N sodium hydroxide aqueous solution (2.92 mL) and hydrogen peroxide solution (14.3 mL) were added to a mixed solution of a methanol (3.12 mL) solution—hexane (6.24 mL) of IY41-1 (1.8 g). The reaction mixture was stirred at room temperature overnight. Hydrogen peroxide solution (1.43 mL) was added thereto. Urea-hydrogen peroxide (1.32 g) was added and the mixture was stirred for 1 hour. The reaction mixture was neutralized with a 6 N hydrochloric acid aqueous solution, a sodium thiosulfate aqueous solution was added, and extraction was performed with ethyl acetate. The organic layer was separated and washed with a 1 N hydrochloric acid aqueous solution, a saturated sodium hydrogencarbonate aqueous solution, and next with a saturated saline solution, and then dried with magnesium sulfate, and the solvent was distilled off. The residue was purified by silica gel column chromatography (ethyl acetate/hexane) to yield 700 mg of the title compound as a mixture of stereoisomers (4α,5α-epoxy, and 4β,5β-epoxy).

The NMR results of the obtained compound are as follows.

$^1$H NMR (300 MHz, $CDCl_3$) δ 0.64-0.73 (3H, m), 0.80-0.93 (9H, m), 0.94-2.47 (31H, m), 2.98 (1H, s, 4-H beta), 3.03 (1H, 2, 4-H alpha).

B) Synthesis of IY41-3

The reaction mixture prepared by adding p-toluenesulfonyl hydrazide (342 mg) in small lots to a mixed solution of the IY41-2 (700 mg) obtained in step A in acetic acid (10 mL) and THF (10 mL) was stirred at room temperature for 4 hours. A saturated saline solution (30 mL) was added to the reaction mixture and the organic layer was separated. The aqueous layer was extracted with ethyl acetate, and washing was performed with a saturated sodium hydrogencarbonate solution, drying was performed with sodium sulfate, and then the solvent was distilled off. The residue was purified by silica gel column chromatography (ethyl acetate/hexane) to yield 560 mg of the title compound.

The NMR results of the obtained compound are as follows.

$^1$H NMR (300 MHz, $CDCl_3$) δ 0.73 (3H, s), 0.82-0.95 (9H, m), 0.96-1.08 (3H, m), 1.09 (3H, s), 1.10-2.39 (25H, m), 2.44-2.62 (1H, m).

C) Synthesis of IY41-4

Sodium borohydride (110 mg) was added at room temperature to a methanol solution (10 mL) of the IY41-3 (560 mg) obtained in step B. The reaction mixture was stirred at room temperature for 30 min and then diluted with ethyl acetate. The organic layer was separated, washed with water and a saturated saline solution, and dried with sodium sulfate, and then the solvent was distilled off. The residue was purified by silica gel column chromatography (ethyl acetate/hexane) to yield 560 mg of the title compound as a mixture of stereoisomers (5a and 5β-hydroxy compounds).

The NMR results of the obtained compound are as follows.

$^1$H NMR (300 MHz, $CDCl_3$) δ 0.65 (9H, d, J=3.4 Hz), 0.74-2.36 (35H, m), 3.43-3.56 (1H, m, 5-H alpha), (1H, d, J=2.4 Hz, 5-H alpha).

D) Synthesis of IY41-5

Palladium/carbon (7.4 mg) was added to an ethanol solution (7 mL) of the IY41-4 (540 mg) obtained in step C, and the mixture was stirred overnight in a hydrogen atmosphere. The reaction mixture was filtrated with an amino-silica pad, and the solvent was distilled off to yield 540 mg of the title compound as a mixture of stereoisomers (5α and 5β-hydroxy compounds).

The NMR results of the obtained compound are as follows.

$^1$H NMR (300 MHz, $CDCl_3$) δ 0.61-0.69 (3H, m), 0.80 (3H, s), 0.81-1.91 (42H, m), 1.92-2.03 (1H, m), 3.43-3.55 (1H, m, 5-H alpha), 3.63 (1H, brs, 5-H beta).

E) Synthesis of IY41

The title compound was prepared as a single isomer in the same manner as in Reference Example 9 using the IY41-5 obtained in step D. The α-hydroxy compound of IY41-5, which was unreacted under the present reaction conditions was removed in the purification process.

The NMR results of the obtained compound are as follows.

$^1$H NMR (300 MHz, $CDCl_3$) δ 0.66 (4H, s), 0.73-2.07 (47H, m), 4.72 (1H, dd, J=11.2, 4.2 Hz), 7.36 (2H, d, J=8.9 Hz), 8.28 (2H, d, J=8.3 Hz).

Reference Example 42

Synthesis of IY42

[Chem 98]

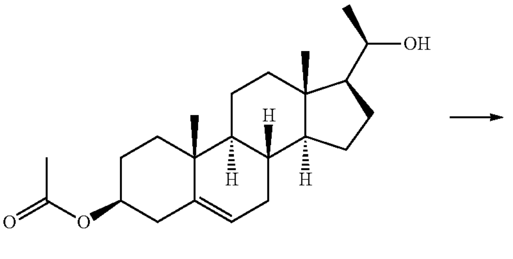

IY42-1

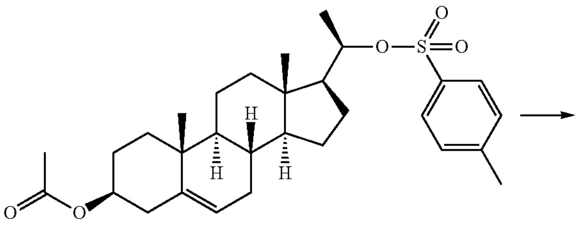

IY42-2

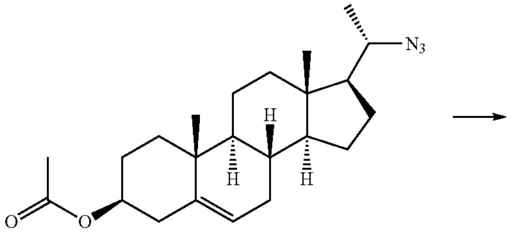

IY42-3

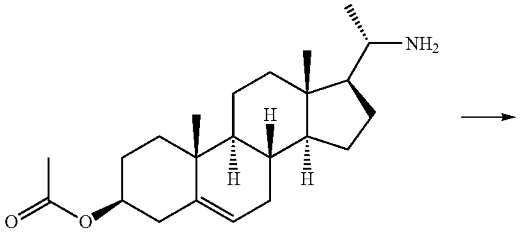

IY42-4

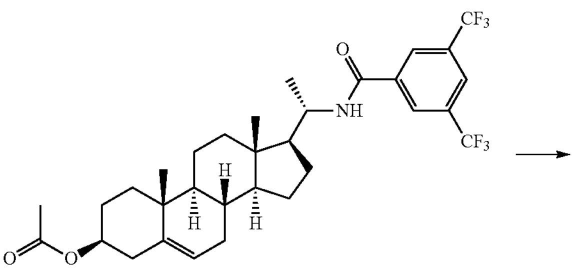

IY42-5

-continued

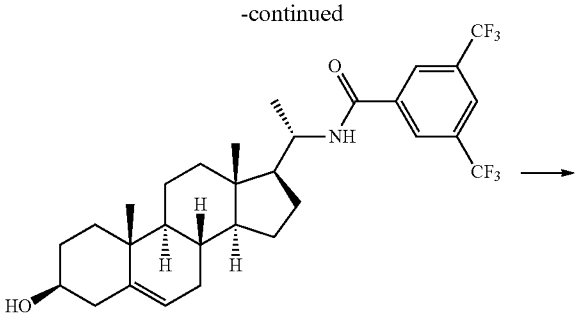

IY42-6

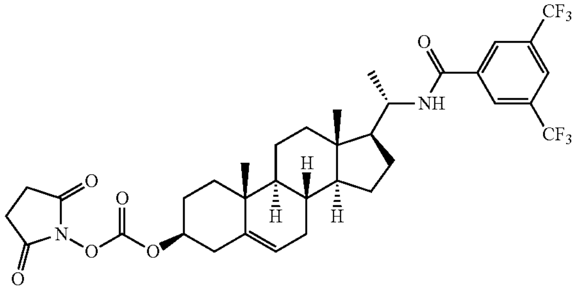

IY42

A) Synthesis of IY42-2

To a pyridine solution (30 mL) of IY42-1 (3.03 g), p-toluenesulfonyl chloride (2.40 g) was added at room temperature. The reaction mixture was stirred for 3 hours, to which p-toluenesulfonyl chloride (2.40 g) was added, and stirred overnight. A 1 N hydrochloric acid solution was added at room temperature to the reaction mixture, which was then extracted with ethyl acetate. The organic layer was separated, washed with a saturated saline solution, and dried with magnesium sulfate, and then the solvent was distilled off. The residue was washed with diisopropyl ether to yield 1.45 g of the title compound. The crude product was used without purification in the next step.

B) Synthesis of IY42-3

Sodium azide (238 mg) was added at room temperature to a DMF solution (3 mL) of the IY42-2 (377 mg) obtained in Step A, and the mixture was stirred at 70 degrees for 4 hours. The reaction mixture was added to water at room temperature, which was then extracted with ethyl acetate. The organic layer was separated, washed with a saturated saline solution, and dried with magnesium sulfate, and then the solvent was distilled off. The residue was washed with diisopropyl ether to yield 310 mg of the title compound. The crude product was used without purification in the next step.

C) Synthesis of IY42-5

To a solution of the IY42-3 (493 mg) obtained in step B in a mixture solvent of THF (10 mL) and water (1 mL), a polymer-supported triphenylphosphine (3 mmol/g) (1.32 g) was added, and the mixture was stirred at 70° C. for 3 hours. The insoluble solids were filtrated and further washed with ethyl acetate. A saturated saline solution was added to the filtrate, the organic layer was separated, and dried with magnesium sulfate, and the solvent was distilled off. The residue was dissolved in pyridine (10 mL), to which 3,5-bis(trifluoromethyl)-benzoyl chloride (0.241 mL) was added at room temperature. The reaction mixture was stirred overnight, to which 1 N hydrochloric acid aqueous solution was added, and then extracted with ethyl acetate. The organic layer was separated, washed with water, then with a saturated saline solution, and dried with magnesium sulfate, and then the solvent was distilled off. The residue was purified by silica gel column chromatography (ethyl acetate/hexane) to yield 370 mg of the title compound.

The NMR results of the obtained compound are as follows.

$^1$H NMR (300 MHz, $CDCl_3$) δ 0.81 (3H, s), 0.94-1.74 (22H, m), 1.74-2.12 (5H, m), 2.33 (2H, d, J=7.3 Hz), 4.20-4.38 (1H, m), 4.62 (1H, brs), 5.39 (1H, brs), 5.96 (1H, d, J=8.9 Hz), 8.00 (1H, s), 8.16 (2H, s).

D) Synthesis of IY42-6

The IY49-5 (370 mg) obtained in step C was dissolved in methanol (3 mL)-THF (3 mL), to which potassium carbonate (256 mg) was added, and the mixture was stirred at room temperature for 2 hours. To the residue obtained by distilling off the solvent in the reaction mixture, a 1 N hydrochloric acid aqueous solution was added, and the mixture was extracted with ethyl acetate. The aqueous layer was neutralized with a saturated sodium hydrogencarbonate aqueous solution at 0° C., and extracted with ethyl acetate. The organic layer was separated, washed with water, then with a saturated saline solution, and dried with magnesium sulfate, and then the solvent was distilled off. The residue was purified by silica gel column chromatography (ethyl acetate/hexane) to yield 183 mg of the title compound.

The NMR results of the obtained compound are as follows.

$^1$H NMR (300 MHz, $CDCl_3$) δ 0.80 (3H, s), 0.90-2.12 (25H, m), 2.16-2.65 (2H, m), 3.53 (1H, brs), 4.25 (1H, d, J=6.8 Hz), 5.36 (1H, brs), 6.08 (1H, d, J=8.7 Hz), 7.99 (1H, s), 8.16 (2H, s).

E) Synthesis of IY42

The title compound was synthesized using the IY42-6 obtained in step D in the same manner as in Reference Example 19.

The NMR results of the obtained compound are as follows.

$^1$H NMR (300 MHz, $CDCl_3$) δ 0.81 (3H, s), 0.90-1.24 (7H, m), 1.32 (3H, d, J=6.4 Hz), 1.41-2.16 (14H, m), 2.49 (2H, d, J=7.0 Hz), 2.84 (4H, s), 4.27 (1H, s), 4.62 (1H, s), 5.42 (1H, d, J=4.7 Hz), 5.92 (1H, d, J=9.4 Hz), 8.00 (1H, s), 8.15 (2H, s).

Reference Example 46

Synthesis of IY46

[Chem 99]

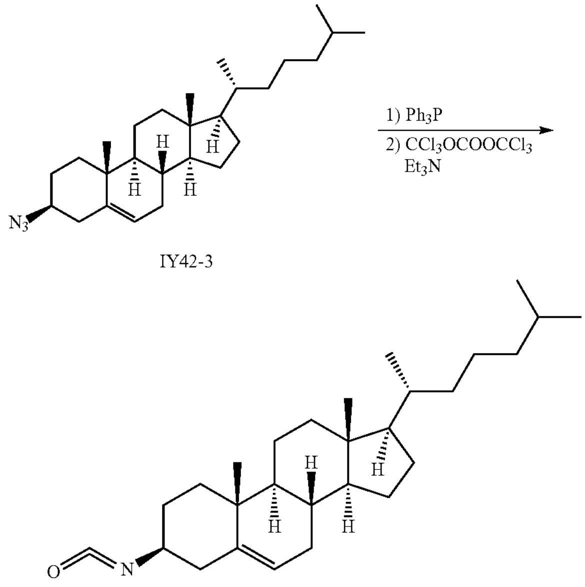

IY42-3

IY46

A mixture of the IY42-3 (830 mg) produced in Step B of Reference Example 42, triphenylphosphine (577 mg), THF (10 mL), and water (1 mL) was stirred at 70° C. for 1 hour. The reaction mixture was added to a 1 N hydrochloric acid aqueous solution, and the insoluble solids were filtered out. The organic layer was separated, washed with a saturated saline solution, and dried with magnesium sulfate, and then the solvent was distilled off. To the residue, THF (20 mL), triethylamine (0.562 mL), and triphosgene (598 mg) were added at 0° C., and the mixture was stirred overnight at room temperature. The reaction mixture was neutralized at 0° C. by adding a saturated sodium hydrogencarbonate aqueous solution, and extracted with a mixed solvent of ethyl acetate and THF. The organic layer was separated, washed with water, then with a saturated saline solution, and dried with magnesium sulfate, and the solvent was distilled off. The residue was purified by silica gel column chromatography (ethyl acetate/hexane) to yield 485 mg of the title compound.

The NMR results of the obtained compound are as follows.

$^1H$ NMR (300 MHz, $CDCl_3$) δ 0.67 (3H, s), 0.78-2.12 (38H, m), 2.35 (2H, d, J=8.3 Hz), 3.24 (1H, d, J=9.0 Hz), 5.37 (1H, d, J=5.1 Hz).

Reference Example 47

Synthesis of IY47

[Chem 100]

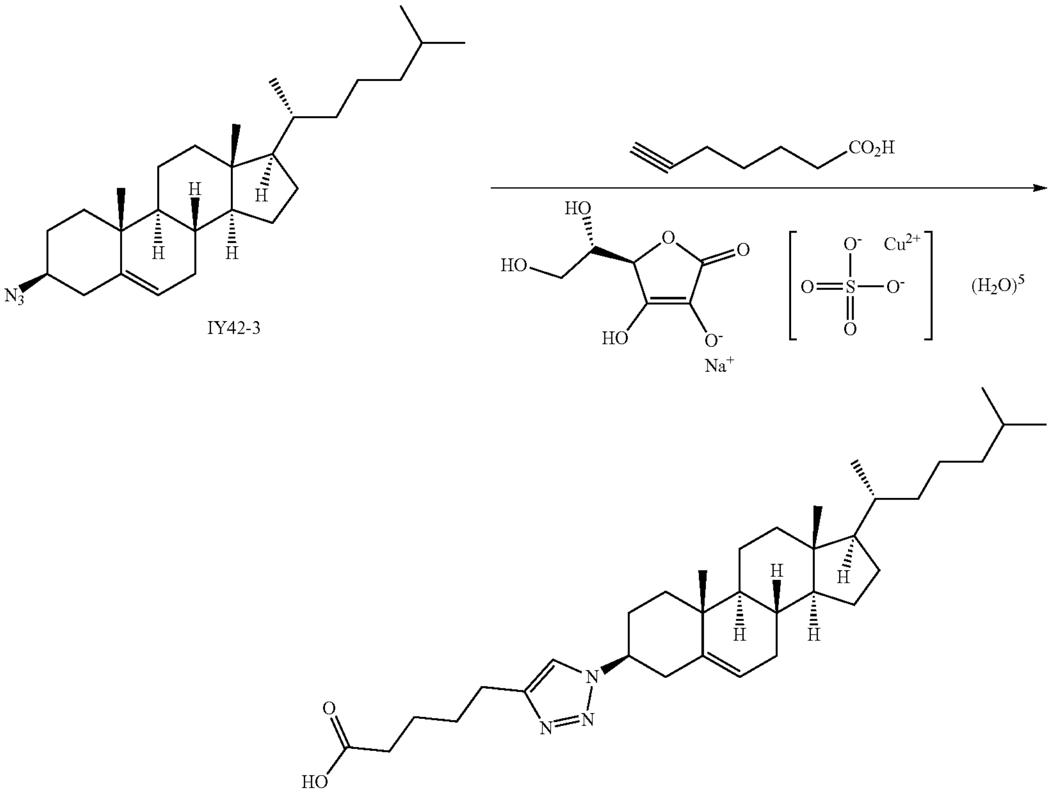

IY42-3

IY47

To a mixture of the IY42-3 (570 mg) produced in step B of Reference Example 42, hept-6-ynoic acid (0.226 mL), copper(II) sulfate pentahydrate (346 mg), ethanol (5 mL), water (5 mL), and THF (10 mL), sodium ascorbate (1920 mg) was added at room temperature, and the mixture was stirred overnight. The insoluble solids were filtered out and the solvent in the filtrate was distilled off under reduced pressure. To the residue, a 1 N hydrochloric acid aqueous solution was added, and then ethyl acetate-THF (4:1) was added. The organic layer was separated, washed with water, then with a saturated saline solution, and dried with magnesium sulfate, and then the solvent was distilled off. The residue was purified by silica gel column chromatography (ethyl acetate/hexane) to yield 188 mg of the title compound.

The NMR results of the obtained compound are as follows.

$^1$H NMR (300 MHz, $CDCl_3$) δ 0.69 (3H, s), 0.79-2.19 (43H, m), 2.27-2.89 (6H, m), 4.34 (1H, brs), 5.45 (1H, brs), 7.32 (1H, s).

Reference Example 49

Synthesis of IY49

[Chem 101]

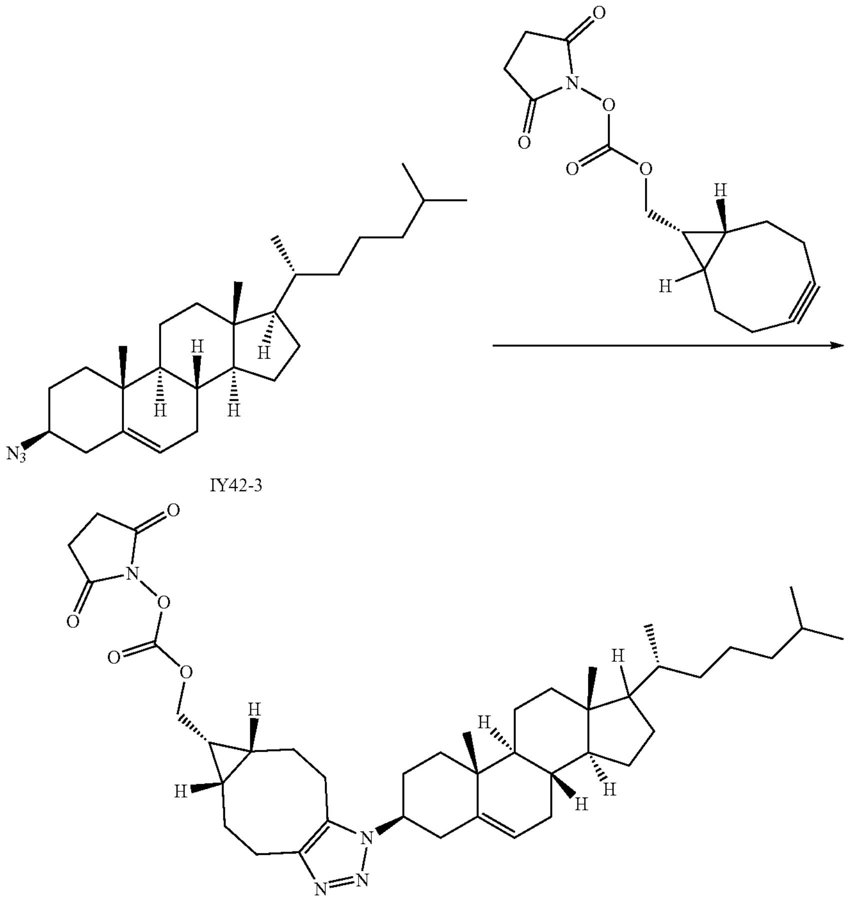

IY42-3

IY49

A mixture of the IY42-3 (200 mg) produced in step B of Reference Example 42, (1R,9S)-bicyclo[6.1.0]non-4-yn-9-ylmethyl (2,5-dioxopyrrolidin-1-yl) carbonate (142 mg), and THF (15 mL) was stirred at room temperature for 2 hours. The reaction mixture was added to water and extracted with ethyl acetate. The organic layer was separated, washed with a saturated saline solution, and dried with magnesium sulfate, and then the solvent was distilled off. The residue was purified by silica gel column chromatography (ethyl acetate/hexane) to yield 134 mg of the title compound.

The NMR results of the obtained compound are as follows.

$^1$H NMR (300 MHz, $CDCl_3$) −0.70 (3H, s), 0.80-1.66 (36H, m), 1.70-2.12 (6H, m), 2.17-2.51 (4H, m), 2.68 (1H, ddt, J=16.0, 10.0, 3.2 Hz), 2.85 (4H, s), 2.89-3.27 (4H, m), 4.01 (1H, tt, J=12.2, 3.9 Hz), 4.29-4.44 (1H, m), 4.47-4.61 (1H, m), 5.42 (1H, d, J=1.9 Hz).

Reference Example 50

Synthesis of IY50

[Chem 102]

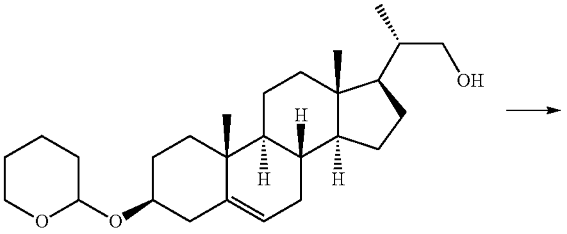

IY50-1

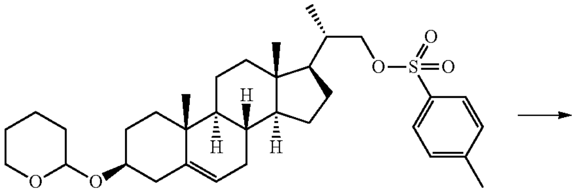

IY50-2

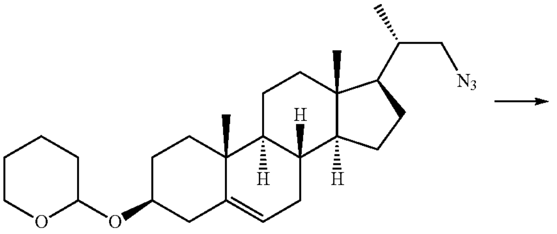

IY50-3

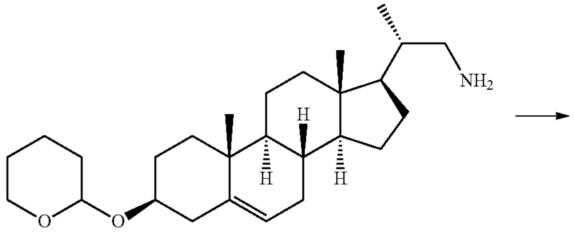

IY50-4

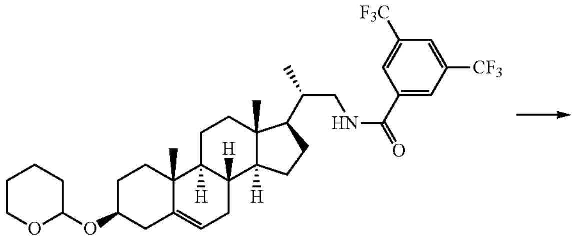

IY50-5

-continued

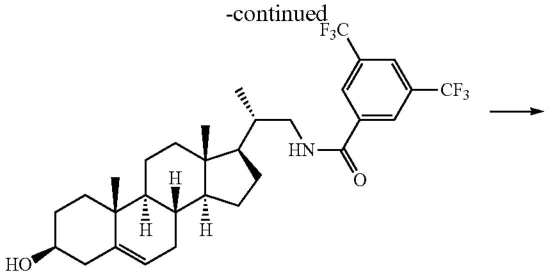

IY50-6

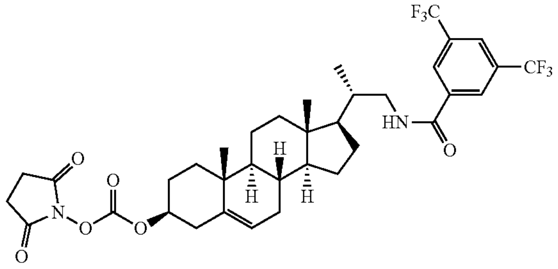

IY50

A) Synthesis of IY50-2

Using IY50-1 (1.02 g) as a starting material, 825 mg of the title compound was produced in the same manner as in step A in Reference Example 42.

The NMR results of the obtained compound are as follows.

$^1$H NMR (300 MHz, $CDCl_3$) δ 0.64 (3H, s), 0.81-2.39 (33H, m), 2.45 (3H, s), 3.50 (2H, brs), 3.67-4.06 (3H, m), 4.71 (1H, brs), 5.33 (1H, brs), 7.34 (2H, d, J=7.5 Hz), 7.78 (2H, d, J=7.9 Hz).

B) Synthesis of IY50-3

Using the IY50-2 (411 mg) obtained in step A as a starting material, 258 mg of the title compound was produced in the same manner as in step B in Reference Example 42.

The NMR results of the obtained compound are as follows.

$^1$H NMR (300 MHz, $CDCl_3$) δ ppm 0.69 (3H, s), 0.82-2.43 (33H, m), 3.04 (1H, dd, J=11.8, 7.4 Hz), 3.28-3.68 (3H, m), 3.81-4.03 (1H, m), 4.72 (1H, brs), 5.35 (1H, brs).

C) Synthesis of IY50-5

Using the IY50-3 (258 mg) obtained in step B as a starting material, 190 mg of the title compound was produced in the same manner as in step C in Reference Example 42.

The NMR results of the obtained compound are as follows.

$^1$H NMR (300 MHz, $CDCl_3$) δ 0.73 (3H, s), 0.87-1.43 (22H, m), 1.63-2.14 (8H, m), 2.37 (1H, s), 3.03-4.03 (7H, m), 4.72 (1H, brs), 5.36 (1H, s), 6.13 (1H, s), 8.01 (1H, s), 8.20 (2H, s).

D) Synthesis of IY50-6

A mixture of the IY50-5 (190 mg) obtained in step C, pyridinium para-toluenesulfonate (101 mg), and methanol (5 mL) was stirred with heating at reflux for 1 hour. The solvent was distilled off under reduced pressure, and the residue was added to water and extracted with ethyl acetate. The organic layer was separated, washed with a saturated saline solution, and dried with magnesium sulfate, and then the solvent was distilled off to yield 170 mg of the title compound. The crude product was used without purification in the next step.

The NMR results of the obtained compound are as follows.

$^1$H NMR (300 MHz, $CDCl_3$) δ 0.74 (3H, s), 0.86-2.45 (28H, m), 3.10-3.33 (1H, m), 3.41-3.69 (2H, m), 5.35 (1H, brs), 6.15 (1H, brs), 8.01 (1H, s), 8.20 (2H, s).

E) Synthesis of IY50

The title compound was produced in the same manner as in Reference Example 19 using the IY53-6 obtained in step D.

The NMR results of the obtained compound are as follows.

$^1$H NMR (300 MHz, $CDCl_3$) δ 0.74 (3H, s), 0.88-2.21 (25H, m), 2.49 (2H, d, J=7.9 Hz), 2.84 (4H, s), 3.09-3.32 (1H, m), 3.59 (1H, d, J=12.8 Hz), 4.60 (1H, brs), 5.43 (1H, brs), 6.15 (1H, brs), 8.01 (1H, s), 8.20 (2H, s).

Other compounds used in Examples are listed in the following Table. Commercial products may be used as they are, respectively, or they may be produced by a publicly known method or a method conforming thereto.

TABLE 6

| Compound name | Structural formula |
|---|---|
| IY2 | 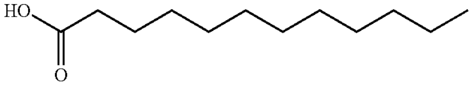 |
| IY3 | 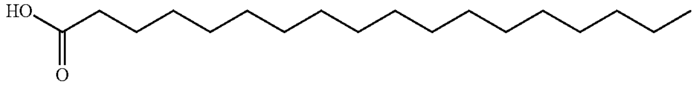 [SMILES: CCCCCCCCCCCCCCCCCC(=O)O] |
| IY4 | 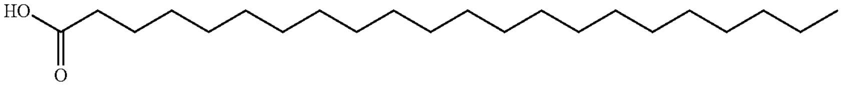 [SMILES: CCCCCCCCCCCCCCCCCCCCCC(=O)O] |
| IY5 | 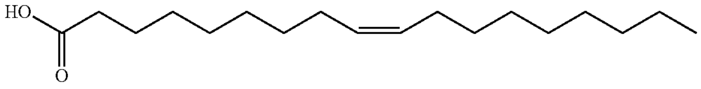 [SMILES: CCCCCCCC/C=C\CCCCCCCC(=O)O] |
| IY6 | 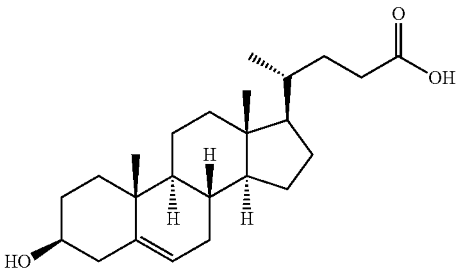 |
| IY12 | 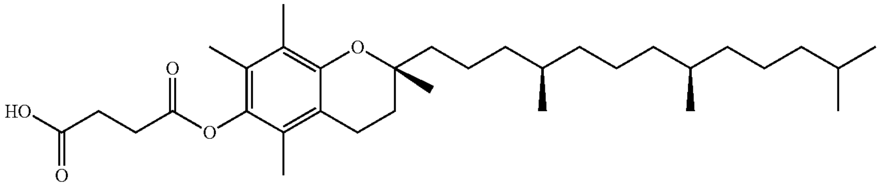 [SMILES: Cc1c(C)c2c(c(C)c1OC(=O)CCC(=O)O)CC[C@@](C)(CCC[C@H](C)CCC[C@H](C)CCCC(C)C)O2] |
| IY13 | 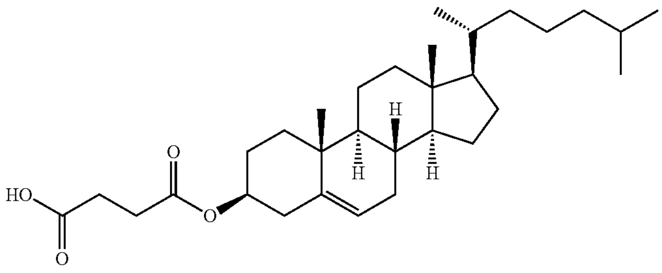 |

TABLE 6-continued

| Compound name | Structural formula |
|---|---|
| IY26 | 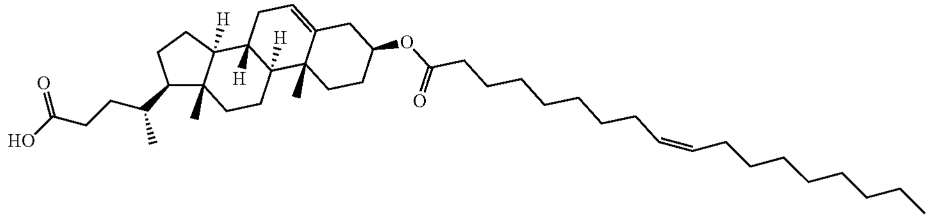 |
| IY45 | 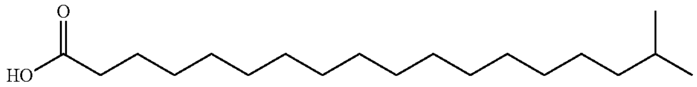 [SMILES: CC(C)CCCCCCCCCCCCCCCC(=O)O] |
| IY53 | 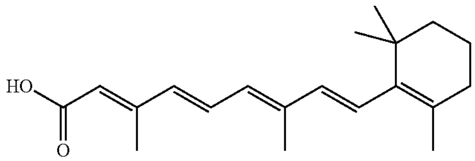 [SMILES: CC1=C(/C=C/C(C)=C/C=C/C(C)=C/C(=O)O)C(C)(C)CCC1] |
| IY54 | 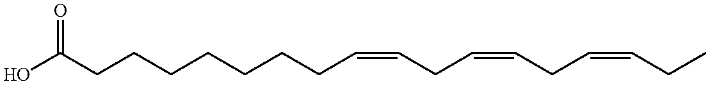 [SMILES: CC/C=C\C/C=C\C/C=C\CCCCCCCC(=O)O] |
| IY55 | 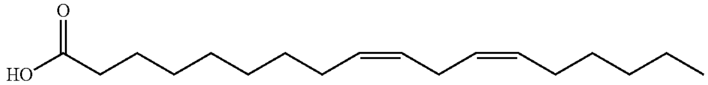 [SMILES: CCCCC/C=C\C/C=C\CCCCCCCC(=O)O] |
| IY57 | 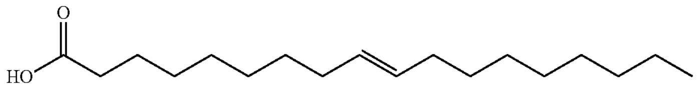 [SMILES: CCCCCCCC/C=C/CCCCCCCC(=O)O] |

Example 1

A) Synthesis of cRNA Bound to Y1- at 5' End (Y1-cRNA (Malat1))

A 50 mM NMP solution of IY1 (800 μL), a 75 mM NMP solution of HATU (800 μL), and a 150 mM NMP solution of DIPEA (800 μL) were mixed in an Eppendorf tube, stirred, precipitated, and then allowed to react at room temperature for 30 min. Thereto an aqueous solution of the RNA strand (Y61-cRNA (Malat1)) listed in Table 1 (2000 nmol), NMP (2100 μL), distilled water (153 μL), and DIPEA (63 μL) were added. Then the mixture was stirred, precipitated, and then allowed to react at room temperature for 1 hour. The reaction solution was purified in an ODS column (column: Purif-Pack®-EX ODS-50 size 60, produced by Shoko Science Co., Ltd., mobile phase: TEAA/acetonitrile), and desalinated by ultrafiltration (Amicon Ultra, 3 kDa, produced by Merck Millipore, distilled water). To the obtained solution, ten times the amount of 1 M meglumine acetate was added, and the mixture was stirred thoroughly and left standing for 5 min for ion exchange. Thereafter, it was desalinated by ultrafiltration (Amicon Ultra, 3 kDa, produced by Merck Millipore, distilled water). The final product was filtrated through a 0.20 μm membrane filter and freeze-dried to yield 690 nmol of the title compound.

B) Synthesis of Double-Stranded Nucleic Acid Agent Y1-HDO

A 16mer single-stranded LNA/DNA gapmer (ASO (Malat1)) targeting metastasis-associated lung adenocarcinoma transcriptional product (Malat1) non-coding RNA comprises three LNA nucleosides at the 5' end, three LNA nucleosides at the 3' end, and ten DNA nucleosides between them. This LNA/DNA gapmer has a base sequence complementary to 1316-1331 of the murine Malat1 non-coding RNA (GenBank Accession number NR 002847, SEQ ID NO: 3). The ASO (Malat1) (first strand) and the Y1-cRNA (Malat1) (second strand) obtained in the previous step A were mixed equimolarly, and the mixed liquid was heated at 70° C. for 5 min. Then, the liquid was slowly cooled to room temperature, to yield the Y1-conjugated heteroduplex oligonucleotide (Y1-HDO), which was a double-stranded nucleic acid agent as described above.

Example 3

A) Synthesis of cRNA Bound to Y3- at 5' End (Y3-cRNA (Malat1))

A 50 mM DMSO solution of IY3 (240 μL), a 75 mM NMP solution of HATU (240 μL), and a 150 mM NMP solution of DIPEA (240 μL) were mixed in an Eppendorf tube, stirred, precipitated, and then allowed to react at room temperature for 15 min. Thereto an aqueous solution of the RNA strand (Y61-cRNA (Malat1)) listed in Table 1 (253 μL, 1200 nmol), DMSO (1980 μL), distilled water (47.4 μL), and DIPEA (38 μL) were added. Then the mixture was stirred, precipitated, and then allowed to react at room temperature for 1 hour. The reaction solution was diluted with distilled water to an NMP concentration of 10 v/v %, and then extracted with ethyl acetate. The aqueous layer was purified by ultrafiltration (Amicon Ultra, 3 kDa, Merck Millipore, distilled water). The final product was filtrated through a 0.20 μm membrane filter and freeze-dried to quantitatively yield the title compound.

B) Synthesis of Double-Stranded Nucleic Acid Agent Y3-HDO

The Y3-conjugated heteroduplex oligonucleotide (Y3-HDO), which was a double-stranded nucleic acid agent was produced in the same manner as in step B of Example 1 using the ASO (Malat1) (first strand) and the Y3-cRNA (Malat1) (second strand) obtained at the previous step A.

Example 4

A) Synthesis of cRNA Bound to Y4- at 5' End (Y4-cRNA (Malat1))

The title compound in an amount of 590 nmol was produced in the same manner as in step A of Example 1 using an aqueous solution of the RNA strand (Y61-cRNA (Malat1)) (2000 nmol) as shown in Table 1, and IY4.

B) Synthesis of Double-Stranded Nucleic Acid Agent Y4-HDO

The Y4-conjugated heteroduplex oligonucleotide (Y4-HDO), which was a double-stranded nucleic acid agent, was prepared in the same manner as in step B of Example 1, using the ASO (Malat1) (first strand) and the Y4-cRNA (Malat1) (second strand) obtained in the previous step A.

Example 5

A) Synthesis of cRNA Bound to Y5- at 5' End (Y5-cRNA (Malat1))

The title compound in an amount of 776 nmol was produced in the same manner as in step A of Example 3 using an aqueous solution of the RNA strand (Y61-cRNA (Malat1)) (1000 nmol) as shown in Table 1, and IY5.

B) Synthesis of Double-Stranded Nucleic Acid Agent Y5-HDO

The Y5-conjugated heteroduplex oligonucleotide (Y5-HDO), which was a double-stranded nucleic acid agent, was prepared in the same manner as in step B of Example 1, using the ASO (Malat1) (first strand) and the Y5-cRNA (Malat1) (second strand) obtained in the previous step A.

Example 6

A) Synthesis of cRNA Bound to Y6- at 5' End (Y6-cRNA (Malat1))

The title compound in an amount of 880 nmol was produced in the same manner as in Step A of Example 3 using an aqueous solution of the RNA strand (Y61-cRNA (Malat1)) (1000 nmol) as shown in Table 1, and IY6.

B) Synthesis of Double-Stranded Nucleic Acid Agent Y6-HDO

The Y6-conjugated heteroduplex oligonucleotide (Y6-HDO), which was a double-stranded nucleic acid agent, was prepared in the same manner as in step B of Example 1, using the ASO (Malat1) (first strand) and the Y6-cRNA (Malat1) (second strand) obtained in the previous step A.

Example 7

A) Synthesis of cRNA Bound to Y7- at 5' End (Y7-cRNA (Malat1))

A 50 mM NMP solution of IY7 (1200 μL), a 75 mM NMP solution of HATU (1200 μL), and a 150 mM NMP solution of DIPEA (1200 μL) were mixed in an Eppendorf tube, stirred, precipitated, and then allowed to react at room temperature for 30 min. Thereto an aqueous solution of the RNA strand (Y61-cRNA (Malat1)) listed in Table 1 (548 μL, 3000 nmol), NMP (3150 μL), distilled water (202 μL), and DIPEA (94 μL) were added. Then the mixture was stirred, precipitated, and then allowed to react at room temperature for 1 hour. The reaction solution was purified in an ODS column (column: Purif-Pack®-EX ODS-50 size 60, produced by Shoko Science Co., Ltd., mobile phase: TEAA/acetonitrile), and desalinated by ultrafiltration (Amicon Ultra, 3 kDa, produced by Merck Millipore, distilled water). The obtained solution was freeze-dried and dissolved in distilled water to yield 780 nmol of the title compound.

B) Synthesis of Double-Stranded Nucleic Acid Agent Y7-HDO

A 16mer single-stranded LNA/DNA gapmer (ASO (Malat1)) targeting metastasis-associated lung adenocarcinoma transcriptional product (Malat1) non-coding RNA comprises three LNA nucleosides at the 5' end, three LNA nucleosides at the 3' end, and ten DNA nucleosides between them. This LNA/DNA gapmer has a base sequence complementary to 1316-1331 of the murine Malat1 non-coding RNA (GenBank Accession number NR 002847, SEQ ID NO: 3). The ASO (Malat1) (first strand) and the Y7-cRNA (Malat1) (second strand) obtained in the previous step A were mixed equimolarly, and the mixed liquid was heated at 70° C. for 5 min. The mixed liquid was then slowly cooled down to room temperature. The same was then subjected to ion exchange to sodium salt using BT AG 50W-X8 Resin, and then freeze-dried. By adding distilled water, the Y7-conjugated heteroduplex oligonucleotide (Y7-HDO), which was a double-stranded nucleic acid agent, was prepared.

Example 8

A) Synthesis of cRNA Bound to Y8- at 5' End (Y8-cRNA (Malat1))

The title compound in an amount of 630 nmol was produced in the same manner as in step A of Example 7 using an aqueous solution of the RNA strand (Y61-cRNA (Malat1)) (3000 nmol) as shown in Table 1, and IY8.

B) Synthesis of Double-Stranded Nucleic Acid Agent Y8-HDO

The Y8-conjugated heteroduplex oligonucleotide (Y8-HDO), which was a double-stranded nucleic acid agent, was prepared in the same manner as in step B of Example 7, using the ASO (Malat1) (first strand) and the Y8-cRNA (Malat1) (second strand) obtained in the previous step A.

Example 9

A) Synthesis of cRNA Bound to Y9- at 5' End (Y9-cRNA (Malat1))

Into an aqueous solution of the RNA strand (Y61-cRNA (Malat1)) (260 μL, 1500 nmol) listed in Table 1, a 50 mM NMP solution of IY9 (900 μL), distilled water (190 μL), NMP (2100 μL), and a Borate Buffer, pH 8.5+/−0.2, 5× Concentrate (375 μL), were admixed in the mentioned order in an Eppendorf tube, and the mixture was stirred, precipitated, and allowed to react at room temperature for 2 hours. The reaction solution was purified in an ODS column (column: Purif-Pack®-EX ODS-50 size 60, produced by Shoko Science Co., Ltd., mobile phase: TEAA/acetonitrile), and desalinated by ultrafiltration (Amicon Ultra, 3 kDa, produced by Merck Millipore, distilled water). The resulting solution was freeze-dried to yield 578 nmol of the title compound.

B) Synthesis of Double-Stranded Nucleic Acid Agent Y9-HDO

The Y9-conjugated heteroduplex oligonucleotide (Y9-HDO), which was a double-stranded nucleic acid agent, was prepared in the same manner as in step B of Example 7 using the ASO (Malat1) (first strand) and the Y9-cRNA (Malat1) (second strand) obtained in the previous step A.

Example 10

A) Synthesis of cRNA Bound to Y10- at 5' End (Y10-cRNA (Malat1))

Into an aqueous solution of the RNA strand (Y61-cRNA (Malat1)) (421 μL, 2000 nmol) listed in Table 1, a 50 mM NMP solution of IY10 (800 μL), distilled water (79 μL), NMP (3200 μL), and a Borate Buffer, pH 8.5+/−0.2, 5× Concentrate (500 μL), were admixed in the mentioned order in an Eppendorf tube, and the mixture was stirred, precipitated, and allowed to react at room temperature for 1 hour. The reaction solution was diluted with distilled water to a NMP concentration of 10 v/v %, and then ultrafiltration (Amicon Ultra, 3 kDa, manufactured by Merck Millipore, distilled water) was performed for concentration, and removal of low-molecular weight reagents such as NMP. The final product was filtrated with a 0.20 μm membrane filter, and freeze-dried to yield 1185 nmol of the title compound.

B) Synthesis of Double-Stranded Nucleic Acid Agent Y10-HDO

The Y10-conjugated heteroduplex oligonucleotide (Y10-HDO), which was a double-stranded nucleic acid agent, was prepared in the same manner as in step B of Example 1 using the ASO (Malat1) (first strand) and the Y10-cRNA (Malat1) (second strand) obtained in the previous step A.

Example 11

A) Synthesis of cRNA Bound to Y11- at 5' End (Y11-cRNA (Malat1))

Into an aqueous solution of the RNA strand (Y61-cRNA (Malat1)) (173.5 μL, 1000 nmol) listed in Table 1, a 50 mM NMP solution of IY11 (400 μL), distilled water (76.5 μL), NMP (1600 μL), a ×10 PBS (250 μL), and DIPEA (31 μL) were admixed in the mentioned order in an Eppendorf tube, and the mixture was stirred, precipitated, and allowed to react at 70° C. for 1 hour. The reaction solution was purified in an ODS column (column: Purif-Pack®-EX ODS-50 size 60, produced by Shoko Science Co., Ltd., mobile phase: TEAA/acetonitrile), and desalinated by ultrafiltration (Amicon Ultra, 3 kDa, produced by Merck Millipore, distilled water). To the obtained solution, ten times the amount of 1 M meglumine acetate was added, and the mixture was stirred thoroughly and left standing for 5 min for ion exchange. Thereafter, it was desalinate by ultrafiltration (Amicon Ultra, 3 kDa, produced by Merck Millipore, distilled water). The final product was filtrated with a 0.20 μm membrane filter and freeze-dried to yield 592 nmol of the title compound.

B) Synthesis of Double-Stranded Nucleic Acid Agent Y11-HDO

The Y11-conjugated heteroduplex oligonucleotide (Y11-HDO), which was a double-stranded nucleic acid agent, was prepared in the same manner as in Step B of Example 1 using the ASO (Malat1) (first strand) and the Y11-cRNA (Malat1) (second strand) obtained in the previous step A.

Example 12

A) Synthesis of cRNA Bound to Y12- at 5' End (Y12-cRNA (Malat1))

The title compound in an amount of 1770 nmol was produced in the same manner as in step A of Example 7 using an aqueous solution of the RNA strand (Y61-cRNA (Malat1)) (3000 nmol) as shown in Table 1, and IY12.

B) Synthesis of Double-Stranded Nucleic Acid Agent Y12-HDO

The Y12-conjugated heteroduplex oligonucleotide (Y12-HDO), which was a double-stranded nucleic acid agent, was prepared in the same manner as in step B of Example 7, using the ASO (Malat1) (first strand) and the Y12-cRNA (Malat1) (second strand) obtained in the previous step A.

Example 13

A) Synthesis of cRNA Bound to Y13- Bound at 5' end (Y13-cRNA (Malat1))

The title compound in an amount of 1230 nmol was produced in the same manner as in step A of Example 7 using an aqueous solution of the RNA strand (Y61-cRNA (Malat1)) (3000 nmol) as shown in Table 1, and IY13.

B) Synthesis of Double-Stranded Nucleic Acid Agent Y13-HDO

The Y13-conjugated heteroduplex oligonucleotide (Y13-HDO), which was a double-stranded nucleic acid agent, was prepared in the same manner as in step B of Example 7, using the ASO (Malat1) (first strand) and the Y13-cRNA (Malat1) (second strand) obtained in the previous step A.

Example 14

A) Synthesis of cRNA Bound to Y14- at 5' End (Y14-cRNA (Malat1))

The title compound in an amount of 1650 nmol was produced in the same manner as in step A of Example 1 using an aqueous solution of the RNA strand (Y61-cRNA (Malat1)) (3000 nmol) as shown in Table 1, and IY14.

B) Synthesis of Double-Stranded Nucleic Acid Agent Y14-HDO

The Y14-conjugated heteroduplex oligonucleotide (Y14-HDO), which was a double-stranded nucleic acid agent, was prepared in the same manner as in step B of Example 1, using the ASO (Malat1) (first strand) and the Y14-cRNA (Malat1) (second strand) obtained in the previous step A.

Example 15

A) Synthesis of cRNA Bound to Y15- at 5' End (Y15-cRNA (Malat1))

The title compound in an amount of 900 nmol was produced in the same manner as in step A of Example 3 using an aqueous solution of the RNA strand (Y61-cRNA (Malat1)) (210 μL, 1000 nmol) as shown in Table 1, and IY15.

B) Synthesis of Double-Stranded Nucleic Acid Agent Y15-HDO

The Y15-conjugated heteroduplex oligonucleotide (Y15-HDO), which was a double-stranded nucleic acid agent, was prepared in the same manner as in step B of Example 1, using the ASO (Malat1) (first strand) and the Y15-cRNA (Malat1) (second strand) obtained in the previous step A.

Example 16

A) Synthesis of cRNA Bound to Y16- at 5' End (Y16-cRNA (Malat1))

The title compound in an amount of 532 nmol was produced in the same manner as in step A of Example 11 using an aqueous solution of the RNA strand (Y61-cRNA (Malat1)) (176 μL, 1000 nmol) as shown in Table 1, and IY16.

B) Synthesis of Double-Stranded Nucleic Acid Agent Y16-HDO

The Y16-conjugated heteroduplex oligonucleotide (Y16-HDO), which was a double-stranded nucleic acid agent, was prepared in the same manner as in step B of Example 1, using the ASO (Malat1) (first strand) and the Y16-cRNA (Malat1) (second strand) obtained in the previous step A.

Example 17

A) Synthesis of cRNA Bound to Y17- at 5' End (Y17-cRNA (Malat1))

The title compound in an amount of 686 nmol was produced in the same manner as in step A of Example 11 using an aqueous solution of the RNA strand (Y61-cRNA (Malat1)) (176 μL, 1000 nmol) as shown in Table 1, and IY17.

B) Synthesis of Double-Stranded Nucleic Acid Agent Y17-HDO

The Y17-conjugated heteroduplex oligonucleotide (Y17-HDO), which was a double-stranded nucleic acid agent, was prepared in the same manner as in step B of Example 1, using the ASO (Malat1) (first strand) and the Y17-cRNA (Malat1) (second strand) obtained in the previous step A.

Example 18

A) Synthesis of cRNA Bound to Y18- at 5' End (Y18-cRNA (Malat1))

The title compound in an amount of 1398 nmol was produced in the same manner as in step A of Example 3 using an aqueous solution of the RNA strand (Y61-cRNA (Malat1)) (274 μL, 1500 nmol) as shown in Table 1, and IY18.

B) Synthesis of Double-Stranded Nucleic Acid Agent Y18-HDO

The Y18-conjugated heteroduplex oligonucleotide (Y18-HDO), which was a double-stranded nucleic acid agent, was prepared in the same manner as in step B of Example 1, using the ASO (Malat1) (first strand) and the Y18-cRNA (Malat1) (second strand) obtained in the previous step A.

Example 19

A) Synthesis of cRNA Bound to Y19- at 5' End (Y19-cRNA (Malat1)

Into an aqueous solution of the RNA strand (Y61-cRNA (Malat1)) (210.5 μL, 1000 nmol) listed in Table 1, a 50 mM NMP solution of IY19 (400 μL), distilled water (39.5 μL), NMP (1600 μL), ×10 PBS (250 μL), and DIPEA (31 μL) were admixed in the mentioned order in an Eppendorf tube, and the mixture was stirred, precipitated, and allowed to react at room temperature for 1 hour. The reaction solution was diluted with distilled water to a NMP concentration of 10 v/v %, and then ultrafiltration (Amicon Ultra, 3 kDa, manufactured by Merck Millipore, distilled water) was performed for concentration and removal of low-molecular weight reagents such as NMP. The final product was filtrated with a 0.20 μm membrane filter, and freeze-dried to yield 927 nmol of the title compound.

B) Synthesis of Double-Stranded Nucleic Acid Agent Y19-HDO

The Y19-conjugated heteroduplex oligonucleotide (Y19-HDO), which was a double-stranded nucleic acid agent, was prepared in the same manner as in step B of Example 1 using the ASO (Malat1) (first strand) and the Y19-cRNA (Malat1) (second strand) obtained at the previous step A.

Example 20

A) Synthesis of cRNA Bound to Y20- at 5' End (Y20-cRNA (Malat1))

The title compound in an amount of 686 nmol was produced in the same manner as in Step A of Example 11 using an aqueous solution of the RNA strand (Y61-cRNA (Malat1)) (260 μL, 1500 nmol) as shown in Table 1, and IY19.

B) Synthesis of Double-Stranded Nucleic Acid Agent Y20-HDO

The Y20-conjugated heteroduplex oligonucleotide (Y20-HDO), which was a double-stranded nucleic acid agent, was prepared in the same manner as in step B of Example 1, using the ASO (Malat1) (first strand) and the Y20-cRNA (Malat1) (second strand) obtained in the previous step A.

Example 21

A) Synthesis of cRNA Bound to Y21- at 5' End (Y21-cRNA (Malat1))

Into an aqueous solution of the RNA strand (Y61-cRNA (Malat1)) (260 μL, 1500 nmol) listed in Table 1, a 50 mM NMP solution of IY21 (300 μL), distilled water (115 μL), NMP (2400 μL), a ×10 PBS (375 μL), and a 50 mM DMAP (300 μL) were admixed in the mentioned order in an Eppendorf tube, and the mixture was stirred, precipitated, and allowed to react at 70° C. for 1 hour. The reaction solution was purified in an ODS column (column: Purif-Pack®-EX ODS-50 size 60, produced by Shoko Science Co., Ltd., mobile phase: TEAA/acetonitrile), and desalinated by ultrafiltration (Amicon Ultra, 3 kDa, produced by Merck Millipore, distilled water). The final product was filtrated with a 0.20 μm membrane filter and freeze-dried to yield 917 nmol of the title compound.

B) Synthesis of Double-Stranded Nucleic Acid Agent Y21-HDO

The Y21-conjugated heteroduplex oligonucleotide (Y21-HDO), which was a double-stranded nucleic acid agent, was prepared in the same manner as in step B of Example 1 using the ASO (Malat1) (first strand) and the Y21-cRNA (Malat1) (second strand) obtained at the previous step A.

Example 22

A) Synthesis of cRNA Bound to Y22- at 5' End (Y22-cRNA (Malat1))

The title compound in an amount of 1253 nmol was produced in the same manner as in step A of Example 21 using an aqueous solution of the RNA strand (Y61-cRNA (Malat1)) (365 μL, 2000 nmol) as shown in Table 1, and IY22.

B) Synthesis of Double-Stranded Nucleic Acid Agent Y22-HDO

The Y22-conjugated heteroduplex oligonucleotide (Y22-HDO), which was a double-stranded nucleic acid agent, was prepared in the same manner as in step B of Example 1, using the ASO (Malat1) (first strand) and the Y22-cRNA (Malat1) (second strand) obtained in the previous step A.

Example 23

A) Synthesis of cRNA Bound to Y23- at 5' End (Y23-cRNA (Malat1))

Into an aqueous solution of the RNA strand (Y61-cRNA (Malat1)) (382 μL, 2200 nmol) listed in Table 1, a 50 mM NMP solution of IY23 (440 μL), distilled water (168 μL), NMP (3520 μL), a ×10 PBS (550 μL), and a 50 mM DMAP (440 μL) were admixed in the mentioned order in an Eppendorf tube, and the mixture was stirred, precipitated, and allowed to react at 70° C. for 1 hour. The reaction solution was purified in an ODS column (column: Purif-Pack®-EX ODS-50 size 60, produced by Shoko Science Co., Ltd., mobile phase: TEAA/acetonitrile), and desalinated by ultrafiltration (Amicon Ultra, 3 kDa, produced by Merck Millipore, distilled water). The resulting solution was diluted to 1000 μL with distilled water, to which distilled water (200 μL), NMP (400 μL), methanol (4400 μL), and a 50 mM DMSO solution of hydrogen fluoride (2000 μL) were admixed in the mentioned order in an Eppendorf tube, and the mixture was stirred, precipitated, and allowed to react at room temperature for 1 hour. To the reaction solution, a 300 mM DMSO solution of trimethylethoxysilane (2000 μL) was added. The reaction mixture was purified in an ODS column (column: Purif-Pack®-EX ODS-50 size 60, manufactured by Shoko Science Co., Ltd., mobile phase: TEAA/acetonitrile), and then desalinated by ultrafiltration (Amicon Ultra, 3 kDa, produced by Merck Millipore, distilled water). The final product was filtrated with a 0.20 μm membrane filter and freeze-dried to yield 1114 nmol of the title compound.

B) Synthesis of Double-Stranded Nucleic Acid Agent Y23-HDO

The Y23-conjugated heteroduplex oligonucleotide (Y23-HDO), which was a double-stranded nucleic acid agent, was prepared in the same manner as in step B of Example 7 using the ASO (Malat1) (first strand) and the Y23-cRNA (Malat1) (second strand) obtained in the previous step A.

Example 24

A) Synthesis of cRNA Bound to Y24- at 5' End (Y24-cRNA (Malat1))

The title compound in an amount of 870 nmol was produced in the same manner as in step A of Example 21 using an aqueous solution of the RNA strand (Y61-cRNA (Malat1)) (174 μL, 1000 nmol) as shown in Table 1, and IY24.

B) Synthesis of Double-Stranded Nucleic Acid Agent Y24-HDO

The Y24-conjugated heteroduplex oligonucleotide (Y24-HDO), which was a double-stranded nucleic acid agent, was prepared in the same manner as in step B of Example 7, using the ASO (Malat1) (first strand) and the Y24-cRNA (Malat1) (second strand) obtained in the previous step A.

Example 25

A) Synthesis of cRNA Bound to Y25- at 5' End (Y25-cRNA (Malat1))

The title compound in an amount of 760 nmol was produced in the same manner as in step A of Example 11 using an aqueous solution of the RNA strand (Y61-cRNA (Malat1)) (274 μL, 1500 nmol) as shown in Table 1, and IY25.

B) Synthesis of Double-Stranded Nucleic Acid Agent Y25-HDO

The Y25-conjugated heteroduplex oligonucleotide (Y25-HDO), which was a double-stranded nucleic acid agent, was prepared in the same manner as in step B of Example 1, using the ASO (Malat1) (first strand) and the Y25-cRNA (Malat1) (second strand) obtained in the previous step A.

Example 26

A) Synthesis of cRNA Bound to Y26- at 5' End (Y26-cRNA (Malat1))

A 50 mM THF solution of IY26 (400 μL), a 75 mM NMP solution of HATU (400 μL), and a 150 mM NMP solution of DIPEA (400 μL) were mixed in an Eppendorf tube. The mixture was stirred and precipitated, and allowed to react at room temperature for 30 min. Thereto an aqueous solution of the RNA strand (Y61-cRNA (Malat1)) listed in Table 1 (315 μL, 2000 nmol), NMP (1450 μL), THF (1850 μL), distilled water (184 μL), and DIPEA (63 μL) were added. Then the mixture was stirred, precipitated, and then allowed to react at room temperature for 1 hour. In addition, a 50 mM THF solution of IY26 (400 μL), a 75 mM NMP solution of HATU (400 μL), and 150 mM NMP solution of DIPEA (400 μL) were mixed in a Falcon tube, and left standing for 15 min, which was then combined with the reaction solution, and, after addition of DIPEA (125 μL), allowed to react at room temperature for 2 hours. The reaction solution was purified in an ODS column (column: Purif-Pack®-EX ODS-50 size 60, produced by Shoko Science Co., Ltd., mobile phase: TEAA/acetonitrile), and desalinated by ultrafiltration (Amicon Ultra, 3 kDa, produced by Merck Millipore, distilled water). To the obtained solution, ten times the amount of 1 M meglumine acetate was added, and the mixture was stirred thoroughly and left standing for 5 min for ion exchange. Thereafter, it was desalinated by ultrafiltration (Amicon Ultra, 3 kDa, produced by Merck Millipore, distilled water). The final product was filtrated with a 0.20 μm membrane filter and freeze-dried to yield 237 nmol of the title compound.

B) Synthesis of Double-Stranded Nucleic Acid Agent Y26-HDO

The Y26-conjugated heteroduplex oligonucleotide (Y26-HDO), which was a double-stranded nucleic acid agent, was prepared in the same manner as in step B of Example 1 using the ASO (Malat1) (first strand) and the Y26-cRNA (Malat1) (second strand) obtained at the previous step A.

Example 27

A) Synthesis of cRNA Bound to Y27- at 5' End (Y27-cRNA (Malat1))

The title compound in an amount of 705 nmol was produced in the same manner as in step A of Example 11 using an aqueous solution (312 μL, 2000 nmol) of the RNA strand (Y61-cRNA (Malat1)) as shown in Table 1, and IY27.

B) Synthesis of Double-Stranded Nucleic Acid Agent Y27-HDO

The Y27-conjugated heteroduplex oligonucleotide (Y27-HDO), which was a double-stranded nucleic acid agent, was prepared in the same manner as in step B of Example 1, using the ASO (Malat1) (first strand) and the Y27-cRNA (Malat1) (second strand) obtained in the previous step A.

Example 28

A) Synthesis of cRNA Bound to Y28- at 5' End (Y28-cRNA (Malat1))

The title compound in an amount of 1046 nmol was produced in the same manner as in step A of Example 11 using an aqueous solution of the RNA strand (Y61-cRNA (Malat1)) (346 μL, 2530 nmol) as shown in Table 1, and IY28.

B) Synthesis of Double-Stranded Nucleic Acid Agent Y28-HDO

The Y28-conjugated heteroduplex oligonucleotide (Y28-HDO), which was a double-stranded nucleic acid agent, was prepared in the same manner as in step B of Example 1, using the ASO (Malat1) (first strand) and the Y28-cRNA (Malat1) (second strand) obtained in the previous step A.

Example 29

A) Synthesis of cRNA Bound to Y29- at 5' End (Y29-cRNA (Malat1))

The title compound in an amount of 903 nmol was produced in the same manner as in step A of Example 21 using an aqueous solution of the RNA strand (Y62-cRNA (Malat1)) (369 μL, 1500 nmol) as shown in Table 1, and IY29.

B) Synthesis of Double-Stranded Nucleic Acid Agent Y29-HDO

The Y29-conjugated heteroduplex oligonucleotide (Y29-HDO), which was a double-stranded nucleic acid agent, was prepared in the same manner as in step B of Example 7, using the ASO (Malat1) (first strand) and the Y29-cRNA (Malat1) (second strand) obtained in the previous step A.

Example 30

A) Synthesis of cRNA Bound to Y30- at 5' End (Y30-cRNA (Malat1))

The title compound in an amount of 1228 nmol was produced in the same manner as in Step A of Example 11 using an aqueous solution of the RNA strand (Y63-cRNA (Malat1)) (358 μL, 1500 nmol) as shown in Table 1 and cholesteryl chloroformate.

B) Synthesis of Double-Stranded Nucleic Acid Agent Y30-HDO

The Y30-conjugated heteroduplex oligonucleotide (Y30-HDO), which was a double-stranded nucleic acid agent, was prepared in the same manner as in step B of Example 1, using the ASO (Malat1) (first strand) and the Y30-cRNA (Malat1) (second strand) obtained in the previous step A.

Example 31

A) Synthesis of cRNA Bound to Y31- at 5' End (Y31-cRNA (Malat1))

The title compound in an amount of 657 nmol was produced in the same manner as in step A of Example 21 using an aqueous solution of the RNA strand (Y64-cRNA (Malat1)) (355 μL, 1400 nmol) as shown in Table 1, and IY29.

B) Synthesis of Double-Stranded Nucleic Acid Agent Y31-HDO

The Y31-conjugated heteroduplex oligonucleotide (Y31-HDO), which was a double-stranded nucleic acid agent, was prepared in the same manner as in step B of Example 7, using the ASO (Malat1) (first strand) and the Y31-cRNA (Malat1) (second strand) obtained in the previous step A.

Example 32

A) Synthesis of cRNA Bound to Y32- at 5' End (Y32-cRNA (Malat1))

The title compound in an amount of 864 nmol was produced in the same manner as in step A of Example 11 using an aqueous solution of the RNA strand (Y61-cRNA (Malat1)) (315 μL, 2000 nmol) as shown in Table 1, and IY32.

B) Synthesis of Double-Stranded Nucleic Acid Agent Y32-HDO

The Y32-conjugated heteroduplex oligonucleotide (Y32-HDO), which was a double-stranded nucleic acid agent, was prepared in the same manner as in step B of Example 1, using the ASO (Malat1) (first strand) and the Y32-cRNA (Malat1) (second strand) obtained in the previous step A.

Example 33

A) Synthesis of cRNA Bound to Y33- at 5' End (Y33-cRNA (Malat1))

To an aqueous solution of the RNA strand (Y61-cRNA (Malat1)) (365 μL, 2000 nmol) listed in Table 1, a 50 mM NMP solution of IY33 (400 μL), distilled water (135 μL), NMP (3200 μL), a ×10 PBS (500 μL), a 50 mM DMAP (400 μL) were added and mixed in an Eppendorf tube. The mixture was stirred and precipitated, and allowed to react at 70° C. for 1 hour. The reaction solution was purified in an ODS column (column: Purif-Pack®-EX ODS-50 size 60, produced by Shoko Science Co., Ltd., mobile phase: TEAA/acetonitrile), and desalinated by ultrafiltration (Amicon Ultra, 3 kDa, produced by Merck Millipore, distilled water). To the obtained solution, ten times the amount of 1 M meglumine acetate was added, and the mixture was stirred thoroughly and left standing for 5 min for ion exchange. Thereafter, it was desalinated by ultrafiltration (Amicon Ultra, 3 kDa, produced by Merck Millipore, distilled water). The final product was filtrated with a 0.20 μm membrane filter and freeze-dried to yield 963 nmol of the title compound.

B) Synthesis of Double-Stranded Nucleic Acid Agent Y33-HDO

The Y33-conjugated heteroduplex oligonucleotide (Y33-HDO), which was a double-stranded nucleic acid agent, was prepared in the same manner as in step B of Example 1 using the ASO (Malat1) (first strand) and the Y33-cRNA (Malat1) (second strand) obtained in the previous step A.

Example 34

A) Synthesis of cRNA Bound to Y34- at 5' End (Y34-cRNA (Malat1))

The title compound in an amount of 1083 nmol was produced in the same manner as in step A of Example 33 using an aqueous solution of the RNA strand (Y61-cRNA (Malat1)) (365 μL, 2000 nmol) as shown in Table 1 and IY34.

B) Synthesis of Double-Stranded Nucleic Acid Agent Y34-HDO

The Y34-conjugated heteroduplex oligonucleotide (Y34-HDO), which was a double-stranded nucleic acid agent, was prepared in the same manner as in step B of Example 1, using the ASO (Malat1) (first strand) and the Y34-cRNA (Malat1) (second strand) obtained in the previous step A.

Example 35

A) Synthesis of cRNA Bound to Y35- at 5' End (Y35-cRNA (Malat1))

The title compound in an amount of 830 nmol was produced in the same manner as in step A of Example 33 using an aqueous solution of the RNA strand (Y61-cRNA (Malat1)) (315 μL, 2000 nmol) as shown in Table 1.

B) Synthesis of Double-Stranded Nucleic Acid Agent Y35-HDO

The Y35-conjugated heteroduplex oligonucleotide (Y35-HDO), which was a double-stranded nucleic acid agent, was prepared in the same manner as in step B of Example 1, using the ASO (Malat1) (first strand) and the Y35-cRNA (Malat1) (second strand) obtained in the previous step A.

Example 36

A) Synthesis of cRNA Bound to Y36- at 5' End (Y36-cRNA (Malat1))

The title compound in an amount of 830 nmol was produced in the same manner as in step A of Example 33 using an aqueous solution of the RNA strand (Y61-cRNA (Malat1)) (329 μL, 2000 nmol) as shown in Table 1, and IY36.

B) Synthesis of Double-Stranded Nucleic Acid Agent Y36-HDO

The Y36-conjugated heteroduplex oligonucleotide (Y36-HDO), which was a double-stranded nucleic acid agent, was prepared in the same manner as in step B of Example 1, using the ASO (Malat1) (first strand) and the Y36-cRNA (Malat1) (second strand) obtained in the previous step A.

Example 37

A) Synthesis of cRNA Bound to Y37- at 5' End (Y37-cRNA (Malat1))

The title compound in an amount of 1189 nmol was produced in the same manner as in Step A of Example 33 using an aqueous solution of the RNA strand (Y61-cRNA (Malat1)) (400 μL, 2000 nmol) as shown in Table 1, and IY37.

B) Synthesis of Double-Stranded Nucleic Acid Agent Y37-HDO

The Y37-conjugated heteroduplex oligonucleotide (Y37-HDO), which was a double-stranded nucleic acid agent, was prepared in the same manner as in step B of Example 1, using the ASO (Malat1) (first strand) and the Y37-cRNA (Malat1) (second strand) obtained in the previous step A.

Example 38

A) Synthesis of cRNA Bound to Y38- at 5' End (Y38-cRNA (Malat1))

The title compound in an amount of 1032 nmol was produced in the same manner as in step A of Example 33 using an aqueous solution of the RNA strand (Y61-cRNA (Malat1)) (329 μL, 2000 nmol) as shown in Table 1, and IY38.

B) Synthesis of Double-Stranded Nucleic Acid Agent Y38-HDO

The Y38-conjugated heteroduplex oligonucleotide (Y38-HDO), which was a double-stranded nucleic acid agent, was prepared in the same manner as in step B of Example 1, using the ASO (Malat1) (first strand) and the Y38-cRNA (Malat1) (second strand) obtained in the previous step A.

Example 39

A) Synthesis of cRNA Bound to Y39- at 5' End (Y39-cRNA (Malat1))

To an aqueous solution of the RNA strand (Y61-cRNA (Malat1)) (329 μL, 2000 nmol) listed in Table 1, a 50 mM NMP solution of IY39 (800 μL), distilled water (270 μL), NMP (2800 μL), and a Borate Buffer, pH 8.5+/−0.2, 5× Concentrate (500 μL) were admixed in the mentioned order in an Eppendorf tube. The mixture was stirred and precipitated, and allowed to react at room temperature for 1 hour. Further, a 50 mM NMP solution (400 μL) of IY39 was added, and a reaction was performed at room temperature for 1 hour. Further, a 50 mM NMP solution (400 μL) of IY39, and a Borate Buffer, pH 8.5+/−0.2, 5× Concentrate (100 μL) were added, and a reaction was performed at room temperature overnight. The reaction solution was purified in an ODS column (column: Purif-Pack®-EX ODS-50 size 60, manufactured by Shoko Science Co., Ltd., mobile phase: TEAA/acetonitrile), and desalinated by ultrafiltration (Amicon Ultra, 3 kDa, produced by Merck Millipore, distilled water). To the obtained solution, ten times the amount of 1 M meglumine acetate was added, and the mixture was stirred thoroughly and left standing for 5 min for ion exchange. Thereafter, it was desalinated by ultrafiltration (Amicon Ultra, 3 kDa, produced by Merck Millipore, distilled water). The final product was filtrated with a 0.20 μm membrane filter and freeze-dried to yield 1554 nmol of the title compound.

B) Synthesis of Double-Stranded Nucleic Acid Agent Y39-HDO

The Y39-conjugated heteroduplex oligonucleotide (Y39-HDO), which was a double-stranded nucleic acid agent, was prepared in the same manner as in step B of Example 1 using the ASO (Malat1) (first strand) and the Y39-cRNA (Malat1) (second strand) obtained in the previous step A.

Example 40

A) Synthesis of cRNA Bound to Y40- at 5' End (Y40-cRNA (Malat1))

The title compound in an amount of 607 nmol was produced in the same manner as in step A of Example 39 using an aqueous solution of the RNA strand (Y61-cRNA (Malat1)) (364 μL, 2000 nmol) as shown in Table 1, and IY40.

B) Synthesis of Double-Stranded Nucleic Acid Agent Y40-HDO

The Y40-conjugated heteroduplex oligonucleotide (Y40-HDO), which was a double-stranded nucleic acid agent, was prepared in the same manner as in step B of Example 1, using the ASO (Malat1) (first strand) and the Y40-cRNA (Malat1) (second strand) obtained in the previous step A.

Example 41

A) Synthesis of cRNA Bound to Y41- at 5' End (Y41-cRNA (Malat1))

The title compound in an amount of 1400 nmol was produced in the same manner as in step A of Example 39 using an aqueous solution of the RNA strand (Y61-cRNA (Malat1)) (329 μL, 2000 nmol) as shown in Table 1, and IY41.

B) Synthesis of Double-Stranded Nucleic Acid Agent Y41-HDO

The Y41-conjugated heteroduplex oligonucleotide (Y41-HDO), which was a double-stranded nucleic acid agent, was prepared in the same manner as in step B of Example 1, using the ASO (Malat1) (first strand) and the Y41-cRNA (Malat1) (second strand) obtained in the previous step A.

Example 42

A) Synthesis of cRNA Bound to Y42- at 5' End (Y42-cRNA (Malat1))

The title compound in an amount of 1061 nmol was produced in the same manner as in step A of Example 39 using an aqueous solution of the RNA strand (Y61-cRNA (Malat1)) (365 μL, 2000 nmol) as shown in Table 1, and IY42.

B) Synthesis of Double-Stranded Nucleic Acid Agent Y42-HDO

The Y42-conjugated heteroduplex oligonucleotide (Y42-HDO), which was a double-stranded nucleic acid agent, was prepared in the same manner as in step B of Example 1, using the ASO (Malat1) (first strand) and the Y42-cRNA (Malat1) (second strand) obtained in the previous step A.

Example 43

A) Synthesis of cRNA Bound to Y43- at 5' End (Y43-cRNA (Malat1))

The title compound in an amount of 820 nmol was produced in the same manner as in step A of Example 39 using an aqueous solution of the RNA strand (Y61-cRNA (Malat1)) (329 μL, 2000 nmol) as shown in Table 1, and IY43.

B) Synthesis of Double-Stranded Nucleic Acid Agent Y43-HDO

The Y43-conjugated heteroduplex oligonucleotide (Y43-HDO), which was a double-stranded nucleic acid agent, was prepared in the same manner as in step B of Example 1, using the ASO (Malat1) (first strand) and the Y43-cRNA (Malat1) (second strand) obtained in the previous step A.

Example 44

A) Synthesis of cRNA Bound to Y44- at 5' End (Y44-cRNA (Malat1))

The title compound in an amount of 969 nmol was produced in the same manner as in step A of Example 39 using an aqueous solution (329 μL, 2000 nmol) of the RNA strand (Y61-cRNA (Malat1)) as shown in Table 1, and IY44.

B) Synthesis of Double-Stranded Nucleic Acid Agent Y44-HDO

The Y44-conjugated heteroduplex oligonucleotide (Y44-HDO), which was a double-stranded nucleic acid agent, was prepared in the same manner as in step B of Example 1, using the ASO (Malat1) (first strand) and the Y44-cRNA (Malat1) (second strand) obtained in the previous step A.

Example 45

A) Synthesis of cRNA Bound to Y45- at 5' End (Y45-cRNA (Malat1))

The title compound in an amount of 653 nmol was produced in the same manner as in step A of Example 1 using an aqueous solution of the RNA strand (Y61-cRNA (Malat1)) (164 μL, 1000 nmol) as shown in Table 1, and IY45.

B) Synthesis of Double-Stranded Nucleic Acid Agent Y45-HDO

The Y45-conjugated heteroduplex oligonucleotide (Y45-HDO), which was a double-stranded nucleic acid agent, was prepared in the same manner as in step B of Example 1, using the ASO (Malat1) (first strand) and the Y45-cRNA (Malat1) (second strand) obtained in the previous step A.

Example 46

A) Synthesis of cRNA Bound to Y46- at 5' End (Y46-cRNA (Malat1))

To an aqueous solution of the RNA strand (Y61-cRNA (Malat1)) (312 μL, 2000 nmol) listed in Table 1, a 50 mM NMP solution of IY46 (400 μL), distilled water (188 μL), NMP (3200 μL), a ×10 PBS (500 μL), and a 50 mM DMAP (400 μL) were added in the mentioned order, and mixed in an Eppendorf tube. The mixture was stirred and precipitated, and allowed to react at 70° C. for 1 hour. Further, a 50 mM NMP solution (400 μL) of IY46 and a 50 mM DMAP (400 μL) were added, and a reaction was performed at 70° C. for 1 hour, and at room temperature overnight. Further, a 50 mM NMP solution (400 μL) of IY46 and a 150 mM DIPEA (400 μL) were added, and a reaction was performed at 70° C. for 1 hour. The reaction solution was purified in an ODS column (column: Purif-Pack®-EX ODS-50 size 60, manufactured by Shoko Science Co., Ltd., mobile phase: TEAA/acetonitrile), and desalinated by ultrafiltration (Amicon Ultra, 3 kDa, produced by Merck Millipore, distilled water). To the obtained solution, ten times the amount of 1 M meglumine acetate was added, and the mixture was stirred thoroughly and left standing for 5 min for ion exchange. Thereafter, it was desalinated by ultrafiltration (Amicon Ultra, 3 kDa, produced by Merck Millipore, distilled water). The final product was filtrated with a 0.20 μm membrane filter and freeze-dried to yield 980 nmol of the title compound.

B) Synthesis of Double-Stranded Nucleic Acid Agent Y46-HDO

The Y46-conjugated heteroduplex oligonucleotide (Y46-HDO), which was a double-stranded nucleic acid agent, was prepared in the same manner as in step B of Example 1 using the ASO (Malat1) (first strand) and the Y46-cRNA (Malat1) (second strand) obtained in the previous step A.

Example 47

A) Synthesis of cRNA Bound to Y47- at 5' End (Y47-cRNA (Malat1))

The title compound in an amount of 569 nmol was produced in the same manner as in step A of Example 1 using an aqueous solution of the RNA strand (Y61-cRNA (Malat1)) (315 μL, 2000 nmol) as shown in Table 1, and IY47.

B) Synthesis of Double-Stranded Nucleic Acid Agent Y47-HDO

The Y47-conjugated heteroduplex oligonucleotide (Y47-HDO), which was a double-stranded nucleic acid agent, was prepared in the same manner as in step B of Example 1, using the ASO (Malat1) (first strand) and the Y47-cRNA (Malat1) (second strand) obtained in the previous step A.

Example 48

A) Synthesis of cRNA Bound to Y48- at 5' End (Y48-cRNA (Malat1))

A 50 mM NMP solution of IY48 (800 μL), a 75 mM NMP solution of HATU (800 μL), and a 150 mM NMP solution of DIPEA (800 μL) were mixed in an Eppendorf tube. The mixture was stirred, precipitated, and allowed to react at room temperature for 30 min. Thereto, an aqueous solution of the RNA strand (Y61-cRNA (Malat1)) (2000 nmol) listed in Table 1, NMP (2100 μL), distilled water (153 μL), and DIPEA (63 μL) were added, and the mixture was stirred and precipitated, and then allowed to react at room for 1 hour. The reaction solution was diluted with distilled water to a NMP concentration of 10 v/v %, and then ultrafiltration (Amicon Ultra, 3 kDa, manufactured by Merck Millipore, distilled water) was performed for concentration and removal of low-molecular weight reagents such as NMP. The final product was filtrated with a 0.20 μm membrane filter, and freeze-dried to yield 1085 nmol of the title compound.

B) Synthesis of Double-Stranded Nucleic Acid Agent Y48-HDO

The Y48-conjugated heteroduplex oligonucleotide (Y48-HDO), which was a double-stranded nucleic acid agent, was prepared in the same manner as in step B of Example 1 using the ASO (Malat1) (first strand) and the Y48-cRNA (Malat1) (second strand) obtained in the previous step A.

Example 49

A) Synthesis of cRNA Bound to Y49- at 5' End (Y49-cRNA (Malat1))

The title compound in an amount of 1176 nmol was produced in the same manner as in step A of Example 39 using an aqueous solution of the RNA strand (Y61-cRNA (Malat1)) (329 μL, 2000 nmol) as shown in Table 1, and IY49.

B) Synthesis of Double-Stranded Nucleic Acid Agent Y49-HDO

The Y49-conjugated heteroduplex oligonucleotide (Y49-HDO), which was a double-stranded nucleic acid agent, was prepared in the same manner as in step B of Example 1, using the ASO (Malat1) (first strand) and the Y49-cRNA (Malat1) (second strand) obtained in the previous step A.

Example 50

A) Synthesis of cRNA Bound to Y50- at 5' End (Y50-cRNA (Malat1))

The title compound in an amount of 674 nmol was produced in the same manner as in step A of Example 1 using an aqueous solution of the RNA strand (Y61-cRNA (Malat1)) (315 μL, 2000 nmol) as shown in Table 1, and IY50.

B) Synthesis of Double-Stranded Nucleic Acid Agent Y50-HDO

The Y50-conjugated heteroduplex oligonucleotide (Y50-HDO), which was a double-stranded nucleic acid agent, was prepared in the same manner as in step B of Example 1, using the ASO (Malat1) (first strand) and the Y50-cRNA (Malat1) (second strand) obtained in the previous step A.

Example 51

A) Synthesis of cRNA Bound to Y51- at 5' End (Y51-cRNA (Malat1))

The title compound in an amount of 827 nmol was produced in the same manner as in step A of Example 39 using an aqueous solution of the RNA strand (Y61-cRNA (Malat1)) (315 μL, 2000 nmol) as shown in Table 1, and IY51.

B) Synthesis of Double-Stranded Nucleic Acid Agent Y51-HDO

The Y51-conjugated heteroduplex oligonucleotide (Y51-HDO), which was a double-stranded nucleic acid agent, was prepared in the same manner as in step B of Example 1, using the ASO (Malat1) (first strand) and the Y51-cRNA (Malat1) (second strand) obtained in the previous step A.

Example 52

A) Synthesis of cRNA Bound to Y52- at 5' End (Y52-cRNA (Malat1))

The title compound in an amount of 653 nmol was produced in the same manner as in step A of Example 1 using an aqueous solution of the RNA strand (Y61-cRNA (Malat1)) (164 μL, 1000 nmol) as shown in Table 1, and IY52.

B) Synthesis of Double-Stranded Nucleic Acid Agent Y52-HDO

The Y52-conjugated heteroduplex oligonucleotide (Y52-HDO), which was a double-stranded nucleic acid agent, was prepared in the same manner as in step B of Example 1, using the ASO (Malat1) (first strand) and the Y52-cRNA (Malat1) (second strand) obtained in the previous step A.

Example 53

A) Synthesis of cRNA Bound to Y53- at 5' End (Y53-cRNA (Malat1))

The title compound in an amount of 865 nmol was produced in the same manner as in step A of Example 1 using an aqueous solution of the RNA strand (Y61-cRNA (Malat1)) (313 μL, 2000 nmol) as shown in Table 1, and IY53.

B) Synthesis of Double-Stranded Nucleic Acid Agent Y53-HDO

The Y53-conjugated heteroduplex oligonucleotide (Y53-HDO), which was a double-stranded nucleic acid agent, was prepared in the same manner as in step B of Example 1, using the ASO (Malat1) (first strand) and the Y53-cRNA (Malat1) (second strand) obtained in the previous step A.

Example 54

A) Synthesis of cRNA Bound to Y54- at 5' End (Y54-cRNA (Malat1))

The title compound in an amount of 1165 nmol was produced in the same manner as in step A of Example 1 using an aqueous solution of the RNA strand (Y61-cRNA (Malat1)) (313 μL, 2000 nmol) as shown in Table 1, and IY54.

B) Synthesis of Double-Stranded Nucleic Acid Agent Y54-HDO

The Y54-conjugated heteroduplex oligonucleotide (Y54-HDO), which was a double-stranded nucleic acid agent, was prepared in the same manner as in step B of Example 1, using the ASO (Malat1) (first strand) and the Y54-cRNA (Malat1) (second strand) obtained in the previous step A.

Example 55

A) Synthesis of cRNA Bound to Y55- at 5' End (Y55-cRNA (Malat1))

The title compound in an amount of 1401 nmol was produced in the same manner as in step A of Example 1 using an aqueous solution of the RNA strand (Y61-cRNA (Malat1)) (313 μL, 2000 nmol) as shown in Table 1, and IY55.

B) Synthesis of Double-Stranded Nucleic Acid Agent Y55-HDO

The Y55-conjugated heteroduplex oligonucleotide (Y55-HDO), which was a double-stranded nucleic acid agent, was prepared in the same manner as in step B of Example 1, using the ASO (Malat1) (first strand) and the Y55-cRNA (Malat1) (second strand) obtained in the previous step A.

Example 57

A) Synthesis of cRNA Bound to Y57- at 5' End (Y57-cRNA (Malat1))

The title compound in an amount of 641 nmol was produced in the same manner as in step A of Example 1 using an aqueous solution of the RNA strand (Y61-cRNA (Malat1)) (394 μL, 2500 nmol) as shown in Table 1, and IY57.

B) Synthesis of Double-Stranded Nucleic Acid Agent Y57-HDO

The Y57-conjugated heteroduplex oligonucleotide (Y57-HDO), which was a double-stranded nucleic acid agent, was prepared in the same manner as in step B of Example 1, using the ASO (Malat1) (first strand) and the Y57-cRNA (Malat1) (second strand) obtained in the previous step A.

Example 58

Synthesis of Double-Stranded Nucleic Acid Agent Y59-HDO

The Y59-conjugated heteroduplex oligonucleotide (Y59-HDO), which was a double-stranded nucleic acid agent, was prepared in the same manner as in step B of Example 1, using the ASO (Malat1) (first strand) and the Y59-cRNA (Malat1) (second strand) listed in Table 1.

Example 59

Synthesis of Double-Stranded Nucleic Acid Agent Y60-HDO

The Y60-conjugated heteroduplex oligonucleotide (Y60-HDO), which was a double-stranded nucleic acid agent, was prepared in the same manner as in step B of Example 1, using the ASO (Malat1) (first strand) and the Y60-cRNA (Malat1) (second strand) listed in Table 1.

Example 60

Synthesis of Double-Stranded Nucleic Acid Agent Chol-HDO

The Chol-conjugated heteroduplex oligonucleotide (Chol-HDO), which was a double-stranded nucleic acid agent, was prepared in the same manner as in step B of Example 1, using the ASO (Malat1) (first strand) and the Chol-cRNA (Malat1) (second strand) listed in Table 1.

Example 61

(A) Experiments In Vivo

Male 7-week-old C57BL/6J mice (Charles River Laboratories Japan Inc.) were used as experimental animals, and two to four mice per group were subjected to experiments. In the experimental group, a solution containing a nucleic acid was administered in a single dose of 5 mL/kg intravenously from the tail vein of a mouse. In the control group, the solvent used for preparing the nucleic acid solution (5% glucose solution) was intravenously administered to the mice in the same procedure as in the experimental group.

(B) Expression Analysis

Seventy-two hours after the administration of the nucleic acid solution, each mouse was anesthetized by intraperitoneal administration of 50 mg/kg of pentobarbital, and sacrificed after collection of the blood sample. The brain (cerebral cortex) was isolated. For extraction of total RNA from the brain tissues, an RNA extraction reagent ISOGEN (Nippon Gene Co., Ltd.) was used. The isolated brain tissue was homogenated in the ISOGEN solution, and then separated RNA fraction with chloroform. Thereafter, a nucleic acid separation system QuickGene RNA tissue kit SII (Kurabo Industries Ltd.) was carried out. For cDNA synthesis from the total RNA, a ReverTra Ace qPCR RT Kit (Toyobo Co., Ltd.) was used, and quantitative PCR was performed using a THUNDERBIRD qPCR Mix (Toyobo Co., Ltd.). For the quantitative PCR, a fluorescent probe method was applied, and as fluorescent probes, murine Malat1 (Integrated DNA Technologies), and murine Gapdh (Thermo Fisher Scientific) were used. Gene fragment amplification reaction conditions for the quantitative PCR were based on the protocol of the aforedescribed THUNDERBIRD qPCR Mix (Toyobo Co., Ltd.). The expression amounts of murine Malat1 and Gapdh (internal standard gene) were calculated using relative calibration curves and the relative expression level was calculated as Malat1/Gapdh. The mean relative expression level was calculated from the results of two to four mice per group. With the mean relative expression level of the control group being 100%, the mean relative expression level of the experimental group was calculated as the relative Malat1 ncRNA expression level.

(C) Results

The results of Example 61 are shown in Table 7. In the table, the dosage indicates the amount of the ASO (Malat1).

All of the double strand numbers 1, 3 to 55, 57, 59, and 60 inhibited expression of Malat1 non-coding RNA in the cerebral cortex. These results demonstrate that the nucleic acid complex of the present invention can be delivered to the brain, where it can produce an antisense effect.

TABLE 7

| Double strand No. | Dosage | Relative Malat1 ncRNA expression level |
|---|---|---|
| 1 | 50 mg/kg | 48% |
| 3 | 50 mg/kg | 82% |
| 4 | 50 mg/kg | 75% |
| 5 | 50 mg/kg | 89% |
| 6 | 50 mg/kg | 85% |
| 7 | 50 mg/kg | 70% |
| 8 | 50 mg/kg | 68% |
| 9 | 50 mg/kg | 90% |
| 10 | 50 mg/kg | 84% |
| 11 | 50 mg/kg | 60% |
| 12 | 50 mg/kg | 86% |
| 13 | 50 mg/kg | 62% |
| 14 | 50 mg/kg | 51% |
| 16 | 50 mg/kg | 66% |
| 17 | 50 mg/kg | 61% |
| 19 | 50 mg/kg | 76% |
| 20 | 50 mg/kg | 78% |
| 59 | 50 mg/kg | 49% |
| 60 | 50 mg/kg | 55% |
| 21 | 50 mg/kg | 90% |
| 22 | 50 mg/kg | 78% |
| 23 | 50 mg/kg | 87% |
| 24 | 50 mg/kg | 73% |
| 25 | 50 mg/kg | 96% |
| 26 | 50 mg/kg | 77% |
| 27 | 50 mg/kg | 67% |
| 28 | 50 mg/kg | 98% |
| 29 | 50 mg/kg | 60% |
| 30 | 50 mg/kg | 71% |
| 31 | 50 mg/kg | 68% |
| 32 | 50 mg/kg | 56% |
| 33 | 50 mg/kg | 62% |
| 34 | 50 mg/kg | 49% |
| 35 | 50 mg/kg | 56% |
| 36 | 50 mg/kg | 72% |
| 37 | 50 mg/kg | 68% |
| 38 | 50 mg/kg | 68% |
| 39 | 50 mg/kg | 61% |
| 40 | 50 mg/kg | 101% |
| 41 | 50 mg/kg | 75% |
| 42 | 50 mg/kg | 62% |
| 43 | 50 mg/kg | 60% |
| 44 | 50 mg/kg | 71% |
| 45 | 50 mg/kg | 79% |
| 46 | 50 mg/kg | 50% |
| 47 | 50 mg/kg | 70% |
| 48 | 50 mg/kg | 75% |
| 49 | 50 mg/kg | 59% |
| 50 | 50 mg/kg | 78% |
| 51 | 50 mg/kg | 62% |
| 52 | 50 mg/kg | 78% |
| 53 | 50 mg/kg | 83% |
| 54 | 50 mg/kg | 62% |
| 55 | 50 mg/kg | 75% |
| 57 | 50 mg/kg | 85% |

Example 62

(A) Experiments In Vivo

Male 10-week-old C57BL/6J mice (Charles River Laboratories Japan Inc.) were used as experimental animals, and three mice per group were subjected to experiments. In the experimental group, a solution containing a nucleic acid was administered in a single dose of 5 mL/kg intravenously from the tail vein of a mouse. In the control group, the solvent (physiological saline) used for preparing the nucleic acid solution was intravenously administered to the mice in the same procedure as in the experimental group.

(B) Isolation of Microglia

Seventy-two hours after the administration of the nucleic acid solution, the abdominal cavity of the mouse was opened under isoflurane anesthesia, the diaphragm was incised to expose the heart, physiological saline was injected into the left ventricle through an injection needle, the right atrium was incised to bleed, and then the brain was isolated. The brain was enzymatically treated using a Neural Tissue Dissociation Kits (Miltenyi Biotec) according to the protocol, and the debris were removed using a Debris Removal Solution (Miltenyi Biotec) to prepare the brain cell liquid. Microglia were isolated from the brain cell liquid using CD11b (Microglia) Microbeads (Miltenyi Biotec) according to the protocol.

(C) Expression Analysis

For extraction of total RNA from the isolated microglia, an RNeasy Micro Kit (QIAGEN) was used. For cDNA synthesis from the total RNA, a High Capacity cDNA RT Kit (Thermo Fisher Scientific) was used, and quantitative PCR was performed using a TaqMan Fast Advanced Master Mix (Thermo Fisher Scientific). For the quantitative PCR, a fluorescent probe method was applied, and as fluorescent probes, murine Malat1 (Thermo Fisher Scientific), and murine Gapdh (Thermo Fisher Scientific) were used. Gene fragment amplification reaction conditions for the quantitative PCR were based on the protocol of the aforedescribed TaqMan Fast Advanced Master Mix (Thermo Fisher Scientific). The expression amounts of murine Malat1 and Gapdh (internal standard gene) were calculated using a comparative Ct method, and the relative expression level was calculated as Malat1/Gapdh. The mean relative expression level was calculated from the results of three mice per group. With the mean relative expression level of the control group being 100%, the mean relative expression level of the experimental group was calculated as the relative Malat1 ncRNA expression level.

(D) Results

The results of Example 62 are shown in Table 8. In the table, the dosage indicates the amount of the ASO (Malat1).

The double strand number 58 inhibited expression of Malat1 non-coding RNA in microglia. These results demonstrate that the nucleic acid complex of the present invention can be delivered to the brain, and it can also produce an antisense effect in the microglia.

TABLE 8

| Double strand No. | Dosage | Relative Malat1 ncRNA expression level |
|---|---|---|
| 58 | 50 mg/kg | 22% |

All publications, patents, and patent applications cited herein are incorporated herein directly by reference.

The invention claimed is:

1. A nucleic acid complex comprising a first nucleic acid strand and a second nucleic acid strand, wherein:

the first nucleic acid strand comprises a base sequence capable of hybridizing to at least part of a target transcriptional product, and has an antisense effect on the target transcriptional product;

the second nucleic acid strand comprises a base sequence complementary to the first nucleic acid strand, and is bound to an analog of cholesterol;

said analog of cholesterol is represented by the following Formula (IIa):

(IIa)

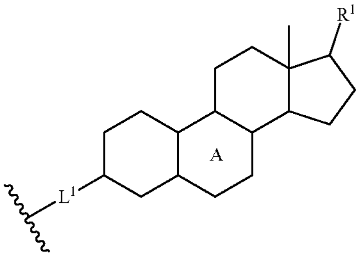

wherein:

the ring A represents a substituted or unsubstituted cyclohexene, $R^1$ represents a substituted or unsubstituted $C_{8-10}$ alkenyl group, or the ring A represents a substituted or unsubstituted cyclohexadiene, $R^1$ represents a substituted or unsubstituted $C_{8-10}$ alkyl group, or a substituted or unsubstituted $C_{8-10}$ alkenyl group, and $L^1$ represents —O—, —NH—, (III)

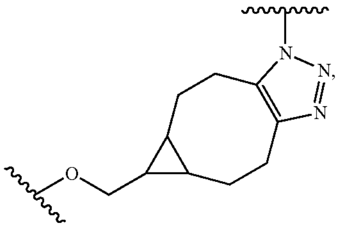

or (IV)

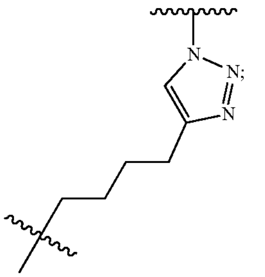

and the first nucleic acid strand is annealed to the second nucleic acid strand; and wherein the first nucleic acid strand and the second nucleic acid strand are at least 8 bases in length.

2. The nucleic acid complex according to claim 1, wherein said analog of cholesterol is represented by Formula (IIa-1):

(IIa-1)

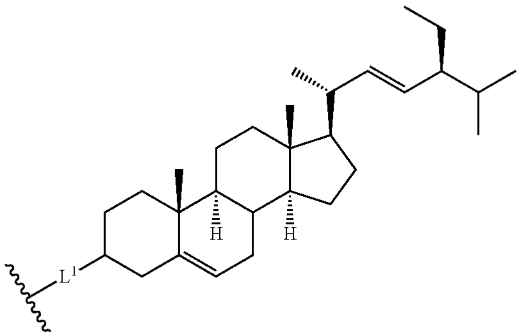

, wherein $L^1$ represents —O—, —NH—, (III)

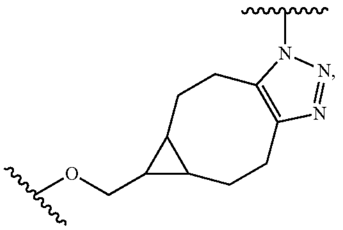

or (IV)

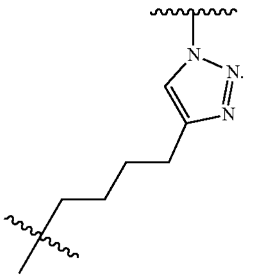

3. The nucleic acid complex according to claim 1, wherein the second nucleic acid strand is bound to the analog of cholesterol via a linker represented by the following Formula (VIII):

(VIII)

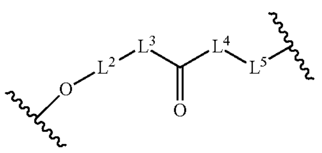

wherein:

$L^2$ represents a substituted or unsubstituted $C_{1-12}$ alkylene group, a substituted or unsubstituted $C_{3-8}$ cycloalkylene group, $—(CH_2)_2—O—(CH_2)_2—O—(CH_2)_2—O—(CH_2)_3—$, or $CH(CH_2—OH)—CH_2—O—(CH_2)_2—O—(CH_2)_2—O—(CH_2)_2—O—(CH_2)_3—$;

$L^3$ represents —NH— or a bond;

$L^4$ represents a substituted or unsubstituted $C_{1-12}$ alkylene group, a substituted or unsubstituted $C_{3-8}$ cycloalkylene group, $—(CH_2)_2—[O—(CH_2)_2]_m—$, or a bond, wherein m represents an integer of 1 to 25; and $L^5$ represents —NH—(C═O)—, —(C═O)—, or a bond).

4. The nucleic acid complex according to claim 1, wherein said first nucleic acid strand comprises at least four contiguous deoxyribonucleosides.

5. The nucleic acid complex according to claim 1, wherein said first nucleic acid strand is a gapmer.

6. The nucleic acid complex according to claim 4, wherein said second nucleic acid strand comprises at least four contiguous ribonucleosides complementary to at least four contiguous deoxyribonucleosides in said first nucleic acid strand.

7. The nucleic acid complex according to claim 1, wherein said first nucleic acid strand is a mixmer.

8. The nucleic acid complex according to claim 1, wherein said first nucleic acid strand is from 13 to 20 bases in length.

9. The nucleic acid complex according to claim 1, wherein said second nucleic acid strand does not comprise a natural ribonucleoside.

10. The nucleic acid complex according to claim 1, wherein said nucleic acid portion in the second nucleic acid strand consists of deoxyribonucleosides and/or sugar-modified nucleosides linked by a modified or unmodified internucleoside bond.

11. A method for regulating expression or editing of a target transcriptional product in the central nervous system of a subject, comprising intravenously or subcutaneously administering the nucleic acid complex according to claim 1 to the subject, wherein said analog of cholesterol bound to the second nucleic acid strand is a blood-brain barrier (BBB)-passing lipid ligand, and wherein said nucleic acid complex crosses the BBB.

12. The method according to claim 11 for treating a central nervous system disease of a subject.

13. The method according to claim 12, wherein said central nervous system disease is an immune-mediated central nervous system disease.

14. A method for delivering a drug to the central nervous system of a subject comprising intravenously or subcutaneously administering the nucleic acid complex according to claim 1 to the subject, wherein the drug is bound to the first nucleic acid strand and/or the second nucleic acid strand, wherein said analog of cholesterol bound to the second nucleic acid strand is a blood-brain barrier (BBB)-passing lipid ligand, and wherein said nucleic acid complex crosses the BBB.

15. The method according to claim 11, wherein said central nervous system is selected from the group consisting of cerebral cortex, basal ganglion, cerebral white matter, diencephalon, brainstem, and cerebellum.

16. The method according to claim 11, wherein said central nervous system is selected from the group consisting of frontal lobe, temporal lobe, hippocampus, parahippocampal gyrus, parietal lobe, occipital lobe, striatum, globus pallidus, claustrum, thalamus, subthalamic nucleus, midbrain, substantia nigra, pons, medulla oblongata, cerebellar cortex, and cerebellar nucleus.

17. The method according to claim 11, wherein 5 mg/kg or more of said nucleic acid complex is administered in a single dose.

18. The method according to claim 13, wherein said immune-mediated central nervous system disease is a microglia-associated disease.

19. The method according to claim 18, wherein said microglia-associated disease is Alzheimer's disease, multiple sclerosis, ALS, or neuropathic pain.

20. The method according to claim 11 for regulating expression or editing of a target transcriptional product in microglia.

21. The method according to claim 14, wherein said central nervous system is selected from the group consisting of cerebral cortex, basal ganglion, cerebral white matter, diencephalon, brainstem, and cerebellum.

22. The method according to claim 14, wherein said central nervous system is selected from the group consisting of frontal lobe, temporal lobe, hippocampus, parahippocampal gyrus, parietal lobe, occipital lobe, striatum, globus pallidus, claustrum, thalamus, subthalamic nucleus, midbrain, substantia nigra, pons, medulla oblongata, cerebellar cortex, and cerebellar nucleus.

23. The method according to claim 14 for intravenous administration or subcutaneous administration.

24. The method according to claim 14, wherein 5 mg/kg or more of said nucleic acid complex is administered in a single dose.

25. The method according to claim 14, wherein said nucleic acid complex crosses the blood-brain barrier (BBB).

26. The method according to claim 14 for regulating expression or editing of a target transcriptional product in microglia.

27. The nucleic acid complex according to claim 1, wherein said analog of cholesterol is represented by Formula (IIa-2):

(IIa-2)

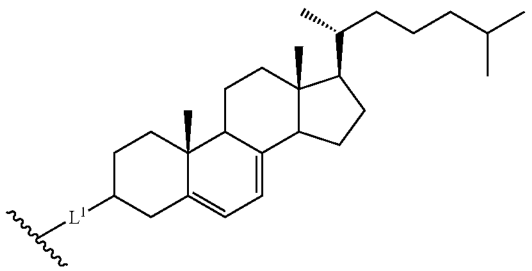

wherein $L^1$ represents —O—, —NH—, (III)

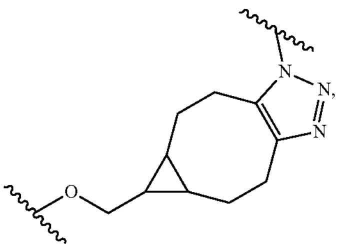

or

-continued
(IV)
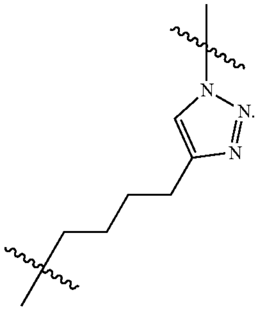
28. The nucleic acid complex according to claim 1, wherein said analog of cholesterol is represented by Formula (IIa-4):
(IIa-4)
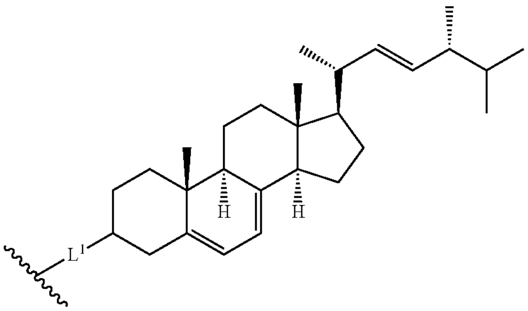
wherein $L^1$ represents —O—, —NH—,
(III)
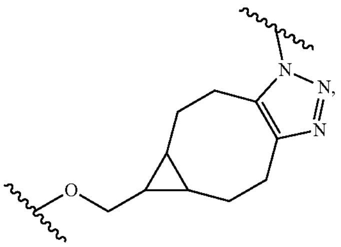
or
(IV)
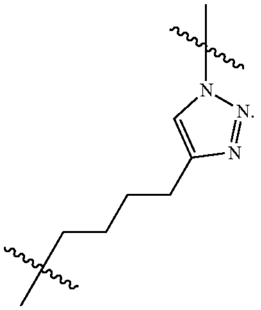
* * * * *

UNITED STATES PATENT AND TRADEMARK OFFICE

CERTIFICATE OF CORRECTION

PATENT NO. : 12,305,169 B2
APPLICATION NO. : 16/982758
DATED : May 20, 2025
INVENTOR(S) : Yokota et al.

It is certified that error appears in the above-identified patent and that said Letters Patent is hereby corrected as shown below:

On the Title Page

"(86) PCT No.: PCT/JP2019/011464" should be --(86) PCT/JP2019/012077--

Under (30) Foreign Application Priority data:
"Mar. 19, 2018 (JP)...........2018-051338" should be --Mar. 22, 2018 (JP) 2018-055372--

Signed and Sealed this
Twenty-sixth Day of August, 2025

Coke Morgan Stewart
*Acting Director of the United States Patent and Trademark Office*

SEQUENCE LISTING

<160> NUMBER OF SEQ ID NOS: 8

<210> SEQ ID NO 1
<211> LENGTH: 16
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (2)..(3), (14)..(15)
<223> OTHER INFORMATION: LNA
<220> FEATURE:
<221> NAME/KEY: misc_feature
<222> LOCATION: (1)..(1), (16)..(16)
<223> OTHER INFORMATION: 5-methylcytosine LNA

<400> SEQUENCE: 1
ctagttcact gaatgc 16

<210> SEQ ID NO 2
<211> LENGTH: 16
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3), (14)..(16)
<223> OTHER INFORMATION: 2'-O-Me RNA

<400> SEQUENCE: 2
gcauucagug aacuag 16

<210> SEQ ID NO 3
<211> LENGTH: 6982
<212> TYPE: DNA
<213> ORGANISM: Mus musculus
<220> FEATURE:
<223> OTHER INFORMATION: Malat1 non-coding RNA

<400> SEQUENCE: 3
aggcattcag gcagcgagag cagagcagcg tagagcagca cagctgagct cgtgaggcag 60
gagactcagc ccgaggaaat cgcagataag tttttaatta aaaagattga gcagtaaaaa 120
gaattagaac tctaaactta agctaataga gtagcttatc gaaatattac ttagtcttaa 180
taatctaaga agatcttaag agataacatg aaggcttatt taaacagttt gaaaaaggaa 240
atgaggagaa aagtatttgt actgtataat ggaggctgac cagagcagtt taggagattg 300
taaagggagg ttttgtgaag ttctaaaagg ttctagtttg aaggtcggcc ttgtagatta 360
aaacgaaggt tacctaaata gaatctaagt ggcatttaaa acagtaaagt tgtagagaat 420
agtttgaaaa tgaggtgtag ttttaaaaga ttgagaaaag taggttaagt tgacggccgt 480
tataaaaatc cttcgactgg cgcatgtacg tttgaaggca tgagttggaa acagggaaga 540
tggaagtgtt aggctagccg ggcgatggtg gcgcacgcct ttaatcctag cacttgggag 600
gcagaggcag gcggatttct gagttcgagg ccagcctggt ctacagagtg agttccagga 660
cagccagggc tacacagaga aaccctgtct tgaaaaaaca aaaaggttag gctagtattt 720
ggagaaagaa gattagaaaa tggaagtgaa agacgaagaa gacatacagg aaggtgaaga 780
aaaagctgtt agagaagata ggaaaataga agacaaagca tctttagaag acagaaaagg 840
tacttaaagg cacaggtagt aggaagccga agaatagaag atagaaagaa gcaagataga 900
aaaacaaaat ggaagttaag acaactttgg atgccagcat tcaagatagg caaagaagat 960

```
aagattgagg ccaaaaggtt ggataagata taaagtcaga aggaaattat ctttaaagcc   1020
ataagttcaa atttctgatg gagcgagcag tttagaagag tctttagaca gccacataca   1080
agattgaagc tagcaatcaa agctactagg actgaagtaa aaagttaagg cagaatgcct   1140
ttgaagagtt agaagaatat taaaagcctt aacttgtagc ttaattttgc ttgatgacaa   1200
aaggactttt gataacagtt tcaagattgt cagcattttg cattggactt gagctgaggt   1260
gcttttaaaa tcctaacgac tagcattggc agctgaccca ggtctacaca gaagtgcatt   1320
cagtgaacta ggaagacagg agcggcagac aggagtcccg aagccagttt ggtgaagcta   1380
ggaaggactg aggagccagc agcagcagtg catggtgaag atagcccagg aaagagtgcg   1440
gttcggtgga ggaagctagg aagaaggagc catacggatg tggtggtgaa gctgggaaag   1500
ggttccagga tggtggagcg agagcgagtt ggtgatgaag ctagctggcg gcttggcttg   1560
tcaactgcgc ggaggaggcg agcaggcatt gtggagagga tagatagcgg ctcctagacc   1620
agcatgccag tgtgcaagaa aggctgcagg gagagcatgc ggtgcggtaa cattccttga   1680
ggtcggcaac atggtggtgg ttttctgtaa cttggatggt aacttgttta ctttgtctta   1740
atagttatgg gggagttgta ggcttctgtg taaagagata tatctggggc tgtatgtagg   1800
cctttgcggg tgttgtaggt ttttcttttt cagggttatg tcctcttgca tcttgtcaga   1860
agcttttgag ggctgactgc caaggcccag aaagaagaat ggtagatggc aagttgtctt   1920
taaccgctca gaggggaatg aatggtagag ccagcacaac ctcccagttt tgtaagacgt   1980
tgtagtttga acagatgacc taccacaagc ctcactcctg tgtaggggag gtaattgggc   2040
aaagtgcttt tgggggaatg gggggcaaaat atattttgag ttcttttccc cttaggtctg   2100
tctagaatcc taaaggcaga tgactcaagg gaaccagaaa aaaggaaatc cactctcagg   2160
ataagcagag ctcgccaggt ttacagtttg taggaagtag aggatggatg ctagctttca   2220
cactgagtgt ggaggagctg gccatggcgg aattgctggt agtttactct ttccccctcc   2280
cttaatgaga tttgtaaaat cctaaacact tttacttgaa atatttggga gtggtcttaa   2340
cagggaggag tgggtggggg aaacgttttt tttctaagat tttccacaga tgctatagtt   2400
gtgttgacac actgggttag agaaggcgtg tactgctatg ctgttggcac gacaccttca   2460
gggactggag ctgccttttg tccttggaag agttttccca gttgccgctg aagtcagcac   2520
agtgcggctt tggttcacag tcacctcagg agaacctcag gagcttggct aggccagagg   2580
ttgaagttaa gttttacagc accgtgattt aaaatatttc attaaagggg aggggtaaaa   2640
cttagttggc tgtggccttg tgtttgggtg ggtgggggtg ttaggtaatt gtttagttta   2700
tgatttcaga taatcatacc agagaactta aatatttgga aaaacaggaa atctcagctt   2760
tcaagttggc aagtaactcc caatccagtt tttgcttctt ttttcctttt tcttttttttg   2820
aggcgggcag ctaaggaagg ttggttcctc tgccggtccc tcgaaagcgt agggcttggg   2880
ggttggtctg gtccactggg atgatgtgat gctacagtgg ggactcttct gaagctgttg   2940
gatgaatata gattgtagtg tgtggttctc ttttgaaatt tttttcaggt gacttaatgt   3000
atcttaataa ctactatagg aacaaaggaa gtggctttaa tgaccctgaa ggaatttctt   3060
ctggtgatag cttttatatt atcaagtaag agatactatc tcagttttgt ataagcaagt   3120
ctttttccta gtgtaggaga aatgattttc cttgtgacta aacaagatgt aaaggtatgc   3180
ttttttttctt cttgtgcatt gtatacttgt gtttatttgt aacttataat ttaagaatta   3240
tgataattca gcctgaatgt cttttagagg gtgggctttt gttgatgagg gaggggaaac   3300
```

-continued

```
cttttttttt ctgtagacct ttttcagata acaccatctg agtcataacc agcctggcag   3360
tgtgatgacg tagatgcaga gggagcagct ccttggtgaa tgagtgataa gtaaaggcag   3420
aaaaaataat gtcatgtctc catggggaat gagcatgagc cagagattgt tcctactgat   3480
gaaaagctgc atatgcaaaa atttaagcaa atgaaagcaa ccagtataaa gttatggcaa   3540
tacctttaaa agttatggct tatctaccaa gctttatcca caaaagtaaa gaattgatga   3600
aaaacagtga agatcaaatg ttcatctcaa aactgctttt acaaaagcag aatagaaatg   3660
aagtgaaaat gctgcattaa gcctggagta aaaagaagct gagcttgttg agatgagtgg   3720
gatcgagcgg ctgcgaggcg gtgcagtgtg ccaatgtttc gtttgcctca gacaggtttc   3780
tcttcataag cagaagagtt gcttcattcc atctcggagc aggaaacagc agactgctgt   3840
tgacagataa gtgtaacttg gatctgcagt attgcatgtt agggatagat aagtgccttt   3900
tttctctttt tccaaaaaga cctgtagagc tgttgaatgt ttgcagctgg cccctcttag   3960
gcagttcaga attttgagta gttttcccat ccagcctctt aaaaattcct aagccttgca   4020
ccgatgggct ttcatgatgg gatagctaat aggcttttgc atcgtaaact tcaacacaaa   4080
agcctacatg attaatgcct actttaatta cattgcttac aagattaagg aatctttatc   4140
ttgaagaccc catgaaaggg atcattatgt gctgaaaatt agatgttcat attgctaaaa   4200
tttaaatgtg ctccaatgta cttgtgctta aaatcattaa attatacaaa ttaataaaat   4260
acttcactag agaatgtatg tatttagaag gctgtctcct tatttaaata aagtcttgtt   4320
tgttgtctgt agttagtgtg ggcaattttg gggggatgtt cttctctaat cttttcagaa   4380
acttgacttc gaacacttaa gtggaccaga tcaggatttg agccagaaga ccgaaattaa   4440
ctttaaggca ggaaagacaa attttattct ccatgcagtg atgagcattt aataattgca   4500
ggcctggcat agaggccgtc taactaagga ctaagtacct taggcaggtg ggagatgatg   4560
gtcagagtaa aaggtaacta catattttgt ttccagaaag tcaggggtct aatttgacca   4620
tggctaaaca tctagggtaa gacacttttc ccccacattt ccaaatatgc atgttgagtt   4680
taaatgctta cgatcatctc atccacttta gccttttgtc acctcacttg agccacgagt   4740
ggggtcaggc atgtgggttt aaagagtttt cctttgcaga gcctcatttc atccttcatg   4800
gagctgctca ggactttgca tataagcgct tgcctctgtc ttctgttctg ctagtgagtg   4860
tgtgatgtga gaccttgcag tgagtttgtt tttcctggaa tgtggaggga ggggggggatg   4920
gggcttactt gttctagctt ttttttttaca gaccacacag aatgcaggtg tcttgacttc   4980
aggtcatgtc tgttctttgg caagtaatat gtgcagtact gttccaatct gctgctatta   5040
gaatgcattg tgacgcgact ggagtatgat taaagaaagt tgtgtttccc caagtgtttg   5100
gagtagtggt tgttggagga aaagccatga gtaacaggct gagtgttgag gaaatggctc   5160
tctgcagctt taagtaaccc gtgtttgtga ttggagccga gtccctttgc tgtgctgcct   5220
taggtaaatg tttttgttca tttctggtga ggggggttgg gagcactgaa gcctttagtc   5280
tcttccagat tcaacttaaa atctgacaag aaataaatca gacaagcaac attcttgaag   5340
aaattttaac tggcaagtgg aaatgttttg aacagttccg tggtctttag tgcattatct   5400
ttgtgtaggt gttctctctc ccctcccttg gtcttaattc ttacatgcag gaacattgac   5460
aacagcagac atctatctat tcaaggggcc agagaatcca gacccagtaa ggaaaaatag   5520
cccatttact ttaaatcgat aagtgaagca gacatgccat tttcagtgtg gggattggga   5580
agccctagtt ctttcagatg tacttcagac tgtagaagga gcttccagtt gaattgaaat   5640
tcaccagtgg acaaaatgag gacaacaggt gaacgagcct tttcttgttt aagattagct   5700
```

-continued actggtaatc tagtgttgaa tcctctccag cttcatgctg gagcagctag catgtgatgt 5760
aatgttggcc ttggggtgga ggggtgaggt gggcgctaag ccttttttta agatttttca 5820
ggtacccctc actaaaggca ctgaaggctt aatgtaggac agcggagcct tcctgtgtgg 5880
caagaatcaa gcaagcagta ttgtatcgag accaaagtgg tatcatggtc ggttttgatt 5940
agcagtgggg actaccctac cgtaacacct tgttggaatt gaagcatcca aagaaaatac 6000
ttgagaggcc ctgggcttgt tttaacatct ggaaaaaagg ctgtttttat agcagcggtt 6060
accagcccaa acctcaagtt gtgcttgcag gggagggaaa agggggaaag cgggcaacca 6120
gtttccccag cttttccaga atcctgttac aaggtctccc cacaagtgat ttctctgcca 6180
catcgccacc atgggccttt ggcctaatca cagacccttc acccctcacc ttgatgcagc 6240
cagtagctgg atccttgagg tcacgttgca tatcggtttc aaggtaacca tggtgccaag 6300
gtcctgtggg ttgcaccaga aaaggccatc aattttcccc ttgcctgtaa tttaacatta 6360
aaaccatagc taagatgttt tatacatagc acctatgcag agtaaacaaa ccagtatggg 6420
tatagtatgt ttgataccag tgctgggtgg gaatgtagga agtcggatga aaagcaagcc 6480
tttgtaggaa gttgttgggg tggattgcaa aaaattctct gctaagactt tttcaggtgg 6540
acataacaga cttggccaag ctagcatctt agtggaagca gattcgtcag tagggttgta 6600
aaggtttttc ttttcctgag aaaacaacct tttgttttct caggttttgc tttttggcct 6660
ttccctagct ttaaaaaaaa aaaagcaaaa gacgctggtg gctggcactc ctggtttcca 6720
ggacggggtt caagtccctg cggtgtcttt gcttgactct tatatcatga ggccattaca 6780
tttttcttgg agggttctaa aggctctggg tatggtagct gatatcactg gaacactccc 6840
cagcctcagt gttgaactct tgataattaa ctgcattgtc tttcaggtta tgcccaattc 6900
gtcttattac ctctgagtcg acacacctcc tactatttat tgaatacttt gattttatga 6960
aataaaaact aaatatctct ca 6982

<210> SEQ ID NO 4
<211> LENGTH: 8758
<212> TYPE: DNA
<213> ORGANISM: Homo sapiens
<220> FEATURE:
<223> OTHER INFORMATION: Malat1 non-coding RNA

<400> SEQUENCE: 4
gtaaaggact ggggccccgc aactggcctc tcctgccctc ttaagcgcag cgccatttta 60
gcaacgcaga agcccggcgc cgggaagcct cagctcgcct gaaggcaggt cccctctgac 120
gcctccggga gcccaggttt cccagagtcc ttgggacgca gcgacgagtt gtgctgctat 180
cttagctgtc cttataggct ggccattcca ggtggtggta tttagataaa accactcaaa 240
ctctgcagtt tggtcttggg gtttggagga aagcttttat ttttcttcct gctccggttc 300
agaaggtctg aagctcatac ctaaccaggc ataacacaga atctgcaaaa caaaaacccc 360
taaaaaagca gacccagagc agtgtaaaca cttctgggtg tgtccctgac tggctgccca 420
aggtctctgt gtcttcggag acaaagccat tcgcttagtt ggtctacttt aaaaggccac 480
ttgaactcgc tttccatggc gatttgcctt gtgagcactt tcaggagagc ctggaagctg 540
aaaaacggta gaaaaatttc cgtgcgggcc gtggggggct ggcggcaact ggggggccgc 600
agatcagagt gggccactgg cagccaacgg cccccggggc tcaggcgggg agcagctctg 660
tggtgtggga ttgaggcgtt ttccaagagt gggttttcac gtttctaaga tttcccaagc 720

-continued

```
agacagcccg tgctgctccg atttctcgaa caaaaaagca aaacgtgtgg ctgtcttggg    780
agcaagtcgc aggactgcaa gcagttgggg gagaaagtcc gccattttgc cacttctcaa    840
ccgtccctgc aaggctgggg ctcagttgcg taatggaaag taaagccctg aactatcaca    900
ctttaatctt ccttcaaaag gtggtaaact atacctactg tccctcaaga gaacacaaga    960
agtgctttaa gaggtatttt aaaagttccg gggttttgt gaggtgtttg atgacccgtt   1020
taaaatatga tttccatgtt tcttttgtct aaagtttgca gctcaaatct ttccacacgc   1080
tagtaattta agtatttctg catgtgtagt ttgcattcaa gttccataag ctgttaagaa   1140
aaatctagaa aagtaaaact agaacctatt tttaaccgaa gaactacttt ttgcctccct   1200
cacaaaggcg gcggaaggtg atcgaattcc ggtgatgcga gttgttctcc gtctataaat   1260
acgcctcgcc cgagctgtgc ggtaggcatt gaggcagcca gcgcaggggc ttctgctgag   1320
ggggcaggcg gagcttgagg aaaccgcaga taagtttttt tctctttgaa agatagagat   1380
taatacaact acttaaaaaa tatagtcaat aggttactaa gatattgctt agcgttaagt   1440
ttttaacgta attttaatag cttaagattt taagagaaaa tatgaagact tagaagagta   1500
gcatgaggaa ggaaaagata aaaggtttct aaaacatgac ggaggttgag atgaagcttc   1560
ttcatggagt aaaaaatgta tttaaaagaa aattgagaga aaggactaca gagccccgaa   1620
ttaataccaa tagaagggca atgcttttag attaaaatga aggtgactta aacagcttaa   1680
agtttagttt aaaagttgta ggtgattaaa ataatttgaa ggcgatcttt taaaaagaga   1740
ttaaaccgaa ggtgattaaa agaccttgaa atccatgacg cagggagaat tgcgtcattt   1800
aaagcctagt taacgcattt actaaacgca gacgaaaatg gaaagattaa ttgggagtgg   1860
taggatgaaa caatttggag aagatagaag tttgaagtgg aaaactggaa gacagaagta   1920
cgggaaggcg aagaaaagaa tagagaagat agggaaatta gaagataaaa acatactttt   1980
agaagaaaaa agataaattt aaacctgaaa agtaggaagc agaagaaaaa agacaagcta   2040
ggaaacaaaa agctaagggc aaaatgtaca aacttagaag aaaattggaa gatagaaaca   2100
agatagaaaa tgaaaatatt gtcaagagtt tcagatagaa aatgaaaaac aagctaagac   2160
aagtattgga gaagtataga agatagaaaa atataaagcc aaaaattgga taaaatagca   2220
ctgaaaaaat gaggaaatta ttggtaacca atttatttta aaagcccatc aatttaattt   2280
ctggtggtgc agaagttaga aggtaaagct tgagaagatg agggtgttta cgtagaccag   2340
aaccaattta gaagaatact tgaagctaga aggggaagtt ggttaaaaat cacatcaaaa   2400
agctactaaa aggactggtg taatttaaaa aaaactaagg cagaaggctt ttggaagagt   2460
tagaagaatt tggaaggcct taaatatagt agcttagttt gaaaaatgtg aaggactttc   2520
gtaacggaag taattcaaga tcaagagtaa ttaccaactt aatgtttttg cattggactt   2580
tgagttaaga ttattttta aatcctgagg actagcatta attgacagct gacccaggtg   2640
ctacacagaa gtggattcag tgaatctagg aagacagcag cagacaggat tccaggaacc   2700
agtgtttgat gaagctagga ctgaggagca agcgagcaag cagcagttcg tggtgaagat   2760
aggaaaagag tccaggagcc agtgcgattt ggtgaaggaa gctaggaaga aggaaggagc   2820
gctaacgatt tggtggtgaa gctaggaaaa aggattccag gaaggagcga gtgcaatttg   2880
gtgatgaagg tagcaggcgg cttggcttgg caaccacacg gaggaggcga gcaggcgttg   2940
tgcgtagagg atcctagacc agcatgccag tgtgccaagg ccacagggaa agcgagtggt   3000
tggtaaaaat ccgtgaggtc ggcaatatgt tgtttttctg gaacttactt atggtaacct   3060
tttatttatt ttctaatata atgggggagt ttcgtactga ggtgtaaagg gatttatatg   3120
```

```
gggacgtagg ccgatttccg ggtgttgtag gtttctcttt ttcaggctta tactcatgaa   3180
tcttgtctga agcttttgag ggcagactgc caagtcctgg agaaatagta gatggcaagt   3240
ttgtgggttt ttttttttta cacgaatttg aggaaaacca aatgaatttg atagccaaat   3300
tgagacaatt tcagcaaatc tgtaagcagt ttgtatgttt agttggggta atgaagtatt   3360
tcagttttgt gaatagatga cctgttttta cttcctcacc ctgaattcgt tttgtaaatg   3420
tagagtttgg atgtgtaact gaggcggggg ggagttttca gtattttttt ttgtgggggt   3480
gggggcaaaa tatgttttca gttctttttc ccttaggtct gtctagaatc ctaaaggcaa   3540
atgactcaag gtgtaacaga aaacaagaaa atccaatatc aggataatca gaccaccaca   3600
ggtttacagt ttatagaaac tagagcagtt ctcacgttga ggtctgtgga agagatgtcc   3660
attggagaaa tggctggtag ttactctttt ttccccccac cccctaatc agactttaaa   3720
agtgcttaac cccttaaact tgttattttt tacttgaagc attttgggat ggtcttaaca   3780
gggaagagag agggtggggg agaaaatgtt tttttctaag attttccaca gatgctatag   3840
tactattgac aaactgggtt agagaaggag tgtaccgctg tgctgttggc acgaacacct   3900
tcagggactg gagctgcttt tatccttgga agagtattcc cagttgaagc tgaaaagtac   3960
agcacagtgc agctttggtt catattcagt catctcagga gaacttcaga agagcttgag   4020
taggccaaat gttgaagtta agttttccaa taatgtgact tcttaaaagt tttattaaag   4080
gggaggggca aatattggca attagttggc agtggcctgt tacggttggg attggtgggg   4140
tgggtttagg taattgttta gtttatgatt gcagataaac tcatgccaga gaacttaaag   4200
tcttagaatg gaaaaagtaa agaaatatca acttccaagt tggcaagtaa ctcccaatga   4260
tttagttttt ttccccccag tttgaattgg gaagctgggg gaagttaaat atgagccact   4320
gggtgtacca gtgcattaat ttgggcaagg aaagtgtcat aatttgatac tgtatctgtt   4380
ttccttcaaa gtatagagct tttggggaag gaaagtattg aactgggggt tggtctggcc   4440
tactgggctg acattaacta caattatggg aaatgcaaaa gttgtttgga tatggtagtg   4500
tgtggttctc ttttggaatt tttttcaggt gatttaataa taatttaaaa ctactataga   4560
aactgcagag caaaggaagt ggcttaatga tcctgaaggg atttcttctg atggtagctt   4620
ttgtattatc aagtaagatt ctattttcag ttgtgtgtaa gcaagttttt ttttagtgta   4680
ggagaaatac ttttccattg tttaactgca aaacaagatg ttaaggtatg cttcaaaaat   4740
tttgtaaatt gtttatttta aacttatctg tttgtaaatt gtaactgatt aagaattgtg   4800
atagttcagc ttgaatgtct cttagagggt gggcttttgt tgatgaggga ggggaaactt   4860
ttttttttc tatagacttt tttcagataa catcttctga gtcataacca gcctggcagt   4920
atgatggcct agatgcagag aaaacagctc cttggtgaat tgataagtaa aggcagaaaa   4980
gattatatgt catacctcca ttggggaata agcataaccc tgagattctt actactgatg   5040
agaacattat ctgcatatgc caaaaaattt taagcaaatg aaagctacca atttaaagtt   5100
acggaatcta ccattttaaa gttaattgct tgtcaagcta taaccacaaa aataatgaat   5160
tgatgagaaa tacaatgaag aggcaatgtc catctcaaaa tactgctttt acaaaagcag   5220
aataaaagcg aaaagaaatg aaaatgttac actacattaa tcctggaata aaagaagccg   5280
aaataaatga gagatgagtt gggatcaagt ggattgagga ggctgtgctg tgtgccaatg   5340
tttcgtttgc ctcagacagg tatctcttcg ttatcagaag agttgcttca tttcatctgg   5400
gagcagaaaa cagcaggcag ctgttaacag ataagtttaa cttgcatctg cagtattgca   5460
```

-continued

```
tgttagggat aagtgcttat ttttaagagc tgtggagttc ttaaatatca accatggcac   5520
tttctcctga ccccttccct aggggatttc aggattgaga aatttttcca tcgagccttt   5580
ttaaaattgt aggacttgtt cctgtgggct tcagtgatgg gatagtacac ttcactcaga   5640
ggcatttgca tctttaaata atttcttaaa agcctctaaa gtgatcagtg ccttgatgcc   5700
aactaaggaa atttgtttag cattgaatct ctgaaggctc tatgaaagga atagcatgat   5760
gtgctgttag aatcagatgt tactgctaaa atttacatgt tgtgatgtaa attgtgtaga   5820
aaaccattaa atcattcaaa ataataaact atttttatta gagaatgtat acttttagaa   5880
agctgtctcc ttatttaaat aaaatagtgt ttgtctgtag ttcagtgttg gggcaatctt   5940
gggggggatt cttctctaat ctttcagaaa ctttgtctgc gaacactctt taatggacca   6000
gatcaggatt tgagcggaag aacgaatgta actttaaggc aggaaagaca aattttattc   6060
ttcataaagt gatgagcata taataattcc aggcacatgg caatagaggc cctctaaata   6120
aggaataaat aacctcttag acaggtggga gattatgatc agagtaaaag gtaattacac   6180
atttatttc cagaaagtca ggggtctata aattgacagt gattagagta atactttttc   6240
acatttccaa agtttgcatg ttaactttaa atgcttacaa tcttagagtg gtaggcaatg   6300
ttttacacta ttgaccttat atagggaagg gagggggtgc ctgtggggtt ttaaagaatt   6360
ttcctttgca gaggcatttc atccttcatg aagccattca ggattttgaa ttgcatatga   6420
gtgcttggct cttccttctg ttctagtgag tgtatgagac cttgcagtga gtttatcagc   6480
atactcaaaa tttttttcct ggaatttgga gggatgggag gagggggtgg ggcttacttg   6540
ttgtagcttt tttttttttt acagacttca cagagaatgc agttgtcttg acttcaggtc   6600
tgtctgttct gttggcaagt aaatgcagta ctgttctgat cccgctgcta ttagaatgca   6660
ttgtgaaacg actggagtat gattaaaagt tgtgttcccc aatgcttgga gtagtgattg   6720
ttgaaggaaa aaatccagct gagtgataaa ggctgagtgt tgaggaaatt tctgcagttt   6780
taagcagtcg tatttgtgat tgaagctgag tacattttgc tggtgtattt ttaggtaaaa   6840
tgctttttgt tcatttctgg tggtgggagg ggactgaagc ctttagtctt ttccagatgc   6900
aaccttaaaa tcagtgacaa gaaacattcc aaacaagcaa cagtcttcaa gaaattaaac   6960
tggcaagtgg aaatgtttaa acagttcagt gatctttagt gcattgttta tgtgtgggtt   7020
tctctctccc ctcccttggt cttaattctt acatgcagga acactcagca gacacacgta   7080
tgcgaagggc cagagaagcc agacccagta agaaaaaata gcctatttac tttaaataaa   7140
ccaaacattc cattttaaat gtggggattg ggaaccacta gttctttcag atggtattct   7200
tcagactata gaaggagctt ccagttgaat tcaccagtgg acaaaatgag gaaaacaggt   7260
gaacaagctt tttctgtatt tacatacaaa gtcagatcag ttatgggaca atagtattga   7320
atagatttca gctttatgct ggagtaactg gcatgtgagc aaactgtgtt ggcgtggggg   7380
tggaggggtg aggtgggcgc taagcctttt tttaagattt ttcaggtacc cctcactaaa   7440
ggcaccgaag gcttaaagta ggacaaccat ggagccttcc tgtggcagga gagacaacaa   7500
agcgctatta tcctaaggtc aagagaagtg tcagcctcac ctgattttta ttagtaatga   7560
ggacttgcct caactccctc tttctggagt gaagcatccg aaggaatgct tgaagtaccc   7620
ctgggcttct cttaacattt aagcaagctg tttttatagc agctcttaat aataaagccc   7680
aaatctcaag cggtgcttga aggggaggga aagggggaaa gcgggcaacc acttttccct   7740
agcttttcca gaagcctgtt aaaagcaagg tctccccaca agcaacttct ctgccacatc   7800
gccaccccgt gcctttttgat ctagcacaga cccttcaccc ctcacctcga tgcagccagt   7860
```

agcttggatc cttgtgggca tgatccataa tcggtttcaa ggtaacgatg gtgtcgaggt 7920
ctttggtggg ttgaactatg ttagaaaagg ccattaattt gcctgcaaat tgttaacaga 7980
agggtattaa aaccacagct aagtagctct attataatac ttatccagtg actaaaacca 8040
acttaaacca gtaagtggag aaataacatg ttcaagaact gtaatgctgg gtgggaacat 8100
gtaacttgta gactggagaa gataggcatt tgagtggctg agagggcttt tgggtgggaa 8160
tgcaaaaatt ctctgctaag actttttcag gtgaacataa cagacttggc caagctagca 8220
tcttagcgga agctgatctc caatgctctt cagtagggtc atgaaggttt ttcttttcct 8280
gagaaaacaa cacgtattgt tttctcaggt tttgcttttt ggcctttttc tagcttaaaa 8340
aaaaaaaaag caaaagatgc tggtggttgg cactcctggt ttccaggacg gggttcaaat 8400
ccctgcggcg tctttgcttt gactactaat ctgtcttcag gactctttct gtatttctcc 8460
ttttctctgc aggtgctagt tcttggagtt ttggggaggt gggaggtaac agcacaatat 8520
ctttgaacta tatacatcct tgatgtataa tttgtcagga gcttgacttg attgtatatt 8580
catatttaca cgagaaccta atataactgc cttgtctttt tcaggtaata gcctgcagct 8640
ggtgttttga gaagccctac tgctgaaaac ttaacaattt tgtgtaataa aaatggagaa 8700
gctctaaatt gttgtggttc ttttgtgaat aaaaaaatct tgattgggga aaaaaaaa 8758

<210> SEQ ID NO 5
<211> LENGTH: 2534
<212> TYPE: DNA
<213> ORGANISM: Mus musculus
<220> FEATURE:
<223> OTHER INFORMATION: SR-B1 mRNA

<400> SEQUENCE: 5
ggaatcccgc gccgaactcg ggggcgggct gcccgggcca tggcgcataa agcctctggc 60
cacctgcagg gctactgctg ctccggccac cgccaggcac acaccttgct gctgagggag 120
tctcggcttc tgtcatctct gtggcctccg tcacctctgt ctccgtctcc ttcaggtcct 180
gagccccgag agccccttcc gcgcacgcgg acatgggcgg cagctccagg gcgcgctggg 240
tggccttggg gttgggcgcc ctggggctgc tgtttgctgc gctcggcgtt gtcatgatcc 300
tcatggtgcc ctccctcatc aagcagcagg tgctcaagaa tgtccgcata gacccgagca 360
gcctgtcctt cgggatgtgg aaggagatcc ccgtcccttt ctacttgtct gtctacttct 420
tcgaagtggt caacccaaac gaggtcctca acggccagaa gccagtagtc cgggagcgtg 480
gaccctatgt ctacagggag ttcagacaaa aggtcaacat caccttcaat gacaacgaca 540
ccgtgtcctt cgtggagaac cgcagcctcc atttccagcc tgacaagtcg catggctcag 600
agagtgacta cattgtactg cctaacatct tggtcctggg gggctcgata ttgatggaga 660
gcaagcctgt gagcctgaag ctgatgatga ccttggcgct ggtcaccatg ggccagcgtg 720
cttttatgaa ccgcacagtt ggtgagatcc tgtggggcta tgacgatccc ttcgtgcatt 780
ttctcaacac gtacctccca gacatgcttc ccataaaggg caaatttggc ctgtttgttg 840
ggatgaacaa ctcgaattct ggggtcttca ctgtcttcac gggcgtccag aatttcagca 900
ggatccatct ggtggacaaa tggaacggac tcagcaagat cgattattgg cattcagagc 960
agtgtaacat gatcaatggg acttccgggc agatgtgggc acccttcatg acacccgaat 1020
cctcgctgga attcttcagc ccggaggcat gcaggtccat gaagctgacc tacaacgaat 1080
caagggtgtt tgaaggcatt cccacgtatc gcttcacggc cccgatact ctgtttgcca 1140 acgggtccgt ctacccaccc aacgaaggct tctgcccatg ccgagagtct ggcattcaga 1200
atgtcagcac ctgcaggttt ggtgcgcctc tgtttctctc ccaccccac ttttacaacg 1260 ccgaccctgt gttgtcagaa gctgttcttg gtctgaaccc taacccaaag gagcattcct 1320
tgttcctaga catccatccg gtcactggga tccccatgaa ctgttctgtg aagatgcagc 1380
tgagcctcta catcaaatct gtcaagggca tcgggcaaac agggaagatc gagccagtag 1440
ttctgccgtt gctgtggttc gaacagagcg gagcaatggg tggcaagccc ctgagcacgt 1500
tctacacgca gctggtgctg atgccccagg ttcttcacta cgcgcagtat gtgctgctgg 1560
ggcttggagg cctcctgttg ctggtgccca tcatctgcca actgcgcagc caggagaaat 1620
gctttttgtt ttggagtggt agtaaaaagg gctcccagga taaggaggcc attcaggcct 1680
actctgagtc cctgatgtca ccagctgcca agggcacggt gctgcaagaa gccaagctat 1740
agggtcctga agacactata agcccccaa acctgatagc ttggtcagac cagccaccca 1800
gtccctacac cccgcttctt gaggactctc tcagcggaca gcccaccagt gccatggcct 1860
gagcccccag atgtcacacc tgtccgcacg cacggcacat ggatgcccac gcatgtgcaa 1920
aaacaactca gggaccaggg acagacctgc tgccaagtga gcctgatggg ccacaggtgt 1980
gctcttctaa atggcctgtg agccaggctg tgggaactct agctgctgtc agcccctcct 2040
gtaggagctg gccctgccca ggctcctgac ttccctcagg aagtctttct gtctttctcc 2100
atcagtctga aagccttagt tcccacagag gacggatctg tcactcctag ggctgggca 2160 tatgtcggcc tcttgtgcca aggccaggca agcagctcca ggtcctgacc agtttgcaca 2220
cacactctgg agctgtatct ggcgcttttt ctatcgtctc tgctatgtca ctgaattaac 2280
cactgtacgt ggcagaggtg gcaggcccct cagggtcctt atttttcagg catggggtca 2340
aagctagagg tatgggccgt ctacaccccc ccgcccccg gcatctagtg tacctcacca 2400
gagggtattc ggaggcccag catcctgcaa ccgacccctt ttttctactg gaagagaaat 2460
tttatcatct tttgaaagga agtcatgact gaagcaataa accttttcac tgattcaaca 2520
aaaaaaaaaa aaaa 2534

<210> SEQ ID NO 6
<211> LENGTH: 2759
<212> TYPE: DNA
<213> ORGANISM: Homo sapiens
<220> FEATURE:
<223> OTHER INFORMATION: SR-B1 mRNA

<400> SEQUENCE: 6
gctcaggccc cgcccctgcc gccggaatcc tgaagcccaa ggctgcccgg gggcggtccg 60
gcggcgccgg cgatggggca taaaaccact ggccacctgc cgggctgctc ctgcgtgcgc 120
tgccgtcccg gatccaccgt gcctctgcgg cctgcgtgcc cggagtcccc gcctgtgtcg 180
tctctgtcgc cgtccccgtc tcctgccagg cgcggagccc tgcgagccgc gggtgggccc 240
caggcgcgca gacatgggct gctccgccaa agcgcgctgg gctgccgggg cgctgggcgt 300
cgcggggcta ctgtgcgctg tgctgggcgc tgtcatgatc gtgatggtgc cgtcgctcat 360
caagcagcag gtccttaaga acgtgcgcat cgaccccagt agcctgtcct tcaacatgtg 420
gaaggagatc cctatcccct tctatctctc cgtctacttc tttgacgtca tgaaccccag 480
cgagatcctg aagggcgaga agccgcaggt gcgggagcgc gggccctacg tgtacaggga 540
gttcaggcac aaaagcaaca tcaccttcaa caacaacgac accgtgtcct tcctcgagta 600
ccgcaccttc cagttccagc cctccaagtc ccacggctcg gagagcgact acatcgtcat 660

-continued

```
gcccaacatc ctggtcttgg gtgcggcggt gatgatggag aataagccca tgaccctgaa    720
gctcatcatg accttggcat tcaccaccct cggcgaacgt gccttcatga accgcactgt    780
gggtgagatc atgtggggct acaaggaccc ccttgtgaat ctcatcaaca agtactttcc    840
aggcatgttc cccttcaagg acaagttcgg attatttgct gagctcaaca actccgactc    900
tgggctcttc acggtgttca cgggggtcca gaacatcagc aggatccacc tcgtggacaa    960
gtggaacggg ctgagcaagg ttgacttctg gcattccgat cagtgcaaca tgatcaatgg   1020
aacttctggg caaatgtggc cgcccttcat gactcctgag tcctcgctgg agttctacag   1080
cccggaggcc tgccgatcca tgaagctaat gtacaaggag tcaggggtgt ttgaaggcat   1140
ccccacctat cgcttcgtgg ctcccaaaac cctgtttgcc aacgggtcca tctacccacc   1200
caacgaaggc ttctgcccgt gcctggagtc tggaattcag aacgtcagca cctgcaggtt   1260
cagtgccccc ttgtttctct cccatcctca cttcctcaac gctgacccgg ttctggcaga   1320
agcggtgact ggcctgcacc ctaaccagga ggcacactcc ttgttcctgg acatccaccc   1380
ggtcacggga atccccatga actgctctgt gaaactgcag ctgagcctct acatgaaatc   1440
tgtcgcaggc attggacaaa ctgggaagat tgagcctgtg gtcctgccgc tgctctggtt   1500
tgcagagagc ggggccatgg agggggagac tcttcacaca ttctacactc agctggtgtt   1560
gatgcccaag gtgatgcact atgcccagta cgtcctcctg gcgctgggct gcgtcctgct   1620
gctggtccct gtcatctgcc aaatccggag ccaagagaaa tgctatttat tttggagtag   1680
tagtaaaaag ggctcaaagg ataaggaggc cattcaggcc tattctgaat ccctgatgac   1740
atcagctccc aagggctctg tgctgcagga agcaaaactg tagggtcctg aggacaccgt   1800
gagccagcca ggcctggccg ctgggcctga ccggcccccc agcccctaca ccccgcttct   1860
cccggactct cccagcggac agccccccag ccccacagcc tgagcctccc agctgccatg   1920
tgcctgttgc acacctgcac acacgccctg gcacacatac acacatgcgt gcaggcttgt   1980
gcagacactc agggatggag ctgctgctga agggacttgt agggagaggc tcgtcaacaa   2040
gcactgttct ggaaccttct ctccacgtgg cccacaggcc tgaccacagg ggctgtgggt   2100
cctgcgtccc cttcctcggg tgagcctggc ctgtcccgtt cagccgttgg gcccaggctt   2160
cctcccctcc aaggtgaaac actgcagtcc cggtgtggtg gctccccatg caggacgggc   2220
caggctggga gtgccgcctt cctgtgccaa attcagtggg gactcagtgc ccaggccctg   2280
gccacgagct ttggccttgg tctacctgcc aggccaggca aagcgccttt acacaggcct   2340
cggaaaacaa tggagtgagc acaagatgcc ctgtgcagct gcccgagggt ctccgcccac   2400
cccggccgga ctttgatccc cccgaagtct tcacaggcac tgcatcgggt tgtctggcgc   2460
ccttttcctc cagcctaaac tgacatcatc ctatggactg agccggccac tctctggccg   2520
aagtggccgc aggctgtgcc cccgagctgc ccccaccccc tcacagggtc cctcagatta   2580
taggtgccca ggctgaggtg aagaggcctg ggggccctgc cttccgggcg ctcctggacc   2640
ctggggcaaa cctgtgaccc ttttctactg gaatagaaat gagttttatc atctttgaaa   2700
aataattcac tcttgaagta ataaacgttt aaaaaaatgg gaaaaaaaaa aaaaaaaaa    2759
```

<210> SEQ ID NO 7
<211> LENGTH: 2761
<212> TYPE: DNA
<213> ORGANISM: Mus musculus
<220> FEATURE:
<223> OTHER INFORMATION: DMPK mRNA

<400> SEQUENCE: 7
gaactggcca gagagaccca agggatagtc agggacgggc agacatgcag ctagggttct 60
ggggcctgga caggggcagc caggccctgt gacgggaaga ccccgagctc cggcccgggg 120
aggggccatg gtgttgcctg cccaacatgt cagccgaagt gcggctgagg cagctccagc 180
agctggtgct ggacccaggc ttcctgggac tggagcccct gctcgacctt ctcctgggcg 240
tccaccagga gctgggtgcc tctcacctag cccaggacaa gtatgtggcc gacttcttgc 300
agtgggtgga gcccattgca gcaaggctta aggaggtccg actgcagagg gatgattttg 360
agattttgaa ggtgatcggg cgtggggcgt tcagcgaggt agcggtggtg aagatgaaac 420
agacgggcca agtgtatgcc atgaagatta tgaataagtg ggacatgctg aagagaggcg 480
aggtgtcgtg cttccgggaa gaaagggatg tattagtgaa aggggaccgg cgctggatca 540
cacagctgca ctttgccttc caggatgaga actacctgta cctggtcatg gaatactacg 600
tgggcgggga cctgctaacg ctgctgagca agtttgggga gcggatcccc gccgagatgg 660
ctcgcttcta cctggccgag attgtcatgg ccatagactc cgtgcaccgg ctgggctacg 720
tgcacaggga catcaaacca gataacattc tgctggaccg atgtgggcac attcgcctgg 780
cagacttcgg ctcctgcctc aaactgcagc ctgatggaat ggtgaggtcg ctggtggctg 840
tgggcacccc ggactacctg tctcctgaga ttctgcaggc cgttggtgga gggcctgggg 900
caggcagcta cgggccagag tgtgactggt gggcactggg cgtgttcgcc tatgagatgt 960
tctatgggca gacccccttc tacgcggact ccacagccga gacatatgcc aagattgtgc 1020
actacaggga acacttgtcg ctgccgctgg cagacacagt tgtccccgag gaagctcagg 1080
acctcattcg tgggctgctg tgtcctgctg agataaggct aggtcgaggt ggggcaggtg 1140
atttccagaa acatcctttc ttctttggcc ttgattggga gggtctccga gacagtgtac 1200
ccccctttac accagacttc gagggtgcca cggacacatg caatttcgat gtggtggagg 1260
accggctcac tgccatggtg agcgggggcg gggagacgct gtcagacatg caggaagaca 1320
tgccccttgg ggtgcgcctg cccttcgtgg gctactccta ctgctgcatg gccttcagag 1380
acaatcaggt cccggacccc accccctatgg aactagaggc cctgcagttg cctgtgtcag 1440
acttgcaagg gcttgacttg cagcccccag tgtccccacc ggatcaagtg gctgaagagg 1500
ctgacctagt ggctgtccct gcccctgtgg ctgaggcaga gaccacggta acgctgcagc 1560
agctccagga agccctggaa gaagaggttc tcacccggca gagcctgagc cgcgagctgg 1620
aggccatccg gaccgccaac cagaacttct ccagccaact acaggaggcc gaggtccgaa 1680
accgagacct ggaggcgcat gttcggcagc tacaggaacg gatggagatg ctgcaggccc 1740
caggagccgc agccatcacg gggtccccca gtccccgggc cacggatcca ccttcccatc 1800
tagatggccc ccggccgtg gctgtgggcc agtgcccgct ggtggggcca ggccccatgc 1860
accgccgtca cctgctgctc cctgccagga tccctaggcc tggcctatcc gaggcgcgtt 1920
gcctgctcct gttcgccgct gctctggctg ctgccgccac actgggctgc actgggttgg 1980
tggcctatac cggcggtctc accccagtct ggtgtttccc gggagccacc ttcgcccccct 2040
gaaccctaag actccaagcc atctttcatt taggcctcct aggaaggtcg agcgaccagg 2100
gagcgaccca aagcgtctct gtgcccatcg cgcccccccc ccccccccac cgctccgctc 2160
cacacttctg tgagcctggg tccccaccca gctccgctcc tgtgatccag gcctgccacc 2220
tggcggccgg ggagggagga acagggctcg tgcccagcac ccctggttcc tgcagagctg 2280
gtagccaccg ctgctgcagc agctgggcat tcgccgacct tgctttactc agccccgacg 2340

```
tggatgggca aactgctcag ctcatccgat ttcacttttt cactctccca gccatcagtt   2400

acaagccata agcatgagcc ccctatttcc agggacatcc cattcccata gtgatggatc   2460

agcaagacct ctgccagcac acacggagtc tttggcttcg gacagcctca ctcctggggg   2520

ttgctgcaac tccttccccg tgtacacgtc tgcactctaa caacggagcc acagctgcac   2580

tccccccctcc cccaaagcag tgtgggtatt tattgatctt gttatctgac tcactgacag   2640

actccgggac ccacgtttta gatgcattga gactcgacat tcctcggtat ttattgtctg   2700

tccccaccta cgacctccac tcccgaccct tgcgaataaa atacttctgg tctgccctaa   2760

a                                                                   2761
```

<210> SEQ ID NO 8
<211> LENGTH: 3243
<212> TYPE: DNA
<213> ORGANISM: Homo sapiens
<220> FEATURE:
<223> OTHER INFORMATION: DMPK mRNA

<400> SEQUENCE: 8

```
gccacaagcc tccaccccag ctggtccccc acccaggctg cccagtttaa cattcctagt     60

cataggacct tgacttctga gaggcctgat tgtcatctgt aaataagggg taggactaaa    120

gcactcctcc tggaggactg agagatgggc tggaccggag cacttgagtc tgggatatgt    180

gaccatgcta cctttgtctc cctgtcctgt tccttccccc agccccaaat ccagggtttt    240

ccaaagtgtg gttcaagaac cacctgcatc tgaatctaga ggtactggat acaaccccac    300

gtctgggccg ttacccagga cattctacat gagaacgtgg gggtggggcc ctggctgcac    360

ctgaactgtc acctggagtc agggtggaag gtggaagaac tgggtcttat ttccttctcc    420

ccttgttctt tagggtctgt ccttctgcag actccgttac cccaccctaa ccatcctgca    480

caccccttgga gccctctggg ccaatgccct gtcccgcaaa gggcttctca ggcatctcac    540

ctctatggga gggcattttt ggcccccaga accttacacg gtgtttatgt ggggaagccc    600

ctgggaagca gacagtccta gggtgaagct gagaggcaga gagaagggga gacagacaga    660

gggtggggct ttccccccttg tctccagtgc cctttctggt gaccctcggt tcttttcccc    720

caccaccccc ccagcggagc ccatcgtggt gaggcttaag gaggtccgac tgcagaggga    780

cgacttcgag attctgaagg tgatcggacg cggggcgttc agcgaggtag cggtagtgaa    840

gatgaagcag acgggccagg tgtatgccat gaagatcatg aacaagtggg acatgctgaa    900

gaggggcgag gtgtcgtgct tccgtgagga gagggacgtg ttggtgaatg gggaccggcg    960

gtggatcacg cagctgcact tcgccttcca ggatgagaac tacctgtacc tggtcatgga   1020

gtattacgtg ggcggggacc tgctgacact gctgagcaag tttggggagc ggattccggc   1080

cgagatggcg cgcttctacc tggcggagat tgtcatggcc atagactcgg tgcaccggct   1140

tggctacgtg cacagggaca tcaaacccga caacatcctg ctggaccgct gtggccacat   1200

ccgcctggcc gacttcggct cttgcctcaa gctgcgggca gatggaacgg tgcggtcgct   1260

ggtggctgtg ggcaccccag actacctgtc cccgagatc ctgcaggctg tgggcggtgg   1320
```

-continued

```
gcctgggaca ggcagctacg ggcccgagtg tgactggtgg gcgctgggtg tattcgccta   1380
tgaaatgttc tatgggcaga cgcccttcta cgcggattcc acggcggaga cctatggcaa   1440
gatcgtccac tacaaggagc acctctctct gccgctggtg gacgaagggg tccctgagga   1500
ggctcgagac ttcattcagc ggttgctgtg tcccccggag acacggctgg gccggggtgg   1560
agcaggcgac ttccggacac atcccttctt ctttggcctc gactgggatg gtctccggga   1620
cagcgtgccc ccctttacac cggatttcga aggtgccacc gacacatgca acttcgactt   1680
ggtggaggac gggctcactg ccatggtgag cgggggcggg gagacactgt cggacattcg   1740
ggaaggtgcg ccgctagggg tccacctgcc ttttgtgggc tactcctact cctgcatggc   1800
cctcagggac agtgaggtcc caggccccac acccatggaa ctggaggccg agcagctgct   1860
tgagccacac gtgcaagcgc ccagcctgga gccctcggtg tccccacagg atgaaacagc   1920
tgaagtggca gttccagcgg ctgtccctgc ggcagaggct gaggccgagg tgacgctgcg   1980
ggagctccag gaagccctgg aggaggaggt gctcacccgg cagagcctga gccgggagat   2040
ggaggccatc cgcacggaca accagaactt cgccagtcaa ctacgcgagg cagaggctcg   2100
gaaccgggac ctagaggcac acgtccggca gttgcaggag cggatggagt tgctgcaggc   2160
agagggagcc acagctgtca cgggggtccc cagtccccgg gccacggatc caccttccca   2220
tctagatggc cccccggccg tggctgtggg ccagtgcccg ctggtggggc caggccccat   2280
gcaccgccgc cacctgctgc tccctgccag ggtccctagg cctggcctat cggaggcgct   2340
ttccctgctc ctgttcgccg ttgttctgtc tcgtgccgcc gccctgggct gcattgggtt   2400
ggtggcccac gccggccaac tcaccgcagt ctggcgccgc ccaggagccg cccgcgctcc   2460
ctgaacccta gaactgtctt cgactccggg gccccgttgg aagactgagt gcccggggca   2520
cggcacagaa gccgcgccca ccgcctgcca gttcacaacc gctccgagcg tgggtctccg   2580
cccagctcca gtcctgtgat ccgggcccgc cccctagcgg ccggggaggg aggggccggg   2640
tccgcggccg gcgaacgggg ctcgaagggt ccttgtagcc gggaatgctg ctgctgctgc   2700
tgctgctgct gctgctgctg ctgctgctgc tgctgctgct gctgctgggg ggatcacaga   2760
ccatttcttt ctttcggcca ggctgaggcc ctgacgtgga tgggcaaact gcaggcctgg   2820
gaaggcagca agccgggccg tccgtgttcc atcctccacg cacccccacc tatcgttggt   2880
tcgcaaagtg caaagctttc ttgtgcatga cgccctgctc tggggagcgt ctggcgcgat   2940
ctctgcctgc ttactcggga aatttgcttt tgccaaaccc gctttttcgg ggatcccgcg   3000
ccccccctcct cacttgcgct gctctcggag ccccagccgg ctccgcccgc ttcggcggtt   3060
tggatattta ttgacctcgt cctccgactc gctgacaggc tacaggaccc ccaacaaccc   3120
caatccacgt tttggatgca ctgagacccc gacattcctc ggtatttatt gtctgtcccc   3180
acctaggacc cccacccccg accctcgcga ataaaaggcc ctccatctgc ccaaagctct   3240
gga                                                                 3243
```